US012486277B2

(12) United States Patent
Lu et al.

(10) Patent No.: US 12,486,277 B2
(45) **Date of Patent: *Dec. 2, 2025**

(54) CDK INHIBITORS AND THEIR USE AS PHARMACEUTICALS

(71) Applicant: Prelude Therapeutics Incorporated, Wilmington, DE (US)

(72) Inventors: Liang Lu, Hockessin, DE (US); Rupa Shetty, Blue Bell, PA (US); Andrew Paul Combs, Kennett Square, PA (US); Chaofeng Dai, Hockessin, DE (US); Raul Andrew Leal, Newark, DE (US); Klare Lazor Bersch, Glen Mills, PA (US)

(73) Assignee: Prelude Therapeutis Incorporated, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/295,394

(22) Filed: Apr. 4, 2023

(65) Prior Publication Data

US 2023/0242543 A1 Aug. 3, 2023

(51) Int. Cl.

| | |
|---|---|
| ***C07D 487/04*** | (2006.01) |
| ***A61P 35/00*** | (2006.01) |
| ***C07D 401/04*** | (2006.01) |
| ***C07D 401/08*** | (2006.01) |
| ***C07D 401/14*** | (2006.01) |
| ***C07D 405/14*** | (2006.01) |
| ***C07D 413/14*** | (2006.01) |
| ***C07D 417/04*** | (2006.01) |
| ***C07D 417/08*** | (2006.01) |
| ***C07D 417/14*** | (2006.01) |
| ***C07D 471/04*** | (2006.01) |
| ***C07D 498/04*** | (2006.01) |

(52) U.S. Cl.

CPC ............ *C07D 487/04* (2013.01); *A61P 35/00* (2018.01); *C07D 401/04* (2013.01); *C07D 401/08* (2013.01); *C07D 401/14* (2013.01); *C07D 405/14* (2013.01); *C07D 413/14* (2013.01); *C07D 417/04* (2013.01); *C07D 417/08* (2013.01); *C07D 417/14* (2013.01); *C07D 471/04* (2013.01); *C07D 498/04* (2013.01)

(58) Field of Classification Search

CPC .. C07D 487/04; C07D 401/08; C07D 401/14; C07D 413/14; C07D 417/08; C07D 417/14; C07D 471/04

See application file for complete search history.

(56) References Cited

U.S. PATENT DOCUMENTS

| | | | | |
|---|---|---|---|---|
| 11,673,893 | B2 * | 6/2023 | Lu ........................ | A61K 31/506 514/234.5 |
| 2010/0056525 | A1 | 3/2010 | Rheault et al. | |
| 2011/0015117 | A1 | 1/2011 | Florjan | |
| 2011/0015173 | A1 | 1/2011 | Florjancic et al. | |
| 2014/0275011 | A1 | 9/2014 | Mastracchio et al. | |
| 2015/0225422 | A1 | 8/2015 | Bharathan | |
| 2016/0009682 | A1 | 1/2016 | Miller et al. | |
| 2016/0333007 | A1 | 11/2016 | Bharathan et al. | |
| 2016/0376287 | A1 | 12/2016 | Barlaam | |
| 2018/0273528 | A1 | 9/2018 | Bálint et al. | |
| 2018/0273852 | A1 | 9/2018 | Balint | |
| 2022/0089608 | A1 | 3/2022 | Buesking | |
| 2022/0267345 | A1 | 8/2022 | Wu | |
| 2022/0324830 | A1 | 10/2022 | Lu | |
| 2023/0144528 | A1 * | 5/2023 | Lu ........................ | C07D 401/04 546/272.7 |
| 2025/0011298 | A1 * | 1/2025 | Cao ...................... | A61K 31/635 |

FOREIGN PATENT DOCUMENTS

| | | | | |
|---|---|---|---|---|
| WO | 2014160017 | A1 | 10/2014 | |
| WO | 2015108861 | A1 | 7/2015 | |
| WO | 2016022312 | A1 | 2/2016 | |
| WO | 2016197078 | A1 | 12/2016 | |
| WO | 2017055530 | A1 | 4/2017 | |
| WO | 2021115335 | A1 | 6/2021 | |
| WO | 2022035799 | A1 | 2/2022 | |
| WO | WO-2023064920 | A1 * | 4/2023 | .............. A61P 35/00 |
| WO | WO-2025076115 | A1 * | 4/2025 | ........... C07D 401/02 |

OTHER PUBLICATIONS

Pubchem. CID 24953600, Oct. 13, 2008, pp. 1-9, Retrieved from the internet , URL: https://pubchem.nlm.nih.gov/compound/24953600.; p. 2, formula.

* cited by examiner

*Primary Examiner* — Daniel R Carcanague
(74) *Attorney, Agent, or Firm* — BakerHostetler

(57) ABSTRACT

The disclosure is directed to, in part, to CDK inhibitors, pharmaceutical compositions comprising the same, as well as methods of their use and preparation.

23 Claims, No Drawings

CDK INHIBITORS AND THEIR USE AS PHARMACEUTICALS

CROSS REFERENCE TO RELATED APPLICATIONS

The present application is a continuation of U.S. patent application Ser. No. 17/018,005, filed Sep. 11, 2020, which claims priority to U.S. Provisional Application No. 63/005,577 filed Apr. 6, 2020 and U.S. Provisional Application No. 62/898,839, filed Sep. 11, 2019. The entirety of each of the foregoing applications is incorporated by reference herein.

TECHNICAL FIELD

The disclosure is directed to CDK inhibitors and methods of their use.

BACKGROUND

Cyclin-dependent kinases (CDK), a family of serine/threonine kinases whose activities are dependent on association and activation by cyclins, play critical roles in regulating cell cycle and gene transcription (Malumbres, M. (2014). "Cyclin-dependent kinases." Genome Biol 15(6): 122). While CDK1, CDK2, CDK4, and CDK6 are directly involved in promoting cell division, other members such as CDK7, CDK8 and CDK9 comprise a second subgroup that regulates transcription.

Upon gene activation, transcription activators, co-activators/mediator complex (MC), and RNA polymerase II (RNA Pol II) first assemble on the gene promoter to form the pre-initiation complex (PIC). RNA Pol II is then released from the complex upon PIC activation to start initial transcription, only to be paused by factors like negative elongation factors (NELF) and DRB sensitivity induced factors (DSIF) shortly after. This is termed promoter pausing. Productive elongation does not occur until paused RNA Pol II is released from pausing by positive transcription elongation factor b (p-TEFb) (Harlen, K. M. and L. S. Churchman (2017). "The code and beyond: transcription regulation by the RNA polymerase II carboxy-terminal domain." Nat Rev Mol Cell Biol 18(4): 263-273). During this process, CDK8, as a subunit of MC, facilitates PIC formation, while CDK7, a component of transcription factor IIH (TFIIH), phosphorylates Serine-5/7 of RNA Pol II C-terminal domain (CTD) to trigger its escape from the promoter region, and CDK9, the catalytic subunit of p-TEFb, phosphorylates Serine-2 of CTD as well as NEFL, DSIF to release RNA Pol II from pausing, allowing it to elicit productive elongation (Franco, L. C., et al. (2018). "CDK9: A key player in cancer and other diseases." J Cell Biochem 119(2): 1273-1284; Soutourina, J. (2018). "Transcription regulation by the Mediator complex." Nat Rev Mol Cell Biol 19(4): 262-274)).

As the master regulator controlling releasing of paused Pol II from the promoter, CDK9 plays pivotal roles in promoting gene expression. Consistently, inhibition of CDK9 triggers global down-regulation of gene expression (Olson, C. M., et al. (2018). "Pharmacological perturbation of CDK9 using selective CDK9 inhibition or degradation." Nat Chem Biol 14(2): 163-170), among which are short-lived transcripts, such as the oncogene, c-Myc, and Mcl-1, a member of pro-survival Bcl-2 family of proteins that promote cancer cell survival (Chen, R., et al. (2005). "Transcription inhibition by flavopiridol: mechanism of chronic lymphocytic leukemia cell death." Blood 106(7): 2513-2519; Youle, R. J. and A. Strasser (2008). "The BCL-2 protein family: opposing activities that mediate cell death." Nat Rev Mol Cell Biol 9(1): 47-59), suggesting an indirect approach to target Mcl-1 to treat cancer (Krystof, V., et al. (2012). "Perspective of cyclin-dependent kinase 9 (CDK9) as a drug target." Curr Pharm Des 18(20): 2883-2890). Indeed, several CDK9 inhibitors have been developed and showed promising anti-cancer activities in preclinical models and have been advanced into the clinic (Boffo, S., et al. (2018). "CDK9 inhibitors in acute myeloid leukemia." J Exp Clin Cancer Res 37(1): 36). Interestingly, a recent study found that CDK9 inhibition also reactivates epigenetically silenced tumor suppressor genes, adding another line of evidence that supports targeting CDK9 for cancer therapy (Zhang, H., et al., (2018). "Targeting CDK9 Reactivates Epigenetically Silenced Genes in Cancer." Cell 175(5): 1244-1258.e1226).

SUMMARY

The disclosure is directed to compounds of Formula (I) or Formula (II),

Formula (I)

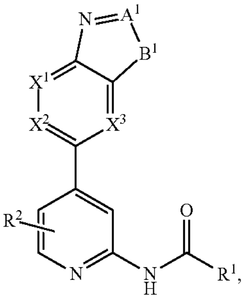

,

Formula (II)

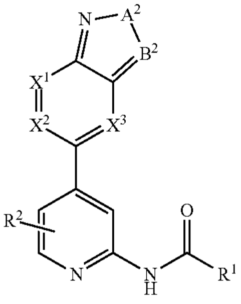

or pharmaceutically acceptable salts or solvates thereof; wherein

- $X^1$, $X^2$, and $X^3$ are each independently N or $CR^3$;
- $A^1$ is N or C—$R^4$;
- $B^1$ is C—$R^6R^7$, N—$R^5$, O, or S;
- $A^2$ is N—$R^8$, S, or O;
- $B^2$ is C—$R^9$ or N;

$R^1$ is selected from $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5.14 membered heteroaryl, 4-10 membered heterocycloalkyl, $C_{6-10}$ aryl-$C_{1-4}$ alkyl, $C_{3-10}$ cycloalkyl$C_{1-4}$ alkyl, (5-14 membered heteroaryl)-$C_{1-4}$ alkyl, and (4-14 membered heterocycloalkyl)-$C_{1-4}$ alkyl;

wherein $R^1$ is optionally substituted with 1, 2, 3, 4, 5, 6, 7 or 8 independently selected $R^b$ substituents;

$R^2$, $R^3$, $R^4$, $R^5$, $R^6$, $R^7$, $R^8$ and $R^9$ are each independently selected from H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl, $C_{1-4}$alkyl, (5-14 membered heteroaryl)-$C_{1-4}$ alkyl, (4-14 membered heterocycloalkyl)-$C_{1-4}$ alkyl, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NHR^{a1}$, $NR^{a1}R^{a1}$, $NR^{a1}C(O)R^{a1}$, $NR^{a1}C(O)OR^{a1}$, $NR^{a1}C(O)NR^{a1}R^{a1}$, $C(=NR^{a1})R^{a1}$, $C(=NR^{a1})NR^{a1}R^{a1}$, $NR^{a1}C(=NR^{a1})NR^{a1}R^{a1}$ $NR^{a1}C(=NOH)NR^{a1}R^{a1}$ $NR^{a1}C(=NCN)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$ $S(O)_2R^{a1}$, $SF_5$, $P(O)R^{a1}R^{a1}$, $P(O)(OR^{a1})(OR^{a1})$, $B(OR^{a1})_2$ and $S(O)_2NR^{a1}R^{a1}$;

wherein when $R^2$, $R^3$, $R^4$, $R^5$, $R^6$, $R^7$, $R^8$ or $R^9$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^2$, $R^3$, $R^4$, $R^5$, $R^6$, $R^7$, $R^8$ or $R^9$ is optionally substituted with 1, 2, 3, 4 or 5 independently selected $R^b$ substituents;

or $R^4$ and $R^5$, together with the atoms to which they are attached, form a 5-, 6-, or 7-membered heterocycloalkyl ring optionally substituted with 1, 2, 3, 4 or 5 independently selected $R^b$ substituents;

or $R^6$ and $R^7$ together with the carbon atom to which they are both attached, form a $C_3$-$C_7$ spirocyclic ring;

or $R^8$ and $R^9$, together with the atoms to which they are attached, form a 5-, 6-, or 7-membered heterocycloalkyl ring optionally substituted with 1, 2, 3, 4 or 5 independently selected $R^b$ substituents;

each $R^{a1}$ is independently selected from H, D, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$alkyl, $C_{3-10}$ cycloalkyl-$C_{1-4}$ alkyl, (5-10 membered heteroaryl)-$C_{1-4}$ alkyl, and (4-14 membered heterocycloalkyl)-$C_{1-4}$ alkyl;

wherein when $R^{a1}$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^{a1}$ is optionally substituted with 1, 2, 3, 4, or 5 independently selected $R^d$ substituents;

each $R^b$ substituent is independently selected from D, halo, oxo, $C_{1-4}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$;

wherein when $R^b$ is $C_{1-4}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents;

each $R^c$ is independently selected from H, D, OH, $C_{1-6}$ alkyl, $C_{1-6}$ alkoxy, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl;

wherein when $R^c$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^c$ is optionally substituted with 1, 2, 3, 4, or 5 independently selected $R^f$ substituents;

each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^g$, ORB, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $NR^gC(=NOH)NR^gR^g$, $NR^gC(=NCN)NR^gR^g$, $SF_5$, $P(O)R^gR^g$, $P(O)(OR^g)(OR^g)$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$;

wherein when $R^f$ is $C_{1-4}$alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R^n$ substituents;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $NR^oC(=NOH)NR^oR^o$, $NR^oC(=NCN)NR^oR^o$, $SF_5$, $P(O)R^oR^o$, $P(O)(OR^o)(OR^o)$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $SF_5$, $P(O)R^eR^e$, $P(O)(OR^e)(OR^e)$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein when $R^d$ is $C_{1-6}$alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected $R^f$ substituents;

each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents;

each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected $R^P$ substituents;

each $R^P$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^rR^r$, $NR^rC(O)R^r$, $NR^rC(O)NR^rR^r$, $NR^eC(O)OR^r$, $C(=NR^r)NR^r$, $NR^rC(=NR^r)NR^rR^r$, $NR^rC(=NOH)NR^rR^r$, $NR^rC(=NCN)NR^rR^r$, $SF_5$, $P(O)R^rR^r$, $P(O)(OR^r)(OR^r)$, $S(O)R^r$, $S(O)NR^rR^r$, $S(O)_2R^r$, $NR^rS(O)_2R^r$, $NR^rS(O)_2NR^rR^r$, and $S(O)_2NR^rR^r$;

each $R^o$ or $R^r$ is independently selected from H, D, $C_{1-4}$ alkyl, $C_{3-6}$cycloalkyl, $C_{6-10}$ aryl, 5 or 6-membered heteroaryl, $C_{1-4}$ haloalkyl, $C_{2-4}$alkenyl, and $C_{2-4}$ alkynyl, wherein when $R^o$ or $R^r$ is $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl, then $R^o$ or $R^r$ is optionally substituted with 1, 2 or 3 independently selected $R^q$ substituents;

each $R^q$ is independently selected from D, OH, CN, —COOH, $NH_2$, halo, $C_{1-6}$alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, $—CONHR^{12}$, $—NHC(O)R^{12}$, $—OC(O)R^{12}$, $—C(O)OR^{12}$, $—C(O)R^{12}$, $—SO_2R^{12}$, $—NHSO_2R^{12}$, $—SO_2NHR^{12}$ and $NR^{12}R^{12}$, wherein when $R^q$ is $C_{1-6}$ alkyl, phenyl, 4-6 membered heterocycloalkyl or 5-6 membered heteroaryl, then $R^g$ is optionally substituted with OH, CN, —COOH, $NH_2$, $C_{1-6}$ alkoxy, $C_{3-6}$cycloalkyl or 4-6 membered heterocycloalkyl; and each $R^{12}$ is independently $C_{1-6}$ alkyl.

In some embodiments, compounds having a formula of

Formula (III)

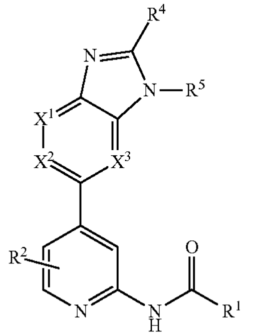

or

Formula (IV)

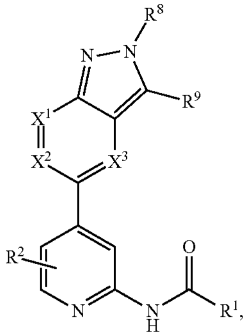

or pharmaceutically acceptable salts or solvates thereof, wherein the variables are as defined herein, are provided.

In some embodiments, compounds having a formula of

Formula (V)

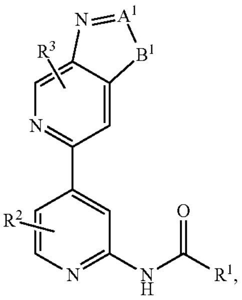

Formula (VI)

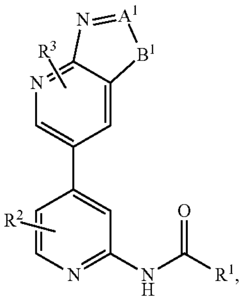

-continued
Formula (VII)
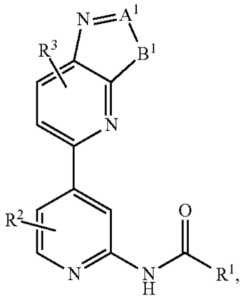
Formula (VIII)
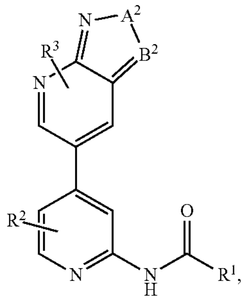
Formula (IX)
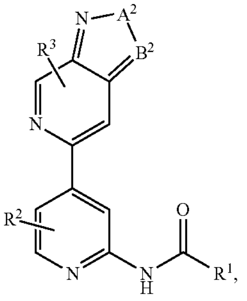
Formula (X)
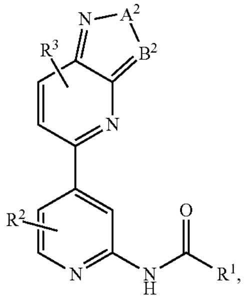
Formula (XI)
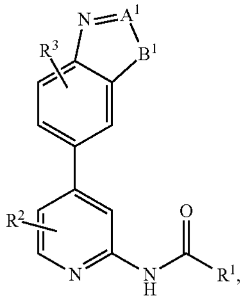
or
-continued
Formula (XII)
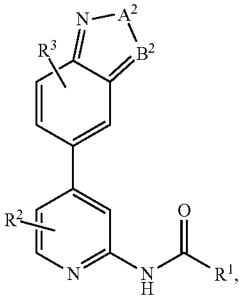
or pharmaceutically acceptable salts or solvates thereof, wherein the variables are as defined herein, are provided
In some embodiments, compounds having a formula of Formula (V), Formula (VI), Formula (VII), or Formula (XI):
Formula (V)
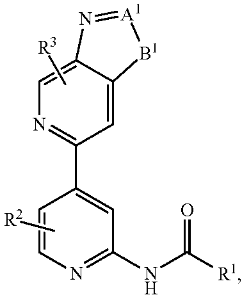
Formula (VI)
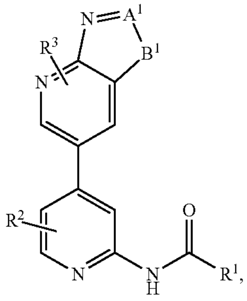
Formula (VII)
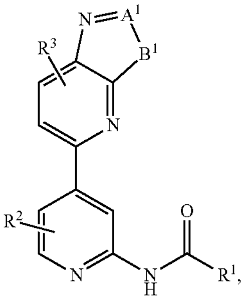
or -continued Formula (XI)

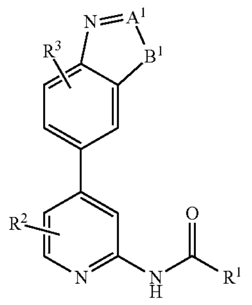

or pharmaceutically acceptable salts or solvates thereof, wherein the variables are as defined herein, are provided.

In some embodiments, compounds having Formula (VIII), Formula (IX), Formula (X), or Formula (XII):

Formula (VIII)

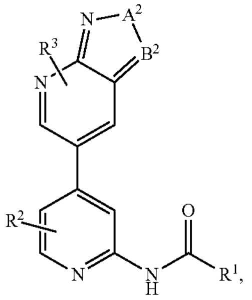

Formula (IX)

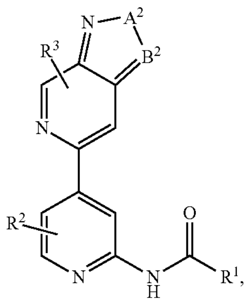

Formula (X)

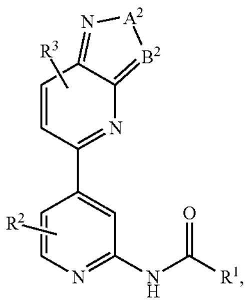

or

-continued

Formula (XII)

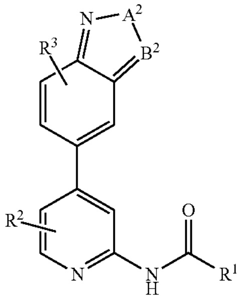

or pharmaceutically acceptable salts or solvates thereof, wherein the variables are as defined herein, are provided.

In some embodiments, compounds having a formula of

Formula (XIV-c)

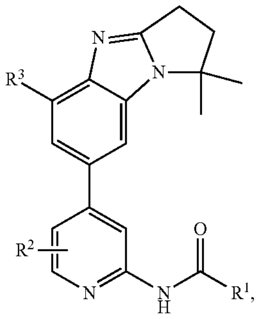

Formula (XV)

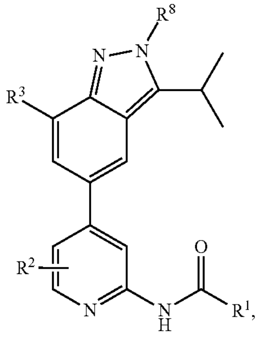

Formula (XVIII)

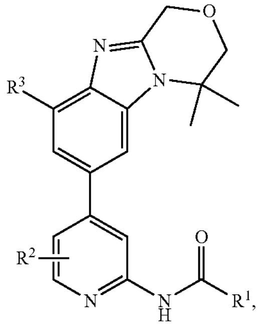

or pharmaceutically acceptable salts or solvates thereof, wherein the variables are as defined herein, are provided and wherein when there are more than one $R^b$, each $R^b$ is independent to others.

In some embodiments, compounds having a formula of solvate thereof, has a formula of Formula (XIX-a)

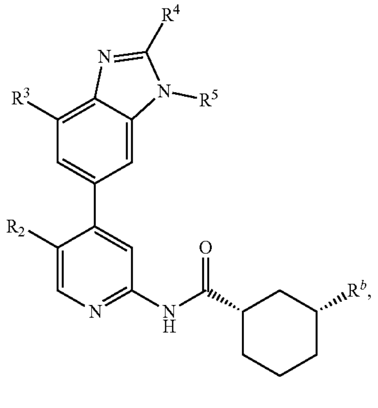

wherein $R^2$ is Me or OMe;

$R^3$ is H, D, or F;

$R^4$ is H or $C_{1-3}$ alkyl;

$R^5$ is isopropyl, —$CF_3(CH)CH_3$, —$C_{3-6}$ cycloalkyl, or —$CH_2$—($C_{3-6}$ cycloalkyl);

$R^b$ is $NHCOR^{13}$ or CN; and $R^{13}$ is H or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl In some embodiments, compounds having a formula of Formula (XXIII-a)

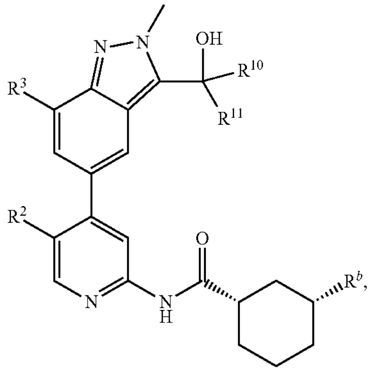

wherein:

$R^2$ is H, D, halogen, or Me;

$R^3$ is H, D, or F;

$R^{10}$ is H, D, Me, or $C_{1-3}$ haloalkyl;

$R^{11}$ is H, D, Me, or $C_{1-3}$ haloalkyl;

$R^b$ is $NHCOR^{14}$; and $R^{14}$ is H, —$CH_2CN$, or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl.

In some embodiments, compounds having a formula of

Formula (XXI-e)

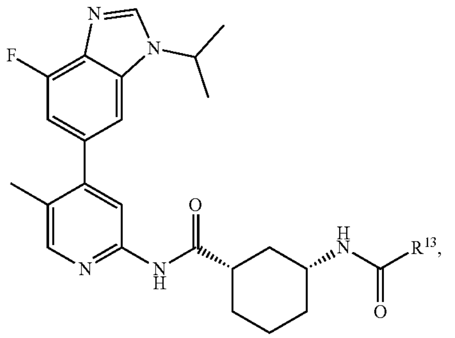

or

Formula (XXVII-e)

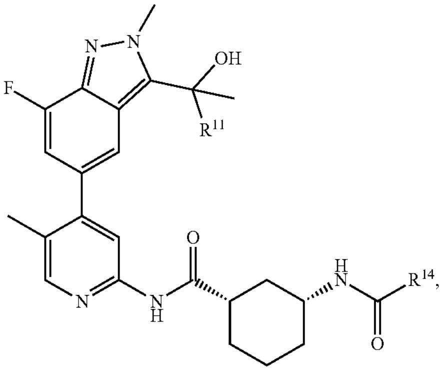

or pharmaceutically acceptable salts or solvates thereof, wherein the variables are as defined herein, are provided.

In some embodiments, methods of inhibiting a CDK enzyme are provided, the method comprising: contacting the CDK enzyme with an effective amount of a compound as provided herein, or a pharmaceutically acceptable salt or solvate thereof, or a pharmaceutical composition comprising the same.

In some embodiments, methods of treating a disease or disorder associated with aberrant CDK activity in a subject or a subject in need thereof are provided, the method comprising administering to the subject, a compound as provided herein, or a pharmaceutically acceptable salt or solvate thereof, or a pharmaceutical composition comprising the same.

In some embodiments, methods of treating cancer in a subject or a subject in need thereof are provided, the method comprising administering to the subject, a compound as provided herein, or a pharmaceutically acceptable salt or solvate a pharmaceutical composition comprising the same In some embodiments, pharmaceutical composition comprising one or more compounds, or a pharmaceutically acceptable salt or solvate thereof, or a compound of the various formula provided herein, or a pharmaceutically acceptable salt or solvate thereof, are provided.

Stereoisomers of the compounds of the various formula provided herein, and pharmaceutical salts and solvates thereof, are also contemplated, described, and encompassed herein. Methods of using compounds of the formula provided herein are described, as well as pharmaceutical compositions including the compounds of the formula provided herein.

DETAILED DESCRIPTION

The disclosure may be more fully appreciated by reference to the following description, including the following definitions and examples. Certain features of the disclosed compositions and methods that are described herein in the context of separate aspects may also be provided in combination in a single aspect. Alternatively, various features of the disclosed compositions and methods that are, for brevity, described in the context of a single aspect, may also be provided separately or in any subcombination.

At various places in the present specification, substituents of compounds are disclosed in groups or in ranges. It is specifically intended that the embodiments include each and every individual subcombination of the members of such groups and ranges. For example, the term "$C_{1-6}$ alkyl" or "$C_1$-$C_6$ alkyl" is specifically intended to individually disclose methyl, ethyl, $C_3$ alkyl, $C_4$ alkyl, $C_5$ alkyl, and $C_6$ alkyl.

It is further appreciated that certain embodiments, which are, for clarity, described in the context of separate embodiments, can also be provided in combination in a single embodiment.

Conversely, various features of the embodiments, which are, for brevity, described in the context of a single embodiment, can also be provided separately or in any suitable sub-combination.

All percentages and ratios used herein, unless otherwise indicated, are by weight.

The term "alkyl," when used alone or as part of a substituent group, refers to a straight- or branched-chain hydrocarbon group, a spirocyclic group, or a fused or bridged bicyclic group, each of which has from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like. The term "spirocyclic group" refers to spirocyclic compounds in which the two rings share only one single atom, the spiro atom, which is usually a quaternary carbon. Examples of spirocyclic compounds are spiro[2,3]undecane, spiro[3,3]heptane, and spiro[5,5]undecane. The term "fused bicyclic group" refers to fused bicyclic compounds, in which two rings share two adjacent atoms. Examples of fused bicyclic compounds include bicyclo[4.4.0]decane, α-thujene and decalin and the like. The term "bridged bicyclic group" refers to bridged bicyclic compounds, in which the two rings share three or more atoms, separating the two bridgehead atoms by a bridge containing at least one atom. Examples of bridged bicyclic compounds include bicyclo[2.2.1]heptane, bicyclo [1,1,1] pentane, bicyclo[2.2.1]heptane, bicyclo[2.2.2]octane, bicyclo-[3.3.1]nonane, bicyclo[3.3.3]undecane, and the like. The term "haloalkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group, wherein one or more of the hydrogen atoms in the group have been replaced by a halogen atom. Examples of haloalkyl groups include trifluoromethyl ($-CF_3$, $C_1$haloalkyl), trifluoroethyl ($-CH_2CF_3$, $C_2$haloalkyl), and the like.

The term "halo" or "halogen" refers to chloro, fluoro, bromo, or iodo.

The term "oxo" refers to an oxygen atom (i.e., =O) as a divalent substituent, forming a carbonyl group when attached to a carbon (e.g. C=O), or attached to a nitrogen or sulfur heteroatom forming a nitroso, sulfinyl or sulfonyl.

The term "cycloalkyl" when used alone or as part of a substituent group refers to monocyclic, bicyclic, or tricyclic, non-aromatic hydrocarbon groups having from 3 to 10 carbon atoms ("$C_3$-$C_{10}$"), preferably from 3 to 6 carbon atoms ("$C_3$-$C_6$"), or from 3 to 7 carbon atoms ("$C_3$-$C_7$"). Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), and the like.

The term "heterocycloalkyl" when used alone or as part of a substituent group refers to any three to fourteen membered monocyclic, bicyclic, or tricyclic saturated ring structure containing at least one heteroatom selected from the group consisting of O, N and S. Heterocycloalkyl groups may be described with respect to the number of atoms in the group, or with respect to the number of carbon atoms in the group. The term "bicyclic" ring structure refers to a spirocyclic, fused bicyclic, or bridged bicyclic ring. For example, the term "4-10 membered heterocycloalkyl" refers to a heterocycloalkyl group containing between 4 and 10 ring atoms. The term $-C_4$-$C_6$ heterocycloalkyl, for example, refers to a heterocycloalkyl group containing four to six carbon atoms. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, Decahydroquinoline, 2-azaspiro[5.5]undecane, 6-oxa-3-azabicyclo[3.1.1]heptane, and the like.

The term "aryl" when used alone or as part of a substituent group refers to a mono- or bicyclic-aromatic hydrocarbon ring structure having 6 or 10 carbon atoms in the ring system. Examples of aryl groups are phenyl and naphthyl.

The term "heteroaryl" when used alone or as part of a substituent group refers to a mono-, bi- or tricyclic-aromatic ring structure including carbon atoms as well as up to four heteroatoms selected from nitrogen, oxygen, and sulfur. Heteroaryl rings can include a total of 5, 6, 9, 10, or 14 ring atoms. Heteroaryl groups may be described with respect to the number of atoms in the group, or with respect to the number of carbon atoms in the group. Thus, the term "5-14 membered heteroaryl" refers to a heteroaryl group containing between 5 and 14 ring atoms. The term $-C_4$-$C_6$ heteroaryl, for example, refers to a heteroaryl group containing four to six carbon atoms. Examples of heteroaryl groups include but are not limited to, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like.

When a range of carbon atoms is used herein, for example, $C_1$-$C_6$ all ranges, as well as individual numbers of carbon atoms are encompassed. For example, "$C_1$-$C_3$" includes $C_1$-$C_3$, $C_1$-$C_2$, $C_2$-$C_3$, $C_1$, $C_2$, and $C_3$. The range of carbon atoms may be expressed with alternative expressions. For example, the term "$C_{1-6}$" is an alternative expression of "$C_1$-$C_6$".

When a ring system is described herein as having a range of members, for example, "5-14-membered", all ranges, as well as individual numbers of atoms are encompassed. For example, "5-14-membered" includes 5-6-membered, 5-10-membered, 6-9-membered, 5-membered, 6-membered, 7-membered, 8-membered, and the like.

As used herein, "alkoxy" refers to an —O-alkyl group. Example alkoxy groups include methoxy, ethoxy, propoxy (e.g., n-propoxy and isopropoxy), t-butoxy, and the like.

The term "alkenyl" when used alone or as part of a substituent group refers to a straight- or branched-chain group having from 2 to 12 carbon atoms ("$C_2$-$C_{12}$"), preferably 2 to 6 carbons atoms ("$C_{2-6}$"), in the group, wherein the group includes at least one carbon-carbon double bond of alkenyl groups include vinyl ($—CH{=}CH_2$; $C_2$alkenyl), allyl ($—CH_2—$ $CH{=}CH_2$; $C_3$alkenyl), propenyl ($—CH{=}CHCH_3$; $C_3$alkenyl); isopropenyl ($—C(CH_3){=}CH_2$; $C_3$alkenyl), butenyl ($—CH{=}CHCH_2CH_3$; $C_4$alkenyl), sec-butenyl ($—C(CH_3){=}CHCH_3$; $C_4$alkenyl), iso-butenyl ($—CH{=}C(CH_3)_2$; $C_4$alkenyl), 2-butenyl ($—CH_2CH{=}CHCH_3$; $C_4$alkyl), pentenyl ($CH{=}CHCH_2CH_2CH_3$ or $CH_2{=}CHCH_2CH_2CH_2—$; $C_5$alkenyl), and the like.

The term "alkynyl" when used alone or as part of a substituent group refers to a straight- or branched-chain group having from 2 to 12 carbon atoms ("$C_2$-$C_{12}$"), preferably 2 to 6 carbons atoms ("$C_2$-$C_6$"), in the group, wherein the group includes at least one carbon-carbon triple bond. Examples of alkynyl groups include ethynyl ($—C{\equiv}CH$; $C_2$alkynyl), propargyl ($—CH_2—$ $CH{\equiv}CH$; $C_3$alkynyl), and the like.

The compounds described herein can be asymmetric (e.g., having one or more stereocenters). All stereoisomers, such as enantiomers and diastereomers, are intended unless otherwise indicated. Compounds provided herein that contain asymmetrically substituted carbon atoms can be isolated in optically active or racemic forms. Methods on how to prepare optically active forms from optically active starting materials are known in the art, such as by resolution of racemic mixtures or by stereoselective synthesis. Geometric isomers of olefins, C═N double bonds, and the like can also be present in the compounds described herein, and all such stable isomers are contemplated in the present embodiments. Geometric isomers of the compounds of the present embodiments are described and may be isolated as a mixture of isomers or as separated isomeric forms.

Compounds provided herein may also include tautomeric forms. All tautomeric forms are encompassed.

In some embodiments, the compounds may exist as rotational isomers. In some embodiments, the compounds exist as mixtures of rotational isomers in any proportion. In other embodiments, the compounds exist as particular rotational isomers, substantially free of other rotational isomers.

Compounds can also include all isotopes of atoms occurring in the intermediates or final compounds. Isotopes include those atoms having the same atomic number but different mass numbers. For example, isotopes of hydrogen include tritium and deuterium.

In some embodiments, the compounds, and salts thereof, are substantially isolated. By "substantially isolated" is meant that the compound is at least partially or substantially separated from the environment in which is formed or detected. Partial separation can include, for example, a composition enriched in the compound. Substantial separation can include compositions containing at least about 50%, at least about 60%, at least about 70%, at least about 80%, at least about 90%, at least about 95%, at least about 97%, or at least about 99% by weight of the compound, or salt thereof. Methods for isolating compounds and their salts are routine in the art.

Also provided herein are pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts t include, but are not limited to, the conventional non-toxic salts of the parent compound formed, for example, from non-toxic inorganic or organic acids. The pharmaceutically acceptable salts can be synthesized from the parent compound, which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* $17^{th}$ ed., Mack Publishing Company, Easton, Pa., 1985, p. 1418 and *Journal of Pharmaceutical Science,* 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound provided herein with one or more solvent molecules.

"Subject" includes humans. The terms "human," "patient," and "subject" are used interchangeably herein.

As used herein, the phrase "in need thereof" means that the animal or mammal (subject) has been identified as having a need for the particular method or treatment. In some embodiments, the identification can be by any means of diagnosis. In any of the methods and treatments described herein, the animal or mammal can be in need thereof. In some embodiments, the animal or mammal is in an environment or will be traveling to an environment in which a particular disease, disorder, or condition is prevalent. In some embodiments, the subject in need thereof is suspected of having the condition that needs to be treated.

"Treating" or "treatment" of any disease or disorder refers, in some embodiments, to ameliorating the disease or disorder (i.e., arresting or reducing the development of the disease or at least one of the clinical symptoms thereof). In another embodiment, "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

As used herein, the phrase "integer from X to Y" means any integer that includes the endpoints. For example, the phrase "integer from X to Y" or "1-5" or "1 to 5" means 1, 2, 3, 4, or 5 or any value therein if not modified by the term "integer."

"Compounds of the present disclosure," and equivalent expressions, are meant to embrace compounds of any formula or structural representation as described herein, as well as their subgenera, which expression includes the stereoisomers (e.g., enantiomers, diastereomers) and constitutional isomers (e.g., tautomers) of the various compounds and formula provided for herein as well as pharmaceutically acceptable salts thereof, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium ($^2H$ or D), carbon-13 ($^{13}C$), nitrogen-15 ($^{15}N$), or the like. It will be understood that, in a compound where such isotopic substitution is made, the following atoms, where present, may vary, so that for example, any hydrogen may be $^2H$/D, any carbon may be $^{13}C$, or any nitrogen may be $^{15}N$, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well known in the art.

Throughout the description, where compositions are described as having, including, or comprising specific components, or where processes are described as having, including, or comprising specific process steps, it is contemplated that compositions described herein also consist essentially of, or consist of, the recited components, and that the processes described herein also consist essentially of, or consist of, the recited processing steps. Further, it should be understood that the order of steps or order for performing certain actions are immaterial so long as the process remains operable. Moreover, two or more steps or actions can be conducted simultaneously.

In some embodiments, compounds of Formula (I) or Formula (II):

(I)

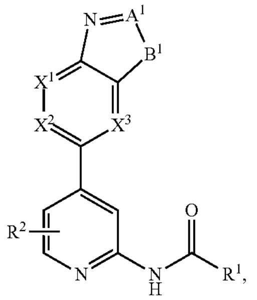

(II)

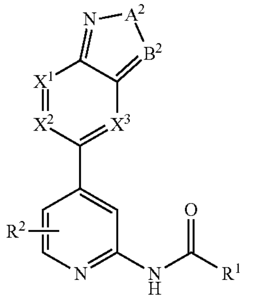

or pharmaceutically acceptable salts or solvates thereof, are provided.

In some embodiments, the disclosure is directed to compounds of Formula (I).

In some embodiments, the disclosure is directed to pharmaceutically acceptable salts or solvates of compounds of Formula (I).

In other embodiments, the disclosure is directed to compounds of Formula (II).

In some embodiments, the disclosure is directed to pharmaceutically acceptable salts or solvates of compounds of Formula (II).

In some embodiments, $X^1$, $X^2$, and $X^3$ in the compounds of Formula (I) or Formula (II) are each independently N or $CR^3$.

In some embodiments $X^1$ is N. In other embodiments, $X^1$ is $CR^3$.

In some embodiments $X^2$ is N. In other embodiments, $X^2$ is $CR^3$.

In some embodiments $X^3$ is N. In other embodiments, $X^3$ is $CR^3$.

In some aspects, $A^1$ in the compounds of Formula (I) is N or C—$R^4$.

In some embodiments, $A^1$ is N.

In other embodiments, $A^1$ is C—$R^4$.

In some aspects, $B^1$ in the compounds of Formula (I) is C—$R^6R^7$, N—$R^5$, O, or S.

In some embodiments, $B^1$ is C—$R^6R^7$.

In other embodiments, $B^1$ is N—$R^5$.

In other embodiments, $B^1$ is O.

In other embodiments, $B^1$ is S.

In some aspects, $A^2$ in the compounds of Formula (II) is N—$R^8$, S, or O.

In some embodiments, $A^2$ is N—$R^8$.

In other embodiments, $A^2$ is S.

In other embodiments, $A^2$ is O.

In some aspects, $B^2$ in the compounds of Formula (II) is C—$R^9$ or N.

In some embodiments, $B^2$ is C—$R^9$.

In other embodiments, $B^2$ is N.

In some aspects, $R^1$ in the compounds of Formula (I) or Formula (II) is selected from $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, and (4-14 membered heterocycloalkyl)-$C_{1-4}$ alkyl; wherein $R^1$ is optionally substituted with 1, 2, 3, 4, 5, 6, 7 or 8 independently selected $R^b$ substituents.

In some embodiments, $R^1$ is $C_{1-6}$alkyl, for example, $C_6$ alkyl, $C_5$ alkyl, $C_4$ alkyl, $C_3$ alkyl, $C_2$ alkyl, $C_1$ alkyl, methyl, ethyl, isopropyl, and the like, wherein $R^1$ is optionally substituted with 1, 2, 3, 4, 5, 6, 7 or 8 independently selected $R^b$ substituents.

In some embodiments, $R^1$ is $C_{1-6}$ alkoxy, for example, $C_6$ alkoxy, $C_5$ alkoxy, $C_4$ alkoxy, $C_3$ alkoxy, $C_2$ alkoxy, $C_1$ alkoxy, methoxy, ethoxy, isopropoxy, and the like, wherein $R^1$ is optionally substituted with 1, 2, 3, 4, 5, 6, 7 or 8 independently selected $R^b$ substituents.

In some embodiments, $R^1$ is $C_{2-6}$ alkenyl, for example, $C_6$ alkenyl, $C_5$ alkenyl, $C_4$ alkenyl, $C_3$ alkenyl, $C_2$ alkenyl, ethenyl, propenyl, isopropenyl, and the like, wherein $R^1$ is optionally substituted with 1, 2, 3, 4, 5, 6, 7 or 8 independently selected $R^b$ substituents.

In some embodiments, $R^1$ is $C_{2-6}$ alkynyl, for example, $C_6$ alkynyl, $C_5$ alkynyl, $C_4$ alkynyl, $C_3$ alkynyl, $C_2$ alkynyl, ethynyl, 2-propynyl (i.e., propargyl), and the like, substituted with 1, 2, 3, 4, 5, 6, 7 or 8 independently selected $R^b$ substituents.

In some embodiments, $R^1$ is $C_{6-10}$ aryl, for example, $C_6$ aryl, $C_7$ aryl, $C_8$ aryl, $C_9$ aryl, $C_{10}$ aryl, phenyl, naphthyl, and the like, optionally substituted with 1, 2, 3, 4, 5, 6, 7 or 8 independently selected $R^b$ substituents.

In some embodiments, $R^1$ is $C_{3-10}$cycloalkyl, for example, $C_{10}$cycloalkyl, $C_9$cycloalkyl, $C_8$cycloalkyl, $C_7$cycloalkyl, $C_6$ cycloalkyl, $C_8$ cycloalkyl, $C_4$ cycloalkyl, $C_3$ cycloalkyl, cyclopropyl, cyclobutyl, cyclopentyl, cyclohexyl, cycloheptyl and the like, optionally substituted with 1, 2, 3, 4, 5, 6, 7 or 8 independently selected $R^b$ substituents.

In some embodiments, $R^1$ is cyclopentyl, optionally substituted with 1, 2, 3, 4, 5, 6, 7 or 8 independently selected $R^b$ substituents.

In some embodiments, $R^1$ is cyclohexyl, optionally substituted with 1, 2, 3, 4, 5, 6, 7 or 8 independently selected $R^b$ substituents.

In other embodiments, $R^1$ is a 5-14 membered heteroaryl, for example, 5 membered heteroaryl, 6 membered heteroaryl, 7 membered heteroaryl, 8 membered heteroaryl, 9 membered heteroaryl, 10 membered heteroaryl, 11 membered heteroaryl, 12 membered heteroaryl, 13 membered heteroaryl, 14 membered heteroaryl, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like, optionally substituted with 1, 2, 3, 4, 5, 6, 7 or 8 independently selected $R^b$ substituents.

In other embodiments, $R^1$ is 4-10 membered heterocycloalkyl, for example, 10 membered heterocycloalkyl, 9 membered heterocycloalkyl, 8 membered heterocycloalkyl; 7 membered heterocycloalkyl, 6 membered heterocycloalkyl, 5 membered heterocycloalkyl, 4 membered heterocycloalkyl, piperidinyl, pyrrolidinyl, tetrahydropyranyl, tetrahydrofuranyl, and the like, optionally substituted with 1, 2, 3, 4, 5, 6, 7 or 8 independently selected $R^b$ substituents.

In other embodiments, $R^1$ is $C_{6-10}$ aryl-$C_{1-4}$ alkyl, for example, $C_{6-10}$ aryl-$C_1$ alkyl, $C_{6-10}$ aryl-$C_2$ alkyl, $C_{6-10}$ aryl-$C_3$ alkyl, $C_{6-10}$ aryl-$C_4$ alkyl, $C_6$ aryl-$C_1$ alkyl, $C_6$ aryl-$C_2$ alkyl, $C_6$ aryl-$C_3$ alkyl, $C_6$ aryl-$C_4$ alkyl, $C_{10}$ aryl-$C_1$ alkyl, $C_{10}$ aryl-$C_2$ alkyl, $C_{10}$ aryl-$C_3$ alkyl, $C_{10}$ aryl-$C_4$ alkyl, —$CH_2$-phenyl, —$CH_2CH_2$-phenyl, —$CH_2$-naphthyl, —$CH_2CH_2$-naphthyl, and the like, optionally substituted with 1, 2, 3, 4, 5, 6, 7 or 8 independently selected $R^b$ substituents.

In other embodiments, $R^1$ is $C_{3-10}$ cycloalkyl-$C_{1-4}$ alkyl, for example, $C_{3-10}$ cycloalkyl-$C_1$ alkyl, $C_{3-10}$ cycloalkyl-$C_2$ alkyl, $C_{3-10}$ cycloalkyl-$C_3$ alkyl, $C_{3-10}$ cycloalkyl-$C_4$ alkyl, $C_{3-6}$ cycloalkyl-$C_1$ alkyl, $C_{3-6}$ cycloalkyl-$C_2$ alkyl, $C_{3-6}$ cycloalkyl-$C_3$ alkyl, $C_{3-6}$ cycloalkyl-$C_4$ alkyl, $C_5$-6 cycloalkyl-$C_1$ alkyl, $C_{5-6}$ cycloalkyl-$C_2$ alkyl, $C_{5-6}$ cycloalkyl-$C_3$ alkyl, $C_{5-6}$ cycloalkyl-$C_4$ alkyl, and the like, optionally substituted with 1, 2, 3, 4, 5, 6, 7 or 8 independently selected $R^b$ substituents.

In other embodiments, $R^1$ is a (5-14 membered heteroaryl)-$C_{1-4}$ alkyl, for example, (5-14 membered heteroaryl)-$C_1$ alkyl, (5-14 membered heteroaryl)-$C_2$ alkyl, (5-14 membered heteroaryl)-$C_3$ alkyl, (5-14 membered heteroaryl)-$C_4$ alkyl, (5 membered heteroaryl)-$C_1$ alkyl, (5 membered heteroaryl)-$C_2$ alkyl, (5 membered heteroaryl)-$C_3$ alkyl, (5 membered heteroaryl)-$C_4$ alkyl, (6 membered heteroaryl)-$C_1$ alkyl, (6 membered heteroaryl)-$C_2$ alkyl, (6 membered heteroaryl)-$C_3$ alkyl, (6 membered heteroaryl)-$C_4$ alkyl, (9 membered heteroaryl)-$C_1$ alkyl, (9 membered heteroaryl)-$C_2$ alkyl, (9 membered heteroaryl)-$C_3$ alkyl, (9 membered heteroaryl)-$C_4$ alkyl, (10 membered heteroaryl)-$C_1$ alkyl, (10 membered heteroaryl)-$C_2$ alkyl, (10 membered heteroaryl)-$C_3$ alkyl, (10 membered heteroaryl)-$C_4$ alkyl, and the like, optionally substituted with 1, 2, 3, 4, 5, 6, 7 or 8 independently selected $R^b$ substituents.

In other embodiments, $R^1$ is (4-14 membered heterocycloalkyl)-$C_{1-4}$ alkyl, for example, (4-14 membered heterocycloalkyl)-$C_1$ alkyl, (4-14 membered heterocycloalkyl)-$C_2$ alkyl, (4-14 membered heterocycloalkyl)-$C_3$ alkyl, (4-14 membered heterocycloalkyl)-$C_4$ alkyl, and the like, optionally substituted with 1, 2, 3, 4, 5, 6, 7 or 8 independently selected $R^b$ substituents.

In some aspects, $R^2$, $R^3$, $R^4$, $R^5$, $R^6$, $R^7$, $R^8$ and $R^9$ in compounds of Formula (I) or Formula (II) are each independently selected from H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, (4-14 membered heterocycloalkyl)-$C_{1-4}$ alkyl, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NHR^{a1}$, $NR^{a1}R^{a1}$, $NR^{a1}C(O)R^{a1}$ $NR^{a1}C(O)OR^{a1}$, $NR^{a1}C(O)NR^{a1}R^{a1}$, $C(=NR^{a1})R^{a1}$, $C(=NR^{a1})NR^{a1}R^{a1}$, $NR^{a1}C(=NR^{a1})N^{a1}R^{a1}$ $NR^{a1}C(=NOH)NR^{a1}R^{a1}$, $NR^{a1}C(=NCN)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$ $S(O)_2R^{a1}$, $SF_5$, $P(O)R^{a1}R^{a1}$, $P(O)(OR^{a1})(OR^{a1})$, $B(OR^{a1})_2$ and $S(O)_2NR^{a1}R^{a1}$;

wherein when $R^2$, $R^3$, $R^4$, $R^5$, $R^6$, $R^7$, $R^8$ or $R^9$ is $C_{1-6}$ alkyl, $C_{1-6}$ alkoxy, $C_{2-6}$alkenyl, $C_{2-6}$ alkynyl, $C_{6-10}$ aryl, $C_3$-10 cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^2$, $R^3$, $R^4$, $R^5$, $R^6$, $R^7$, $R^8$ or $R^9$ is optionally substituted with 1, 2, 3, 4 or 5 independently selected $R^b$ substituents. In some embodiments, $R^2$, $R^3$, $R^4$, $R^5$, $R^6$, $R^7$, $R^8$ or $R^9$ is H.

In some embodiments, $R^2$ is not halo. In some embodiments, $R^2$ is optionally substituted $C_{1-6}$ alkyl. In some embodiments, $R^2$ is optionally substituted $C_{1-4}$ alkyl. In some embodiments, $R^2$ is optionally substituted $C_{1-3}$ alkyl.

In some embodiments, $R^5$ is optionally $C_{1-6}$ alkyl. In some embodiments, $R^5$ is optionally substituted $C_{1-4}$ alkyl. In some embodiments, $R^5$ is optionally substituted $C_{1-3}$ alkyl. In some embodiments, the optionally substituted $C_{1-6}$ alkyl, the optionally substituted $C_{1-4}$ alkyl, or the optionally substituted $C_{1-3}$ alkyl is substituted with two $R^b$ substituents. In some embodiments, the optionally substituted $C_{1-6}$ alkyl, the optionally substituted $C_{1-4}$ alkyl, or the optionally substituted $C_{1-3}$ alkyl is substituted with one $R^b$ substituent. In some embodiments, $R^b$ is not a carbocycle, a heterocycle, or an aryl.

In some embodiments, $R^2$ is H.

In some embodiments, $R^3$ is H.

In some embodiments, $R^4$ is H.

In some embodiments, $R^2$, $R^3$, $R^4$, $R^5$, $R^6$, $R^7$, $R^8$ or $R^9$ is D.

In some embodiments, $R^2$, $R^3$, $R^4$, $R^5$, $R^6$, $R^7$, $R^8$ or $R^9$ is halo, (i.e., F, Cl, Br, or I).

In some embodiments, $R^2$ is halo. In some embodiments, $R^2$ is F. In other embodiments, $R^2$ is Cl.

In some embodiments, $R^3$ is halo. In some embodiments, $R^3$ is F. In other embodiments, $R^3$ is Cl.

In some embodiments, $R^2$, $R^3$, $R^4$, $R^5$, $R^6$, $R^7$, $R^8$ or $R^9$ is oxo.

In some embodiments, $R^2$, $R^3$, $R^4$, $R^5$, $R^6$, $R^7$, $R^8$ or $R^9$ is $C_{1-6}$ alkyl, e.g., $C_6$ alkyl, $C_5$ alkyl, $C_4$ alkyl, $C_3$ alkyl, $C_2$ alkyl, $C_1$ alkyl, -methyl, -ethyl, -isopropyl, and the like, optionally substituted with 1, 2, 3, 4 or 5 independently selected $R^b$ substituents.

In some embodiments, $R^2$ is methyl.

In some embodiments, $R^3$ is methyl.

In some embodiments, $R^4$ is methyl.

In some embodiments, $R^5$ is methyl. In other embodiments, $R^5$ is isopropyl.

In some embodiments, $R^8$ is methyl.

In some embodiments, $R^9$ is methyl. In other embodiments, $R^9$ is isopropyl.

In some embodiments, $R^2$, $R^3$, $R^4$, $R^5$, $R^6$, $R^7$, $R^8$ or $R^9$ is $C_{1-6}$ alkoxy, for example, $C_6$ alkoxy, $C_5$ alkoxy, $C_4$ alkoxy, $C_3$ alkoxy, $C_2$ alkoxy, $C_1$ alkoxy, methoxy, ethoxy, isopropoxy, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{2-6}$ alkenyl, for example, $C_6$ alkenyl, $C_5$ alkenyl, $C_4$ alkenyl, $C_3$ alkenyl, $C_2$ alkenyl, -ethenyl, -propenyl, -isopropenyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{2-6}$ alkynyl, for example, $C_6$ alkynyl, $C_5$ alkynyl, $C_4$ alkynyl, $C_3$ alkynyl, $C_2$ alkynyl, -ethynyl, 2-propynyl (i.e., propargyl), and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{1-6}$ haloalkyl, e.g., $C_6$ haloalkyl, $C_5$haloalkyl, $C_4$ haloalkyl, $C_3$ haloalkyl, $C_2$ haloalkyl, $C_1$ haloalkyl, halomethyl, haloethyl, haloisopropyl, and the like.

In some embodiments, $R^2$, $R^3$, $R^4$, $R^5$, $R^6$, $R^7$, $R^8$ or $R^9$ is $C_{1-6}$ haloalkoxy, for example, $C_6$ haloalkoxy, $C_5$ haloalkoxy, $C_4$ haloalkoxy, $C_3$ haloalkoxy, $C_2$ haloalkoxy, $C_1$ haloalkoxy, halomethoxy, haloethoxy, haloisopropxy, and the like.

In some embodiments, $R^2$, $R^3$, $R^4$, $R^5$, $R^6$, $R^7$, $R^8$ or $R^9$ is $C_{6-10}$ aryl, for example, $C_6$ aryl, $C_7$ aryl, $C_8$ aryl, $C_9$ aryl, $C_{10}$ aryl, phenyl, naphthyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{3-10}$ cycloalkyl, for example, $C_{10}$cycloalkyl, $C_9$cycloalkyl, $C_8$cycloalkyl, $C_7$cycloalkyl, $C_6$ cycloalkyl, $C_5$ cycloalkyl, $C_4$ cycloalkyl, $C_3$ cycloalkyl, cyclopropyl, cyclobutyl, cyclopentyl, cyclohexyl, cycloheptyl and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is 5-10 membered heteroaryl, for example, 5 membered heteroaryl, 6 membered heteroaryl, 7 membered heteroaryl, 8 membered heteroaryl, 9 membered heteroaryl, 10 membered heteroaryl, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is 4-14 membered heterocycloalkyl, for example, 10 membered heterocycloalkyl, 9 membered heterocycloalkyl, 8 membered heterocycloalkyl; 7 membered heterocycloalkyl, 6 membered heterocycloalkyl, 5 membered heterocycloalkyl, 4 membered heterocycloalkyl, piperidinyl, pyrrolidinyl, tetrahydropyranyl, tetrahydrofuranyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{6-10}$ aryl-$C_{1-4}$ alkyl, for example, $C_{6-10}$ aryl-$C_1$ alkyl, $C_{6-10}$ aryl-$C_2$ alkyl, $C_{6-10}$ aryl-$C_3$ alkyl, $C_{6-10}$ aryl-$C_4$ alkyl, $C_6$ aryl-$C_1$ alkyl, $C_6$ aryl-$C_2$ alkyl, $C_6$ aryl-$C_3$ alkyl, $C_6$ aryl-$C_4$ alkyl, $C_{10}$ aryl-$C_1$ alkyl, $C_{10}$ aryl-$C_2$ alkyl, $C_{10}$ aryl-$C_3$ alkyl, $C_{10}$ aryl-$C_4$ alkyl, —$CH_2$-phenyl, —$CH_2CH_2$-phenyl, —$CH_2$-naphthyl, —$CH_2CH_2$-naphthyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is $C_{3-10}$ cycloalkyl-$C_{1-4}$alkyl, for example, $C_{3-10}$ cycloalkyl-$C_1$ alkyl, $C_{3-10}$ cycloalkyl-$C_2$ alkyl, $C_{3-10}$ cycloalkyl-$C_3$ alkyl, $C_{3-10}$ cycloalkyl-$C_4$ alkyl, $C_{3-6}$ cycloalkyl-$C_1$ alkyl, $C_{3-6}$ cycloalkyl-$C_2$ alkyl, $C_{3-6}$ cycloalkyl-$C_3$ alkyl, $C_{3-6}$ cycloalkyl-$C_4$ alkyl, $C_{5-6}$ cycloalkyl-$C_1$ alkyl, $C_{5-6}$ cycloalkyl-$C_2$ alkyl, $C_{5-6}$ cycloalkyl-$C_3$ alkyl, $C_{5-6}$ cycloalkyl-$C_4$ alkyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is (5-14 membered heteroaryl)-$C_{1-4}$ alkyl, for example, (5-14 membered heteroaryl)-$C_1$ alkyl, (5-14 membered heteroaryl)-$C_2$ alkyl, (5-14 membered heteroaryl)-$C_3$ alkyl, (5-14 membered heteroaryl)-$C_4$ alkyl, (5 membered heteroaryl)-$C_1$ alkyl, (5 membered heteroaryl)-$C_2$ alkyl, (5 membered heteroaryl)-$C_3$ alkyl, (5 membered heteroaryl)-$C_4$ alkyl, (6 membered heteroaryl)-$C_1$ alkyl, (6 membered heteroaryl)-$C_2$ alkyl, (6 membered heteroaryl)-$C_3$ alkyl, (6 membered heteroaryl)-$C_4$ alkyl, (9 membered heteroaryl)-$C_1$ alkyl, (9 membered heteroaryl)-$C_2$ alkyl, (9 membered heteroaryl)-$C_3$ alkyl, (9 membered heteroaryl)-$C_4$ alkyl, (10 membered heteroaryl)-$C_1$ alkyl, (10 membered heteroaryl)-$C_2$ alkyl, (10 membered heteroaryl)-$C_3$ alkyl, (10 membered heteroaryl)-$C_4$ alkyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is (4-14 membered heterocycloalkyl)-$C_{1-4}$ alkyl, for example, (4-14 membered heterocycloalkyl)-$C_1$ alkyl, (4-14 membered heterocycloalkyl)-$C_2$ alkyl, (4-14 membered heterocycloalkyl)-$C_3$ alkyl, (4-14 membered heterocycloalkyl)-$C_4$ alkyl, and the like, optionally substituted with 1, 2, 3, 4 or 5 independently selected $R^b$ substituents.

In some embodiments, $R^2$, $R^3$, $R^4$, $R^5$, $R^6$, $R^7$, $R^8$ or $R^9$ is CN.

In some embodiments, $R^2$, $R^3$, $R^4$, $R^5$, $R^6$, $R^7$, $R^8$ or $R^9$ is, $NO_2$.

In some embodiments, $R^2$, $R^3$, $R^4$, $R^5$, $R^6$, $R^7$, $R^8$ or $R^9$ is $OR^{a1}$.

In some embodiments, $R^2$, $R^3$, $R^4$, $R^5$, $R^6$, $R^7$, $R^8$ or $R^9$ is $SR^{a1}$.

In some embodiments, $R^2$, $R^3$, $R^4$, $R^5$, $R^6$, $R^7$, $R^8$ or $R^9$ is $NHOR^{a1}$.

In some embodiments, $R^2$, $R^3$, $R^4$, $R^5$, $R^6$, $R^7$, $R^8$ or $R^9$ is $C(O)R^{a1}$.

In some embodiments, $R^2$, $R^3$, $R^4$, $R^5$, $R^6$, $R^7$, $R^8$ or $R^9$ is $C(O)NR^{a1}R^{a1}$.

In some embodiments, $R^2$, $R^3$, $R^4$, $R^5$, $R^6$, $R^7$, $R^8$ or $R^9$ is $C(O)OR^{a1}$.

In some embodiments, $R^2$, $R^3$, $R^4$, $R^5$, $R^6$, $R^7$, $R^8$ or $R^9$ is $OC(O)R^{a1}$.

In some embodiments, $R^2$, $R^3$, $R^4$, $R^5$, $R^6$, $R^7$, $R^8$ or $R^9$ is $OC(O)NR^{a1}R^{a1}$.

In some embodiments, $R^2$, $R^3$, $R^4$, $R^5$, $R^6$, $R^7$, $R^8$ or $R^9$ is $NHR^{a1}$.

In some embodiments, $R^2$, $R^3$, $R^4$, $R^5$, $R^6$, $R^7$, $R^8$ or $R^9$ is $NR^{a1}R^{a1}$.

In some embodiments, $R^2$, $R^3$, $R^4$, $R^5$, $R^6$, $R^7$, $R^8$ or $R^9$ is $NR^{a1}C(O)R^{a1}$.

In some embodiments, $R^2$, $R^3$, $R^4$, $R^5$, $R^6$, $R^7$, $R^8$ or $R^9$ is $NR^{a1}C(O)OR^{a1}$.

In some embodiments, $R^2$, $R^3$, $R^4$, $R^5$, $R^6$, $R^7$, $R^8$ or $R^9$ is $NR^{a1}C(O)NR^{a1}R^{a1}$.

In some embodiments, $R^2$, $R^3$, $R^4$, $R^5$, $R^6$, $R^7$, $R^8$ or $R^9$ is $C(=NR^{a1})R^{a1}$.

In some embodiments, $R^2$, $R^3$, $R^4$, $R^5$, $R^6$, $R^7$, $R^8$ or $R^9$ is $C(=NR^{a1})NR^{a1}R^{a1}$.

In some embodiments, $R^2$, $R^3$, $R^4$, $R^5$, $R^6$, $R^7$, $R^8$ or $R^9$ is $NR^{a1}C(=NR^{a1})NR^{a1}R^{a1}$.

In some embodiments, $R^2$, $R^3$, $R^4$, $R^5$, $R^6$, $R^7$, $R^8$ or $R^9$ is $NR^{a1}C(=NOH)NR^{a1}R^{a1}$.

In some embodiments, $R^2$, $R^3$, $R^4$, $R^5$, $R^6$, $R^7$, $R^8$ or $R^9$ is $NR^{a1}C(=NCN)NR^{a1}R^{a1}$.

In some embodiments, $R^2$, $R^3$, $R^4$, $R^5$, $R^6$, $R^7$, $R^8$ or $R^9$ is $NR^{a1}S(O)R^{a1}$.

In some embodiments, $R^2$, $R^3$, $R^4$, $R^5$, $R^6$, $R^7$, $R^8$ or $R^9$ is $NR^{a1}S(O)_2R^{a1}$.

In some embodiments, $R^2$, $R^3$, $R^4$, $R^5$, $R^6$, $R^7$, $R^8$ or $R^9$ is $NR^{a1}S(O)_2NR^{a1}R^{a1}$.

In some embodiments, $R^2$, $R^3$, $R^4$, $R^5$, $R^6$, $R^7$, $R^8$ or $R^9$ is $S(O)R^{a1}$.

In some embodiments, $R^2$, $R^3$, $R^4$, $R^5$, $R^6$, $R^7$, $R^8$ or $R^9$ is $S(O)NR^{a1}R^{a1}$ $S(O)_2R^{a1}$.

In some embodiments, $R^2$, $R^3$, $R^4$, $R^5$, $R^6$, $R^7$, $R^8$ or $R^9$ is $SF_5$.

In some embodiments, $R^2$, $R^3$, $R^4$, $R^5$, $R^6$, $R^7$, $R^8$ or $R^9$ is $P(O)R^{a1}R^{a1}$.

In some embodiments, $R^2$, $R^3$, $R^4$, $R^5$, $R^6$, $R^7$, $R^8$ or $R^9$ is $P(O)(OR^{a1})(OR^{a1})$.

In some embodiments, $R^2$, $R^3$, $R^4$, $R^5$, $R^6$, $R^7$, $R^8$ or $R^9$ is $B(OR^{a1})$.

In some embodiments, $R^2$, $R^3$, $R^4$, $R^5$, $R^6$, $R^7$, $R^8$ or $R^9$ is $S(O)_2NR^{a1}R^{a1}$.

In some embodiments, $R^4$ and $R^5$, together with the atoms to which they are attached, form a 5-, 6-, or 7-membered heterocycloalkyl ring, optionally substituted with 1, 2, 3, 4 or 5 independently selected $R^b$ substituents.

In some embodiments, $R^6$ and $R^7$ together with the carbon atom to which they are both attached, form a $C_3$-$C_7$ spirocyclic ring, optionally substituted with 1, 2, 3, 4 or 5 independently selected $R^b$ substituents.

In some embodiments, $R^8$ and $R^9$, together with the atoms to which they are attached, form a 5-, 6-, or 7-membered heterocycloalkyl ring, optionally substituted with 1, 2, 3, 4 or 5 independently selected $R^b$ substituents.

In some aspects of the disclosure, each $R^{a1}$ is independently selected from H, D, $C_{1-6}$ alkyl, $C_{14}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$alkyl, $C_{3-10}$ cycloalkyl-$C_{1-4}$ alkyl, (5-10 membered heteroaryl)-$C_{1-4}$ alkyl, and (4-14 membered heterocycloalkyl)-$C_{1-4}$ alkyl; wherein when $R^{a1}$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^{a1}$ is optionally substituted with 1, 2, 3, 4, or 5 independently selected $R^d$ substituents.

In some aspects of the disclosure, each $R^b$ substituent is independently selected from D, halo, oxo, $C_{1-4}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^e$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$;

wherein when $R^b$ is $C_{1-4}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents.

In some embodiments, $R^b$ is $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$.

In other embodiments, $R^b$ is $NR^cC(O)R^c$, $NR^cC(O)NR^cR^c$, or $NR^cS(O)_2R^c$.

In some aspects of the disclosure, each $R^c$ is independently selected from H, D, OH, $C_{1-6}$ alkyl, $C_{1-6}$alkoxy, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl; wherein when $R^c$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^c$ is optionally substituted with 1, 2, 3, 4, or 5 independently selected $R^f$ substituents.

In some aspects of the disclosure, each $R^f$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $NR^gC(=NOH)NR^gR^g$, $NR^gC(=NCN)NR^gR^g$, $SF_5$, $P(O)R^gR^g$, $P(O)(OR^g)(OR^g)$, $S(O)R^g$, $S(O)NR^gR^g$, $S(O)_2R^g$, $NR^gS(O)_2R^g$, $NR^g$ $S(O)_2NR^gR^g$, and $S(O)_2NR^gR^g$;

wherein when $R^f$ is $C_{1-4}$alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R^n$ substituents.

In some aspects of the disclosure, each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $NR^oC(=NOH)NR^oR^o$, $NR^oC(=NCN)NR^oR^o$, $SF_5$, $P(O)R^oR^o$, $P(O)(OR^o)(OR^o)$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$.

In some aspects of the disclosure, each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^eC(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $SF_5$, $P(O)R^eR^e$, $P(O)(OR^e)(OR^e)$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein when $R^d$ is $C_{1-6}$alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected $R^f$ substituents.

In some aspects of the disclosure, each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents.

In some aspects of the disclosure, each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected $R^P$ substituents.

In some aspects of the disclosure, each $R^P$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^r$, OR, $SR^r$, $C(O)R^r$, $C(O)NR^rR^r$, $C(O)OR^r$, $OC(O)R^r$, $OC(O)NR^rR^r$, $NHR^rNR^rR^r$ $NR^rC(O)R^r$, $NR^rC(O)NR^r$, $NR^rC(O)OR^r$, $C(=NR^r)NR^rR^r$, $NR^rC(=NR^r)NR^r$, $NR^rC(=NOH)NR^rR^r$ $NR^rC(=NCN)NR^rR^r$, $SF_5$, $P(O)R^rR^r$, $P(O)(OR^r)(OR^r)$, $S(O)R^r$, $S(O)NR^rR^r$, $S(O)_2R^r$, $NR^rS(O)_2R^r$, $NR^rS(O)_2NR^rR^r$, and $S(O)_2NR^rR^r$.

In some aspects of the disclosure, each $R^o$ or $R^r$ is independently selected from H, D, $C_{1-4}$ alkyl, $C_{3-6}$cycloalkyl, $C_{6-10}$ aryl, 5 or 6-membered heteroaryl, $C_{1-4}$ haloalkyl, $C_{2-4}$alkenyl, and $C_{2-4}$ alkynyl, wherein when $R^o$ or $R^r$ is $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl, then $R^o$ or $R^r$ is optionally substituted with 1, 2 or 3 independently selected $R^q$ substituents.

In some aspects of the disclosure, each $R^q$ is independently selected from D, OH, CN, —COOH, $NH_2$, halo, $C_{1-6}$alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, $—CONHR^{12}$, $—NHC(O)R^{12}$, $—OC(O)R^{12}$, $—C(O)OR^{12}$, $—C(O)R^{12}$, $—SO_2R^{12}$, $—NHSO_2R^{12}$, $—SO_2NHR^{12}$ and $NR^{12}R^{12}$ wherein when $R^q$ is $C_{1-6}$ alkyl, phenyl, 4-6 membered heterocycloalkyl or 5-6 membered heteroaryl, then $R^g$ is optionally substituted with OH, CN, —COOH, $NH_2$, $C_{1-6}$ alkoxy, $C_{3-6}$cycloalkyl or 4-6 membered heterocycloalkyl.

In some aspects of the disclosure, each $R^{12}$ is independently $C_{1-6}$ alkyl.

In some embodiments, the compound has the formula of Formula (I) or Formula (II), or a pharmaceutically acceptable salt or solvate thereof, wherein $X^1$, $X^2$, and $X^3$ are each independently N or $CR^3$;

$A^1$ is N or $C—R^4$;

$B^1$ is $C—R^6R^7$, $N—R^5$;

$A^2$ is $N—R^8$, S, or O;

$B^2$ is $C—R^9$; $R_1$ is $C_{3-10}$cycloalkyl or 4-10 membered heterocycloalkyl optionally substituted with 1, 2, 3, 4, 5, 6, 7 or 8 independently selected $R^b$ substituents;

$R^2$ is H, D, OH, halogen, CN, $C_{1-6}$ alkyl, $C_{3-10}$ cycloalkyl, $C_{1-6}$ alkoxyl, $C_{1-6}$ haloalkyl or 4-14 membered heterocycloalkyl;

$R^3$ is H, D, OH, halogen, CN, $C_{1-6}$ alkyl, $C_{3-10}$ cycloalkyl, $C_{1-6}$ alkoxyl, or 4-14 membered heterocycloalkyl;

$R^4$ is H, D, $C_{1-6}$ alkyl, $C_{1-6}$ alkoxy, $C_{3-10}$ cycloalkyl, or 4-6 membered heterocycloalkyl;

$R^5$ is $C_{1-6}$ alkyl, $C_{1-6}$ alkoxy, $C_{3-6}$ cycloalkyl, or 4-6 membered heterocycloalkyl;

or $R^4$ and $R^5$, together with the atoms to which they are attached, form an 5-, 6-, or 7-membered heterocycloalkyl ring optionally substituted with 1, 2, 3, 4 or 5 independently selected $R^b$ substituents;

$R^6$ is $C_{1-6}$ alkyl, $C_{1-6}$ alkoxy, $C_{3-6}$ cycloalkyl, or 4-6 membered heterocycloalkyl;

$R^7$ is $C_{1-6}$ alkyl, $C_{1-6}$ alkoxy, $C_{3-6}$ cycloalkyl, or 4-6 membered heterocycloalkyl;

or $R^6$ and $R^7$ together with the carbon atom to which they are both attached, form a $C_{4-7}$ spirocyclic ring;

$R^8$ is $C_{1-6}$ alkyl; and $R^9$ is $C_{1-6}$ alkyl, $C_{1-6}$ alkoxy, $C_{3-6}$ cycloalkyl, or 4-6 membered heterocycloalkyl;

or $R^8$ and $R^9$, together with the atoms to which they are attached, form an 5-, 6-, or 7-membered heterocycloalkyl ring optionally substituted with 1, 2, 3, 4 or 5 independently selected $R^b$ substituents;

$R^b$ is 5-10 membered heteroaryl, 4-14 membered heterocycloalkyl, $NR^cC(=NR^c)NR^cR^c$, $NR^cC(=NOH)NR^cR^c$, $NR^cC(=NCN)NR^c$, $NR^cC(O)R^c$, $NR^cC(O)OR^c$, $NR^cC(O)NR^c$, $NR^cS(O)R^c$, $NR^cS(O)(=NR^c)R^c$, $NR^cS(O)_2R^c$, or $NR^cS(O)_2NR^cR^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, or $OR^g$; and each $R^g$ is independently H or $C_{1-6}$ alkyl.

In some embodiments, the compound has the formula of Formula (I) or Formula (II), or a pharmaceutically acceptable salt or solvate thereof, wherein $X^1$, $X^2$, and $X^3$ are each independently N or $CR^3$;

$A^1$ is N or C—$R^4$;

$B^1$ is C—$R^6R^7$, N—$R^5$;

$A^2$ is N—$R^8$, S, or O;

$B^2$ is C—$R^9$;

$R_1$ is $C_{3-10}$cycloalkyl optionally substituted with 1, 2, 3, 4, 5, 6, 7 or 8 independently selected $R^b$ substituents;

$R^2$ is H, D, OH, halogen, CN, $C_{1-6}$ alkyl, $C_{3-10}$ cycloalkyl, $C_{1-6}$ alkoxyl, or 4-14 membered heterocycloalkyl;

$R^3$ is H, D, OH, halogen, CN, $C_{1-6}$ alkyl, $C_{3-10}$ cycloalkyl, $C_{1-6}$ alkoxyl, or 4-14 membered heterocycloalkyl;

$R^4$ is H, D, $C_{1-6}$ alkyl, or $C_{1-6}$ alkoxy;

$R^5$ is $C_{1-6}$ alkyl or $C_{1-6}$ alkoxy;

or $R^4$ and $R^5$, together with the atoms to which they are attached, form an 5-, 6-, or 7-membered heterocycloalkyl ring optionally substituted with 1, 2, 3, 4 or 5 independently selected $R^b$ substituents;

$R^6$ is $C_{1-6}$ alkyl;

$R^7$ is $C_{1-6}$ alkyl;

or $R^6$ and $R^7$ together with the carbon atom to which they are both attached, form a $C_{4-7}$ spirocyclic ring;

$R^8$ is $C_{1-6}$ alkyl; and $R^9$ is $C_{1-6}$ alkyl;

or $R^8$ and $R^9$, together with the atoms to which they are attached, form an 5-, 6-, or 7-membered heterocycloalkyl ring optionally substituted with 1, 2, 3, 4 or 5 independently selected $R^b$ substituents;

$R^b$ is $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, or $NR^cS(O)_2NR^cR^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

In some embodiments, the compounds of Formula (I) or Formula (II), or a pharmaceutically acceptable salt or solvate thereof; are those wherein $X^1$, $X^2$, and $X^3$ are each independently N or $CR^3$;

$A^1$ is N or C—$R^4$;

$B^1$ is C—$R^6R^7$, N—$R^5$;

$A^2$ is N—$R^8$, S, or O;

$B^2$ is C—$R^9$;

$R_1$ is $C_3$-$C_7$cycloalkyl substituted with 1 $R^b$ substituent;

$R^b$ is $NR^cC(O)R^c$, $NR^cC(O)NR^cR^c$, or $NR^cS(O)_2R$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $C_{1-4}$ alkyl or $OR^g$;

each $R^g$ is independently H or $C_{1-6}$ alkyl;

$R^2$ is H, halogen, or $C_{1-6}$ alkyl;

$R^3$ is H, halogen, $C_{1-6}$ alkyl;

$R^4$ is H or $C_{1-6}$ alkyl;

$R^5$ is $C_{1-6}$ alkyl;

or $R^4$ and $R^5$, together with the atoms to which they are attached, form an 5-, 6-, or 7-membered heterocycloalkyl ring optionally substituted with 1 or 2 methyl groups;

$R^6$ is $C_{1-6}$ alkyl;

$R^7$ is $C_{1-6}$ alkyl;

or $R^6$ and $R^7$ together with the carbon atom to which they are both attached, form a $C_{4-7}$ spirocyclic ring;

$R^8$ is $C_1$-$C_6$ alkyl; and $R^9$ is $C_1$-$C_6$ alkyl;

or $R^8$ and $R^9$, together with the atoms to which they are attached, form an 5-, 6-, or 7-membered heterocycloalkyl ring optionally substituted with 1 or 2 methyl groups.

In some embodiments, the compounds of Formula (I) or Formula (II), or a pharmaceutically acceptable salt or solvate thereof, are those wherein $X^1$, $X^2$, and $X^3$ are each independently N or $CR^3$;

$A^1$ is N or C—$R^4$;

$B^1$ is C—$R^6R^7$, N—$R^5$, O, or S;

$A^2$ is N—$R^8$, S, or O;

$B^2$ is C—$R^9$ or N;

$R_1$ is $C_3$-$C_7$cycloalkyl substituted with acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

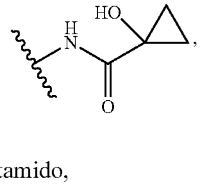

2-(thiazol-4-yl)acetamido,

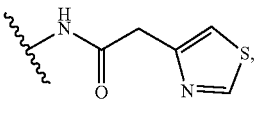 [SMILES: *NC(=O)Cc1cscn1]

methylsulfonamido (—$NSO_2CH_3$), 3-methylureido (—NC(O)$NHCH_3$), 3-methoxyureido (—NC(O)$NHOCH_3$), 3,3-dimethylureido (—NC(O)$N(CH_3)_2$), or 3-ethylureido (—NC(O)$NHCH_2CH_3$), morpholine-4-carboxamido, i.e.,

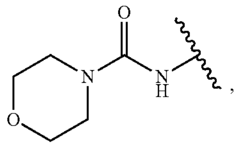, or 4-methylpiperazine-1-carboxamide, i.e.,

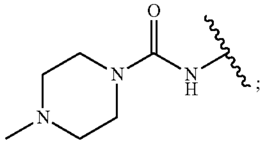 [SMILES: *NC(=O)N1CCN(C)CC1];

$R^2$ is H, halogen, or $C_1$-$C_6$ alkyl;

$R^3$ is H, halogen, $C_1$-$C_6$ alkyl;

$R^4$ is H or $C_1$-$C_6$ alkyl;

$R^5$ is $C_1$-$C_6$ alkyl;

or $R^4$ and $R^5$, together with the atoms to which they are attached, form an 5-membered heterocycloalkyl ring optionally substituted with 1 or 2 methyl groups;

$R^6$ is $C_1$-$C_6$ alkyl;

$R^7$ is $C_1$-$C_6$ alkyl;

or $R^6$ and $R^7$ together with the carbon atom to which they are both attached, form a $C_4$-$C_7$ spirocyclic ring;

$R^8$ is $C_1$-$C_6$ alkyl; and $R^9$ is $C_1$-$C_6$ alkyl;

or $R^8$ and $R^9$, together with the atoms to which they are attached, form a 5-, 6-, or 7-membered heterocycloalkyl ring optionally substituted with 1 or 2 methyl groups.

In some embodiments, $R^1$ in the compounds of Formula (I) or Formula (II) is

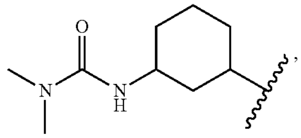,

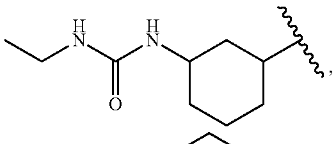,

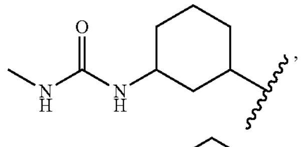,

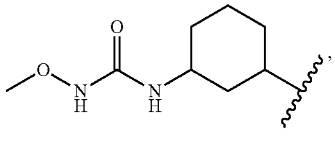,

-continued

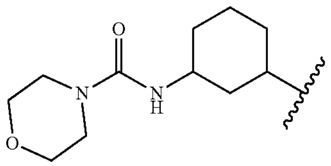,

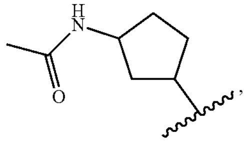,

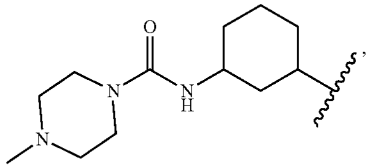, or

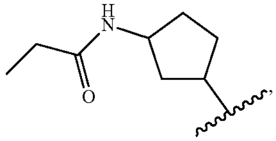,

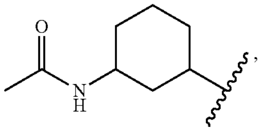,

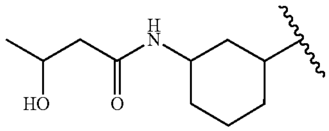,

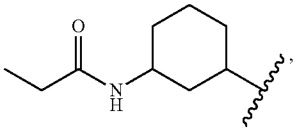,

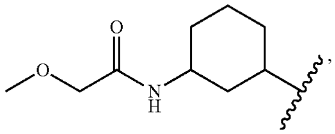,

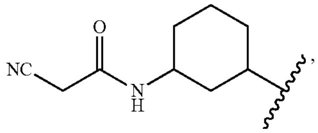,

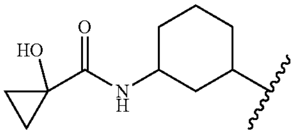,

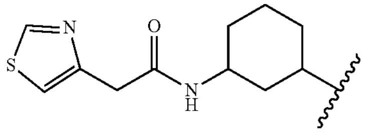,

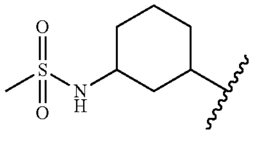,

In other embodiments, $R^1$ is
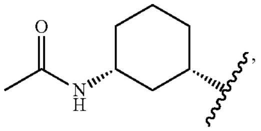
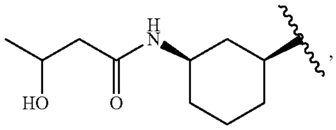
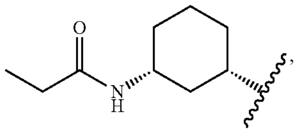
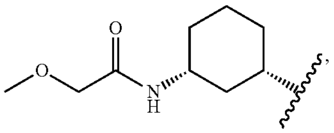
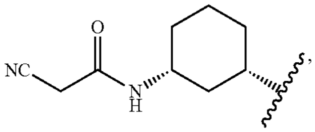
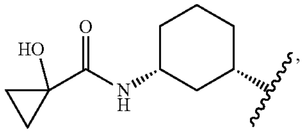
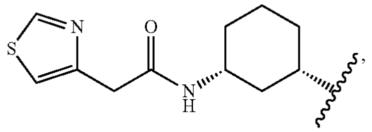
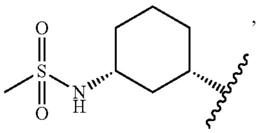
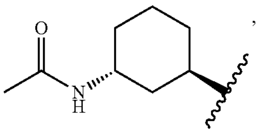
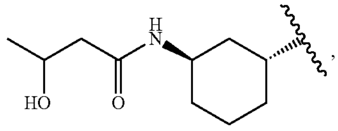
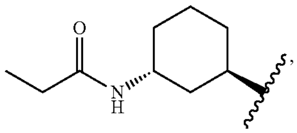
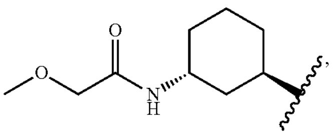
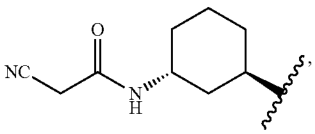
-continued
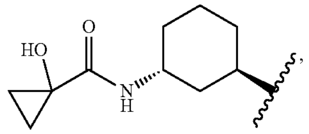
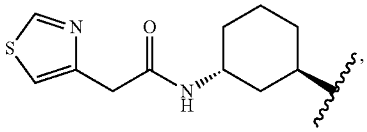
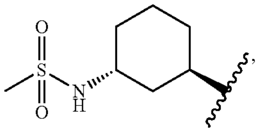
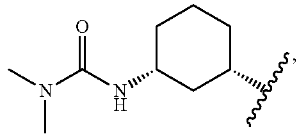
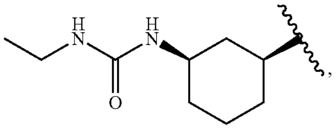
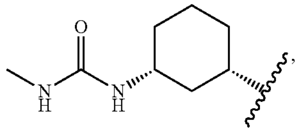
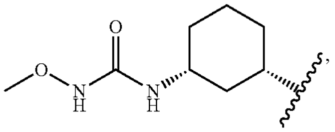
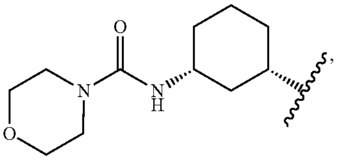
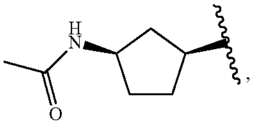
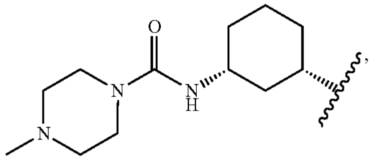
or
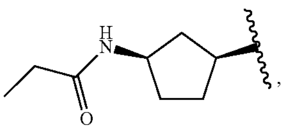
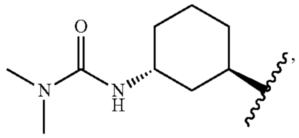
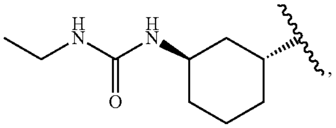

-continued

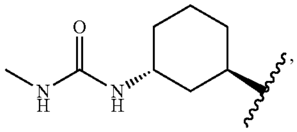,

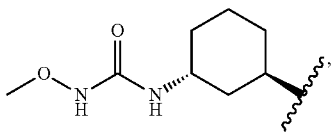,

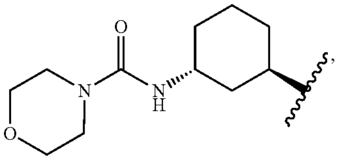,

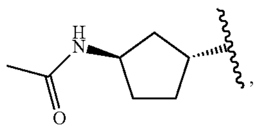,

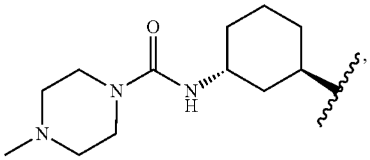, or

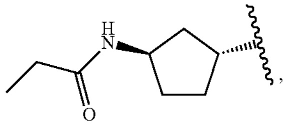,

In some embodiments, the compound has a formula of

Formula (III)

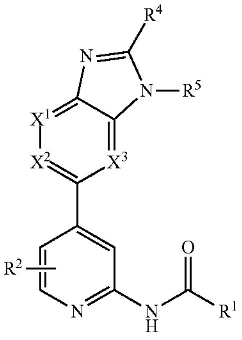

or

Formula (IV)

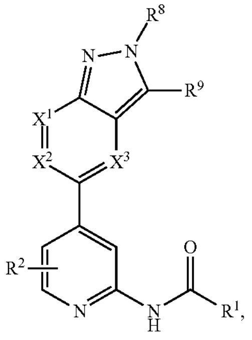, or a pharmaceutically acceptable salt or solvate thereof, wherein $R^1$, $R^2$, $R^4$, $R^5$, $R^1$, $R^9$, $X^1$, $X^2$, and $X^3$ are as defined herein and throughout.

In some embodiments, the compound has the formula of Formula (III) or a pharmaceutically acceptable salt or solvate thereof, wherein $X^1$ is N, $X^2$ is $CR^3$, and $X^3$ is $CR^3$.

In some embodiments, the compound has the formula of Formula (III) or a pharmaceutically acceptable salt or solvate thereof, wherein $X^1$ is $CR^3$, $X^2$ is N, and $X^3$ is $CR^3$.

In some embodiments, the compound has the formula of Formula (III) or a pharmaceutically acceptable salt or solvate thereof, wherein $X^1$ is $CR^3$, $X^2$ is $CR^3$, and $X^3$ is N.

In some embodiments, the compound has the formula of Formula (III) or a pharmaceutically acceptable salt or solvate thereof, wherein $X^1$ is $CR^3$, $X^2$ is $CR^3$, and $X^3$ is $CR^3$.

In some embodiments, the compound has the formula of Formula (IV) or a pharmaceutically acceptable salt or solvate thereof, wherein $X^1$ is N, $X^2$ is $CR^3$, and $X^3$ is $CR^3$.

In some embodiments, the compound has the formula of Formula (IV) or a pharmaceutically acceptable salt or solvate thereof, wherein $X^1$ is $CR^3$, $X^2$ is N, and $X^3$ is $CR^3$.

In some embodiments, the compound has the formula of Formula (IV) or a pharmaceutically acceptable salt or solvate thereof, wherein $X^1$ is $CR^3$, $X^2$ is $CR^3$, and $X^3$ is N.

In some embodiments, the compound has the formula of Formula (IV) or a pharmaceutically acceptable salt or solvate thereof, wherein $X^1$ is $CR^3$, $X^2$ is $CR^3$, and $X^3$ is $CR^3$.

In some embodiments, the compound has the formula of Formula (III) or Formula (IV), or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has the formula of Formula (III) or Formula (IV), or a pharmaceutically acceptable salt or solvate thereof, wherein $R^2$ is halogen or $C_{1-6}$ alkyl.

In some embodiments, the compound has the formula of Formula (III) or Formula (IV), or a pharmaceutically acceptable salt or solvate thereof, wherein $R^2$ is $C_{1-6}$ alkyl.

In some embodiments, the compound has the formula of Formula (III) or Formula (IV), or a pharmaceutically acceptable salt or solvate thereof, wherein $R^2$ is chloro or fluoro.

In some embodiments, the compound has the formula of Formula (III) or Formula (IV), or a pharmaceutically acceptable salt or solvate thereof, wherein $R^2$ is $C_{3-10}$ cycloalkyl, $C_{1-6}$ alkoxyl.

In some embodiments, the compound has the formula of Formula (III) or a pharmaceutically acceptable salt or solvate thereof, wherein $R^4$ is H or $C_{1-6}$ alkyl; $R^5$ is $C_{1-6}$ alkyl; or $R^4$ and $R^5$, together with the atoms to which they are attached, form an 5- or 6-membered heterocycloalkyl ring optionally substituted with 1, 2, 3, 4 or 5 independently selected $R^b$ substituents, wherein each $R^b$ is, independently $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

In some embodiments, the compound has the formula of Formula (III) or a pharmaceutically acceptable salt or solvate thereof, wherein $R^4$ is H.

In some embodiments, the compound has the formula of Formula (III) or a pharmaceutically acceptable salt or solvate thereof, wherein $R^4$ is $C_{1-6}$alkyl, such as, but not limited to, $CH_3$.

In some embodiments, the compound has the formula of Formula (III), or a pharmaceutically acceptable salt or solvate thereof, wherein $R^5$ is $C_{1-6}$alkyl, such as, but not limited to, $CH(CH_3)_2$.

In some embodiments, the compound has the formula of Formula (III), or a pharmaceutically acceptable salt or solvate thereof, wherein $R^4$ and $R^5$, together with the atoms to which they are attached, form an a 5- or 6-membered heterocycloalkyl ring optionally substituted with 1, 2, 3, 4 or 5 independently selected $R^b$ substituents.

In some embodiments, the compound has the formula of Formula (III), or a pharmaceutically acceptable salt or solvate thereof, wherein $R^4$ and $R^5$, together with the atoms to which they are attached, form an optionally substituted 6-membered heterocycloalkyl ring optionally substituted with 1 or 2 $R^b$ substituents. In some embodiments, the 1 or 2 $R^b$ substituents are $C_{1-4}$ alkyl, such as, but not limited to, $CH_3$.

In some embodiments, the compound has the formula of Formula (III), or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has the formula of Formula (III), or a pharmaceutically acceptable salt or solvate thereof, wherein $R^2$ is halogen or $C_{1-6}$ alkyl.

In some embodiments, the compound has the formula of Formula (III), or a pharmaceutically acceptable salt or solvate thereof, wherein $R^2$ is $C_{1-6}$ alkyl.

In some embodiments, the compound has the formula of Formula (III) or a pharmaceutically acceptable salt or solvate thereof, wherein $R^2$ is chloro or fluoro.

In some embodiments, the compound has the formula of Formula (III) or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents;

wherein each $R^b$ is, independently, $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

In some embodiments, the compound has the Formula (III), or a pharmaceutically acceptable salt or solvate thereof, wherein $R^1$ is $C_{3-10}$ cycloalkyl optionally substituted with 1 $R^b$ substituent.

In some embodiments, the compound has the formula of Formula (III) or a pharmaceutically acceptable salt or solvate thereof, wherein $R^1$ is $C_3$ cycloalkyl optionally substituted with 1 $R^b$ substituent.

In some embodiments, the compound has the formula of Formula (III) or a pharmaceutically acceptable salt or solvate thereof, wherein $R^1$ is $C_6$ cycloalkyl optionally substituted with 1 $R^b$ substituent.

In some embodiments, the compound has the formula of Formula (III) or a pharmaceutically acceptable salt or solvate thereof, wherein $R^1$ is cyclopentanyl or cyclohexanyl optionally substituted with 1 $R^b$ substituent. In other embodiments, $R^b$ substituent on $R^1$ is $NR^cC(O)R^c$, $NR^cC(O)NR^cR^c$, or $NR^cS(O)_2NR^cR^c$. In some embodiments, the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents. In some embodiments, the $R^f$ substituents are independently halogen, CN or $OR^g$. In some embodiments, the $R^g$ is independently H or $C_{1-6}$ alkyl.

In some embodiments, the compound has the formula of Formula (III) or a pharmaceutically acceptable salt or solvate thereof, wherein the 1 $R^b$ substituent on $R^1$ is acetamido ($-NHC(O)CH_3$), 3-hydroxybutanamido ($-NHC(O)CH_2CH(OH)CH_3$), propionamido ($-NHC(O)CH_2CH_3$), 2-methoxyacetamido ($-NHC(O)CH_2-OCH_3$), 2-cyanoacetamido ($-NHC(O)CH_2-CN$), 1-hydroxycyclopropane-1-carboxamido,

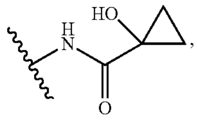

, 2-(thiazol-4-yl)acetamido,

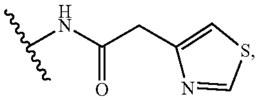 [SMILES: *NC(=O)Cc1cscn1]

, methylsulfonamido ($-NSO_2CH_3$), 3-methylureido ($-NC(O)NHCH_3$), 3-methoxyureido ($-NC(O)NHOCH_3$), 3,3-dimethylureido ($-NC(O)N(CH_3)_2$), or 3-ethylureido ($-NC(O)NHCH_2CH_3$), morpholine-4-carboxamido, i.e.,

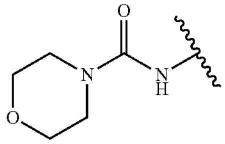

, or 4-methylpiperazine-1-carboxamide, i.e.,

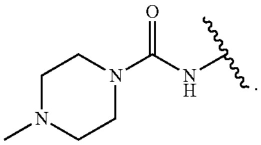 [SMILES: *NC(=O)N1CCN(C)CC1]

.

In some embodiments, the compound has the formula of Formula (IV) or a pharmaceutically acceptable salt or solvate thereof, wherein $R^8$ is $C_{1-6}$ alkyl; and $R^9$ is $C_{1-6}$ alkyl; or $R^8$ and $R^9$, together with the atoms to which they are attached, form an 5- or 6-membered heterocycloalkyl ring optionally substituted with 1, 2, 3, 4 or 5 independently selected $R^b$ substituents; wherein:

each $R^b$ is, independently, $C_{1-4}$ alkyl, $NR^eC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^e$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and
each $R^g$ is independently H or $C_{1-6}$ alkyl.

In some embodiments, the compound has the formula of Formula (IV) or a pharmaceutically acceptable salt or solvate thereof, wherein $R^8$ is $C_{1-6}$alkyl, preferably $CH_3$.

In some embodiments, the compound has the formula of Formula (IV) or a pharmaceutically acceptable salt or solvate thereof, wherein $R^9$ is $C_{1-6}$alkyl, preferably $CH(CH_3)_2$.

In some embodiments, the compound has the formula of Formula (IV) or a pharmaceutically acceptable salt or solvate thereof, wherein $R^8$ and $R^9$, together with the atoms to which they are attached, form a 5- or 6-membered heterocycloalkyl ring optionally substituted with 1, 2, 3, 4 or 5 independently selected $R^b$ substituents. In some embodiments, $R^8$ and $R^9$, together with the atoms to which they are attached, form a 5-membered heterocycloalkyl ring optionally substituted with 1 or 2 $R^b$ substituents. In some embodiments, the 1 or 2 $R^b$ substituents are $C_{1-4}$ alkyl, preferably $CH_3$.

In some embodiments, the compound has the formula of Formula (IV) or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has the formula of Formula (IV) or a pharmaceutically acceptable salt or solvate thereof, wherein $R^2$ is halogen or $C_{1-6}$ alkyl.

In some embodiments, the compound has the formula of Formula (IV) or a pharmaceutically acceptable salt or solvate thereof, wherein $R^2$ is $C_{1-6}$ alkyl.

In some embodiments, the compound has the formula of Formula (IV) or a pharmaceutically acceptable salt or solvate thereof, wherein $R^2$ is chloro or fluoro.

In some embodiments, the compound has the formula of Formula (IV) or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents;

wherein each $R^b$ is, independently, $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;
each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;
each $R^f$ is independently halogen, CN or $OR^g$; and
each $R^g$ is independently H or $C_{1-6}$ alkyl.

In some embodiments, the compound has the formula of Formula (IV) or a pharmaceutically acceptable salt thereof, wherein $R^1$ is $C_{3-10}$ cycloalkyl optionally substituted with 1 $R^b$ substituent.

In some embodiments, the compound has the formula of Formula (IV) or a pharmaceutically acceptable salt or solvate thereof, wherein $R^1$ is $C_{3-7}$ cycloalkyl optionally substituted with 1 $R^b$ substituent.

In some embodiments, the compound has the formula of Formula (IV) or a pharmaceutically acceptable salt or solvate thereof, wherein $R^1$ is $C_{5-6}$ cycloalkyl optionally substituted with 1 $R^b$ substituent.

In some embodiments, the compound has the formula of Formula (IV) or a pharmaceutically acceptable salt thereof, wherein $R^1$ is cyclopentanyl or cyclohexanyl optionally substituted with 1 $R^b$ substituent.

In some embodiments, the compound has the formula of Formula (IV) or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$. In some embodiments, the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents. In some embodiments, the $R^f$ substituents are independently halogen, CN or $OR^g$. In some embodiments, the $R^g$ is independently H or $C_{1-6}$ alkyl. In other embodiments, $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

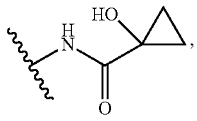 [SMILES: *NC(=O)C1(O)CC1]
, 2-(thiazol-4-yl)acetamido,

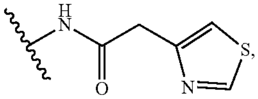 [SMILES: *NC(=O)Cc1cscn1]
, methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido, i.e.,

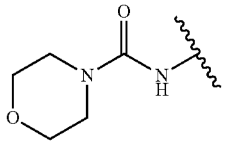
, or 4-methylpiperazine-1-carboxamide, i.e.,

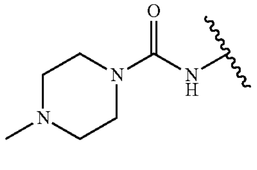
.

In some embodiments, the compound has the formula of Formula (III) or Formula (IV), or a pharmaceutically acceptable salt or solvate thereof, wherein each $R^3$ is, independently, H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has the formula of Formula (III) or Formula (IV), or a pharmaceutically acceptable salt or solvate thereof, wherein each $R^3$ is, independently, H or halogen, such as, but not limited to, Cl or F.

In some embodiments, the compound has the formula of Formula (III) or Formula (IV), or a pharmaceutically acceptable salt or solvate thereof, wherein only one of the $R^3$ is OH, halogen, CN, $C_{1-6}$ alkyl, $C_{3-10}$ cycloalkyl, $C_{1-6}$ alkoxyl, or 4-14 membered heterocycloalkyl and the remainder are H.

In some embodiments, the compound has the formula of Formula (III) or Formula (IV), or a pharmaceutically acceptable salt or solvate thereof, wherein one of the $R^3$ is halogen, preferably Cl or F, and the remainder are H.

In some embodiments, $R^1$ is the stereoisomers provided herein and above, such as in paragraph 00160.

In some embodiments, the compound has a formula of

Formula (V)

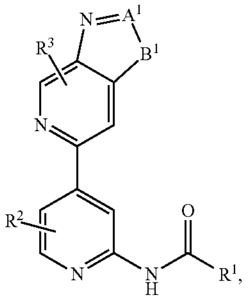

Formula (VI)

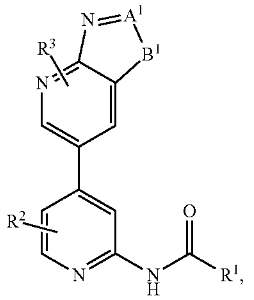

Formula (VII)

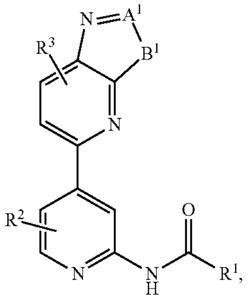

(VIII)

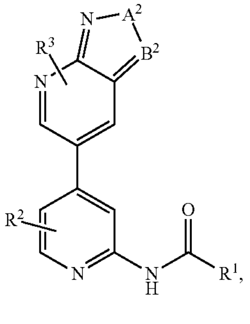

-continued (IX)

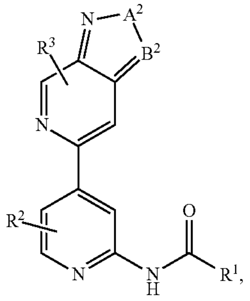

Formula (X)

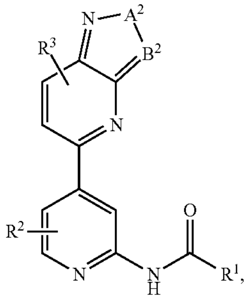

Formula (XI)

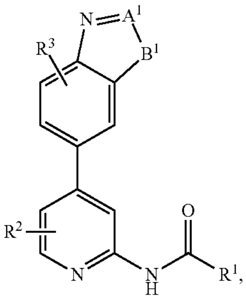

or

Formula (XII)

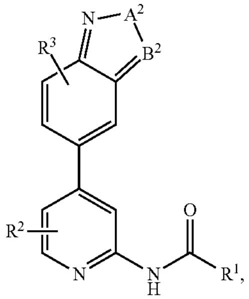

or a pharmaceutically acceptable salt or solvate thereof, wherein the variables are as defined herein and throughout.

In some embodiments, the compound has a formula of any one of Formula (V)-(XII) or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has a formula of any one of Formula (V)-(XII) or a pharmaceutically acceptable salt or solvate thereof, wherein $R^2$ is halogen or $C_{1-6}$ alkyl.

In some embodiments, the compound has a formula of any one of Formula (V)-(XII) or a pharmaceutically acceptable salt or solvate thereof, wherein $R^2$ is $C_{1-6}$ alkyl.

In some embodiments, the compound has a formula of any one of Formula (V)-(XII) or a pharmaceutically acceptable salt or solvate thereof, wherein $R^2$ is chloro or fluoro.

In some embodiments, the compound has a formula of any one of Formula (V)-(XII) or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents, wherein:

each $R^b$ is, independently, $C_{1-4}$ alkyl, $NR^eC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^e$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

In some embodiments, the compound has a formula of any one of Formula (V)-(XII) or a pharmaceutically acceptable salt or solvate thereof, wherein $R^1$ is $C_{3-10}$ cycloalkyl optionally substituted with 1 $R^b$ substituent.

In some embodiments, the compound has a formula of any one of Formula (V)-(XII) or a pharmaceutically acceptable salt or solvate thereof, wherein $R^1$ is $C_{3-7}$ cycloalkyl optionally substituted with 1 $R^b$ substituent.

In some embodiments, the compound has a formula of any one of Formula (V)-(XII) or a pharmaceutically acceptable salt or solvate thereof, wherein $R^1$ is $C_{5-6}$ cycloalkyl optionally substituted with 1 $R^b$ substituent.

In some embodiments, the compound has a formula of any one of Formula (V)-(XII) or a pharmaceutically acceptable salt or solvate thereof, wherein $R^1$ is cyclopentanyl or cyclohexanyl optionally substituted with 1 $R^b$ substituent.

In some embodiments, the compound has a formula of any one of Formula (V)-(XII) or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$. In some embodiments, the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents. In some embodiments, the $R^f$ substituents are independently halogen, CN or $OR^g$. In some embodiments, the $R^g$ is independently H or $C_{1-6}$ alkyl.

In other embodiments, $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

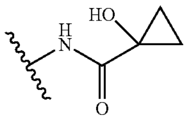

, 2-(thiazol-4-yl)acetamido,

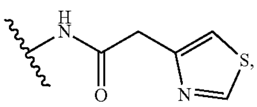 [SMILES: *NC(=O)Cc1cscn1]

methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido,

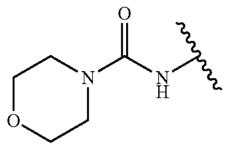

, i.e., or 4-methylpiperazine-1-carboxamide, i.e.,

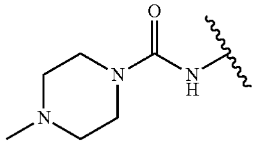

.

In some embodiments, the compound has a formula of

Formula (V)

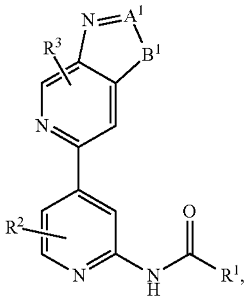

Formula (VI)

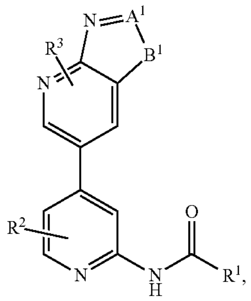

Formula (VII)

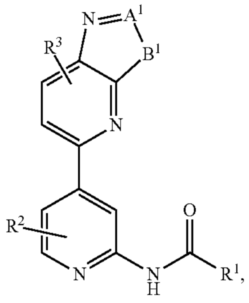

or

-continued

Formula (XI)

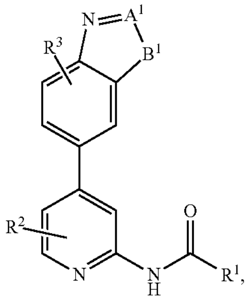

or a pharmaceutically acceptable salt or solvate thereof, wherein $A^1$ is N.

In some embodiments, the compound has a formula of Formula (V), Formula (VI), Formula (VII), or Formula (XI), or a pharmaceutically acceptable salt or solvate thereof, wherein $A^1$ is C—$R^4$.

In some embodiments, the compound has a formula of Formula (V), Formula (VI), Formula (VII), or Formula (XI), or a pharmaceutically acceptable salt or solvate thereof, wherein $B^1$ is C—$R^6R^7$.

In some embodiments, the compound has a formula of Formula (V), Formula (VI), Formula (VII), or Formula (XI), or a pharmaceutically acceptable salt or solvate thereof, wherein $B^1$ is N—$R^5$.

In some embodiments, the compound has a formula of Formula (V), Formula (VI), Formula (VII), or Formula (XI), or a pharmaceutically acceptable salt or solvate thereof, wherein $B^1$ is O.

In some embodiments, the compound has a formula of Formula (V), Formula (VI), Formula (VII), or Formula (XI), or a pharmaceutically acceptable salt or solvate thereof, wherein $B^1$ is S.

In some embodiments, the compound has a formula of Formula (V), Formula (VI), Formula (VII), or Formula (XI), or a pharmaceutically acceptable salt or solvate thereof, wherein $R^4$ is H.

In some embodiments, the compound has a formula of Formula (V), Formula (VI), Formula (VII), or Formula (XI), or a pharmaceutically acceptable salt or solvate thereof wherein $R^4$ is $C_{1-6}$alkyl, preferably $CH_3$.

In some embodiments, the compound has a formula of Formula (V), Formula (VI), Formula (VII), or Formula (XI), or a pharmaceutically acceptable salt or solvate thereof, wherein $R^5$ is $C_{1-6}$alkyl, preferably $CH(CH_3)_2$.

In some embodiments, the compound has a formula of Formula (V), Formula (VI), Formula (VII), or Formula (XI), or a pharmaceutically acceptable salt or solvate thereof, wherein $R^4$ and $R^5$, together with the atoms to which they are attached, form a 5- or 6-membered heterocycloalkyl ring optionally substituted with 1, 2, 3, 4 or 5 independently selected $R^b$ substituents.

In some embodiments, $R^4$ and $R^5$, together with the atoms to which they are attached, form an optionally substituted 5-membered heterocycloalkyl ring optionally substituted with 1 or 2 $R^b$ substituents. In some embodiments, the 1 or 2 $R^b$ substituents are $C_{1-4}$ alkyl, preferably $CH_3$. In some embodiments, $R^6$ is $C_{1-6}$ alkyl, preferably $CH_3$; and $R^7$ is $C_{1-6}$ alkyl, preferably $CH_3$. In some embodiments, wherein $R^6$ and $R^7$ together with the carbon atom to which they are both attached, form a $C_4$-$C_7$ spirocyclic ring. In some embodiments, wherein the $C_4$-$C_7$ spirocyclic ring is a spirocyclopentane ring.

In some embodiments, the compound has a formula of

Formula (VIII)

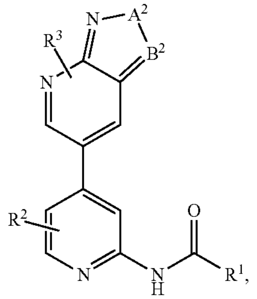

Formula (IX)

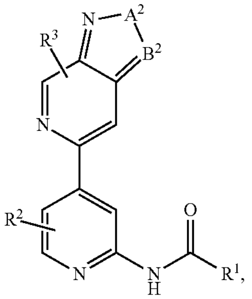

Formula (X)

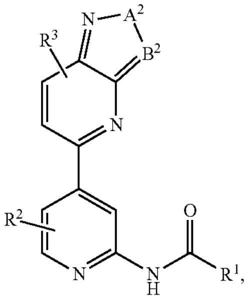

or

Formula (XII)

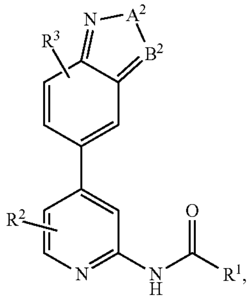

or a pharmaceutically acceptable salt or solvate thereof, wherein $A^2$ is N—$R^8$.

In some embodiments, the compound has a formula of Formula (VIII), Formula (IX), Formula (X), or Formula (XII), or a pharmaceutically acceptable salt or solvate thereof, wherein $A^2$ is S.

In some embodiments, the compound has a formula of Formula (VIII), Formula (IX), Formula (X), or Formula (XII), or a pharmaceutically acceptable salt or solvate thereof, wherein $A^2$ is O.

In some embodiments, the compound has a formula of Formula (VIII), Formula (IX), Formula (X), or Formula (XII), or a pharmaceutically acceptable salt or solvate thereof, wherein $B^2$ is C—$R^9$.

In some embodiments, the compound has a formula of Formula (VIII), Formula (IX), Formula (X), or Formula (XII), or a pharmaceutically acceptable salt or solvate thereof, wherein $B^2$ is N.

In some embodiments, the compound has a formula of Formula (VIII), Formula (IX), Formula (X), or Formula (XII), or a pharmaceutically acceptable salt or solvate thereof, wherein $R^8$ is $C_{1-6}$alkyl, preferably $CH_3$.

In some embodiments, the compound has a formula of Formula (VIII), Formula (IX), Formula (X), or Formula (XII), or a pharmaceutically acceptable salt or solvate thereof, wherein $R^9$ is $C_{1-6}$alkyl, preferably $CH(CH_3)_2$.

In some embodiments, the compound has a formula of Formula (VIII), Formula (IX), Formula (X), or Formula (XII), or a pharmaceutically acceptable salt or solvate thereof, wherein $R^1$ and $R^9$, together with the atoms to which they are attached, form a 5- or 6-membered heterocycloalkyl ring optionally substituted with 1, 2, 3, 4 or 5 independently selected $R^b$ substituents.

In some embodiments, the compound has a formula of Formula (VIII), Formula (IX), Formula (X), or Formula (XII), or a pharmaceutically acceptable salt or solvate thereof, wherein $R^1$ and $R^9$, together with the atoms to which they are attached, form a 5-membered heterocycloalkyl ring optionally substituted with 1 or 2 $R^b$ substituents. In some embodiments, the 1 or 2 $R^b$ substituents are $C_{1-4}$ alkyl, preferably $CH_3$.

In some embodiments, the compound has a formula of any one of Formula (V)-(XII) or a pharmaceutically acceptable salt or solvate thereof, wherein $R^3$ is H, OH, halogen, CN, $C_{1-6}$ alkyl, $C_{3-10}$ cycloalkyl, $C_{1-6}$ alkoxyl, or 4-14 membered heterocycloalkyl.

In some embodiments, the compound has a formula of any one of Formula (V)-(XII) or a pharmaceutically acceptable salt or solvate thereof, wherein $R^3$ is, H or halogen, preferably Cl or F.

In some embodiments, the compound has a formula of any one of Formula (I)-(XII) or a pharmaceutically acceptable salt or solvate thereof, wherein $R^1$ is

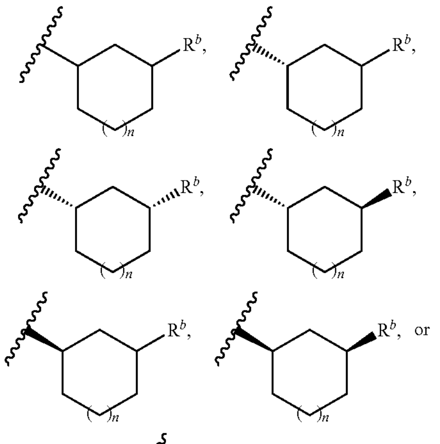

or

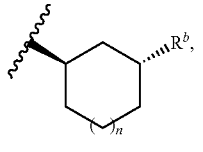

wherein n is 0 or 1 and $R^b$ is as defined in herein and throughout. In some embodiments, $R^b$ substituent on $R^1$ is $NR^cC(O)R^c$, $NR^cC(O)NR^cR^c$, or $NR^cS(O)_2NR^cR^c$. In some embodiments, $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents. In some embodiments, $R^f$ substituents are independently halogen, CN or $OR^g$. In other embodiments, $R^g$ is independently, H or $C_{1-6}$ alkyl. In other embodiments, $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

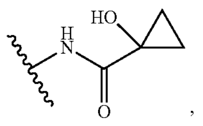 [SMILES: *NC(=O)C1(O)CC1]

, 2-(thiazol-4-yl)acetamido,

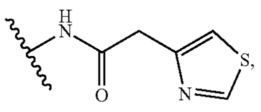 [SMILES: *NC(=O)Cc1cscn1]

methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido, i.e.,

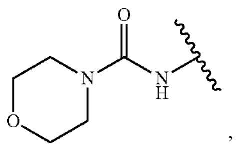 [SMILES: *NC(=O)N1CCOCC1]

, or 4-methylpiperazine-1-carboxamide, i.e.,

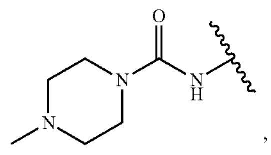 [SMILES: *NC(=O)N1CCN(C)CC1]

,

In some aspects, the disclosure is directed to compounds of Formula (I-A):

Formula (I-A)

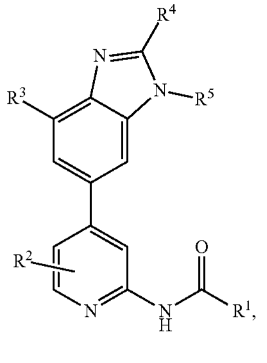

wherein $R_1$ is $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, and (4-14 membered heterocycloalkyl)-$C_{1-4}$ alkyl; wherein $R^1$ is optionally substituted with 1, 2, 3, 4, 5, 6, 7 or 8 independently selected $R^b$ substituents;

$R^2$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents.

$R^3$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents.

$R^4$ is H; and $R^5$ is $C_1$-$C_6$ alkyl;

or $R^4$ and $R^5$, together with the atoms to which they are attached, form a 5-, 6-, or 7-membered heterocycloalkyl ring optionally substituted with 1, 2, 3, 4 or 5 independently selected $R^b$ substituents; and $R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

In some embodiments, the compounds of Formula (I-A) are those wherein $R_1$ is $C_3$-$C_7$cycloalkyl substituted with 1 $R^b$ substituent;

$R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $CH_3$, OH, or $OCH_3$;

$R^2$ is H, halogen, or $C_1$-$C_6$ alkyl;

$R^3$ is H or halogen;

$R^4$ is H or $C_1$-$C_6$ alkyl; and $R^5$ is $C_1$-$C_6$ alkyl;

or $R^4$ and $R^5$, together with the atoms to which they are attached, form 5-, 6-, or 7-membered heterocycloalkyl ring substituted with one or two methyl groups.

In some embodiments, the compounds of Formula (I-A) are those wherein $R^1$ is $C_3$-$C_7$cycloalkyl substituted with acetamido ($-NHC(O)CH_3$), 3-hydroxybutanamido ($-NHC(O)CH_2CH(OH)CH_3$), propionamido ($-NHC(O)CH_2CH_3$), 2-methoxyacetamido ($-NHC(O)CH_2-OCH_3$), 2-cyanoacetamido ($-NHC(O)CH_2-CN$), 1-hydroxycyclopropane-1-carboxamido,

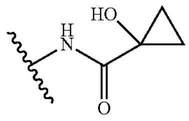
, 2-(thiazol-4-yl)acetamido,

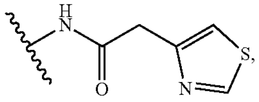 [SMILES: *NC(=O)Cc1cscn1]

methylsulfonamido ($-NSO_2CH_3$), 3-methylureido ($-NC(O)NHCH_3$), 3-methoxyureido ($-NC(O)NHOCH_3$), 3,3-dimethylureido ($-NC(O)N(CH_3)_2$), or 3-ethylureido ($-NC(O)NHCH_2CH_3$), morpholine-4-carboxamido, i.e.,

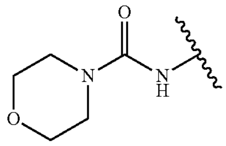
, or 4-methylpiperazine-1-carboxamide, i.e.

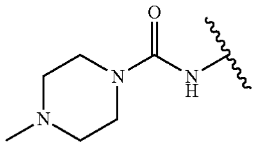
;

$R^2$ is H, Cl, or $C_{1-3}$; $R^3$ is F; $R^4$ is H; and $R^5$ is $C_1$-$C_6$ alkyl;

or $R^4$ and $R^5$, together with the atoms to which they are attached, form a 5-, 6-, or 7-membered heterocycloalkyl ring substituted with one or two methyl groups.

In some embodiments, the compounds of Formula (I-A) are those wherein $R^1$ is $C_5$-$C_6$cycloalkyl substituted with acetamido ($-NHC(O)CH_3$), 3-hydroxybutanamido ($-NHC(O)CH_2CH(OH)CH_3$), propionamido ($-NHC(O)CH_2CH_3$), 2-methoxyacetamido ($-NHC(O)CH_2-OCH_3$), 2-cyanoacetamido ($-NHC(O)CH_2-CN$), 1-hydroxycyclopropane-1-carboxamido,

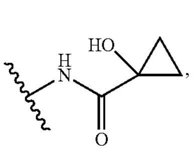 [SMILES: *NC(=O)C1(O)CC1]

2-(thiazol-4-yl)acetamido,

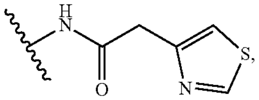 [SMILES: *NC(=O)Cc1cscn1]

methylsulfonamido ($-NSO_2CH_3$), 3-methylureido ($-NC(O)NHCH_3$), 3-methoxyureido ($-NC(O)NHOCH_3$), 3,3-dimethylureido (—NC(O)N($CH_3$ z or 3-ethylureido (—NC(O)$NHCH_2CH_3$), morpholine-4-carboxamido, i.e.,

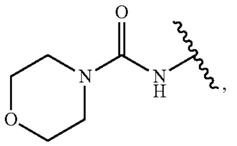 [SMILES: *NC(=O)N1CCOCC1]

or 4-methylpiperazine-1-carboxamide, i.e.

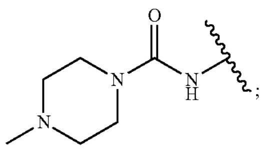 [SMILES: *NC(=O)N1CCN(C)CC1]

$R^2$ is H, Cl, or $C_{1-3}$; $R^3$ is F; $R^4$ is H; and $R^5$ is isopropyl.

In some embodiments, the compounds of Formula (I-A) are those wherein $R^1$ is $C_5$-$C_6$cycloalkyl substituted with acetamido (—NHC(O)$CH_3$), 3-hydroxybutanamido (—NHC(O)$CH_2$CH(OH)$CH_3$), propionamido (—NHC(O)$CH_2CH_3$), 2-methoxyacetamido (—NHC(O)$CH_2$—$OCH_3$), 2-cyanoacetamido (—NHC(O)$CH_2$—CN), 1-hydroxycyclopropane-1-carboxamido,

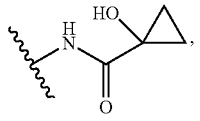 [SMILES: *NC(=O)C1(O)CC1]

2-(thiazol-4-yl)acetamido,

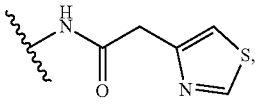 [SMILES: *NC(=O)Cc1cscn1]

ethylsulfonamido (—$NSO_2CH_3$), 3-methylureido (—NC(O)$NHCH_3$), 3-methoxyureido (—NC(O)$NHOCH_3$), 3,3-dimethylureido (—NC(O)N$(CH_3)_2$), or 3-ethylureido (—NC(O)$NHCH_2CH_3$), morpholine-4-carboxamido, i.e.,

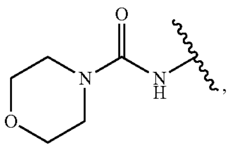 [SMILES: *NC(=O)N1CCOCC1]

or 4-methylpiperazine-1-carboxamide, i.e.,

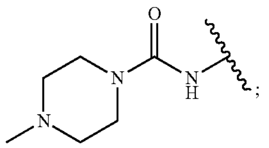 [SMILES: *NC(=O)N1CCN(C)CC1]

$R^2$ is H, Cl, or $C_{1-3}$; $R^3$ is F; and $R^4$ and $R^5$, together with the atoms to which they are attached, form a 5-membered heterocycloalkyl ring substituted with one or two methyl groups.

In some aspects, the disclosure is directed to compounds of Formula (XIII):

Formula (XIII)

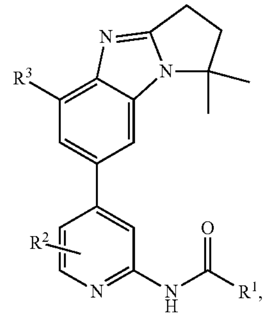

wherein $R_1$ is $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, and (4-14 membered heterocycloalkyl)-$C_{1-4}$ alkyl; wherein $R^1$ is optionally substituted with 1, 2, 3, 4, 5, 6, 7 or 8 independently selected $R^b$ substituents;

$R^2$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents.

$R^3$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents;

$R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

In some embodiments, the compounds of Formula (XIII) are those wherein $R_1$ is $C_3$-$C_7$cycloalkyl substituted with 1 $R^b$ substituent;

$R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $CH_3$, OH, or $OCH_3$;

$R^2$ is H, halogen, or $C_1$-$C_6$ alkyl; and $R^3$ is H or halogen.

In some embodiments, the compounds of Formula (XIII) are those wherein $R^1$ is $C_5$-$C_6$cycloalkyl substituted with acetamido (—NHC(O)$CH_3$), 3-hydroxybutanamido (—NHC(O)$CH_2$CH(OH)$CH_3$), propionamido (—NHC(O)$CH_2CH_3$), 2-methoxyacetamido (—NHC(O)$CH_2$—$OCH_3$), 2-cyanoacetamido (—NHC(O)$CH_2$—CN), 1-hydroxycyclopropane-1-carboxamido,

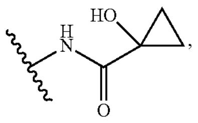 [SMILES: *NC(=O)C1(O)CC1]

2-(thiazol-4-yl)acetamido,

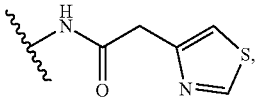 [SMILES: *NC(=O)Cc1cscn1]

methylsulfonamido (—$NSO_2CH_3$), 3-methylureido (—NC(O)$NHCH_3$), 3-methoxyureido (—NC(O)$NHOCH_3$), 3,3-dimethylureido (—NC(O)$N(CH_3)_2$), or 3-ethylureido (—NC(O)$NHCH_2CH_3$), morpholine-4-carboxamido, i.e.,

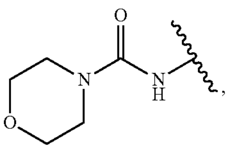 [SMILES: *NC(=O)N1CCOCC1]

or 4-methylpiperazine-1-carboxamide, i.e.,

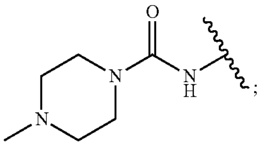 [SMILES: *NC(=O)N1CCN(C)CC1]

$R^2$ is H, Cl, or $C_{1-3}$; and $R^3$ is F.

In some aspects, the disclosure is directed to compounds Formula (II-A):

Formula (II-A)

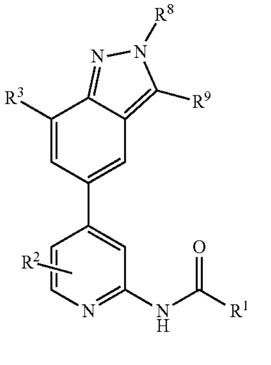

wherein $R_1$ is $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, and (4-14 membered heterocycloalkyl)-$C_{1-4}$ alkyl; wherein $R^1$ is optionally substituted with 1, 2, 3, 4, 5, 6, 7 or 8 independently selected $R^b$ substituents;

$R^2$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents.

$R^3$ is H, hydroxyl, halogen, CN, $C_1$-$C_6$ alkyl, $C_3$-$C_{10}$ cycloalkyl, $C_1$-$C_6$ alkoxyl, or 4-14 membered heterocycloalkyl; wherein the $C_1$-$C_6$ alkyl, $C_3$-$C_{10}$ cycloalkyl, $C_1$-$C_6$ alkoxyl, or 4-14 membered heterocycloalkyl is optionally substituted with 1, 2, 3, 4 or 5 independently selected $R^b$ substituents;

$R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $C_{1-4}$alkyl, or $OR^g$; and each $R^g$ is independently H or $C_{1-6}$ alkyl.

$R^8$ is $C_1$-$C_6$ alkyl; and $R^9$ is $C_1$-$C_6$ alkyl;

or $R^8$ and $R^9$, together with the atoms to which they are attached, form 5-, 6-, or 7-membered heterocycloalkyl ring optionally substituted with one or two methyl groups.

In some embodiments, the compounds of Formula (II-A) are those wherein $R_1$ is $C_3$-$C_7$cycloalkyl substituted with 1 $R^b$ substituent;

$R^b$ is $C_{1-6}$ alkyl, $NR^cC(O)R^c$, $NR^cC(O)NR^cR^c$, or $NR^cS(O)_2R^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN, $CH_3$, OH, or $OCH_3$;

$R^2$ is H, halogen, or $C_1$-$C_6$ alkyl;

$R^3$ is H or halogen;

$R^8$ is $C_1$-$C_6$ alkyl; and $R^9$ is $C_1$-$C_6$ alkyl;

or $R^8$ and $R^9$, together with the atoms to which they are attached, form a 5-, 6-, or 7-membered heterocycloalkyl ring substituted with one or two methyl groups.

In some embodiments, the compounds of Formula (II-A) are those wherein $R^1$ is $C_5$-$C_6$cycloalkyl substituted with acetamido (—NHC(O)$CH_3$), 3-hydroxybutanamido (—NHC(O)$CH_2$CH(OH)$CH_3$), propionamido (—NHC(O)$CH_2CH_3$), 2-methoxyacetamido (—NHC(O)$CH_2$—$OCH_3$), 2-cyanoacetamido (—NHC(O)$CH_2$—CN), 1-hydroxycyclopropane-1-carboxamido,

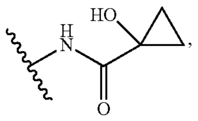 [SMILES: *NC(=O)C1(O)CC1]

2-(thiazol-4-yl)acetamido,

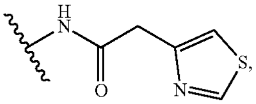 [SMILES: *NC(=O)Cc1cscn1]

methylsulfonamido (—$NSO_2CH_3$), 3-methylureido (—NC(O)$NHCH_3$), 3-methoxyureido (—NC(O)$NHOCH_3$), 3,3-dimethylureido (—NC(O)$N(CH_3)_2$), or 3-ethylureido (—NC(O)$NHCH_2CH_3$), morpholine-4-carboxamido, i.e.,

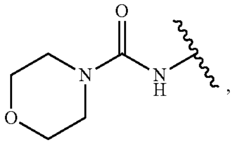 [SMILES: *NC(=O)N1CCOCC1]

or 4-methylpiperazine-1-carboxamide, i.e.,

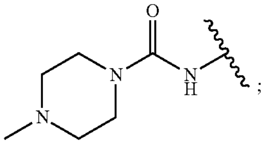 [SMILES: *NC(=O)N1CCN(C)CC1]

$R^2$ is H, Cl, or $C_{1-3}$;

$R^3$ is H or F;

$R^8$ is $C_{1-3}$; and $R^9$ is isopropyl (i.e., $C_1(CH_3)_2$).

In other embodiments, the compounds of Formula (II-A) are those wherein $R^1$ is $C_5$-$C_6$cycloalkyl substituted with acetamido (—NHC(O)$CH_3$), 3-hydroxybutanamido (—NHC(O)$CH_2CH(OH)CH_3$), propionamido (—NHC(O)$CH_2CH_3$), 2-methoxyacetamido (—NHC(O)$CH_2$—$OCH_3$), 2-cyanoacetamido (—NHC(O)$CH_2$—CN), 1-hydroxycyclopropane-1-carboxamido,

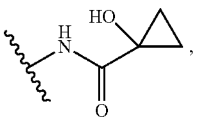 [SMILES: *NC(=O)C1(O)CC1]

2-(thiazol-4-yl)acetamido,

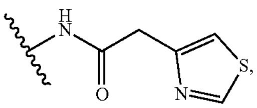 [SMILES: *NC(=O)Cc1cscn1]

methylsulfonamido (—$NSO_2CH_3$), 3-methylureido (—NC(O)$NHCH_3$), 3-methoxyureido (—NC(O)$NHOCH_3$), 3,3-dimethylureido (—NC(O)$N(CH_3)_2$), or 3-ethylureido (—NC(O)$NHCH_2CH_3$), morpholine-4-carboxamido, i.e.,

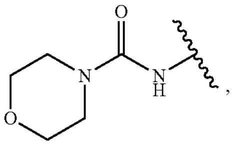 [SMILES: *NC(=O)N1CCOCC1]

or 4-methylpiperazine-1-carboxamide, i.e.,

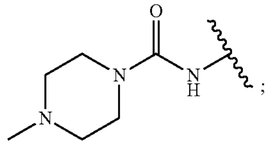 [SMILES: *NC(=O)N1CCN(C)CC1]

$R^2$ is H, Cl, or $C_{1-3}$;

$R^3$ is H or F; and $R^8$ and $R^9$, together with the atoms to which they are attached, form a 5-membered heterocycloalkyl ring substituted with one or two methyl groups.

In some embodiments, the disclosure is directed to compounds having a formula of Formula (XIII)

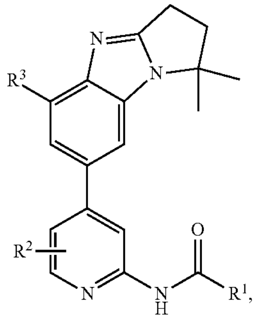

Formula (XIV-a)

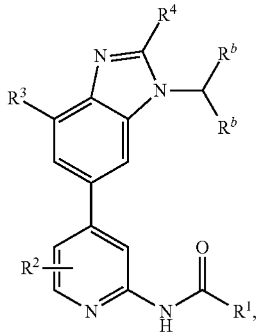

-continued

Formula (XIV-b)

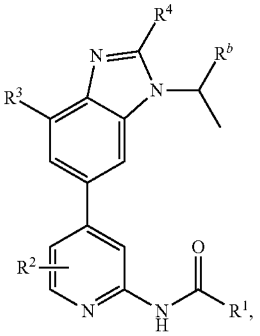

Formula (XIV-c)

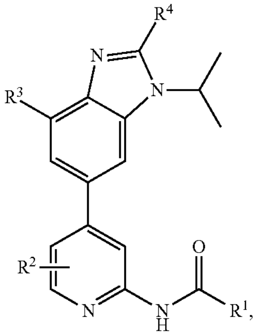

Formula (XV)

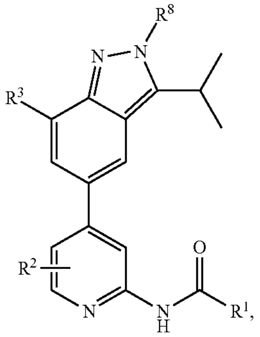

Formula (XVI)

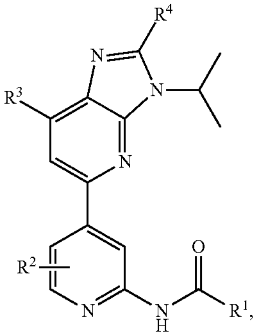

-continued

Formula (XVII)

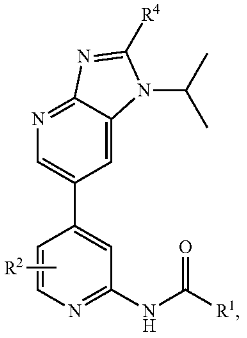

or

Formula (XVIII)

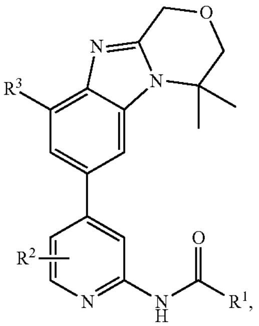

or pharmaceutically acceptable salts or solvates thereof, wherein the variables are as defined herein, are provided and wherein when there are more than one $R^b$, each $R^b$ is independent to others.

In some embodiments, the disclosure is directed to compounds having a formula of Formula (XIX)

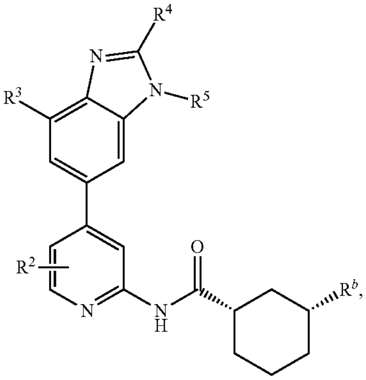

-continued
Formula (XIX-a)
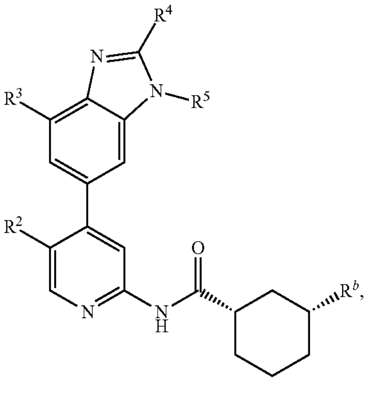
Formula (XX-a)
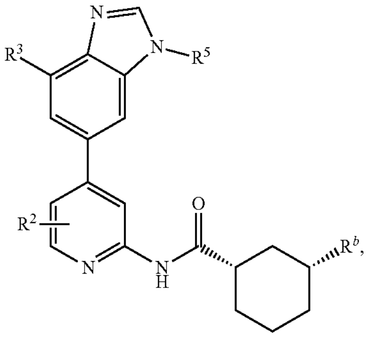
Formula (XX-b)
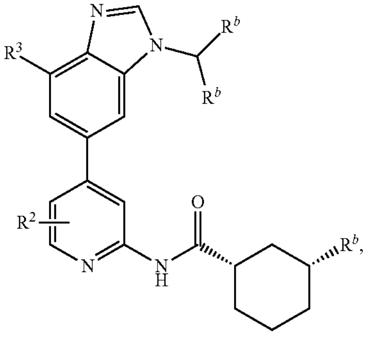
Formula (XX-c)
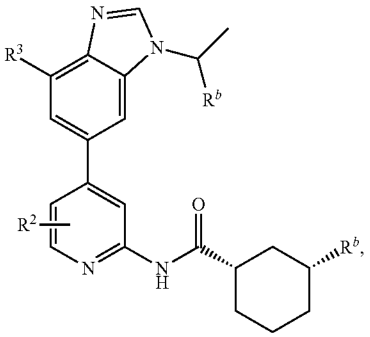
-continued
Formula (XXI)
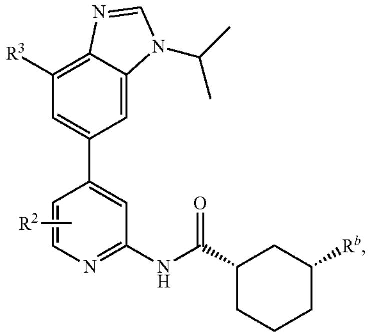
Formula (XXI-a)
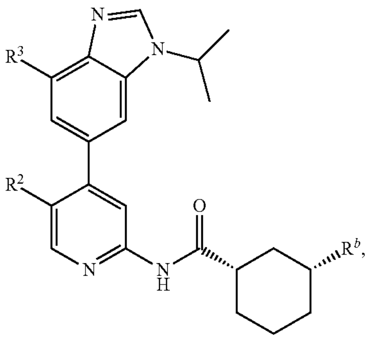
Formula (XXI-b)
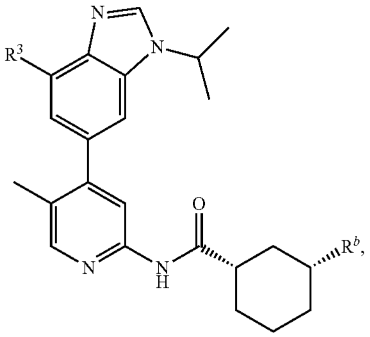
Formula (XXI-c)
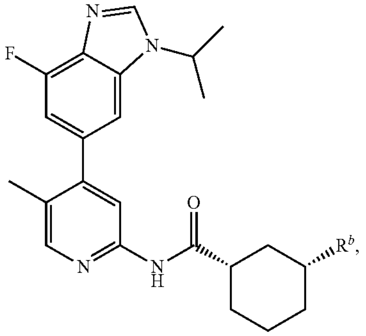
or -continued Formula (XXI-d)

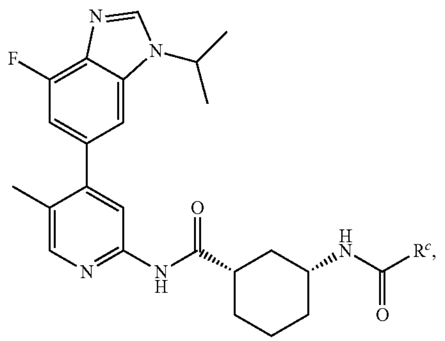

or pharmaceutically acceptable salts or solvates thereof, wherein the variables are as defined herein, are provided and wherein when there are more than one $R^b$, each $R^b$ is independent to others. In some embodiments, $R^2$ is not halo. In some embodiments, $R^2$ is optionally substituted $C_{1-6}$ alkyl. In some embodiments, $R^2$ is optionally substituted $C_{1-4}$ alkyl. In some embodiments, $R^2$ is optionally substituted $C_{1-3}$ alkyl. In some embodiments, $R^2$ is optionally substituted $C_{1-3}$ alkoxyl. In some embodiments, $R^5$ is optionally $C_{1-6}$ alkyl. In some embodiments, $R^5$ is optionally substituted $C_{1-4}$ alkyl. In some embodiments, $R^5$ is optionally substituted $C_{1-3}$ alkyl. In some embodiments, the optionally substituted $C_{1-6}$ alkyl, the optionally substituted $C_{1-4}$ alkyl, or the optionally substituted $C_{1-3}$ alkyl is substituted with two $R^b$ substituents. In some embodiments, the optionally substituted $C_{1-6}$ alkyl, the optionally substituted $C_{1-4}$ alkyl, or the optionally substituted $C_{1-3}$ alkyl is substituted with one $R^b$ substituent. In some embodiments, $R^b$ is not a carbocycle, a heterocycle, or an aryl. In some embodiments, $R^2$ is Me or OMe. In some embodiments, $R^3$ is H, D, or F. In some embodiments, $R^4$ is H or $C_{1-3}$ alkyl. In some embodiments, $R^5$ is isopropyl, $-CF_3(CH)CH_3$, $-C_{3-6}$ cycloalkyl, or $-CH_2-(C_{3-6}$ cycloalkyl). In some embodiments, $R^b$ is $NHCOR^{13}$ or CN. In some embodiments, and $R^{13}$ is H or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl.

In some embodiments, the disclosure is directed to the compound having a formula of Formula (XXI-e)

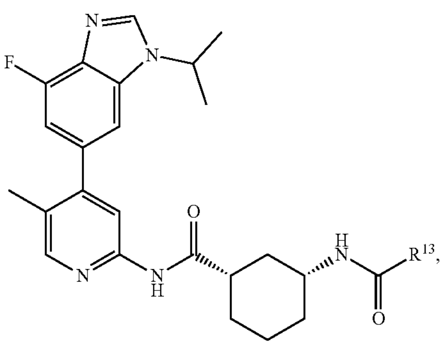

or a pharmaceutically acceptable salt or solvate thereof.

In some embodiments, the disclosure is directed to compounds having a formula of Formula (XXII)

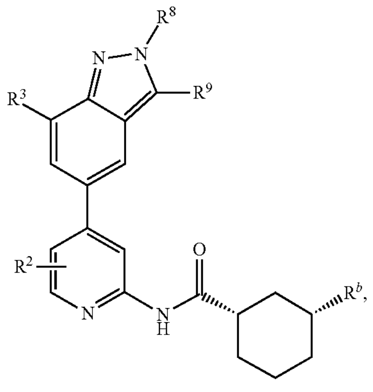

Formula (XXIII)

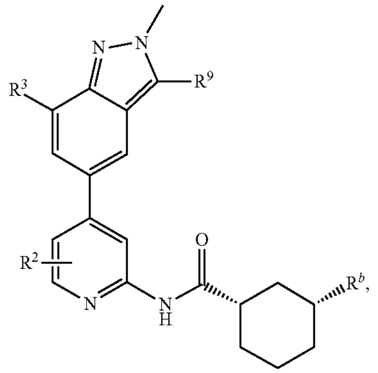

Formula (XXIII-a)

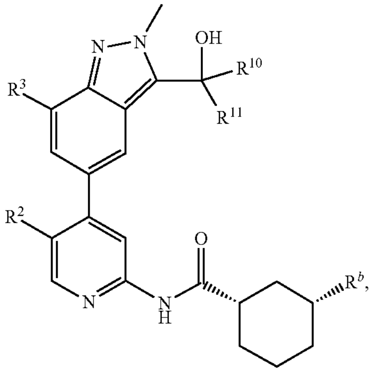

Formula (XXIV)

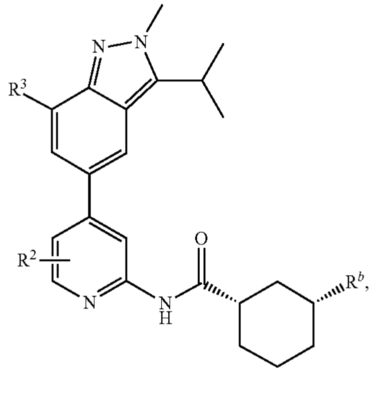

-continued

Formula (XXV)

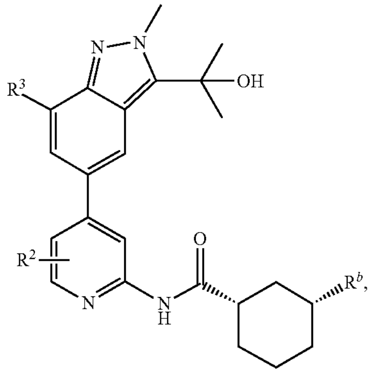

Formula (XXVI)

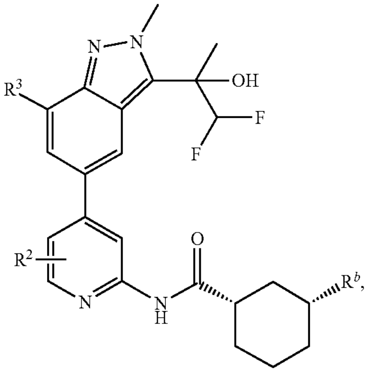

Formula (XXVII)

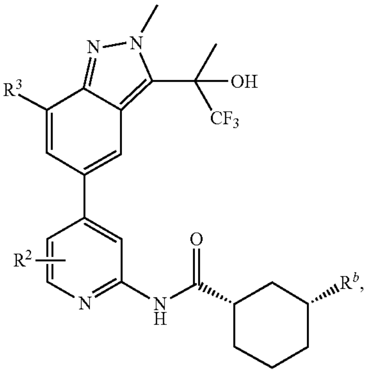

Formula (XXVII-a)

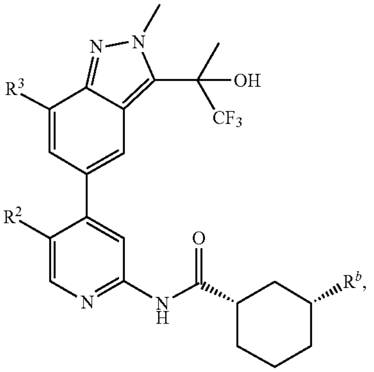

-continued

Formula (XXVII-b)

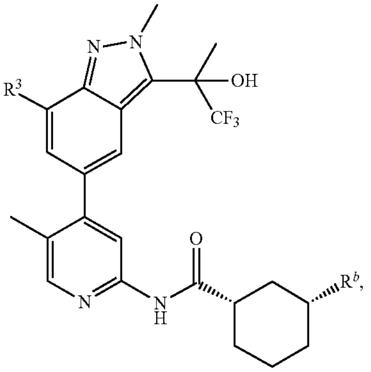

Formula (XXVII-c)

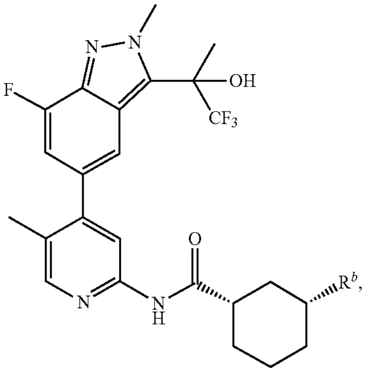

or

Formula (XXVII-d)

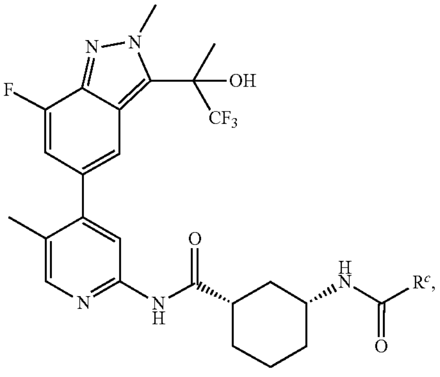

or pharmaceutically acceptable salts or solvates thereof, wherein the variables are as defined herein, are provided. In some embodiments, $R^2$ is H, D, halogen, or Me. In some embodiments, $R^3$ is H, D, or F. In some embodiments, $R^{10}$ is H, D, Me, or $C_{1-3}$ haloalkyl. In some embodiments, $R^{11}$ is H, D, Me, or $C_{1-3}$ haloalkyl. In some embodiments, $R^b$ is $NHCOR^{14}$. In some embodiments, and $R^{14}$ is H, —$CH_2CN$, or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl or (4-10 membered heterocycloalkyl)-$C_{1-4}$ alkyl.

In some embodiments, the disclosure is directed to the compound having a
Formula (XXVII-e)
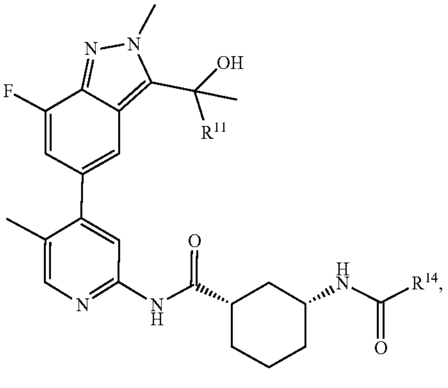
or a pharmaceutically acceptable salt or solvate thereof.
In some embodiments, the compound has a formula of
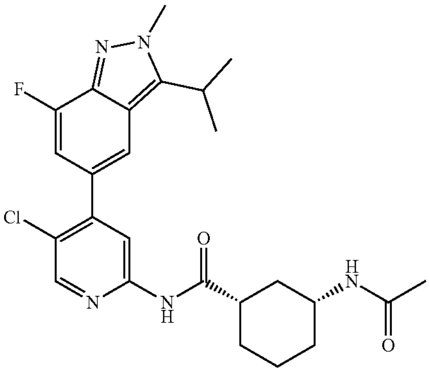
,
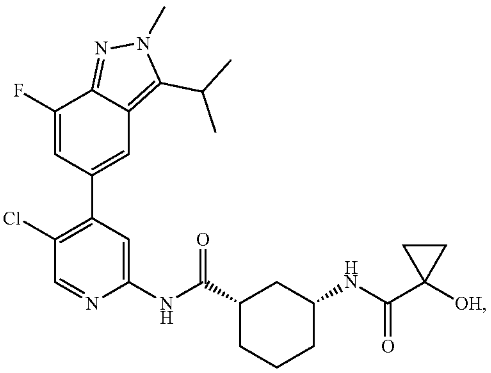
-continued
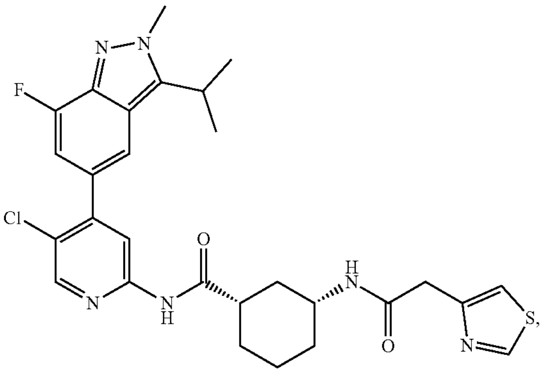
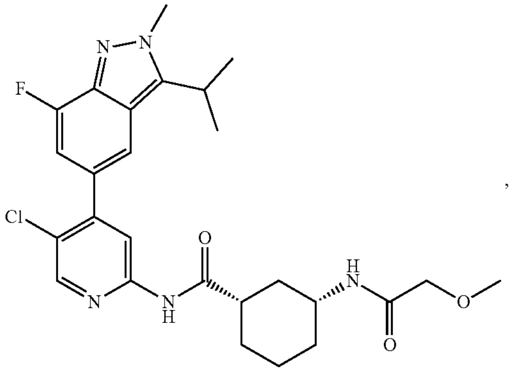
,
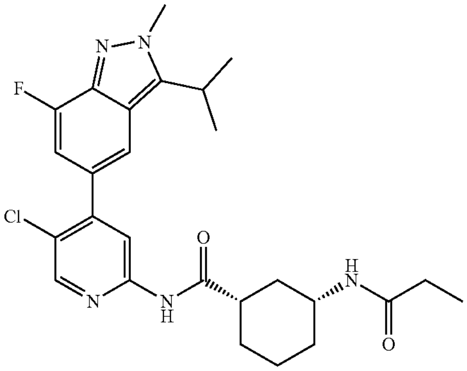
,
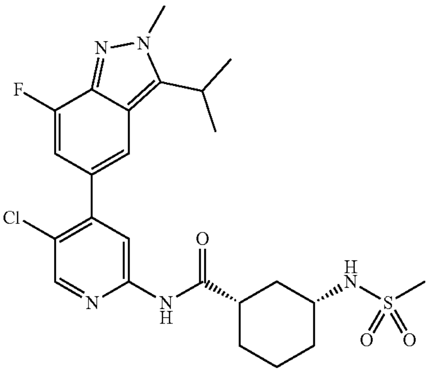
, -continued
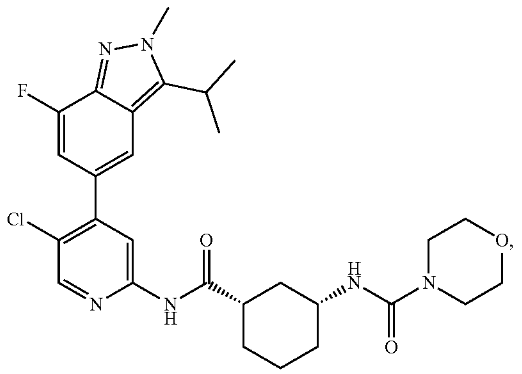
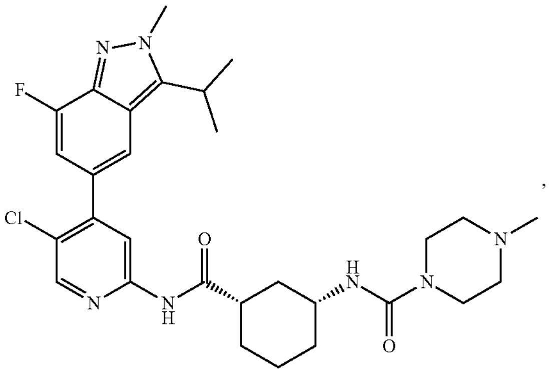
,
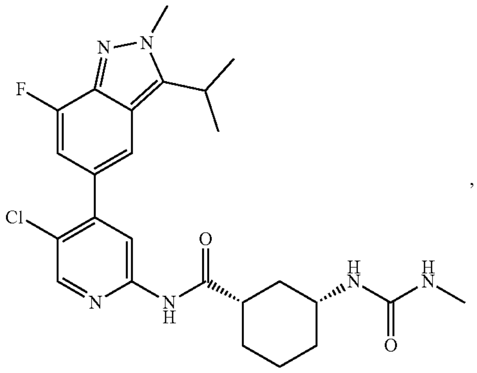
,
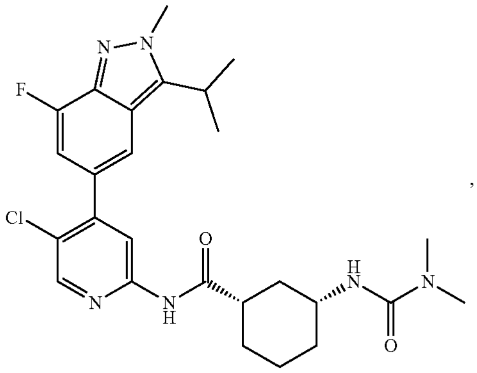
,
-continued
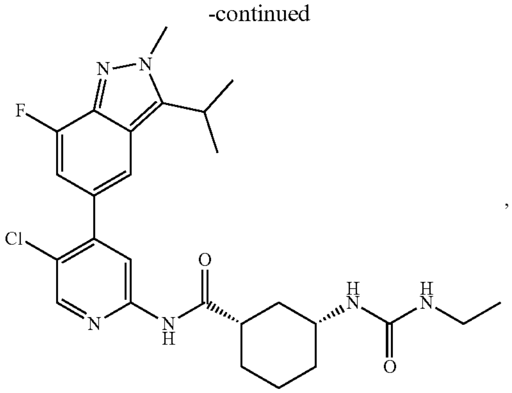
,
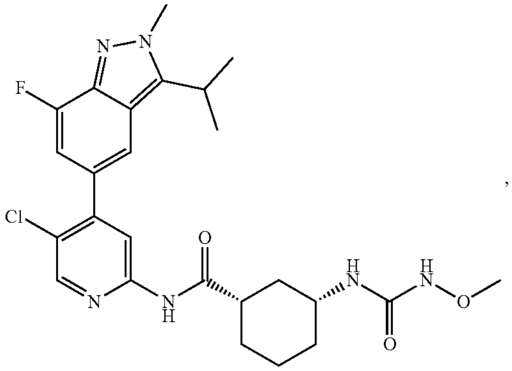
,
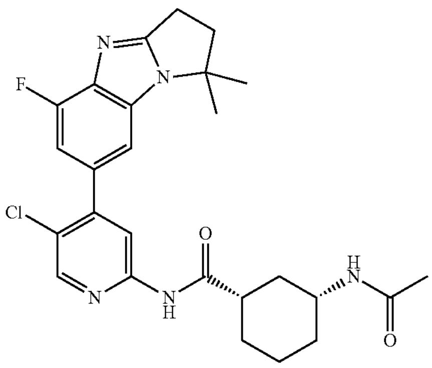
,
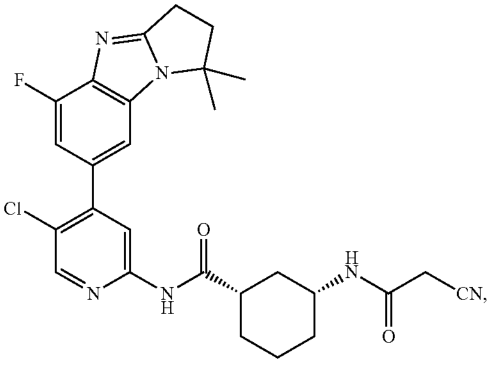

-continued
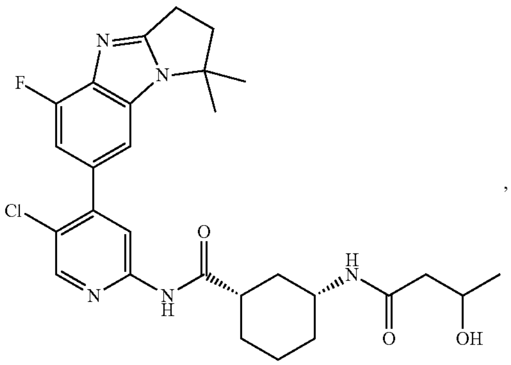
,
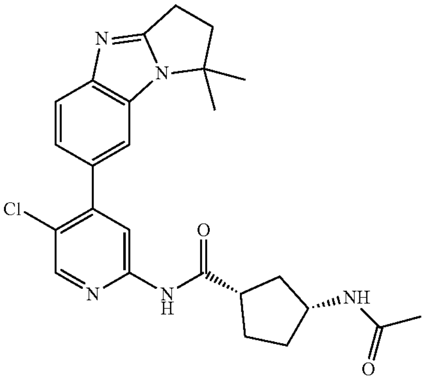
,
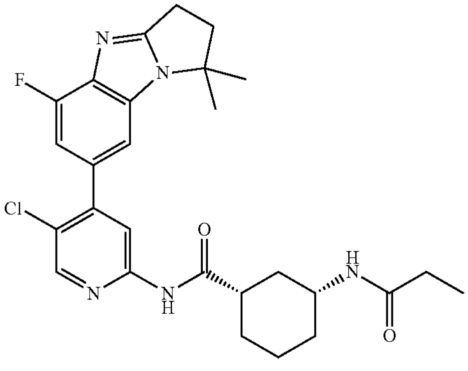
,
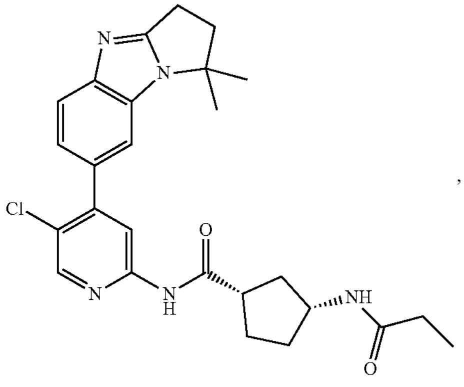
,
-continued
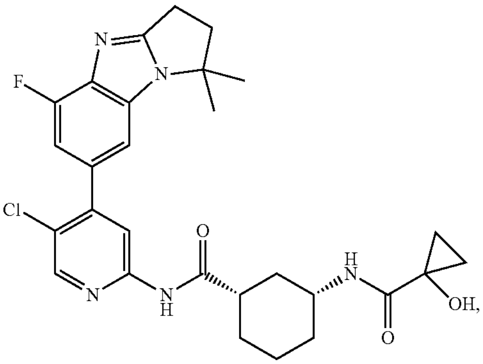
,
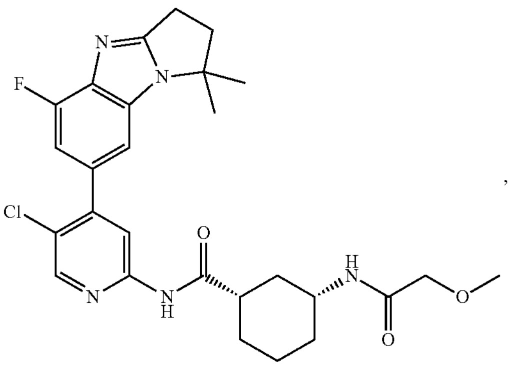
,
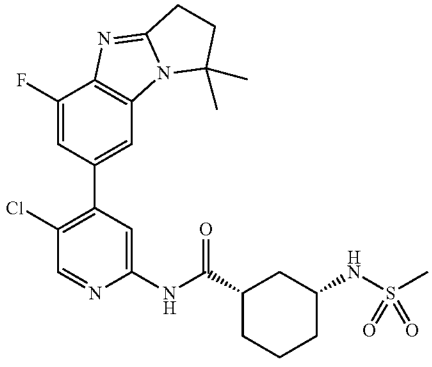
,
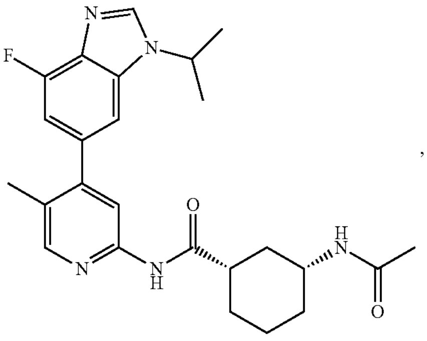
, -continued
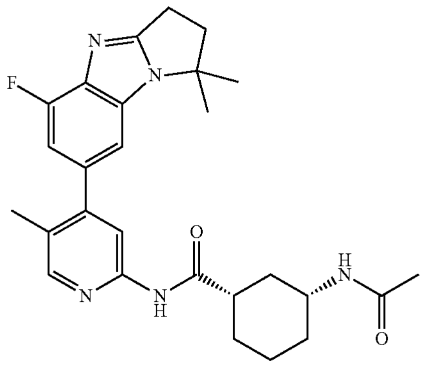
,
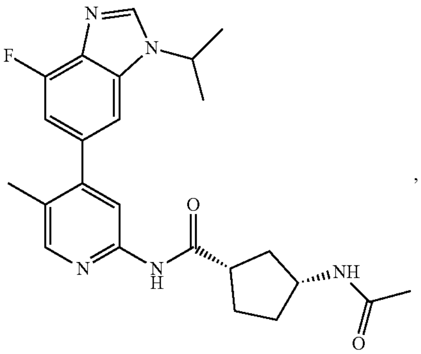
,
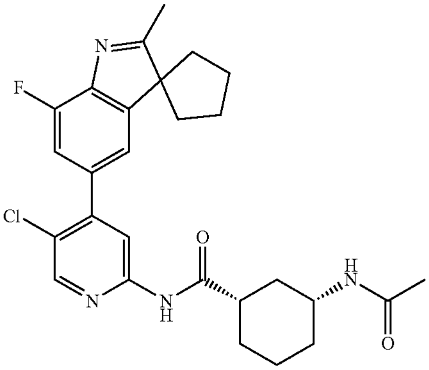
,
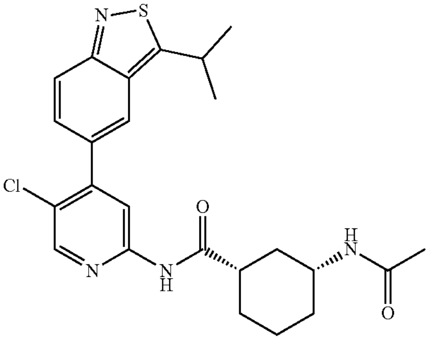
,
-continued
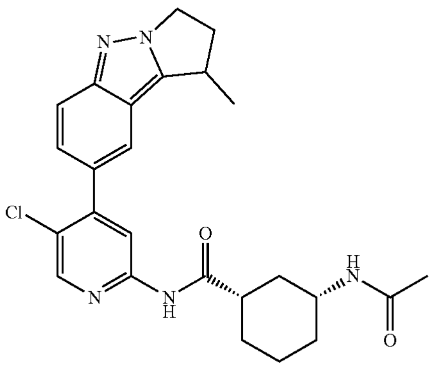
,
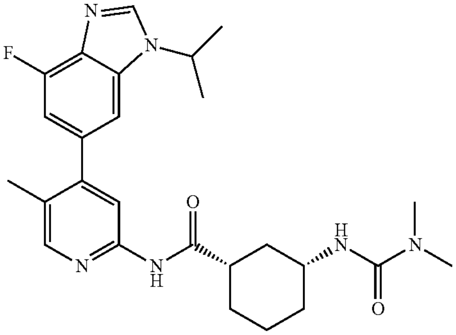
,
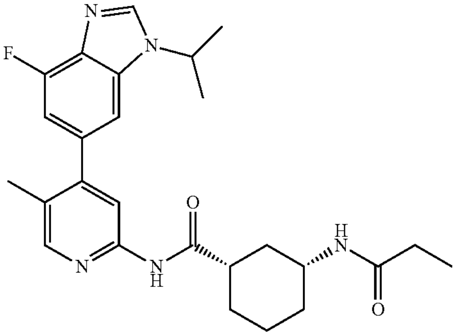
,
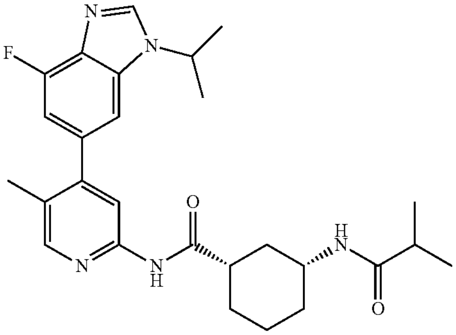
,
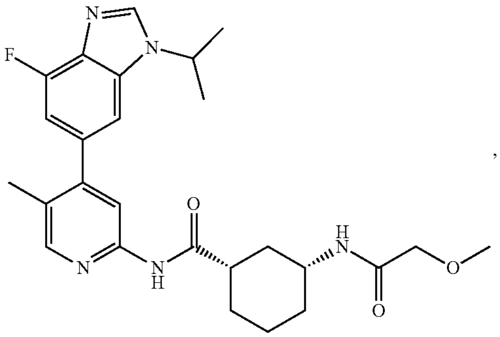
, -continued
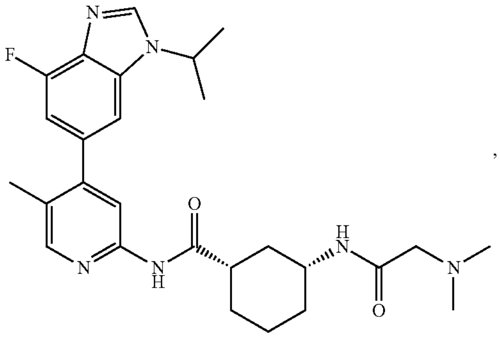
,
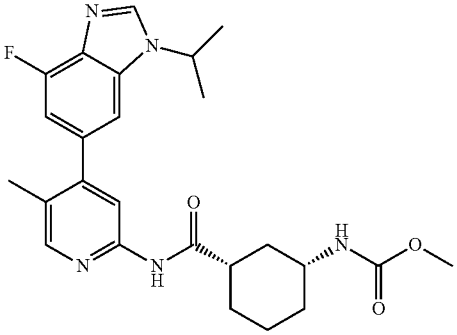
,
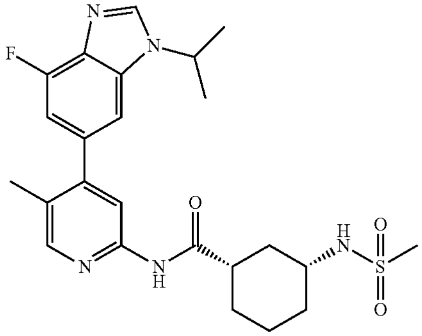
,
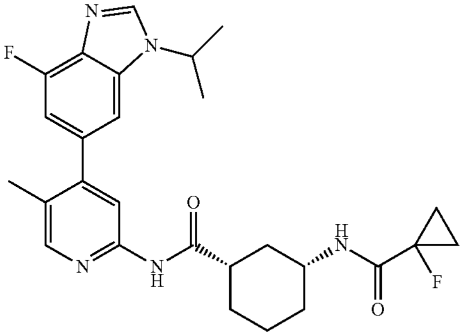
,
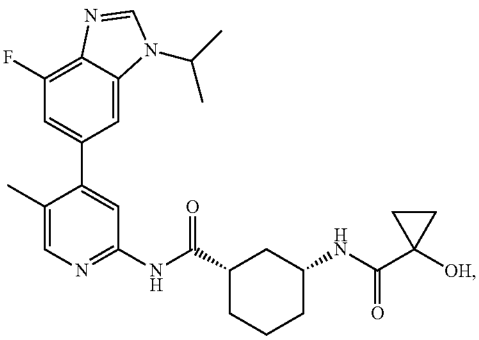
-continued
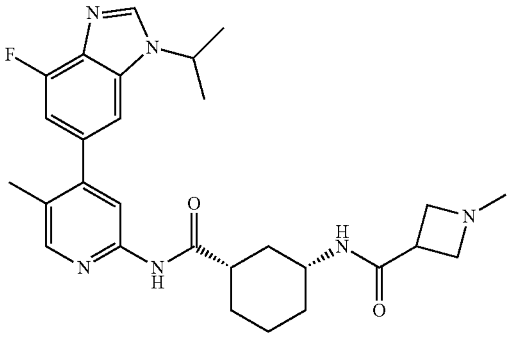
,
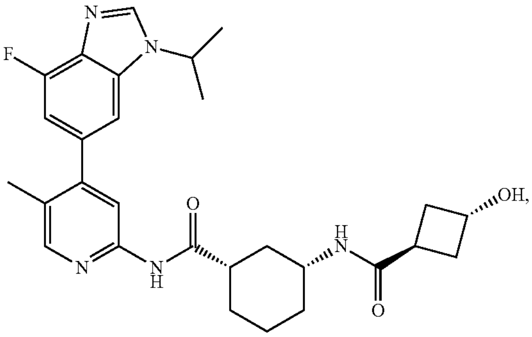
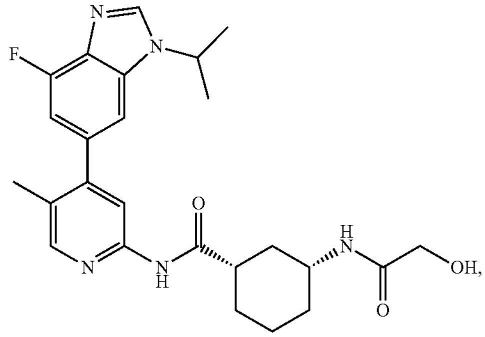
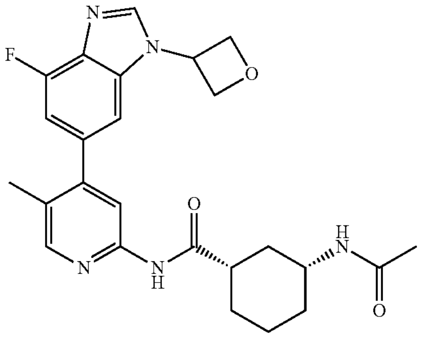
,
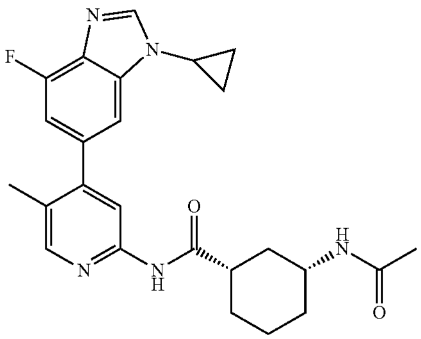
, -continued
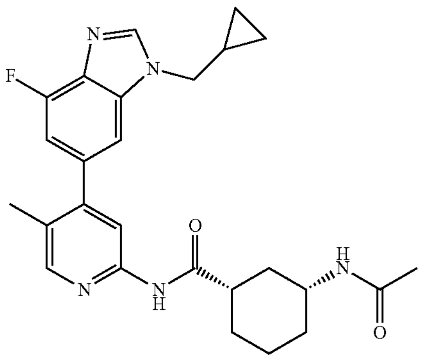
,
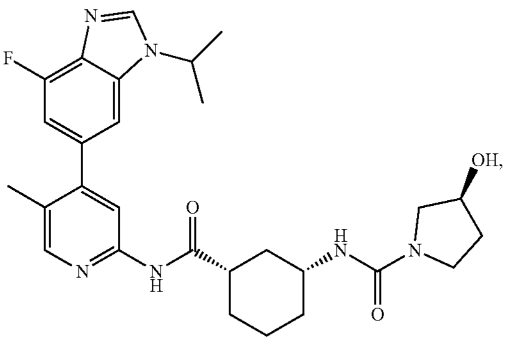
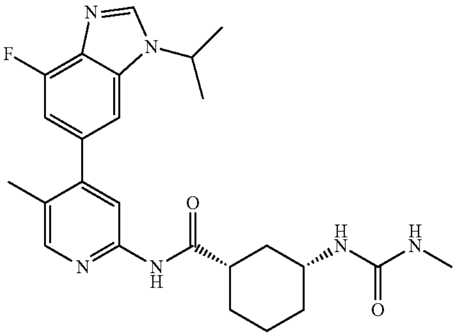
,
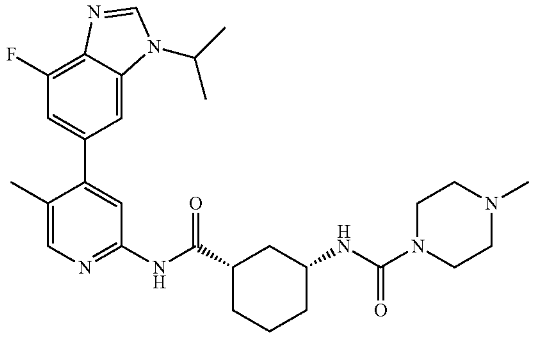
,
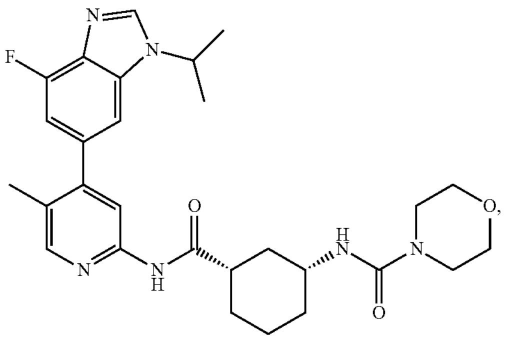
-continued
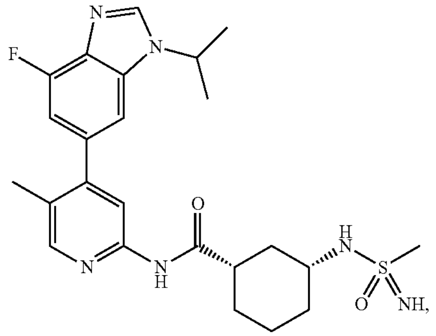
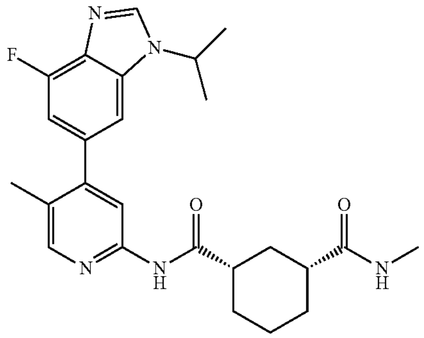
,
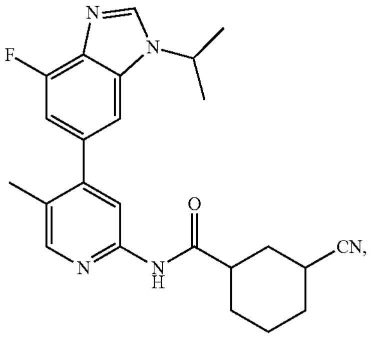
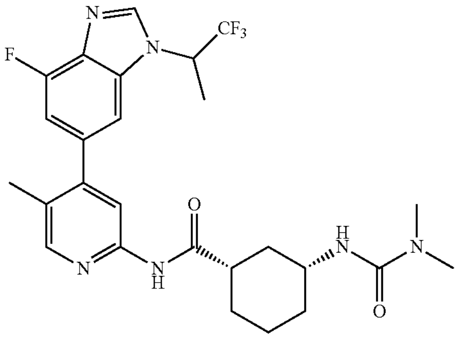
,
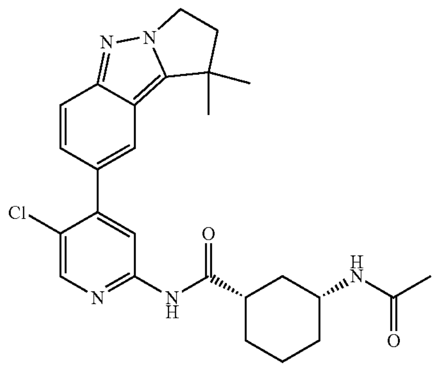
, -continued
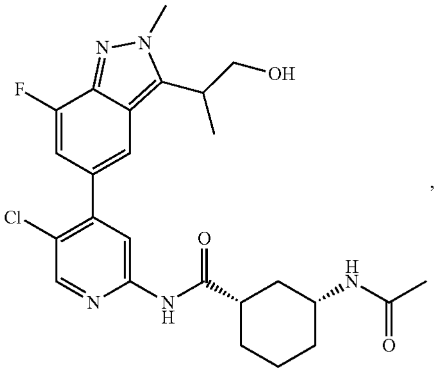
,
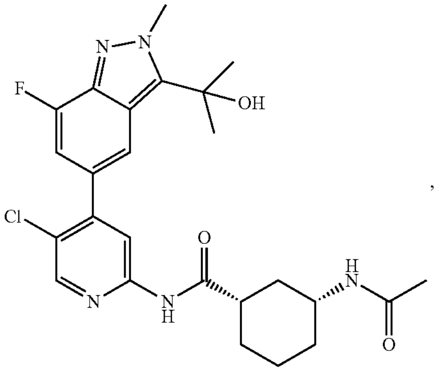
,
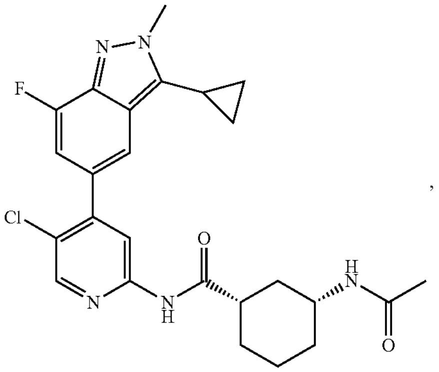
,
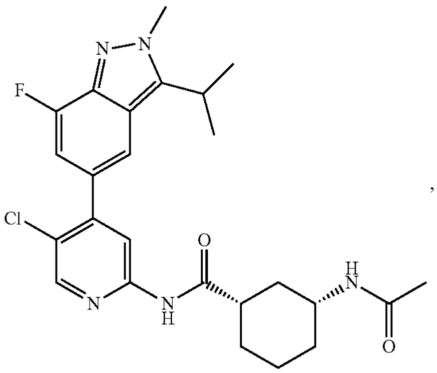
,
-continued
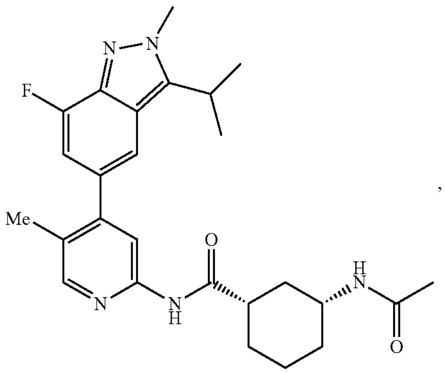
,
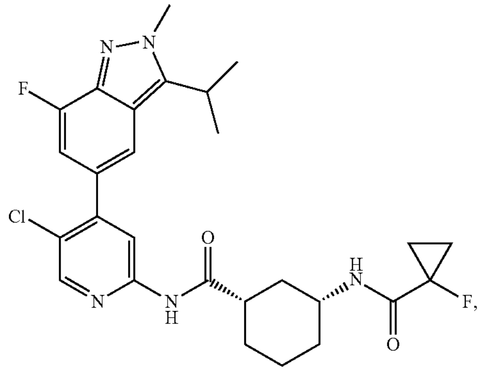
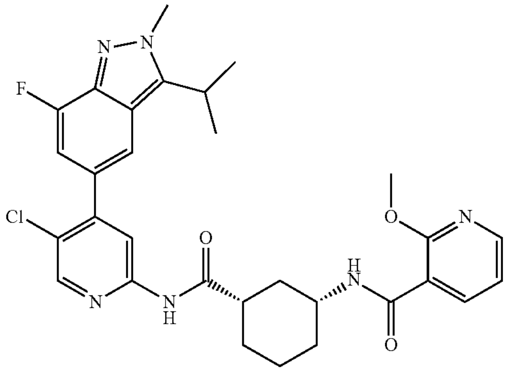
,
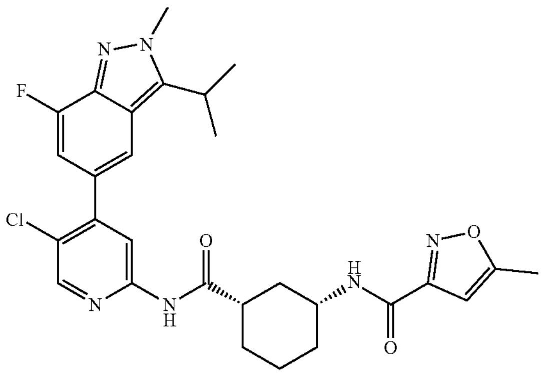
, -continued
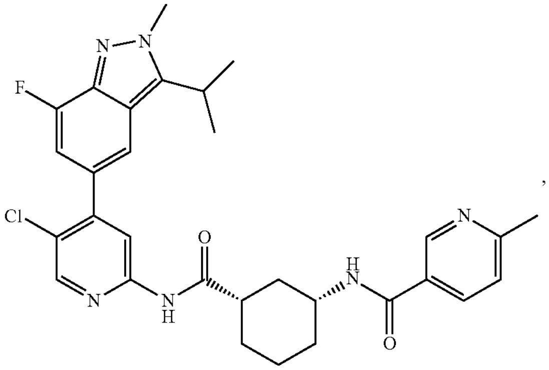
,
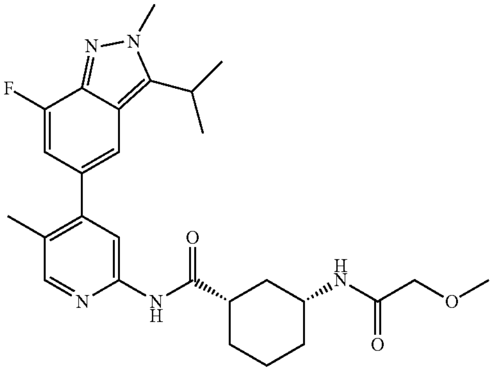
,
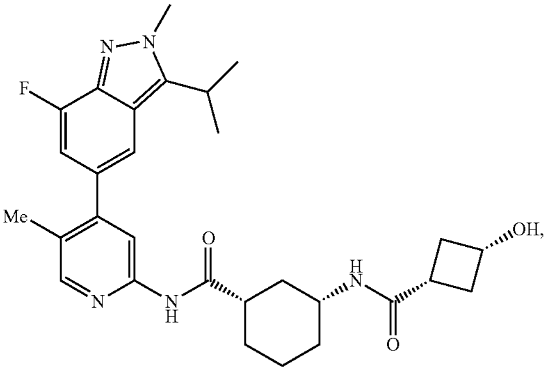
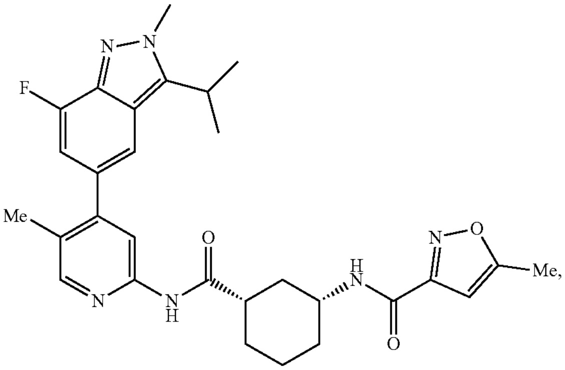
-continued
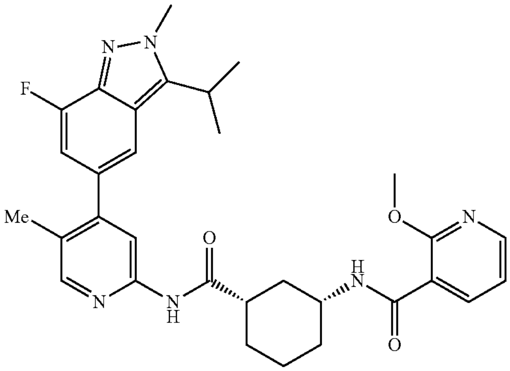
,
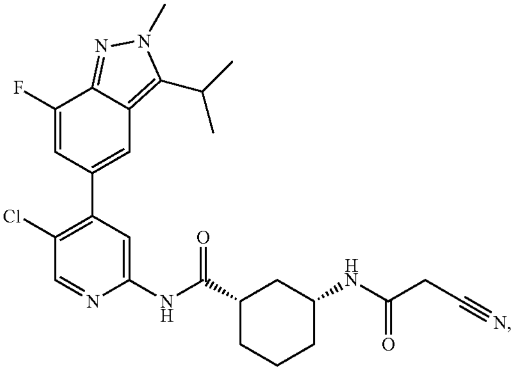
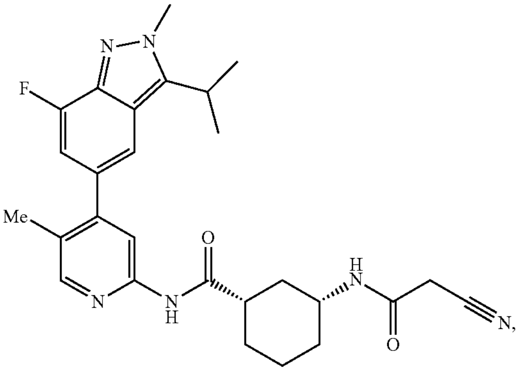
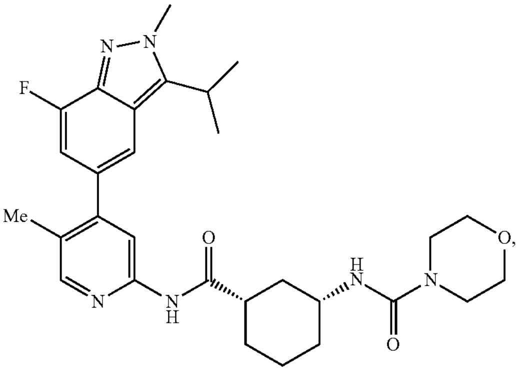

-continued
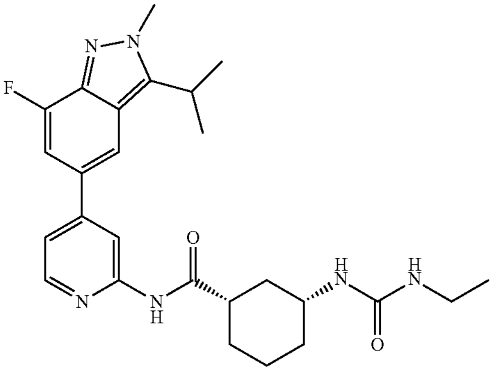
,
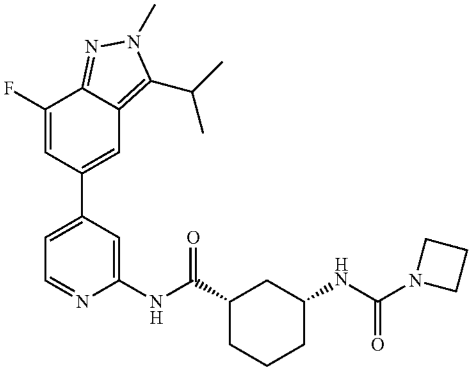
,
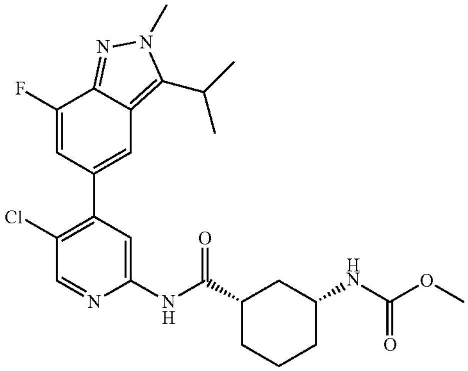
,
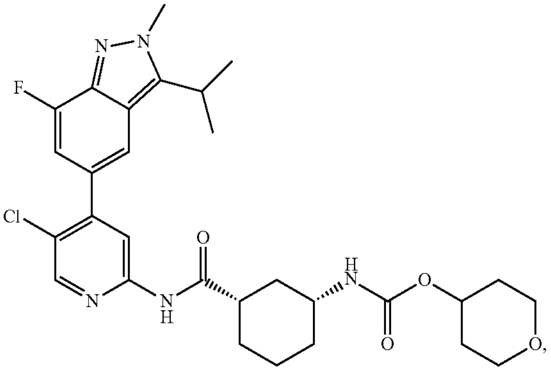
,
-continued
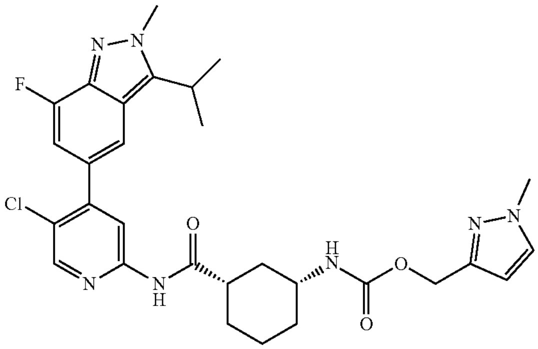
,
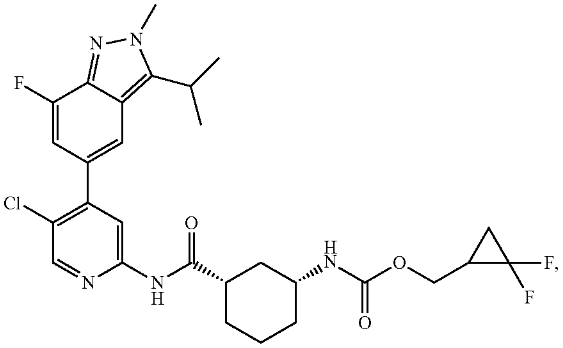
,
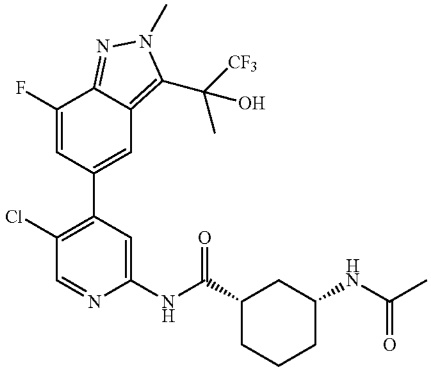
,
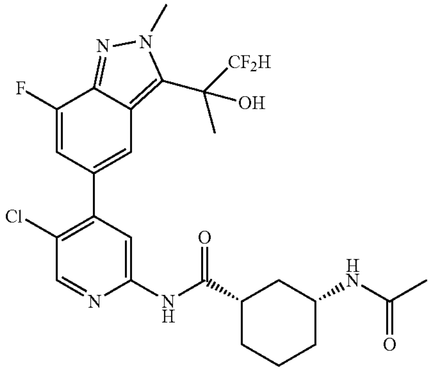
, -continued
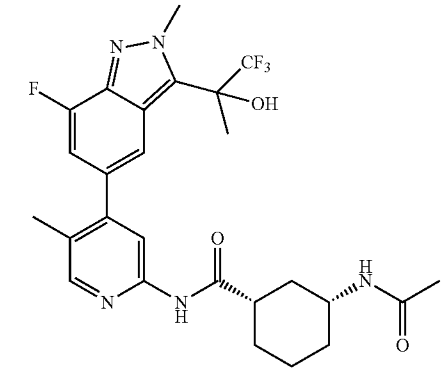
,
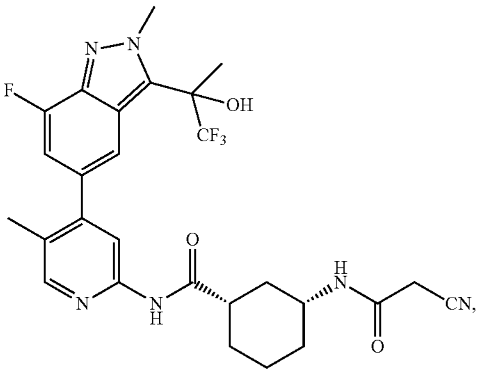
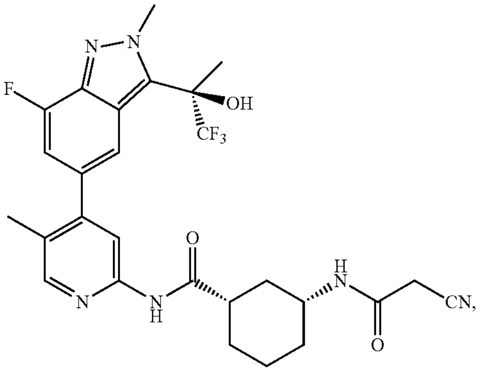
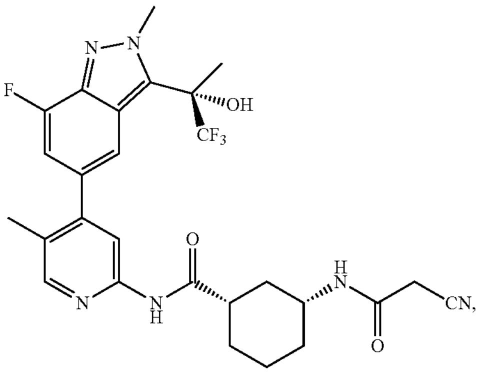
-continued
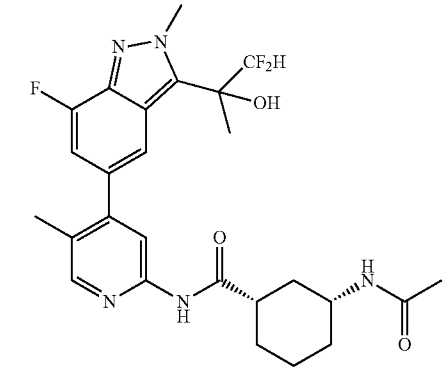
,
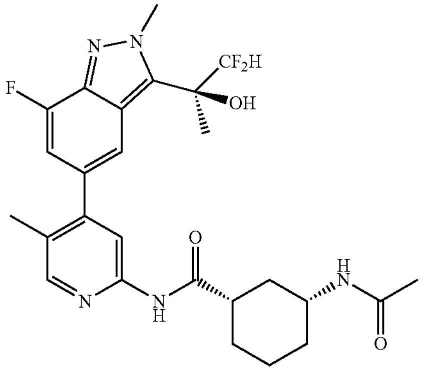
,
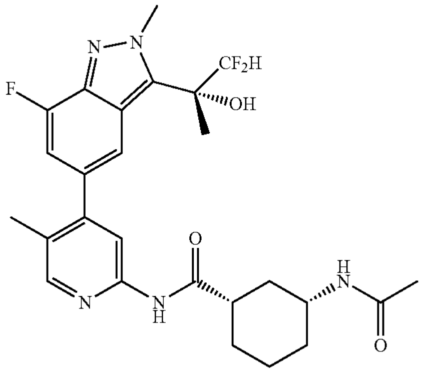
,
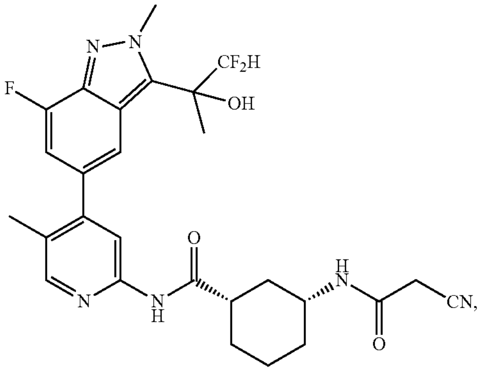

-continued
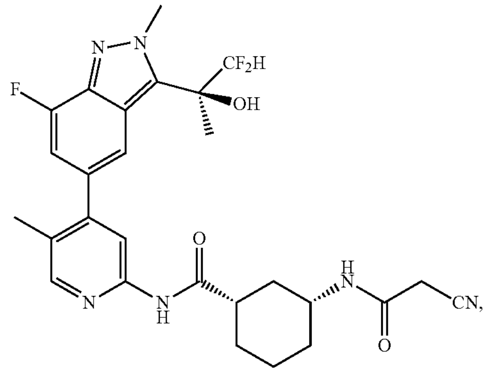
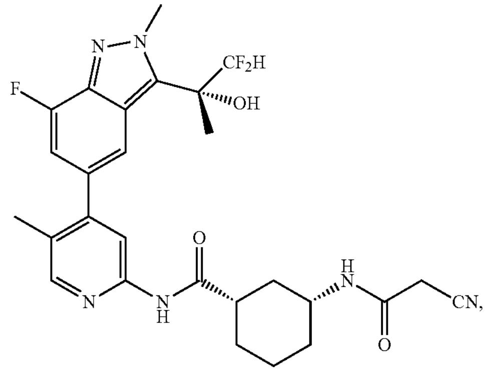
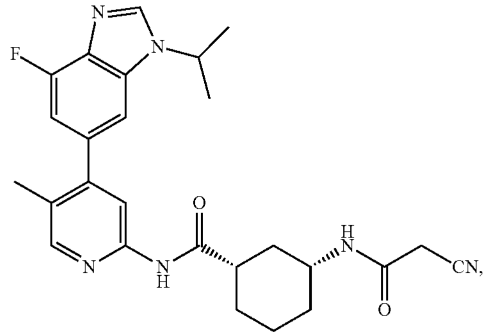
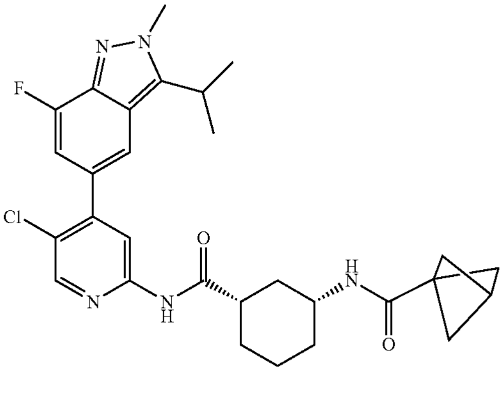
,
-continued
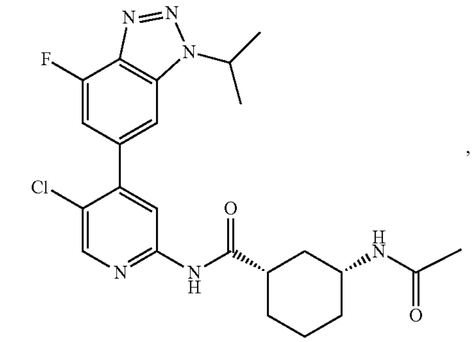
,
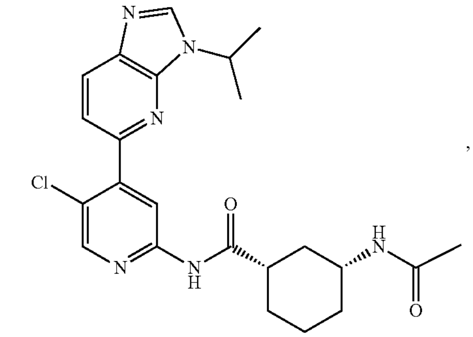
,
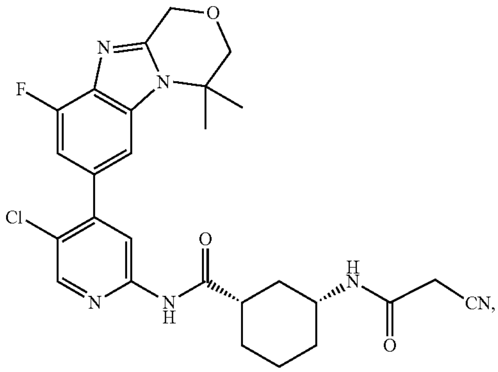
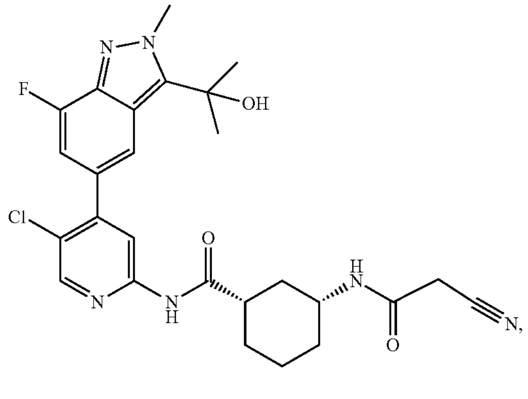
or -continued

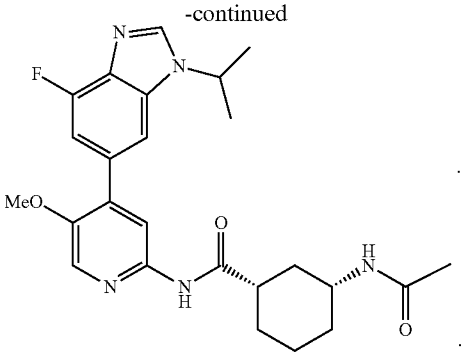

In some embodiments, the disclosure is directed to the compound selected from the group consisting of:

(1S,3R)-3-acetamido-N-[5-chloro-4-(7-fluoro-3-isopropyl-2-methyl-indazol-5-yl)-2-pyridyl]cyclohexanecarboxamide;

(1S,3R)—N-[5-chloro-4-(7-fluoro-3-isopropyl-2-methyl-indazol-5-yl)-2-pyridyl]-3-[(1-hydroxycyclopropanecarbonyl)amino]-cyclohexanecarboxamide;

(1S,3R)—N-(5-chloro-4-(7-fluoro-3-isopropyl-2-methyl-2H-indazol-5-yl)pyridin-2-yl)-3-(2-(thiazol-4-yl)acetamido)cyclohexane-1-carboxamide;

(1S,3R)—N-(5-chloro-4-(7-fluoro-3-isopropyl-2-methyl-2H-indazol-5-yl)pyridin-2-yl)-3-(2-methoxyacetamido) cyclohexane-1-carboxamide;

(1S,3R)—N-(5-chloro-4-(7-fluoro-3-isopropyl-2-methyl-2H-indazol-5-yl)pyridin-2-yl)-3-propionamido-cyclohexane-1-carboxamide;

(1S,3R)—N-[5-chloro-4-(7-fluoro-3-isopropyl-2-methyl-indazol-5-yl)-2-pyridyl]-3-(methanesulfonamido)cyclohexanecarboxamide;

N-[(1R,3S)-3-[[5-chloro-4-(7-fluoro-3-isopropyl-2-methyl-indazol-5-yl)-2-pyridyl]carbamoyl]cyclohexyl]morpholine-4-carboxamide;

N-((1R,3S)-3-((5-chloro-4-(7-fluoro-3-isopropyl-2-methyl-2H-indazol-5-yl)pyridin-2-yl)carbamoyl)-cyclohexyl)-4-methylpiperazine-1-carboxamide;

(1S,3R)—N-(5-chloro-4-(7-fluoro-3-isopropyl-2-methyl-2H-indazol-5-yl)pyridin-2-yl)-3-(3-methylureido)cyclohexane-1-carboxamide;

(1S,3R)—N-(5-chloro-4-(7-fluoro-3-isopropyl-2-methyl-2H-indazol-5-yl)pyridin-2-yl)-3-(3,3-dimethylureido)cyclohexane-1-carboxamide;

(1S,3R)—N-(5-chloro-4-(7-fluoro-3-isopropyl-2-methyl-2H-indazol-5-yl)pyridin-2-yl)-3-(3-ethylureido)cyclohexane-1-carboxamide;

(1S,3R)—N-(5-chloro-4-(7-fluoro-3-isopropyl-2-methyl-2H-indazol-5-yl)pyridin-2-yl)-3-(3-methoxyureido)cyclohexane-1-carboxamide;

(1S,3R)-3-acetamido-N-[5-chloro-4-(5-fluoro-1,1-dimethyl-2,3-dihydropyrrolo[1,2-a]benzimidazol-7-yl)-2-pyridyl]cyclohexanecarboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(2-cyanoacetamido)cyclohexane-1-carboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(3-hydroxybutanamido)cyclohexane-1-carboxamide;

(1S,3R)-3-acetamido-N-(5-chloro-4-(1,1-dimethyl-2,3-dihydro-1H-benzo[d]pyrrolo[1,2-a]imidazol-7-yl)pyridin-2-yl)cyclopentane-1-carboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-propionamidocyclohexane-1-carboxamide;

(1S,3R)—N-(5-chloro-4-(1,1-dimethyl-2,3-dihydro-1H-benzo[d]pyrrolo[1,2-a]imidazol-7-yl)pyridin-2-yl)-3-propionamidocyclopentane-1-carboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(1-hydroxycyclopropane-1-carboxamido)cyclohexane-1-carboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(2-methoxyacetamido)cyclohexane-1-carboxamide;

(1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(methylsulfonamido)cyclohexane-1-carboxamide;

(1S,3R)-3-acetamido-N-(4-(4-fluoro-1-isopropyl-1H-benzo[d]imidazol-6-yl)-5-methylpyridin-2-yl)cyclohexane-1-carboxamide;

(1S,3R)-3-acetamido-N-(4-(5-fluoro-1,1-dimethyl-2,3-dihydro-1H-benzo[d]pyrrolo[1,2-a]imidazol-7-yl)-5-methylpyridin-2-yl)cyclohexane-1-carboxamide;

(1S,3R)-3-acetamido-N-(4-(4-fluoro-1-isopropyl-1H-benzo[d]imidazol-6-yl)-5-methylpyridin-2-yl)cyclopentane-1-carboxamide;

(1S,3R)-3-acetamido-N-(5-chloro-4-(7'-fluoro-2'-methyl-spiro[cyclopentane-1,3'-indol]-5'-yl)pyridin-2-yl)cyclohexane-1-carboxamide;

(1S,3R)-3-acetamido-N-(5-chloro-4-(3-isopropylbenzo[c]isothiazol-5-yl)pyridin-2-yl)cyclohexane-1-carboxamide;

(1S,3R)-3-acetamido-N-(5-chloro-4-(1-methyl-2,3-dihydro-1H-pyrrolo[1,2-b]indazol-8-yl)pyridin-2-yl)cyclohexane-1-carboxamide (1S,3R)-3-(3,3-dimethylureido)-N-(4-(4-fluoro-1-isopropyl-1H-benzo[d]imidazol-6-yl)-5-methylpyridin-2-yl)cyclohexane-1-carboxamide;

(1S,3R)—N-(4-(4-fluoro-1-isopropyl-1H-benzo[d]imidazol-6-yl)-5-methylpyridin-2-yl)-3-propionamidocyclohexane-1-carboxamide;

(1S,3R)—N-(4-(4-fluoro-1-isopropyl-1H-benzo[d]imidazol-6-yl)-5-methylpyridin-2-yl)-3-isobutyramidocyclohexane-1-carboxamide;

(1S,3R)—N-(4-(4-fluoro-1-isopropyl-1H-benzo[d]imidazol-6-yl)-5-methylpyridin-2-yl)-3-(2-methoxyacetamido) cyclohexane-1-carboxamide;

(1S,3R)-3-(2-(dimethylamino)acetamido)-N-(4-(4-fluoro-1-isopropyl-1H-benzo[d]imidazol-6-yl)-5-methylpyridin-2-yl)cyclohexane-1-carboxamide;

methyl ((1R,3S)-3-((4-(4-fluoro-1-isopropyl-1H-benzo[d]imidazol-6-yl)-5-methylpyridin-2-yl)carbamoyl)cyclohexyl)carbamate;

(1S,3R)—N-(4-(4-fluoro-1-isopropyl-1H-benzo[d]imidazol-6-yl)-5-methylpyridin-2-yl)-3-(methylsulfonamido) cyclohexane-1-carboxamide;

(1S,3R)—N-(4-(4-fluoro-1-isopropyl-1H-benzo[d]imidazol-6-yl)-5-methylpyridin-2-yl)-3-(1-fluorocyclopropane-1-carboxamido)cyclohexane-1-carboxamide;

(1S,3R)—N-(4-(4-fluoro-1-isopropyl-1H-benzo[d]imidazol-6-yl)-5-methylpyridin-2-yl)-3-(1-hydroxycyclopropane-1-carboxamido)cyclohexane-1-carboxamide;

N-((1R,3S)-3-((4-(4-fluoro-1-isopropyl-1H-benzo[d]imidazol-6-yl)-5-methylpyridin-2-yl)carbamoyl)cyclohexyl)-1-methylazetidine-3-carboxamide;

(1S,3R)—N-(4-(4-fluoro-1-isopropyl-1H-benzo[d]imidazol-6-yl)-5-methylpyridin-2-yl)-3-((1r,3R)-3-hydroxycyclobutane-1-carboxamido)cyclohexane-1-carboxamide;

(1S,3R)—N-(4-(4-fluoro-1-isopropyl-1H-benzo[d]imidazol-6-yl)-5-methylpyridin-2-yl)-3-(2-hydroxyacetamido)cyclohexane-1-carboxamide;

(1S,3R)-3-acetamido-N-(4-(4-fluoro-1-(oxetan-3-yl)-1H-benzo[d]imidazol-6-yl)-5-methylpyridin-2-yl)cyclohexane-1-carboxamide;

(1S,3R)-3-acetamido-N-(4-(1-cyclopropyl-4-fluoro-1H-benzo[d]imidazol-6-yl)-5-methylpyridin-2-yl)cyclohexane-1-carboxamide;

(1S,3R)-3-acetamido-N-(4-(1-(cyclopropylmethyl)-4-fluoro-1H-benzo[d]imidazol-6-yl)-5-methylpyridin-2-yl)cyclohexane-1-carboxamide;

(S)—N-((1R,3S)-3-((4-(4-fluoro-1-isopropyl-1H-benzo[d]imidazol-6-yl)-5-methylpyridin-2-yl)carbamoyl)cyclohexyl)-3-hydroxypyrrolidine-1-carboxamide;

(1S,3R)—N-(4-(4-fluoro-1-isopropyl-1H-benzo[d]imidazol-6-yl)-5-methylpyridin-2-yl)-3-(3-methylureido)cyclohexane-1-carboxamide;

N-((1R,3S)-3-((4-(4-fluoro-1-isopropyl-1H-benzo[d]imidazol-6-yl)-5-methylpyridin-2-yl)carbamoyl)cyclohexyl)morpholine-4-carboxamide;

N-((1R,3S)-3-((4-(4-fluoro-1-isopropyl-1H-benzo[d]imidazol-6-yl)-5-methylpyridin-2-yl)carbamoyl)cyclohexyl)-4-methylpiperazine-1-carboxamide;

(1S,3R)—N-[4-(7-fluoro-3-isopropyl-benzimidazol-5-yl)-5-methyl-2-pyridyl]-3-[(methylsulfonimidoyl)amino]cyclohexanecarboxamide;

(1S,3R)—N1-(4-(4-fluoro-1-isopropyl-1H-benzo[d]imidazol-6-yl)-5-methylpyridin-2-yl)-N3-methylcyclohexane-1,3-dicarboxamide;

3-cyano-N-(4-(4-fluoro-1-isopropyl-1H-benzo[d]imidazol-6-yl)-5-methylpyridin-2-yl)cyclohexane-1-carboxamide;

(1S,3R)-3-(3,3-dimethylureido)-N-(4-(4-fluoro-1-(1,1,1-trifluoropropan-2-yl)-1H-benzo[d]imidazol-6-yl)-5-methylpyridin-2-yl)cyclohexane-1-carboxamide;

(1S,3R)-3-acetamido-N-(5-chloro-4-(1,1-dimethyl-2,3-dihydro-1H-pyrrolo[1,2-b]indazol-8-yl)pyridin-2-yl)cyclohexane-1-carboxamide;

(1S,3R)-3-acetamido-N-(5-chloro-4-(7-fluoro-3-(1-hydroxypropan-2-yl)-2-methyl-2H-indazol-5-yl)pyridin-2-yl)cyclohexane-1-carboxamide;

(1S,3R)-3-acetamido-N-(5-chloro-4-(7-fluoro-3-(2-hydroxypropan-2-yl)-2-methyl-2H-indazol-5-yl)pyridin-2-yl)cyclohexane-1-carboxamide;

(1S,3R)-3-acetamido-N-(5-chloro-4-(3-cyclopropyl-7-fluoro-2-methyl-2H-indazol-5-yl)pyridin-2-yl)cyclohexane-1-carboxamide;

(1S,3R)-3-acetamido-N-(5-chloro-4-(3-isopropyl-2-methyl-2H-pyrazolo[4,3-b]pyridin-5-yl)pyridin-2-yl)cyclohexane-1-carboxamide;

(1S,3R)-3-acetamido-N-(4-(7-fluoro-3-isopropyl-2-methyl-2H-indazol-5-yl)-5-methylpyridin-2-yl)cyclohexane-1-carboxamide;

(1S,3R)—N-(5-chloro-4-(7-fluoro-3-isopropyl-2-methyl-2H-indazol-5-yl)pyridin-2-yl)-3-(1-fluorocyclopropane-1-carboxamido)cyclohexane-1-carboxamide;

N-((1R,3S)-3-((5-chloro-4-(7-fluoro-3-isopropyl-2-methyl-2H-indazol-5-yl)pyridin-2-yl)carbamoyl)cyclohexyl)-2-methoxynicotinamide;

N-((1R,3S)-3-((5-chloro-4-(7-fluoro-3-isopropyl-2-methyl-2H-indazol-5-yl)pyridin-2-yl)carbamoyl)cyclohexyl)-5-methylisoxazole-3-carboxamide;

N-((1R,3S)-3-((5-chloro-4-(7-fluoro-3-isopropyl-2-methyl-2H-indazol-5-yl)pyridin-2-yl)carbamoyl)cyclohexyl)-6-methylnicotinamide;

(1S,3R)—N-(4-(7-fluoro-3-isopropyl-2-methyl-2H-indazol-5-yl)-5-methylpyridin-2-yl)-3-(2-methoxyacetamido)cyclohexane-1-carboxamide;

(1S,3R)—N-(4-(7-fluoro-3-isopropyl-2-methyl-2H-indazol-5-yl)-5-methylpyridin-2-yl)-3-(2-methoxyacetamido)cyclohexane-1-carboxamide;

N-((1R,3S)-3-((4-(7-fluoro-3-isopropyl-2-methyl-2H-indazol-5-yl)-5-methylpyridin-2-yl)carbamoyl)cyclohexyl)-5-methylisoxazole-3-carboxamide;

N-((1R,3S)-3-((4-(7-fluoro-3-isopropyl-2-methyl-2H-indazol-5-yl)-5-methylpyridin-2-yl)carbamoyl)cyclohexyl)-2-methoxynicotinamide;

(1S,3R)—N-(5-chloro-4-(7-fluoro-3-isopropyl-2-methyl-2H-indazol-5-yl)pyridin-2-yl)-3-(2-cyanoacetamido)cyclohexane-1-carboxamide;

(1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide;

N-((1R,3S)-3-((4-(7-fluoro-3-isopropyl-2-methyl-2H-indazol-5-yl)-5-methylpyridin-2-yl)carbamoyl)cyclohexyl)morpholine-4-carboxamide;

(1S,3R)-3-(3-ethylureido)-N-(4-(7-fluoro-3-isopropyl-2-methyl-2H-indazol-5-yl)pyridin-2-yl)cyclohexane-1-carboxamide;

N-((1R,3S)-3-((4-(7-fluoro-3-isopropyl-2-methyl-2H-indazol-5-yl)pyridin-2-yl)carbamoyl)cyclohexyl)azetidine-1-carboxamide;

methyl ((1R,3S)-3-((5-chloro-4-(7-fluoro-3-isopropyl-2-methyl-2H-indazol-5-yl)pyridin-2-yl)carbamoyl)cyclohexyl)carbamate;

tetrahydro-2H-pyran-4-yl ((1R,3S)-3-((5-chloro-4-(7-fluoro-3-isopropyl-2-methyl-2H-indazol-5-yl)pyridin-2-yl)carbamoyl)cyclohexyl)carbamate;

(1-methyl-1H-pyrazol-3-yl)methyl ((1R,3S)-3-((5-chloro-4-(7-fluoro-3-isopropyl-2-methyl-2H-indazol-5-yl)pyridin-2-yl)carbamoyl)cyclohexyl)carbamate;

(2,2-difluorocyclopropyl)methyl ((1R,3S)-3-((5-chloro-4-(7-fluoro-3-isopropyl-2-methyl-2H-indazol-5-yl)pyridin-2-yl)carbamoyl)cyclohexyl)carbamate;

(1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide;

(1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide;

(1S,3R)-3-(2-cyanoacetamido)-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide (P1);

(1S,3R)-3-(2-cyanoacetamido)-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide (P2);

(1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide;

(1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide;

(1S,3R)—N-(5-chloro-4-(3-(1,1-difluoro-2-hydroxypropan-2-yl)-7-fluoro-2-methyl-2H-indazol-5-yl)pyridin-2-yl)-3-(2-cyanoacetamido)cyclohexane-1-carboxamide;

(1S,3R)-3-(2-cyanoacetamido)-N-(4-(4-fluoro-1-isopropyl-1H-benzo[d]imidazol-6-yl)-5-methylpyridin-2-yl)cyclohexane-1-carboxamide;

(1S,3R)-3-acetamido-N-(4-(4-fluoro-1-isopropyl-1H-benzo[d]imidazol-6-yl)-5-methoxypyridin-2-yl)cyclohexane-1-carboxamide;

N-((1R,3S)-3-((5-chloro-4-(7-fluoro-3-isopropyl-2-methyl-2H-indazol-5-yl)pyridin-2-yl)carbamoyl)cyclohexyl)bicyclo[1.1.1]pentane-1-carboxamide;

(1S,3R)-3-acetamido-N-(5-chloro-4-(4-fluoro-1-isopropyl-1H-benzo[d][1,2,3]triazol-6-yl)pyridin-2-yl)cyclohexane-1-carboxamide;

(1S,3R)-3-Acetamido-N-(5-chloro-4-(3-isopropyl-3H-imidazo[4,5-b]pyridin-5-yl)pyridin-2-yl)cyclohexane-1-carboxamide;

(1S,3R)—N-(5-chloro-4-(9-fluoro-4,4-dimethyl-3,4-dihydro-1H-benzo[4,5]imidazo[2,1-c][1,4]oxazin-7-yl)pyridin-2-yl)-3-(2-cyanoacetamido)cyclohexane-1-carboxamide;

(1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide;

(1S,3R)-3-acetamido-N-(5-chloro-4-(4-fluoro-1-isopropyl-1H-benzo[d]imidazol-6-yl)pyridin-2-yl)cyclohexane-1-carboxamide;

(1S,3R)-3-acetamido-N-(4-(4-fluoro-1-isopropyl-1H-benzo[d]imidazol-6-yl)pyridin-2-yl)cyclohexane-1-carboxamide; and pharmaceutically acceptable salts thereof.

It will be apparent that the compounds provided herein, including all subgenera described herein, may have multiple stereogenic centers. As a result, there exist multiple stereoisomers (enantiomers and diastereomers) of the compounds of the various formula provided herein (and subgenera provided herein). The present disclosure contemplates and encompasses each stereoisomer of any compound of any formula provided herein (and subgenera provided herein), as well as mixtures of said stereoisomers. All enantiomers, diastereomers, and mixtures thereof, are included within the scope of compounds described herein.

Pharmaceutically acceptable salts and solvates of the compounds of any formula provided herein (including all subgenera provided herein) are also within the scope of the disclosure. Isotopic variants of the compounds of any formula provided herein (including all subgenera provided herein) are also contemplated by the present disclosure.

Pharmaceutical Compositions and Methods of Administration

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds and other agent(s) may be mixed into a preparation or both components may be formulated into separate preparations to use them in combination separately or at the same time.

In some embodiments, the concentration of one or more compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds is in the range of 0.0001-10 g, 0.0005-9 g, 0.001-8 g, 0.005-7 g, 0.01-6 g, 0.05-5 g, 0.1-4 g, 0.5-4 g, or 1-3 g.

In some embodiments, a pharmaceutical composition comprising the R enantiomer is free or substantially free of the S enantiomer.

In some embodiments, a pharmaceutical composition comprising the S enantiomer is free or substantially free of the R enantiomer.

In some embodiments, a pharmaceutical composition comprises an enantiomeric excess of at least, or about, 80, 85, 90, 91, 92, 93, 94, 95, 96, 97, 98, 99% of a specific enantiomer of a compound provided herein, such as the R or the S enantiomer. In some embodiments, the enantiomeric excess is at least, or about 90%. In some embodiments, the enantiomeric excess is at least, or about 95%. In some embodiments, the enantiomeric excess is at least, or about 98%. In some embodiments, the enantiomeric excess is at least, or about 99%.

The compounds can be effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition can contain an active ingredient (i.e., a compound of the disclosure) provided for herein or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, pharmaceutical compositions for oral administration are provided that contain a compound provided herein, and a pharmaceutical excipient suitable for oral administration.

In some embodiments, embodiments provide a solid pharmaceutical composition for oral administration containing: (i) an amount (e.g., effective amount) of a compound; optionally (ii) an amount of a second agent; and (iii) a pharmaceutical excipient suitable for oral administration. In some embodiments, the composition further contains: (iv) an amount of a third agent.

In some embodiments, the pharmaceutical composition may be a liquid pharmaceutical composition suitable for oral consumption. Pharmaceutical compositions suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

Embodiments provided for herein further encompass anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. Pharmaceutical compositions and dosage forms that contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrose, kaolin, mannitol, silicic acid, sorbitol, starch, pre-gelatinized starch, and mixtures thereof.

Disintegrants may be used in the compositions provided for herein to provide tablets that disintegrate when exposed to an aqueous environment. Too much of a disintegrant may produce tablets, which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactants that can be used to form pharmaceutical compositions and dosage forms include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic and have greater solubility in oils, while surfactants with higher HLB values are more hydrophilic and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof, carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof, polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-1Ooleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In some embodiments, the composition may include a solubilizer to ensure good solubilization and/or dissolution of the compound(s) and to minimize precipitation of the compound(s). This can be used, for example, for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, S-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject or a subject in need thereof using conventional techniques, such as distillation or evaporation. Thus, if present, the solubilizer can be in a weight ratio of 10%, 25%, 50%), 100%, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used.

When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, pharmaceutical composition for injection are provided containing a compound and a pharmaceutical excipient suitable for injection. Components and amounts of agents in the compositions are as described herein.

The forms in which the compositions may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound(s) in an amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques, which yield a powder of the active ingredient plus any additional desired ingredient from a previously sterile-filtered solution thereof.

Pharmaceutical Compositions for Topical (e.g. Transdermal) Delivery.

In some embodiments, pharmaceutical compositions for transdermal delivery are provided containing a compound(s) and a pharmaceutical excipient suitable for transdermal delivery.

Compositions can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods employs transdermal delivery devices ("patches"). Such transdermal patches may be used to provide continuous or discontinuous infusion of a compound in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure-breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins, 2000; Martindale, The Extra Pharmacopoeia, Thirty-Second Edition (The Pharmaceutical Press, London, 1999); all of which are incorporated by reference herein in their entirety.

Administration of the compounds or pharmaceutical compositions can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound is administered in a single dose.

Typically, such administration can be by injection, e.g., intravenous injection, in order to introduce the agent quickly. However, other routes, such as oral, may be used as appropriate. A single dose of a compound may also be used for treatment of an acute condition.

In some embodiments, a compound is administered in multiple doses. Dosing may be about once, twice, three times, four times, five times, six times, or more than six times per day. Dosing may be about once a month, once every two weeks, once a week, or once every other day. In some embodiments a compound and another agent are administered together about once per day to about 6 times per day. In some embodiments, the administration of a compound and an agent continues for less than about 7 days. In yet another embodiment, the administration continues for more than about 6, 10, 14, 28 days, two months, six months, or one year. In some cases, continuous dosing is achieved and maintained as long as necessary.

Administration of the compounds may continue as long as necessary. In some embodiments, a compound is administered for more than 1, 2, 3, 4, 5, 6, 7, 14, or 28 days. In some embodiments, a compound is administered for less than 28, 14, 7, 6, 5, 4, 3, 2, or 1 day. In some embodiments, a compound is administered chronically on an ongoing basis, e.g., for the treatment of chronic effects.

A compound may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds may slow or inhibit the migration and proliferation of smooth muscle cells in the arterial wall, which contribute to restenosis. A compound may be administered, for example, by local delivery from the struts of a stent, from a stent graft, from grafts, or from the cover or sheath of a stent. In some embodiments, a compound is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound in a suitable solvent, followed by evaporation of the solvent. Excess drug on the surface of the stent may be removed via an additional brief solvent wash. In yet other embodiments, compounds may be covalently linked to a stent or graft. A covalent linker may be used which degrades in vivo, leading to the release of the compound. Any bio-labile linkage may be used for such a purpose, such as ester, amide or anhydride linkages. Compounds may additionally be administered intravascularly from a balloon used during angioplasty. Extravascular administration of the compounds via the pericardial or via adventitial application of formulations may also be performed to decrease restenosis.

A variety of stent devices, which may be used as described are disclosed, for example, in the following references, all of which are hereby incorporated by reference:

U.S. Pat. Nos. 5,451,233; 5,040,548; 5,061,273; 5,496,346; 5,292,331; 5,674,278; 3,657,744; 4,739,762; 5,195,984; 5,292,331; 5,674,278; 5,879,382; 6,344,053.

The compounds may be administered in dosages. It is known in the art that due to intersubject variability in compound pharmacokinetics, individualization of dosing regimen is necessary for optimal therapy. Dosing for a compound may be found by routine experimentation in light of the instant disclosure.

When a compound is administered in a composition that comprises one or more agents, which has a shorter half-life than the compound unit dose forms of the agent and the compound may be adjusted accordingly.

The subject pharmaceutical composition may, for example, be in a form suitable for oral administration as a tablet, capsule, pill, powder, sustained release formulations, solution, and suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition can include a conventional pharmaceutical carrier or excipient and a compound as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

In some embodiments, the method comprises administering to a subject or a subject in need thereof an amount, such as a therapeutically effective amount, of a compound, or a pharmaceutically acceptable salt or solvate thereof. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half-maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half-maximal (50%) inhibitory concentration (IC) of a substance (50% IC, or IC50). EC50 refers to the plasma concentration required for obtaining 50%> of a maximum effect in vivo.

In some embodiments, the subject methods utilize a CDK inhibitor with an IC50 value of about or less than a predetermined value, as ascertained in an in vitro assay. In some embodiments, the CDK inhibitor inhibits CDK with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 μM or less, 1.1 μM or less, 1.2 μM or less, 1.3 μM or less, 1.4 μM or less, 1.5 μM or less, 1.6 μM or less, 1.7 μM or less, 1.8 μM or less, 1.9 μM or less, 2 μM or less, 5 μM or less, 10 μM or less, 15 μM or less, 20 μM or less, 25 μM or less, 30 μM or less, 40 μM or less, 50 μM, 60 μM, 70 μM, 80 μM, 90 μM, 100 μM, 200 μM, 300 μM, 400 μM, or 500 μM, or less, (or a number in the range defined by and including any two numbers above). In some embodiments, the CDK enzyme is CDK9.

In some embodiments, the subject method of inhibiting CDK enzyme comprises contacting the CDK enzyme with an effective amount of a compound or a pharmaceutically acceptable salt thereof as described herein. In some embodiments, the CDK enzyme is CDK9.

In some embodiments, the CDK inhibitor selectively inhibits CDK with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other CDKs. In some embodiments, the CDK inhibitor is a CDK9 inhibitor.

In some embodiments, the CDK inhibitor selectively inhibits CDK with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 μM, 1.1 μM, 1.2 μM, 1.3 μM, 1.4 μM, 1.5 μM, 1.6 μM, 1.7 μM, 1.8 μM, 1.9 μM, 2 μM, 5 μM, 10 μM, 15 μM, 20 μM, 25 μM, 30 μM, 40 μM, 50 μM, 60 μM, 70 μM, 80 μM, 90 μM, 100 μM, 200 μM, 300 μM, 400 μM, or 500 μM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other CDKs. In some embodiments, the CDK inhibitor is a CDK9 inhibitor.

In some embodiments, compounds described herein are in use for inhibiting a CDK enzyme in a subject, wherein the use comprises administering to the subject an effective amount of one or more compounds as described herein, pharmaceutically acceptable salts, solvates, pharmaceutical compositions, or prodrugs thereof.

In some embodiments, are provided pharmaceutical compositions as described herein are in use for inhibiting a CDK enzyme in a subject, wherein the use comprises administering to the subject an effective amount of one or more pharmaceutical compositions as described In some embodiments, are provided uses of compounds as described herein in the manufacture of a formulation inhibiting a CDK enzyme in a subject, wherein the use comprises administering to the subject an effective amount of one or more compounds as described herein, pharmaceutically acceptable salts, solvates, pharmaceutical compositions, or prodrugs thereof.

In some embodiments, are provided uses of a pharmaceutical composition as described herein for inhibiting a CDK enzyme in a subject, wherein the use comprises administering to the subject an effective amount of one or more pharmaceutical compositions as described herein. In some embodiments, the CDK enzyme is CDK9.

The subject methods are useful for treating a disease or disorder condition associated with CDK. Any disease or disorder condition that results directly or indirectly from an abnormal activity or expression level of CDK can be an intended disease or disorder condition. In some embodiments, the said method for treating disease or disorder condition associated with CDK in a subject or a subject in need thereof comprises administering to the subject, a compound or a pharmaceutically acceptable salt thereof as described herein.

Different disease or disorder conditions associated with CDK have been reported. CDK has been implicated, for example, auto-immune diseases, neurodegeneration (such as Parkinson's disease, Alzheimer's disease and ischaemia), inflammatory diseases, viral infections and cancer such as, for example, colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, *Glomus* tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene on Chromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer. In some embodiments, the said method comprises administering to a subject or a subject in need thereof, a compound or a pharmaceutically acceptable salt thereof as described herein.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MN), myelodysplastic syndrome (MDS) or epidermoid cancer.

In some embodiments, are provided Compounds as described herein in use for treating a disease or disorder associated with aberrant CDK activity in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided pharmaceutical compositions as described herein in use for treating a disease or disorder associated with aberrant CDK activity in a subject or a subject in need thereof, wherein the use comprises administering to the subject an effective amount of one or more pharmaceutical compositions as described herein.

In some embodiments, are provided uses of compounds as described herein in the manufacture of a formulation treating a disease or disorder associated with aberrant CDK activity in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, use of pharmaceutical compositions as described herein for treating a disease or disorder associated with aberrant CDK activity in a subject or a subject in need thereof, wherein the use comprises administering to the subject an effective amount of one or more pharmaceutical composition as described herein. In some embodiments, the disease or disorder associated with aberrant CDK activity is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

In some embodiments, are provided compounds as described herein in use for treating cancer in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided pharmaceutical compositions as described herein in use for treating cancer in a subject or a subject in need thereof, wherein the use comprises administering to the subject an effective amount of one or more pharmaceutical compositions as described herein.

In some embodiments, are provided uses of compounds as described herein in the manufacture of a formulation treating cancer in a subject or a subject in need thereof, wherein the use comprises administering to the subject an effective amount of one or more compounds as described herein, pharmaceutically acceptable salts, solvates, pharmaceutical compositions, or prodrugs thereof.

In some embodiments, are provided uses of pharmaceutical compositions as described herein for treating cancer in a subject or a subject in need thereof, wherein the use comprises administering to the subject an effective amount of one or more pharmaceutical compositions as described herein.

In some embodiments, the cancer is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising thereof, can be administered to treat any of the described diseases, alone or in combination with one or more other agents.

In other methods, the compounds of the disclosure, as well as pharmaceutical compositions comprising thereof, can be administered in combination with agonists of nuclear receptors agents.

In other methods, the compounds of the disclosure, as well as pharmaceutical compositions comprising thereof, can be administered in combination with antagonists of nuclear receptors agents.

In other methods, the compounds of the disclosure, as well as pharmaceutical compositions comprising thereof, can be administered in combination with an anti-proliferative agent.

Combination Therapies

For treating cancer and other proliferative diseases, the compounds can be used in combination with chemotherapeutic agents, agonists or antagonists of nuclear receptors, or other anti-proliferative agents. The compounds can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), 5 BCL2 inhibitors (e.g. venetoclax), dual BCL2 family inhibitors (e.g. BCL2/BCLxL), PARP inhibitors, FLT3 inhibitors, orLSDI inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the compound can be administered in combination with a corticosteroid such as triamcinolone, dexamethasone, fluocinolone, cortisone, prednisolone, or flumetholone.

For treating autoimmune or inflammatory conditions, the compound can be administered in combination with an immune suppressant such as fluocinolone acetonide (Retisert®), rimexolone (AL-2178, Vexol, Alcon), or cyclosporine (Restasis®).

In some embodiments, the compounds are used in methods of prevention (prevent or preventing) or prophalyxis of the diseases, disorders, or conditions provided herein. In some embodiments, the compounds are used to prevent the recurrence of a condition or disease provided herein.

The present disclosure also provides the following non-limiting embodiments:

1. A compound having Formula (I) or Formula (II), or a pharmaceutically acceptable salt or solvate thereof:

Formula (I)

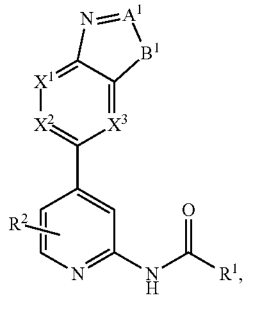

or

-continued

Formula (II)

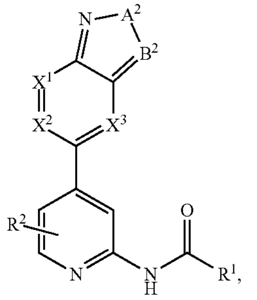

wherein $X^1$, $X^2$, and $X^3$ are each independently N or $CR^3$;

$A^1$ is N or C—$R^4$; $B^1$ is C—$R^6R^7$, N—$R^5$, O, or S;

$A^2$ is N—$R^8$, S, or O;

$B^2$ is C—$R^9$ or N;

$R^1$ is selected from $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 5-14 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, and (4-14 membered heterocycloalkyl)-$C_{1-4}$ alkyl;

wherein $R^1$ is optionally substituted with 1, 2, 3, 4, 5, 6, 7 or 8 independently selected $R^b$ substituents;

$R^2$, $R^3$, $R^4$, $R^5$, $R^6$, $R^7$, $R^8$ and $R^9$ are each independently selected from H, D, halo, oxo, $C_{1-6}$ alkyl, $C_{1-6}$ alkoxy, $C_{2-6}$ alkenyl, $C_{2-6}$ alkynyl, $C_{1-6}$ haloalkyl, $C_{1-6}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-14 membered heteroaryl)-$C_{1-4}$ alkyl, (4-14 membered heterocycloalkyl)-$C_{1-4}$ alkyl, CN, $NO_2$, $OR^{a1}$, $SR^{a1}$, $NHOR^{a1}$, $C(O)R^{a1}$, $C(O)NR^{a1}R^{a1}$, $C(O)OR^{a1}$, $OC(O)R^{a1}$, $OC(O)NR^{a1}R^{a1}$, $NHR^{a1}$, $NR^{a1}R^{a1}$, $NR^{a1}C(O)R^{a1}$, $NR^{a1}C(O)OR^{a1}$, $NR^{a1}C(O)NR^{a1}R^{a1}$, $C(=NR^{a1})R^{a1}$, $C(=NR^{a1})NR^{a1}R^{a1}$, $NR^{a1}C(=NR^{a1})NR^{a1}R^{a1}$, $NR^{a1}C(=NOH)NR^{a1}R^{a1}$, $NR^{a1}C(=NCN)NR^{a1}R^{a1}$, $NR^{a1}S(O)R^{a1}$, $NR^{a1}S(O)_2R^{a1}$, $NR^{a1}S(O)_2NR^{a1}R^{a1}$, $S(O)R^{a1}$, $S(O)NR^{a1}R^{a1}$, $S(O)_2R^{a1}$, $SF_5$, $P(O)R^{a1}R^{a1}$, $P(O)(OR^{a1})(OR^{a1})$, $B(OR^{a1})_2$ and $S(O)_2NR^{a1}R^{a1}$.

wherein when $R^2$, $R^3$, $R^4$, $R^5$, $R^6$, $R^7$, $R^8$ or $R^9$ is $C_{1-6}$ alkyl, $C_{1-6}$ alkoxy, $C_{2-6}$alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$alkyl, (5-14 membered heteroaryl)-$C_{1-4}$ alkyl, or (4-14 membered heterocycloalkyl)-$C_{1-4}$ alkyl, then $R^2$, $R^3$, $R^4$, $R^5$, $R^6$, $R^7$, $R^8$ or $R^9$ is optionally substituted with 1, 2, 3, 4 or 5 independently selected $R^b$ substituents;

or $R^4$ and $R^5$, together with the atoms to which they are attached, form a 5-, 6-, or 7-membered heterocycloalkyl ring optionally substituted with 1, 2, 3, 4 or 5 independently selected $R^b$ substituents;

or $R^6$ and $R^7$ together with the carbon atom to which they are both attached, form a $C_3$-$C_7$ spirocyclic ring;

or $R^8$ and $R^9$, together with the atoms to which they are attached, form a 5-, 6-, or 7-membered heterocycloalkyl ring optionally substituted with 1, 2, 3, 4 or 5 independently selected $R^b$ substituents;

each $R^{a1}$ is independently selected from H, D, $C_{1-6}$ alkyl, $C_{1-4}$haloalkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$alkyl, $C_{3-10}$ cycloalkyl-$C_{1-4}$ alkyl, (5-10 membered heteroaryl)-$C_{1-4}$ alkyl, and (4-14 membered heterocycloalkyl)-$C_{1-4}$ alkyl;

wherein when $R^{a1}$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^{a1}$ is optionally substituted with 1, 2, 3, 4, or 5 independently selected $R^d$ substituents;

each $R^b$ substituent is independently selected from D, halo, oxo, $C_{1-4}$ alkyl, $C_{1-6}$ alkoxy, $C_{1-4}$ haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, (4-14 membered heterocycloalkyl)-$C_{1-4}$ alkyl, CN, OH, $NH_2$, $NO_2$, $NHOR^c$, $OR^c$, $SR^c$, $C(O)R^c$, $C(O)NR^cR^c$, $C(O)OR^c$, $OC(O)R^c$, $OC(O)NR^cR^c$, $C(=NR^c)NR^cR^c$, $NR^cC(=NR^c)NR^cR^c$, $NR^cC(=NOH)NR^cR^c$, $NR^cC(=NCN)NR^cR^c$, $SF_5$, $P(O)R^cR^c$, $P(O)(OR^c)(OR^c)$, $NHR^c$, $NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, $NR^cS(O)_2NR^cR^c$, $S(O)R^c$, $S(O)NR^cR^c$, $S(O)_2R^c$ or $S(O)_2NR^cR^c$;

wherein when $R^b$ is $C_{1-4}$ alkyl, $C_{1-6}$ alkoxy, $C_{1-4}$haloalkyl, $C_{1-4}$ haloalkoxy, $C_{6-10}$ aryl, $C_{3-10}$ cycloalkyl, 5-10 membered heteroaryl, 4-14 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-14 membered heterocycloalkyl)-$C_{1-4}$ alkyl, then $R^b$ is optionally substituted with 1, 2, or 3 independently selected $R^d$ substituents;

each $R^c$ is independently selected from H, D, —OH, $C_{1-6}$ alkyl, $C_{1-6}$ alkoxy, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl;

wherein when $R^c$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^c$ is optionally substituted with 1, 2, 3, 4, or 5 independently selected $R^f$ substituents;

each $R^f$ is independently selected from halogen, $C_{1-4}$ alkyl, $C_{1-4}$ haloalkyl, $C_{2-6}$ alkenyl, $C_{2-6}$ alkynyl, $C_{6-10}$ aryl, $C_3$-10 cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^g$, $OR^g$, $SR^g$, $C(O)R^g$, $C(O)NR^gR^g$, $C(O)OR^g$, $OC(O)R^g$, $OC(O)NR^gR^g$, $NHR^g$, $NR^gR^g$, $NR^gC(O)R^g$, $NR^gC(O)NR^gR^g$, $NR^gC(O)OR^g$, $C(=NR^g)NR^gR^g$, $NR^gC(=NR^g)NR^gR^g$, $NR^gC(=NOH)NR^gR^g$, $NR^gC(=NCN)NR^gR^g$, $SF_5$, $P(O)R^gR^g$, $P(O)(OR^g)(OR^g)$, $S(O)R^g$, $S(O)NR^gR^g$, $S(O)_2R^g$, $NR^gS(O)_2R^g$, $NR^gS(O)_2NR^gR^g$, and $S(O)_2NR^gR^g$;

wherein when $R^f$ is $C_{1-4}$alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, then $R^f$ is optionally substituted with 1, 2, 3, 4, or 5 independently selected $R^n$ substituents;

each $R^n$ is independently selected from $C_{1-4}$ alkyl, $C_{1-4}$ haloalkyl, halo, CN, $R^o$, $NHOR^o$, $OR^o$, $SR^o$, $C(O)R^o$, $C(O)NR^oR^o$, $C(O)OR^o$, $OC(O)R^o$, $OC(O)NR^oR^o$, $NHR^o$, $NR^oR^o$, $NR^oC(O)R^o$, $NR^oC(O)NR^oR^o$, $NR^oC(O)OR^o$, $C(=NR^o)NR^oR^o$, $NR^oC(=NR^o)NR^oR^o$, $NR^oC(=NOH)NR^oR^o$, $NR^oC(=NCN)NR^oR^o$, $SF_5$, $P(O)R^oR^o$, $P(O)(OR^o)(OR^o)$, $S(O)R^o$, $S(O)NR^oR^o$, $S(O)_2R^o$, $NR^oS(O)_2R^o$, $NR^oS(O)_2NR^oR^o$, and $S(O)_2NR^oR^o$;

each $R^d$ is independently selected from D, oxo, $C_{1-6}$ alkyl, $C_{1-6}$ haloalkyl, halo, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, CN, $NH_2$, $NHOR^e$, $OR^e$, $SR^e$, $C(O)R^e$, $C(O)NR^eR^e$, $C(O)OR^e$, $OC(O)R^e$, $OC(O)NR^eR^e$, $NHR^e$, $NR^eR^e$, $NR^eC(O)R^e$, $NR^e(C(O)NR^eR^e$, $NR^eC(O)OR^e$, $C(=NR^e)NR^eR^e$, $NR^eC(=NR^e)NR^eR^e$, $NR^eC(=NOH)NR^eR^e$, $NR^eC(=NCN)NR^eR^e$, $SF_5$, $P(O)R^eR^e$, $P(O)(OR^e)(OR^e)$, $S(O)R^e$, $S(O)NR^eR^e$, $S(O)_2R^e$, $NR^eS(O)_2R^e$, $NR^eS(O)_2NR^eR^e$, and $S(O)_2NR^eR^e$, wherein when $R^d$ is $C_{1-6}$alkyl, $C_{3-10}$ cycloalkyl, $C_{6-10}$ aryl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, or (4-10 membered heterocycloalkyl)-$C_{1-4}$ alkyl, then $R^d$ is optionally substituted with 1, 2, or 3 independently selected $R^f$ substituents;

each $R^e$ is independently selected from H, D, CN, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^e$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^e$ is optionally substituted with 1, 2 or 3 independently selected $R^g$ substituents;

each $R^g$ is independently selected from H, D, $C_{1-6}$ alkyl, $C_{1-4}$ haloalkyl, $C_{2-6}$alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$alkyl, (5-10 membered heteroaryl)-$C_{1-4}$ alkyl, and (4-10 membered heterocycloalkyl)-$C_{1-4}$ alkyl, wherein when $R^g$ is $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl, then $R^g$ is optionally substituted with 1, 2 or 3 independently selected $R^p$ substituents;

each $R^p$ is independently selected from $C_{1-4}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl, and (4-10 membered heterocycloalkyl)-$C_{1-4}$ alkyl, halo, CN, $NHOR^r$, $OR^r$, $SR^r$, $C(O)R^r$, $C(O)NR^rR^r$, $C(O)OR^r$, $OC(O)R^r$, $OC(O)NR^rR^r$, $NHR^r$, $NR^r$, $NR^rC(O)R^r$, $NR^rC(O)NR^r$, $NR^rC(O)OR^r$, $C(=NR^r)NR^rR^r$, $NR^rC(=NR^r)NR^r$, $NR^rC(=NOH)NR^rR^r$ $NR^rC(=NCN)NR^rR^r$, $SF_5$, $P(O)R^rR^r$, $P(O)(OR^r)(OR^r)$, $S(O)R^r$, $S(O)NR^rR^r$, $S(O)_2R^r$, $NR^rS(O)_2R^r$, $NR^rS(O)_2NR^rR^r$, and $S(O)_2NR^rR^r$;

each $R^o$ or $R^r$ is independently selected from H, D, $C_{1-4}$ alkyl, $C_{3-6}$cycloalkyl, $C_{6-10}$ aryl, 5 or 6-membered heteroaryl, $C_{1-4}$ haloalkyl, $C_{2-4}$alkenyl, and $C_{2-4}$ alkynyl, wherein when $R^o$ or $R^r$ is $C_{1-4}$ alkyl, $C_{3-6}$ cycloalkyl, $C_{6-10}$ aryl, 5 or 6-membered heteroaryl, $C_{2-4}$ alkenyl, and $C_{2-4}$ alkynyl, then $R^o$ or $R^r$ is optionally substituted with 1, 2 or 3 independently selected $R^q$ substituents;

each $R^q$ is independently selected from D, OH, CN, —COOH, $NH_2$, halo, $C_{1-6}$alkyl, $C_{1-6}$ haloalkyl, $C_{1-6}$ alkoxy, $C_{1-6}$ haloalkoxy, $C_{1-4}$ alkylthio, phenyl, 5-6 membered heteroaryl, $C_{3-6}$ cycloalkyl, 4-6 membered heterocycloalkyl, $—CONHR^{12}$, $—NHC(O)R^{12}$, $—OC(O)R^{12}$, $—C(O)OR^{12}$, $—C(O)R^{12}$, $—SO_2R^{12}$, $—NHSO_2R^{12}$, $—SO_2NHR^{12}$ and $NR^{12}R^{12}$, wherein when $R^q$ is $C_{1-6}$ alkyl, phenyl, 4-6 membered heterocycloalkyl or 5-6 membered heteroaryl, then $R^q$ is optionally substituted with OH, CN, —COOH, $NH_2$, $C_{1-6}$ alkoxy, $C_{3-6}$cycloalkyl or 4-6 membered heterocycloalkyl; and each $R^{12}$ is independently $C_{1-6}$ alkyl.

2. The compound of embodiment 1, wherein the compound has a formula of

Formula (I)

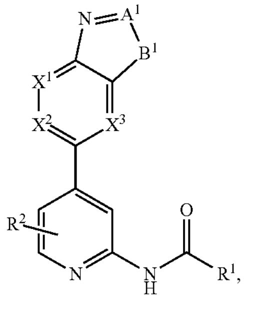

or

Formula (II)

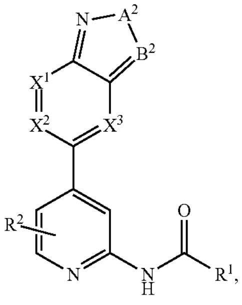

or a pharmaceutically acceptable salt or solvate thereof, wherein:

$X^1$, $X^2$, and $X^3$ are each independently N or $CR^3$;

A is N or C—$R^4$;

$B^1$ is C—$R^6R^7$, N—$R^5$;

$A^2$ is N—$R^8$, S, or O;

$B^2$ is C—$R^9$;

$R_1$ is $C_{3-10}$cycloalkyl or 4-10 membered heterocycloalkyl optionally substituted with 1, 2, 3, 4, 5, 6, 7 or 8 independently selected $R^b$ substituents;

$R^2$ is H, D, OH, halogen, CN, $C_{1-6}$ alkyl, $C_{3-10}$ cycloalkyl, $C_{1-6}$ alkoxyl, $C_{1-6}$ haloalkyl, or 4-14 membered heterocycloalkyl;

$R^3$ is H, D, OH, halogen, CN, $C_{1-6}$ alkyl, $C_{3-10}$ cycloalkyl, $C_{1-6}$ alkoxyl, $C_{1-6}$ haloalkyl, or 4-14 membered heterocycloalkyl;

$R^4$ is H, D, $C_{1-6}$ alkyl, $C_{1-6}$ alkoxy, $C_{3-6}$ cycloalkyl, or 4-6 membered heterocycloalkyl;

$R^5$ is $C_{1-6}$ alkyl, $C_{1-6}$ alkoxy, $C_{3-6}$ cycloalkyl, or 4-6 membered heterocycloalkyl; or $R^4$ and $R^5$, together with the atoms to which they are attached, form a 5-, 6-, or 7-membered heterocycloalkyl ring optionally substituted with 1, 2, 3, 4 or 5 independently selected $R^b$ substituents;

$R^6$ is $C_{1-6}$ alkyl, $C_{1-6}$ alkoxy, $C_{3-6}$ cycloalkyl, or 4-6 membered heterocycloalkyl;

$R^7$ is $C_{1-6}$ alkyl, $C_{1-6}$ alkoxy, $C_{3-6}$ cycloalkyl, or 4-6 membered heterocycloalkyl; or $R^6$ and $R^7$ together with the carbon atom to which they are both attached, form a $C_{4-7}$ spirocyclic ring;

$R^8$ is $C_{1-6}$ alkyl, $C_{1-6}$ alkoxy, $C_{3-6}$ cycloalkyl, or 4-6 membered heterocycloalkyl; and $R^9$ is $C_{1-6}$ alkyl, $C_{1-6}$ alkoxy, $C_{3-6}$ cycloalkyl, or 4-6 membered heterocycloalkyl; or $R^8$ and $R^9$, together with the atoms to which they are attached, form an 5- or 6-membered heterocycloalkyl ring optionally substituted with 1, 2, 3, 4 or 5 independently selected $R^b$ substituents;

$R^b$ is $C_{1-4}$ alkyl, 5-10 membered heteroaryl, 4-14 membered heterocycloalkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^e$, or $NR^cS(O)_2R^c$, $NR^cS(O)_2NR^cR^c$;

each $R^c$ is independently H, OH, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl;

wherein when $R^c$ is $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl, then $R^c$ is optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

3. The compound of embodiment 1, wherein the compound has a formula:

Formula (I)

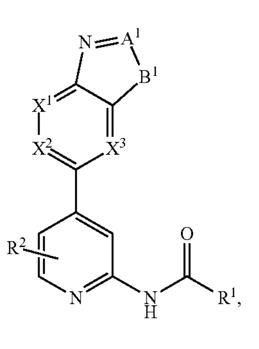

or

-continued

Formula (II)

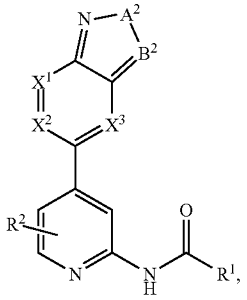

or a pharmaceutically acceptable salt or solvate thereof, wherein:

$X^1$, $X^2$, and $X^3$ are each independently N or $CR^3$;

$A^1$ is N or C—$R^4$;

$B^1$ is C—$R^6R^7$, N—$R^5$;

$A^2$ is N—$R^8$, S, or O;

$B^2$ is C—$R^9$;

$R_1$ is $C_{3-10}$cycloalkyl optionally substituted with 1, 2, 3, 4, 5, 6, 7 or 8 independently selected $R^b$ substituents;

$R^2$ is H, D, OH, halogen, CN, $C_{1-6}$ alkyl, $C_{3-10}$ cycloalkyl, $C_{1-6}$ alkoxyl, or 4-14 membered heterocycloalkyl;

$R^3$ is H, D, OH, halogen, CN, $C_{1-6}$ alkyl, $C_{3-10}$ cycloalkyl, $C_{1-6}$ alkoxyl, or 4-14 membered heterocycloalkyl;

$R^4$ is H, D, $C_{1-6}$ alkyl, or $C_{1-6}$ alkoxy;

$R^5$ is $C_{1-6}$ alkyl or $C_{1-6}$ alkoxy;

or $R^4$ and $R^5$, together with the atoms to which they are attached, form an 5-, 6-, or 7-membered heterocycloalkyl ring optionally substituted with 1, 2, 3, 4 or 5 independently selected $R^b$ substituents;

$R^6$ is $C_{1-6}$ alkyl;

$R^7$ is $C_{1-6}$ alkyl;

or $R^6$ and $R^7$ together with the carbon atom to which they are both attached, form a $C_{4-7}$ spirocyclic ring;

$R^8$ is $C_{1-6}$ alkyl; and $R^9$ is $C_{1-6}$ alkyl;

or $R^8$ and $R^9$, together with the atoms to which they are attached, form an 5-, 6-, or 7-membered heterocycloalkyl ring optionally substituted with 1, 2, 3, 4 or 5 independently selected $R^b$ substituents;

$R^b$ is $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, or $NR^cS(O)_2NR^cR^c$;

each $R^c$ is independently H, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl;

wherein when $R^c$ is $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl, then $R^c$ is optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

4. The compound of embodiments 1-3, or a pharmaceutically acceptable salt or solvate thereof, wherein $X^1$ is N.

5. The compound of any one of the preceding embodiments, or a pharmaceutically acceptable salt or solvate thereof, wherein $X^2$ is N.

6. The compound of any one of the preceding embodiments, or a pharmaceutically acceptable salt or solvate thereof, wherein $X^3$ is N.

7. The compound of any one of the preceding embodiments, or a pharmaceutically acceptable salt or solvate thereof, wherein $X^1$ is $CR^3$.

8. The compound of any one of the preceding embodiments, or a pharmaceutically acceptable salt or solvate thereof, wherein $X^2$ is $CR^3$.

9. The compound of any one of the preceding embodiments, or a pharmaceutically acceptable salt or solvate thereof, wherein $X^3$ is $CR^3$.

10. The compound of any one of the preceding embodiments, or a pharmaceutically acceptable salt or solvate thereof, wherein $R^1$ is $C_{3-10}$ cycloalkyl optionally substituted with 1, 2, 3, or 4 independently selected $R^b$ substituents.

11. The compound according to embodiment 10, or a pharmaceutically acceptable salt or solvate thereof, wherein $R^1$ is $C_{3-7}$ cycloalkyl optionally substituted with 1, 2, 3, or 4 independently selected $R^b$ substituents.

12. The compound according to embodiment 11, or a pharmaceutically acceptable salt or solvate thereof, wherein $R^1$ is $C_{5-6}$ cycloalkyl optionally substituted with 1 $R^b$ substituent.

13. The compound according to embodiment 12, or a pharmaceutically acceptable salt or solvate thereof, wherein the $C_{5-6}$cycloalkyl is cyclopentanyl or cyclohexanyl.

14. The compound according to any one of embodiments 10-13, or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$.

15. The compound according to embodiment 14, or a pharmaceutically acceptable salt or solvate thereof, wherein the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; wherein when $R^c$ is $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl, then $R^c$ is optionally substituted with 1, 2, 3, 4, or 5 independently selected $R^f$ substituents.

16. The compound according to embodiment 15, or a pharmaceutically acceptable salt or solvate thereof, wherein the $R^f$ substituents are independently halogen, CN or $OR^g$.

17. The compound according to embodiment 16, or a pharmaceutically acceptable salt or solvate thereof, wherein the $R^g$ is independently H or $C_{1-6}$ alkyl.

18. The compound according to any one of embodiments 10-13, or a pharmaceutically acceptable salt or solvate thereof, wherein the 1 $R^b$ substituent on $R^1$ acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

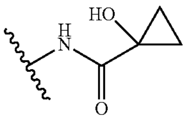

, 2-(thiazol-4-yl)acetamido,

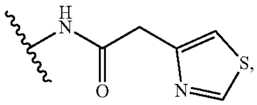 [SMILES: *NC(=O)Cc1cscn1]

, methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido, i.e.,

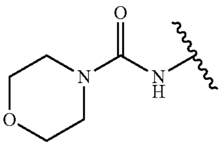

, or 4-methylpiperazine-1-carboxamide, i.e.,

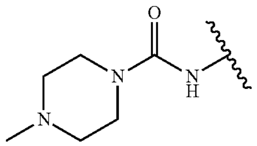

.

19. The compound according to any one of the preceding embodiments, or a pharmaceutically acceptable salt or solvate thereof, wherein $R^2$ is H, halogen (preferably $C_1$), or $C_{1-6}$ alkyl (preferably $CH_3$).

20. The compound according to any one of the preceding embodiments, or a pharmaceutically acceptable salt or solvate thereof, wherein $R^2$ is $C_{1-6}$ alkyl, preferably $CH_3$ or $CH_2CH_3$.

21. The compound according to any one of the preceding embodiments, or a pharmaceutically acceptable salt or solvate thereof, wherein $R^3$ is H or halogen, preferably F.

22. The compound according to any one of the preceding embodiments, or a pharmaceutically acceptable salt or solvate thereof, wherein said compound is a compound of Formula (I):

Formula (I)

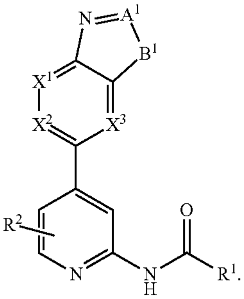

.

23. The compound of embodiment 22, or a pharmaceutically acceptable salt or solvate thereof, wherein $A^1$ is N.

24. The compound of embodiment 22, or a pharmaceutically acceptable salt or solvate thereof, wherein $A^1$ is C—$R^4$.

25. The compound of any one of embodiments 22-24, or a pharmaceutically acceptable salt or solvate thereof, wherein $B^1$ is C—$R^6R^7$.

26. The compound of any one of embodiments 22-24, or a pharmaceutically acceptable salt or solvate thereof, wherein $B^1$ is N—$R^5$.

27. The compound of any one of embodiments 22-24, or a pharmaceutically acceptable salt or solvate thereof, wherein $B^1$ is O.

28. The compound of any one of embodiments 22-24, or a pharmaceutically acceptable salt or solvate thereof, wherein $B^1$ is S.

29. The compound according to any one of embodiments 24-28, or a pharmaceutically acceptable salt or solvate thereof, wherein $R^4$ is H.

30. The compound according to any one of embodiments 24-28, or a pharmaceutically acceptable salt or solvate thereof, wherein $R^4$ is $C_{1-6}$alkyl, preferably $CH_3$.

31. The compound according to embodiment 26, or a pharmaceutically acceptable salt or solvate thereof, wherein $R^5$ is $C_{1-6}$alkyl, preferably $CH(CH_3)_2$.

32. The compound according to any one of embodiments 24 or 26, or a pharmaceutically acceptable salt or solvate thereof, wherein $R^4$ and $R^5$, together with the atoms to which they are attached, form a 5- or 6-membered heterocycloalkyl ring optionally substituted with 1, 2, 3, 4 or 5 independently selected $R^b$ substituents.

33. The compound according to embodiment 32, or a pharmaceutically acceptable salt or solvate thereof, wherein $R^4$ and $R^5$, together with the atoms to which they are attached, form an optionally substituted 5-membered heterocycloalkyl ring optionally substituted with 1 or 2 $R^b$ substituents.

34. The compound according to embodiment 33, or a pharmaceutically acceptable salt or solvate thereof, wherein the 1 or 2 $R^b$ substituents are ($C_4$ alkyl, preferably (C-b.

35. The compound of embodiment 25, or a pharmaceutically acceptable salt or solvate thereof, wherein $R^6$ is $C_{1-6}$ alkyl, preferably $CH_3$; and $R^7$ is $C_{1-6}$ alkyl, preferably $CH_3$.

36. The compound of embodiment 25, or a pharmaceutically acceptable salt or solvate thereof, wherein $R^6$ and $R^7$ together with the carbon atom to which they are both attached, form a $C_4$-$C_7$ spirocyclic ring.

37. The compound of embodiment 36, or a pharmaceutically acceptable salt or solvate thereof, wherein the $C_4$-$C_7$ spirocyclic ring is a spirocyclopentane ring.

38. The compound according to any one of embodiments 1-21, or a pharmaceutically acceptable salt or solvate thereof, wherein said compound is a compound of Formula (II):

Formula (II)

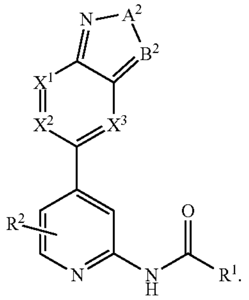

39. The compound of embodiment 38, or a pharmaceutically acceptable salt or solvate thereof, wherein $A^2$ is N—$R^8$.

40. The compound of embodiment 38, or a pharmaceutically acceptable salt or solvate thereof, wherein $A^2$ is S.

41. The compound of embodiment 38, or a pharmaceutically acceptable salt or solvate thereof, wherein $A^2$ is O.

42. The compound of any one of embodiments 38-41, or a pharmaceutically acceptable salt or solvate thereof, wherein $B^2$ is C—$R^9$.

43. The compound of any one of embodiments 38-41, or a pharmaceutically acceptable salt or solvate thereof, wherein $B^2$ is N.

44. The compound according to embodiment 39, or a pharmaceutically acceptable salt or solvate thereof, wherein $R^8$ is $C_{1-6}$alkyl, preferably $CH_3$.

45. The compound according to embodiment 42, or a pharmaceutically acceptable salt or solvate thereof, wherein $R^9$ is $C_{1-6}$alkyl, preferably $CH(CH_3)_2$.

46. The compound according to any one of embodiments 39 or 42, or a pharmaceutically acceptable salt or solvate thereof, wherein $R^8$ and $R^9$, together with the atoms to which they are attached, form a 5- or 6-membered heterocycloalkyl ring optionally substituted with 1, 2, 3, 4 or 5 independently selected $R^b$ substituents.

47. The compound according to embodiment 46, or a pharmaceutically acceptable salt or solvate thereof, wherein $R^8$ and $R^9$, together with the atoms to which they are attached, form a 5-membered heterocycloalkyl ring optionally substituted with 1 or 2 $R^b$ substituents.

48. The compound according to embodiment 47, or a pharmaceutically acceptable salt or solvate thereof, wherein the 1 or 2 $R^b$ substituents are $C_{1-4}$ alkyl, preferably $CH_3$.

49. The compound of embodiment 1, wherein the compound has a formula of

Formula (III)

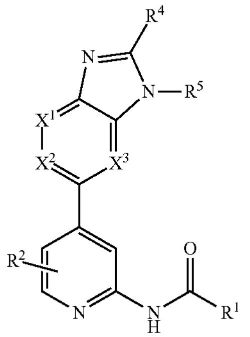

or

Formula (IV)

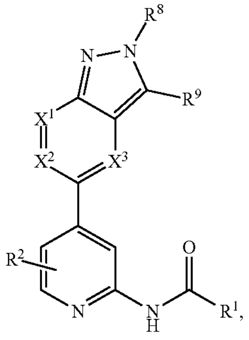

or a pharmaceutically acceptable salt or solvate thereof, wherein the variables are as defined in embodiment 1.

50. The compound of embodiment 49, or a pharmaceutically acceptable salt or solvate thereof, wherein the compound has the formula of Formula (III) and wherein $X^1$ is N, $X^2$ is $CR^3$, and $X^3$ is $CR^3$.

51. The compound of embodiment 49, or a pharmaceutically acceptable salt or solvate thereof, wherein the compound has the formula of Formula (III) and wherein $X^1$ is $CR^3$, $X^2$ is N, and $X^3$ is $CR^3$.

52. The compound of embodiment 49, or a pharmaceutically acceptable salt or solvate thereof, wherein the compound has the formula of Formula (III) and wherein $X^1$ is $CR^3$, $X^2$ is $CR^3$, and $X^3$ is N.

53. The compound of embodiment 49, or a pharmaceutically acceptable salt or solvate thereof, wherein the compound has the formula of Formula (III) and wherein $X^1$ is $CR^3$, $X^2$ is $CR^3$, and $X^3$ is $CR^3$.

54. The compound of embodiment 49, or a pharmaceutically acceptable salt or solvate thereof, wherein the compound has the formula of Formula (IV) and wherein $X^1$ is N, $X^2$ is $CR^3$, and $X^3$ is $CR^3$.

55. The compound of embodiment 49, or a pharmaceutically acceptable salt or solvate thereof, wherein the compound has the formula of Formula (IV) and wherein $X^1$ is $CR^3$, $X^2$ is N, and $X^3$ is $CR^3$.

56. The compound of embodiment 49, or a pharmaceutically acceptable salt or solvate thereof, wherein the compound has the formula of Formula (IV) and wherein $X^1$ is $CR^3$, $X^2$ is $CR^3$, and $X^3$ is N.

57. The compound of embodiment 49, or a pharmaceutically acceptable salt or solvate thereof, wherein the compound has the formula of Formula (IV) and wherein $X^1$ is $CR^3$, $X^2$ is $CR^3$, and $X^3$ is $CR^3$.

58. The compound of any one of embodiments 49-57, or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

59. The compound of any one of embodiments 49-57, or a pharmaceutically acceptable salt or solvate thereof, wherein $R^2$ is halogen or $C_{1-6}$ alkyl.

60. The compound of any one of embodiments 49-57, or a pharmaceutically acceptable salt or solvate thereof, wherein $R^2$ is $C_{1-6}$ alkyl.

61. The compound of any one of embodiments 49-57, or a pharmaceutically acceptable salt or solvate thereof, wherein $R^2$ is chloro or fluoro.

62. The compound of any one of embodiments 49-53 of Formula (III), or a pharmaceutically acceptable salt or solvate thereof, wherein $R^4$ is H or $C_{1-6}$ alkyl; $R^5$ is $C_{1-6}$ alkyl; or $R^4$ and $R^5$, together with the atoms to which they are attached, form an 5- or 6-membered heterocycloalkyl ring optionally substituted with 1, 2, 3, 4 or 5 independently selected $R^b$ substituents, wherein each $R^b$ is, independently $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

63. The compound of any one of embodiments 49-53 of Formula (III), or a pharmaceutically acceptable salt or solvate thereof, wherein $R^4$ is H.

64. The compound of any one of embodiments 49-53 of Formula (III), or a pharmaceutically acceptable salt or solvate thereof, wherein $R^4$ is $C_{1-6}$alkyl, preferably $CH_3$.

65. The compound of any one of embodiments 49-53 of Formula (III), or a pharmaceutically acceptable salt or solvate thereof, wherein $R^5$ is $C_{1-6}$alkyl, preferably $CH(CH_3)_2$.

66. The compound of any one of embodiments 49-53 of Formula (III), or a pharmaceutically acceptable salt or solvate thereof, wherein $R^4$ and $R^5$, together with the atoms to which they are attached, form an a 5- or 6-membered heterocycloalkyl ring optionally substituted with 1, 2, 3, 4 or 5 independently selected $R^b$ substituents.

67. The compound of any one of embodiments 49-53 of Formula (III), or a pharmaceutically acceptable salt or solvate thereof, wherein $R^4$ and $R^5$, together with the atoms to which they are attached, form an optionally substituted 5-membered heterocycloalkyl ring optionally substituted with 1 or 2 $R^b$ substituents.

68. The compound according to embodiment 67, or a pharmaceutically acceptable salt or solvate thereof, wherein the 1 or 2 $R^b$ substituents are $C_{1-4}$ alkyl, preferably $CH_3$.

69. The compound of any one of embodiments 62-68, or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

70. The compound of any one of embodiments 62-68, or a pharmaceutically acceptable salt or solvate thereof, wherein $R^2$ is halogen or $C_{1-6}$ alkyl.

71. The compound any one of embodiments 62-68, or a pharmaceutically acceptable salt or solvate thereof, wherein $R^2$ is $C_{1-6}$ alkyl.

72. The compound any one of embodiments 62-68, or a pharmaceutically acceptable salt or solvate thereof, wherein $R^2$ is chloro or fluoro.

73. The compound of any one of embodiments 49-53 and 58-72, wherein the compound, has a compound of Formula (III), or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents;

wherein each $R^b$ is, independently, $C_{1-4}$ alkyl, $NR^cC(=NR^c)NR^cR^c$, $NR^cC(=NOH)NR^cR^c$, $NR^cC(=NCN)NR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

74. The compound of any one of embodiments 49-53 and 58-72 of Formula (III), or a pharmaceutically acceptable salt or solvate thereof, wherein $R^1$ is $C_{3-10}$ cycloalkyl optionally substituted with 1 $R^b$ substituent.

75. The compound of any one of embodiments 49-53 and 58-72 of Formula (III), or a pharmaceutically acceptable salt or solvate thereof, wherein $R^1$ is $C_{3-7}$ cycloalkyl optionally substituted with 1 $R^b$ substituent.

76. The compound of any one of embodiments 49-53 and 58-72 of Formula (III), or a pharmaceutically acceptable salt or solvate thereof, wherein $R^1$ is $C_{5-6}$ cycloalkyl optionally substituted with 1 $R^b$ substituent.

77. The compound of any one of embodiments 49-53 and 58-72 of Formula (III), or a pharmaceutically acceptable salt or solvate thereof, wherein $R^1$ is cyclopentanyl or cyclohexanyl optionally substituted with 1 $R^b$ substituent.

78. The compound according to any one of embodiments 73, or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$.

79. The compound according to embodiment 78, or a pharmaceutically acceptable salt or solvate thereof, wherein the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents.

80. The compound according to embodiment 79, or a pharmaceutically acceptable salt or solvate thereof, wherein the $R^f$ substituents are independently halogen, CN or $OR^g$.

81. The compound according to embodiment 80, or a pharmaceutically acceptable salt or solvate thereof, wherein the $R^g$ is independently H or $C_{1-6}$ alkyl.

82. The compound according to any one of embodiments 73-77, or a pharmaceutically acceptable salt or solvate thereof, wherein the 1 $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

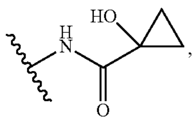 [SMILES: *NC(=O)C1(O)CC1], 2-(thiazol-4-yl)acetamido,

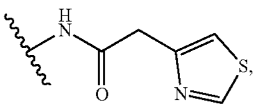 [SMILES: *NC(=O)Cc1cscn1], methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido, i.e.,

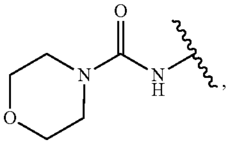 [SMILES: *NC(=O)N1CCOCC1], or 4-methylpiperazine-1-carboxamide, i.e.,

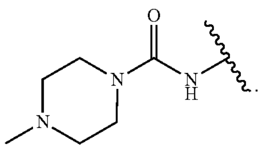 [SMILES: *NC(=O)N1CCN(C)CC1].

83. The compound of any one of embodiments 49 or 54-57 of Formula (IV), or a pharmaceutically acceptable salt or solvate thereof, wherein $R^8$ is $C_{1-6}$ alkyl; and $R^9$ is $C_{1-6}$ alkyl; or $R^8$ and $R^9$, together with the atoms to which they are attached, form an 5- or 6-membered heterocycloalkyl ring optionally substituted with 1, 2, 3, 4 or 5 independently selected $R^b$ substituents; wherein:

each $R^b$ is, independently, $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

84. The compound of any one of embodiments 49, 54-57, and 83 of Formula (IV), or a pharmaceutically acceptable salt or solvate thereof, wherein $R^8$ is $C_{1-6}$alkyl, preferably $CH_3$.

85. The compound of any one of embodiments 49, 54-57, and 83 of Formula (IV), or a pharmaceutically acceptable salt or solvate thereof, wherein $R^9$ is $C_{1-6}$alkyl, preferably $CH(CH_3)_2$.

86. The compound of any one of embodiments 49, 54-57, and 83 of Formula (IV), or a pharmaceutically acceptable salt or solvate thereof, wherein $R^8$ and $R^9$, together with the atoms to which they are attached, form a 5- or 6-membered heterocycloalkyl ring optionally substituted with 1, 2, 3, 4 or 5 independently selected $R^b$ substituents.

87. The compound according to embodiment 86, or a pharmaceutically acceptable salt or solvate thereof, wherein $R^8$ and $R^9$, together with the atoms to which they are attached, form a 5-membered heterocycloalkyl ring optionally substituted with 1 or 2 $R^b$ substituents.

88. The compound according to embodiment 87, or a pharmaceutically acceptable salt or solvate thereof, wherein the 1 or 2 $R^b$ substituents are $C_{1-4}$ alkyl preferably $CH_3$.

89. The compound of any one of embodiments 83-88, or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl or 4-14 membered heterocycloalkyl.

90. The compound of any one of embodiments 83-88, or a pharmaceutically acceptable salt or solvate thereof, wherein $R^2$ is halogen or $C_{1-6}$ alkyl.

91. The compound any one of embodiments 83-88, or a pharmaceutically acceptable salt or solvate thereof, wherein $R^2$ is $C_{1-6}$ alkyl.

92. The compound any one of embodiments 83-88, or a pharmaceutically acceptable salt or solvate thereof, wherein $R^2$ is chloro or fluoro.

93. The compound of any one of embodiments 49, 54-57, and 83-92 of Formula (IV), or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents;

wherein each $R^b$ is, independently, $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

94. The compound of any one of embodiments 49, 54-57, and 83-92 of Formula (IV), or a pharmaceutically acceptable salt or solvate thereof, wherein $R^1$ is $C_{3-10}$ cycloalkyl optionally substituted with 1 $R^b$ substituent.

95. The compound of any one of embodiments 49, 54-57, and 83-92 of Formula (IV), or a pharmaceutically acceptable salt or solvate thereof, wherein $R^1$ is $C_{3-7}$ cycloalkyl optionally substituted with 1 $R^b$ substituent.

96. The compound of any one of embodiments 49, 54-57, and 83-92 of Formula (IV), or a pharmaceutically acceptable salt or solvate thereof, wherein $R^1$ is $C_{5-6}$ cycloalkyl optionally substituted with 1 $R^b$ substituent.

97. The compound of any one of embodiments 49, 54-57, and 83-92 of Formula (IV), or a pharmaceutically acceptable salt or solvate thereof, wherein $R^1$ is cyclopentanyl or cyclohexanyl optionally substituted with 1 $R^b$ substituent.

98. The compound according to any one of embodiments 93-97, or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$.

99. The compound according to embodiment 98, or a pharmaceutically acceptable salt or solvate thereof, wherein the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents.

100. The compound according to embodiment 99, or a pharmaceutically acceptable salt or solvate thereof, wherein the $R^f$ substituents are independently halogen, CN or $OR^g$.

101. The compound according to embodiment 100, or a pharmaceutically acceptable salt or solvate thereof, wherein the $R^g$ is independently H or $C_{1-6}$ alkyl.

102. The compound according to any one of embodiments 93-97, or a pharmaceutically acceptable salt or solvate thereof, wherein the 1 $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

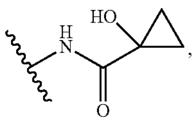 [SMILES: *NC(=O)C1(O)CC1]

, 2-(thiazol-4-yl)acetamido,

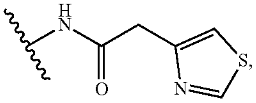 [SMILES: *NC(=O)Cc1cscn1]

, methylsulfonamido (—$NSO_2CH_3$), 3-methylureido (—$NC(O)NHCH_3$), 3-methoxyureido (—$NC(O)NHOCH_3$), 3,3-dimethylureido (—$NC(O)N(CH_3)_2$), or 3-ethylureido (—$NC(O)NHCH_2CH_3$), morpholine-4-carboxamido, i.e.,

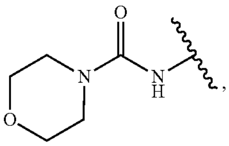 [SMILES: *NC(=O)N1CCOCC1]

, or 4-methylpiperazine-1-carboxamide, i.e.,

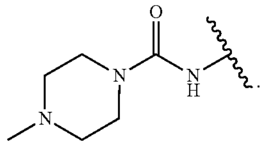 [SMILES: *NC(=O)N1CCN(C)CC1]

.

103. The compound according to any one of embodiments 49-102, or a pharmaceutically acceptable salt or solvate thereof, wherein each $R^3$ is, independently, H, OH, halogen, CN, $C_{1-6}$ alkyl, $C_{3-10}$ cycloalkyl, $C_{1-6}$ alkoxyl, or 4-14 membered heterocycloalkyl.

104. The compound according to any one of embodiments 49-102, or a pharmaceutically acceptable salt or solvate thereof, wherein each $R^3$ is, independently, H or halogen, preferably Cl or F.

105. The compound of according to any one of embodiments 49-102, or a pharmaceutically acceptable salt or solvate thereof, wherein only one of the $R^3$ is OH, halogen, CN, $C_{1-6}$ alkyl, $C_{3-10}$ cycloalkyl, $C_{1-6}$ alkoxyl, or 4-14 membered heterocycloalkyl and the remainder are H.

106. The compound according to any one of embodiments 49-102, or a pharmaceutically acceptable salt or solvate thereof, wherein one of the $R^3$ is halogen, preferably Cl or F, and the remainder are H.

107. The compound of embodiment 1, wherein the compound has a formula of

Formula (V)

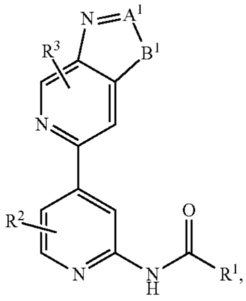

,

Formula (VI)

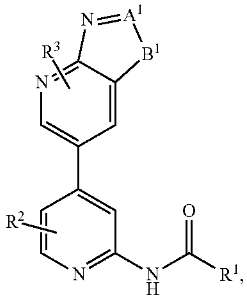

,

Formula (VII)

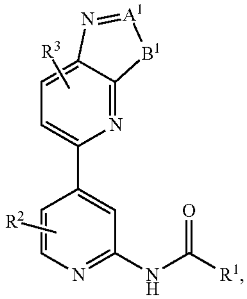

,

-continued

Formula (VIII)

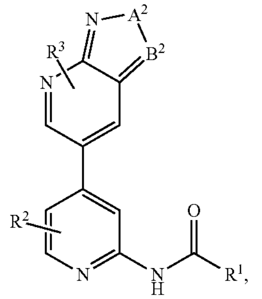

Formula (IX)

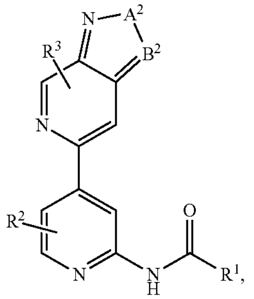

Formula (X)

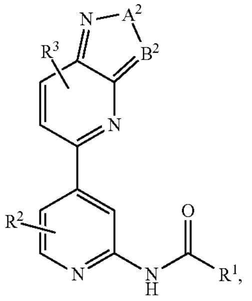

Formula (XI)

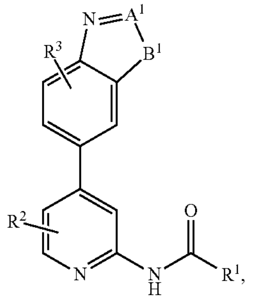

or

Formula (XII)

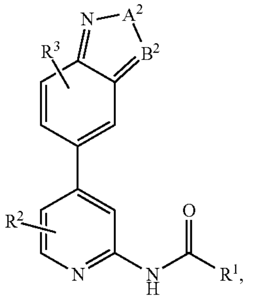

or a pharmaceutically acceptable salt or solvate thereof, wherein the variables are as defined in embodiment 1.

108. The compound of Formula (V)-(XII) of embodiment 107, or a pharmaceutically acceptable salt or solvate thereof, wherein $R^2$ is H, OH, halogen, CN, $C_{1-6}$ alkyl, $C_{3-10}$ cycloalkyl, $C_{1-6}$ alkoxyl, or 4-14 membered heterocycloalkyl.

109. The compound of Formula (V)-(XII) of embodiment 106, or a pharmaceutically acceptable salt or solvate thereof, wherein $R^2$ is halogen or $C_{1-6}$ alkyl.

110. The compound of Formula (V)-(XII) of embodiment 106, or a pharmaceutically acceptable salt or solvate thereof, wherein $R^2$ is $C_{1-6}$ alkyl.

111. The compound of Formula (V)-(XII) of embodiment 106, or a pharmaceutically acceptable salt or solvate thereof, wherein $R^2$ is chloro or fluoro.

112. The compound of any one of embodiments 107-111, or a pharmaceutically acceptable salt or solvate thereof, wherein $R_1$ is $C_{3-10}$cycloalkyl optionally substituted with 1, 2, 3, 4, 5, 6, 7 or 8 independently selected $R^b$ substituents, wherein:

each $R^b$ is, independently, $C_{1-4}$ alkyl, $NR^eC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^e$, or $NR^cS(O)_2R^c$, $NR^cS(O)_2NR^c$;

each $R^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents;

each $R^f$ is independently halogen, CN or $OR^g$; and each $R^g$ is independently H or $C_{1-6}$ alkyl.

113. The compound of any one of embodiments 107-111, or a pharmaceutically acceptable salt or solvate thereof, wherein $R^1$ is $C_{3-10}$ cycloalkyl optionally substituted with 1 $R^b$ substituent.

114. The compound of any one of embodiments 107-111, or a pharmaceutically acceptable salt or solvate thereof, wherein $R^1$ is $C_{3-7}$ cycloalkyl optionally substituted with 1 $R^b$ substituent.

115. The compound of any one of embodiments 107-111, or a pharmaceutically acceptable salt or solvate thereof, wherein $R^1$ is $C_{5-6}$ cycloalkyl optionally substituted with 1 $R^b$ substituent.

116. The compound of any one of embodiments 107-111, or a pharmaceutically acceptable salt or solvate thereof, wherein $R^1$ is cyclopentanyl or cyclohexanyl optionally substituted with 1 $R^b$ substituent.

117. The compound according to any one of embodiments 112-116, or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$.

118. The compound according to embodiment 117, or a pharmaceutically acceptable salt or solvate thereof, wherein the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents.

119. The compound according to embodiment 118, or a pharmaceutically acceptable salt or solvate thereof, wherein the $R^f$ substituents are independently halogen, CN or $OR^g$.

120. The compound according to embodiment 119, or a pharmaceutically acceptable salt or solvate thereof, wherein the $R^g$ is independently H or $C_{1-6}$ alkyl.

121. The compound according to any one of embodiments 112-116, or a pharmaceutically acceptable salt or solvate thereof, wherein the 1 $R^b$ substituent on $R^1$ is acetamido (—$NHC(O)CH_3$), 3-hydroxybutanamido (—$NHC(O)CH_2CH(OH)CH_3$), propionamido (—$NHC(O)CH_2CH_3$), 2-methoxyacetamido (—$NHC(O)CH_2$—$OCH_3$), 2-cyanoacetamido (—$NHC(O)CH_2$—CN), 1-hydroxycyclopropane-1-carboxamido,

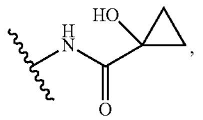 [SMILES: *NC(=O)C1(O)CC1]

2-(thiazol-4-yl)acetamido,

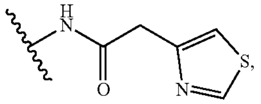 [SMILES: *NC(=O)Cc1cscn1]

methylsulfonamido ($-NSO_2CH_3$), 3-methylureido ($-NC(O)NHCH_3$), 3-methoxyureido ($-NC(O)NHOCH_3$), 3,3-dimethylureido ($-NC(O)N(CH_3)_2$), or 3-ethylureido ($-NC(O)NHCH_2CH_3$), morpholine-4-carboxamido, i.e.,

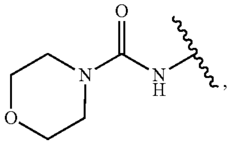 [SMILES: *NC(=O)N1CCOCC1]

or 4-methylpiperazine-1-carboxamide, i.e.,

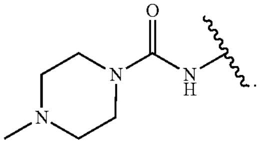 [SMILES: *NC(=O)N1CCN(C)CC1]

122. The compound according to any one of embodiments 107-121, or a pharmaceutically acceptable salt or solvate thereof, wherein said compound is a compound of Formula (V), Formula (VI), Formula (VII), or Formula (XI):

Formula (V)

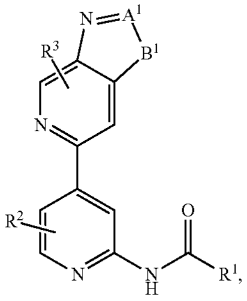

-continued

Formula (VI)

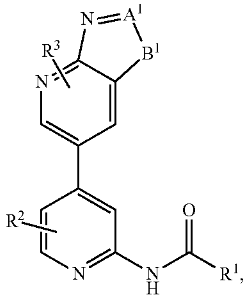

Formula (VII)

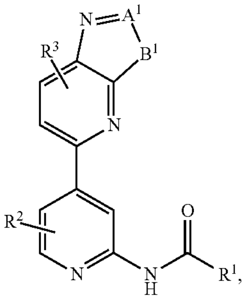

or

Formula (XI)

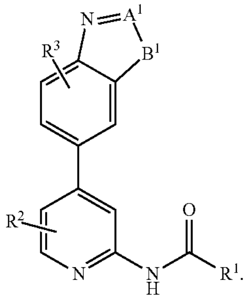

123. The compound of embodiment 122, or a pharmaceutically acceptable salt or solvate thereof, wherein $A^1$ is N.

124. The compound of embodiment 122, or a pharmaceutically acceptable salt or solvate thereof, wherein $A^1$ is $C-R^4$.

125. The compound of any one of embodiments 122-124, or a pharmaceutically acceptable salt or solvate thereof, wherein $B^1$ is $C-R^6R^7$.

126. The compound of any one of embodiments 122-124, or a pharmaceutically acceptable salt or solvate thereof, wherein $B^1$ is $N-R^5$.

127. The compound of any one of embodiments 122-124, or a pharmaceutically acceptable salt or solvate thereof, wherein $B^1$ is O.

128. The compound of any one of embodiments 122-124, or a pharmaceutically acceptable salt or solvate thereof, wherein $B^1$ is S.

129. The compound according to any one of embodiments 124-128, or a pharmaceutically acceptable salt or solvate thereof, wherein $R^4$ is H.

130. The compound according to any one of embodiments 124-128, or a pharmaceutically acceptable salt or solvate thereof, wherein $R^4$ is $C_{1-6}$alkyl, preferably $CH_3$.

131. The compound according to embodiment 126, or a pharmaceutically acceptable salt or solvate thereof, wherein $R^5$ is $C_{1-6}$alkyl, preferably $CH(CH_3)_2$.

132. The compound according to any one of embodiments 124 or 126, or a pharmaceutically acceptable salt or solvate thereof, wherein $R^4$ and $R^5$, together with the atoms to which they are attached, form a 5- or 6-membered heterocycloalkyl ring optionally substituted with 1, 2, 3, 4 or 5 independently selected $R^b$ substituents.

133. The compound according to embodiment 132, or a pharmaceutically acceptable salt or solvate thereof, wherein $R^4$ and $R^5$, together with the atoms to which they are attached, form an optionally substituted 5-membered heterocycloalkyl ring optionally substituted with 1 or 2 $R^b$ substituents.

134. The compound according to embodiment 133, or a pharmaceutically acceptable salt or solvate thereof, wherein the 1 or 2 $R^b$ substituents are $C_{1-4}$ alkyl, preferably $CH_3$.

135. The compound of embodiment 125, or a pharmaceutically acceptable salt or solvate thereof, wherein $R^6$ is $C_{1-6}$ alkyl, preferably $CH_3$; and $R^7$ is $C_{1-6}$ alkyl, preferably $CH_3$.

136. The compound of embodiment 125, or a pharmaceutically acceptable salt or solvate thereof, wherein $R^6$ and $R^7$ together with the carbon atom to which they are both attached, form a $C_4$-$C_7$ spirocyclic ring.

137. The compound of embodiment 136, or a pharmaceutically acceptable salt or solvate thereof, wherein the $C_4$-$C_7$ spirocyclic ring is a spirocyclopentane ring.

138. The compound according to any one of embodiments 107-121, or a pharmaceutically acceptable salt or solvate thereof, wherein said compound is a compound of Formula (VIII), Formula (IX), Formula (X), or Formula (XII):

Formula (VIII)

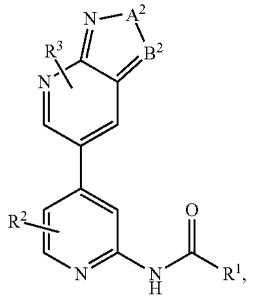

Formula (IX)

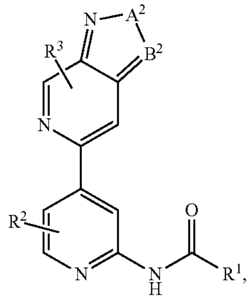

Formula (X)

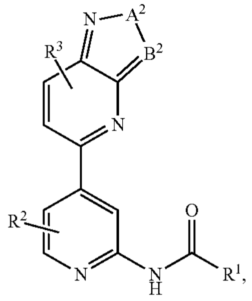

or

-continued

Formula (XII)

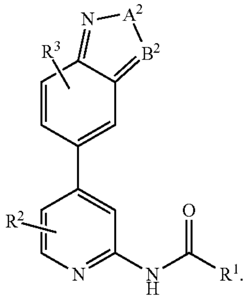

139. The compound of embodiment 138, or a pharmaceutically acceptable salt or solvate thereof, wherein $A^2$ is N—$R^8$.

140. The compound of embodiment 138, or a pharmaceutically acceptable salt or solvate thereof, wherein $A^2$ is S.

141. The compound of embodiment 138, or a pharmaceutically acceptable salt or solvate thereof, wherein $A^2$ is O.

142. The compound of any one of embodiments 138-141, or a pharmaceutically acceptable salt or solvate thereof, wherein $B^2$ is C—$R^9$.

143. The compound of any one of embodiments 138-141, or a pharmaceutically acceptable salt or solvate thereof, wherein $B^2$ is N.

144. The compound according to embodiment 139, or a pharmaceutically acceptable salt or solvate thereof, wherein $R^8$ is $C_{1-6}$alkyl, preferably $CH_3$.

145. The compound according to embodiment 142, or a pharmaceutically acceptable salt or solvate thereof, wherein $R^9$ is $C_{1-6}$alkyl, preferably $CH(CH_3)_2$.

146. The compound according to any one of embodiments 139 or 142, or a pharmaceutically acceptable salt or solvate thereof, wherein $R^8$ and $R^9$, together with the atoms to which they are attached, form a 5- or 6-membered heterocycloalkyl ring optionally substituted with 1, 2, 3, 4 or 5 independently selected $R^b$ substituents.

147. The compound according to embodiment 146, or a pharmaceutically acceptable salt or solvate thereof, wherein $R^8$ and $R^9$, together with the atoms to which they are attached, form a 5-membered heterocycloalkyl ring optionally substituted with 1 or 2 $R^b$ substituents.

148. The compound according to embodiment 147, or a pharmaceutically acceptable salt or solvate thereof, wherein the 1 or 2 $R^b$ substituents are $C_{1-4}$ alkyl, preferably $CH_3$.

149. The compound of any one of embodiments 107-148, or a pharmaceutically acceptable salt or solvate thereof, wherein $R^3$ is H, OH, halogen, CN, $C_{1-6}$ alkyl, $C_{3-10}$ cycloalkyl, $C_{1-6}$ alkoxyl, or 4-14 membered heterocycloalkyl.

150. The compound of any one of embodiments 107-148, or a pharmaceutically acceptable salt or solvate thereof, wherein $R^3$ is H or halogen, preferably Cl or F.

151. The compound of any one of embodiments 1-13, 19-77, 83-97, 103-116, and 122-150, or a pharmaceutically acceptable salt or solvate thereof, wherein $R^1$ is

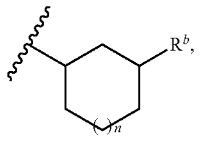

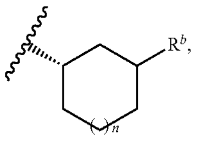

-continued

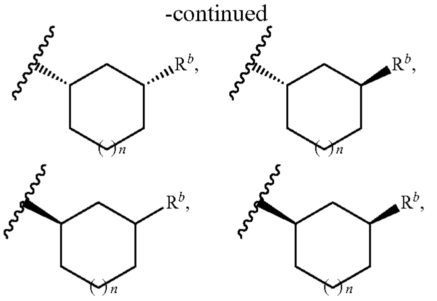

or

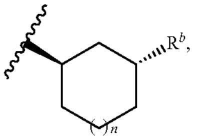

wherein n is 0 or 1 and $R^b$ is as defined in embodiment 1.

152. The compound of embodiment 151, or a pharmaceutically acceptable salt or solvate thereof, wherein the 1 $R^b$ substituent on $R^1$ is $NR^cC(O)R^c$, $NR^cC(O)NR^cR^c$, or $NR^cS(O)_2NR^cR^c$.

153. The compound of embodiment 152, or a pharmaceutically acceptable salt or solvate thereof, wherein the $R^c$ in $NR^cC(O)R^c$, $NR^cC(O)NR^cR^c$, or $NR^cS(O)_2NR^cR^c$ is independently H, $C_{1-6}$ alkyl, $C_{3-10}$ cycloalkyl, 4-10 membered heterocycloalkyl, or (5-10 membered heteroaryl)-$C_{1-4}$ alkyl; optionally substituted with 1, 2, 3, 4, or 5 independently selected $R^f$ substituents.

154. The compound of embodiment 153, or a pharmaceutically acceptable salt or solvate thereof, wherein the $R^f$ substituents are independently halogen, CN or $OR^g$.

155. The compound of embodiment 154, or a pharmaceutically acceptable salt or solvate thereof, wherein the $R^g$ is independently H or $C_{1-6}$ alkyl.

156. The compound of any one of embodiments 1-155, or a pharmaceutically acceptable salt or solvate thereof, wherein the 1 $R^b$ substituent on $R^1$ is acetamido ($-NHC(O)CH_3$), 3-hydroxybutanamido ($-NHC(O)CH_2CH(OH)CH_3$), propionamido ($-NHC(O)CH_2CH_3$), 2-methoxyacetamido ($-NHC(O)CH_2-OCH_3$), 2-cyanoacetamido ($-NHC(O)CH_2-CN$), 1-hydroxycyclopropane-1-carboxamido,

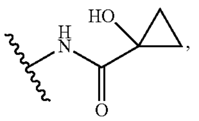 [SMILES: *NC(=O)C1(O)CC1]

2-(thiazol-4-yl)acetamido,

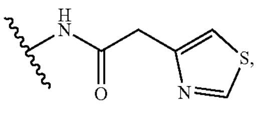 [SMILES: *NC(=O)Cc1cscn1]

methylsulfonamido ($-NSO_2CH_3$), 3-methylureido ($-NC(O)NHCH_3$), 3-methoxyureido ($-NC(O)NHOCH_3$), 3,3-dimethylureido ($-NC(O)N(CH_3)_2$), or 3-ethylureido ($-NC(O)NHCH_2CH_3$), morpholine-4-carboxamido, i.e.,

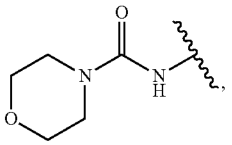 [SMILES: *NC(=O)N1CCOCC1]

or 4-methylpiperazine-1-carboxamide, i.e.

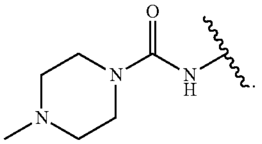 [SMILES: *NC(=O)N1CCN(C)CC1]

157. The compound of embodiment 1, wherein the compound, or a pharmaceutically acceptable salt or solvate thereof, has a formula of Formula (XIII)

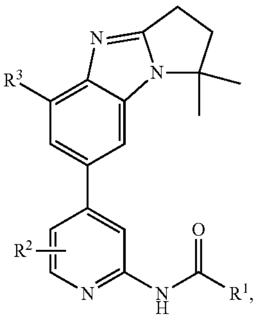

Formula (XV)

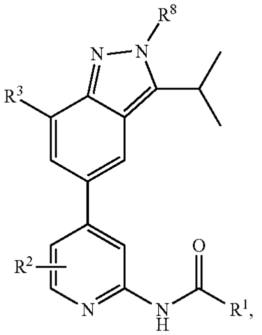

or

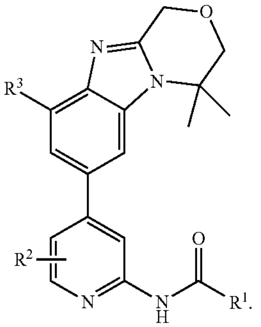

158. The compound of embodiment 1, wherein the compound, or a pharmaceutically acceptable salt or solvate thereof, has a formula of Formula (XIX-a)

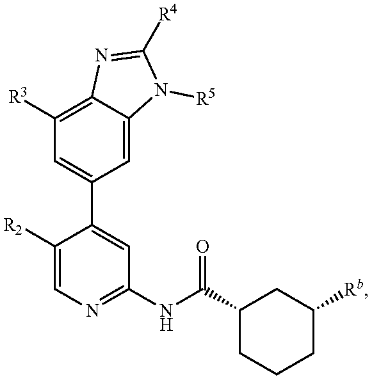

wherein $R^2$ is Me or OMe;

$R^3$ is H, D, or F;

$R^4$ is H or $C_{1-3}$ alkyl;

$R^5$ is isopropyl, —$CF_3(CH)CH_3$, —$C_{3-6}$ cycloalkyl, or —$CH_2$—($C_{3-6}$ cycloalkyl);

$R^b$ is $NHCOR^{13}$ or CN; and $R^{13}$ is H or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl.

159. The compound of embodiment 1, wherein the compound, or a pharmaceutically acceptable salt or solvate thereof, has a formula of Formula (XIX-e)

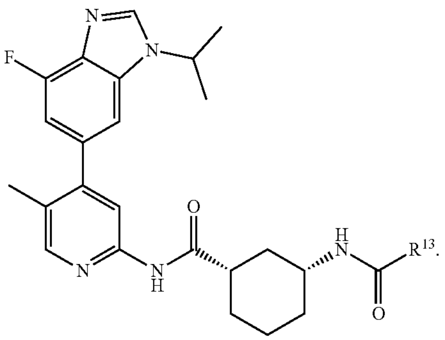

160. The Compound of embodiment 1, wherein the compound or a pharmaceutically acceptable salt or solvate thereof, has a formula of Formula (XXIII-a)

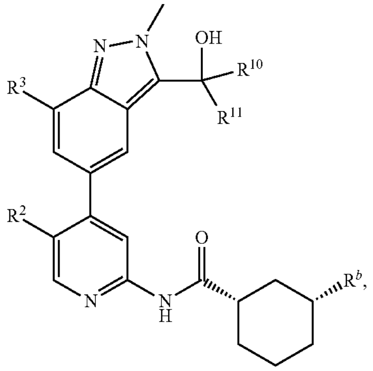

wherein:

$R^2$ is H, D, halogen, or Me;

$R^3$ is H, D, or F;

$R^{10}$ is H, D, Me, or $C_{1-3}$ haloalkyl;

$R^{11}$ is H, D, Me, or $C_{1-3}$ haloalkyl;

$R^b$ is $NHCOR^{14}$; and $R^{14}$ is H, —$CH_2CN$, or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl.

161. The compound of embodiment 1, wherein the compound, or a pharmaceutically acceptable salt or solvate thereof, has a formula of Formula (XXVII-e)

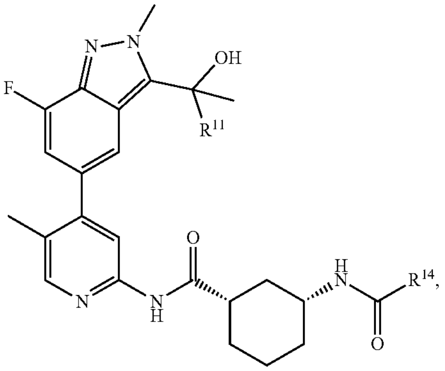

162. The compound of embodiment 1, wherein the compound is selected from the group consisting of:

(1S,3R)-3-acetamido-N-[5-chloro-4-(7-fluoro-3-isopropyl-2-methyl-indazol-5-yl)-2-pyridyl]cyclohexanecarboxamide;

(1S,3R)—N-[5-chloro-4-(7-fluoro-3-isopropyl-2-methyl-indazol-5-yl)-2-pyridyl]-3-[(1-hydroxycyclopropanecarbonyl)amino]-cyclohexanecarboxamide;

(1S,3R)—N-(5-chloro-4-(7-fluoro-3-isopropyl-2-methyl-2H-indazol-5-yl)pyridin-2-yl)-3-(2-(thiazol-4-yl)acetamido)cyclohexane-1-carboxamide;

(1S,3R)—N-(5-chloro-4-(7-fluoro-3-isopropyl-2-methyl-2H-indazol-5-yl)pyridin-2-yl)-3-(2-methoxyacetamido) cyclohexane-1-carboxamide;

(1S,3R)—N-(5-chloro-4-(7-fluoro-3-isopropyl-2-methyl-2H-indazol-5-yl)pyridin-2-yl)-3-propionamido-cyclohexane-1-carboxamide;

(1S,3R)—N-[5-chloro-4-(7-fluoro-3-isopropyl-2-methyl-indazol-5-yl)-2-pyridyl]-3-(methanesulfonamido)cyclo-hexanecarboxamide;

N-[(1R,3S)-3-[[5-chloro-4-(7-fluoro-3-isopropyl-2-methyl-indazol-5-yl)-2-pyridyl]carbamoyl]cyclohexyl]morpho-line-4-carboxamide;

N-((1R,3S)-3-((5-chloro-4-(7-fluoro-3-isopropyl-2-methyl-2H-indazol-5-yl)pyridin-2-yl)carbamoyl)-cyclohexyl)-4-methylpiperazine-1-carboxamide;

(1S,3R)—N-(5-chloro-4-(7-fluoro-3-isopropyl-2-methyl-2H-indazol-5-yl)pyridin-2-yl)-3-(3-methylureido)cyclo-hexane-1-carboxamide;

(1S,3R)—N-(5-chloro-4-(7-fluoro-3-isopropyl-2-methyl-2H-indazol-5-yl)pyridin-2-yl)-3-(3,3-dimethylureido)cy-clohexane-1-carboxamide;

(1S,3R)—N-(5-chloro-4-(7-fluoro-3-isopropyl-2-methyl-2H-indazol-5-yl)pyridin-2-yl)-3-(3-ethylureido)cyclo-hexane-1-carboxamide;

(1S,3R)—N-(5-chloro-4-(7-fluoro-3-isopropyl-2-methyl-2H-indazol-5-yl)pyridin-2-yl)-3-(3-methoxyureido)cy-clohexane-1-carboxamide;

(1S,3R)-3-acetamido-N-[5-chloro-4-(5-fluoro-1,1-dim-ethyl-2,3-dihydropyrrolo[1,2-a]benzimidazol-7-yl)-2-pyridyl]cyclohexanecarboxamide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-(2-cyanoacetamido)cyclohexane-1-carboxamide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-(3-hydroxybutanamido)cyclohexane-1-carbox-amide;

(1S,3R)-3-acetamido-N-(5-chloro-4-(1,1-dimethyl-2,3-di-hydro-1H-benzo[d]pyrrolo[1,2-a]imidazol-7-yl)pyridin-2-yl)cyclopentane-1-carboxamide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-propionamidocyclohexane-1-carboxamide;

(1S,3R)—N-(5-chloro-4-(1,1-dimethyl-2,3-dihydro-1H-benzo[d]pyrrolo[1,2-a]imidazol-7-yl)pyridin-2-yl)-3-pro-pionamidocyclopentane-1-carboxamide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-(1-hydroxycyclopropane-1-carboxamido)cyclo-hexane-1-carboxamide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-(2-methoxyacetamido)cyclohexane-1-carboxam-ide;

(1S,3R)—N-(5-chloro-4-(5-fluoro-1,1-dimethyl-2,3-di-hydro-1H-benzo[d]pyrrolo[1,2-a]imidazol-7-yl)pyridin-2-yl)-3-(methylsulfonamido)cyclohexane-1-carboxam-ide;

(1S,3R)-3-acetamido-N-(4-(4-fluoro-1-isopropyl-1H-benzo[d]imidazol-6-yl)-5-methylpyridin-2-yl)cyclohexane-1-carboxamide;

(1S,3R)-3-acetamido-N-(4-(5-fluoro-1,1-dimethyl-2,3-di-hydro-1H-benzo[d]pyrrolo[1,2-a]imidazol-7-yl)-5-meth-ylpyridin-2-yl)cyclohexane-1-carboxamide;

(1S,3R)-3-acetamido-N-(4-(4-fluoro-1-isopropyl-1H-benzo[d]imidazol-6-yl)-5-methylpyridin-2-yl)cyclopentane-1-carboxamide;

(1S,3R)-3-acetamido-N-(5-chloro-4-(7'-fluoro-2'-methyl-spiro[cyclopentane-1,3'-indol]-5'-yl)pyridin-2-yl)cyclo-hexane-1-carboxamide;

(1S,3R)-3-acetamido-N-(5-chloro-4-(3-isopropylbenzo[c]isothiazol-5-yl)pyridin-2-yl)cyclohexane-1-carboxamide;

(1S,3R)-3-acetamido-N-(5-chloro-4-(1-methyl-2,3-dihydro-1H-pyrrolo[1,2-b]indazol-8-yl)pyridin-2-yl)cyclohexane-1-carboxamide (1S,3R)-3-(3,3-dimethylureido)-N-(4-(4-fluoro-1-isopro-pyl-1H-benzo[d]imidazol-6-yl)-5-methylpyridin-2-yl)cy-clohexane-1-carboxamide;

(1S,3R)—N-(4-(4-fluoro-1-isopropyl-1H-benzo[d]imida-zol-6-yl)-5-methylpyridin-2-yl)-3-propionamidocyclo-hexane-1-carboxamide;

(1S,3R)—N-(4-(4-fluoro-1-isopropyl-1H-benzo[d]imida-zol-6-yl)-5-methylpyridin-2-yl)-3-isobutyramidocyclo-hexane-1-carboxamide;

(1S,3R)—N-(4-(4-fluoro-1-isopropyl-1H-benzo[d]imida-zol-6-yl)-5-methylpyridin-2-yl)-3-(2-methoxyacetamido)cyclohexane-1-carboxamide;

(1S,3R)-3-(2-(dimethylamino)acetamido)-N-(4-(4-fluoro-1-isopropyl-1H-benzo[d]imidazol-6-yl)-5-methylpyridin-2-yl)cyclohexane-1-carboxamide;

methyl ((1R,3S)-3-((4-(4-fluoro-1-isopropyl-1H-benzo[d]imidazol-6-yl)-5-methylpyridin-2-yl)carbamoyl)cyclo-hexyl)carbamate;

(1S,3R)—N-(4-(4-fluoro-1-isopropyl-1H-benzo[d]imida-zol-6-yl)-5-methylpyridin-2-yl)-3-(methylsulfonamido)cyclohexane-1-carboxamide;

(1S,3R)—N-(4-(4-fluoro-1-isopropyl-1H-benzo[d]imida-zol-6-yl)-5-methylpyridin-2-yl)-3-(1-fluorocyclopro-pane-1-carboxamido)cyclohexane-1-carboxamide;

(1S,3R)—N-(4-(4-fluoro-1-isopropyl-1H-benzo[d]imida-zol-6-yl)-5-methylpyridin-2-yl)-3-(1-hydroxycyclopro-pane-1-carboxamido)cyclohexane-1-carboxamide;

N-((1R,3S)-3-((4-(4-fluoro-1-isopropyl-1H-benzo[d]imida-zol-6-yl)-5-methylpyridin-2-yl)carbamoyl)cyclohexyl)-1-methylazetidine-3-carboxamide;

(1S,3R)—N-(4-(4-fluoro-1-isopropyl-1H-benzo[d]imida-zol-6-yl)-5-methylpyridin-2-yl)-3-((1r,3R)-3-hydroxycy-clobutane-1-carboxamido)cyclohexane-1-carboxamide;

(1S,3R)—N-(4-(4-fluoro-1-isopropyl-1H-benzo[d]imida-zol-6-yl)-5-methylpyridin-2-yl)-3-(2-hydroxyacetamido)cyclohexane-1-carboxamide;

(1S,3R)-3-acetamido-N-(4-(4-fluoro-1-(oxetan-3-yl)-1H-benzo[d]imidazol-6-yl)-5-methylpyridin-2-yl)cyclo-hexane-1-carboxamide;

(1S,3R)-3-acetamido-N-(4-(1-cyclopropyl-4-fluoro-1H-benzo[d]imidazol-6-yl)-5-methylpyridin-2-yl)cyclo-hexane-1-carboxamide;

(1S,3R)-3-acetamido-N-(4-(1-(cyclopropylmethyl)-4-fluoro-1H-benzo[d]imidazol-6-yl)-5-methylpyridin-2-yl)cyclohexane-1-carboxamide;

(S)—N-((1R,3S)-3-((4-(4-fluoro-1-isopropyl-1H-benzo[d]imidazol-6-yl)-5-methylpyridin-2-yl)carbamoyl)cyclo-hexyl)-3-hydroxypyrrolidine-1-carboxamide;

(1S,3R)—N-(4-(4-fluoro-1-isopropyl-1H-benzo[d]imida-zol-6-yl)-5-methylpyridin-2-yl)-3-(3-methylureido)cy-clohexane-1-carboxamide;

N-((1R,3S)-3-((4-(4-fluoro-1-isopropyl-1H-benzo[d]imida-zol-6-yl)-5-methylpyridin-2-yl)carbamoyl)cyclohexyl)morpholine-4-carboxamide;

N-((1R,3S)-3-((4-(4-fluoro-1-isopropyl-1H-benzo[d]imida-zol-6-yl)-5-methylpyridin-2-yl)carbamoyl)cyclohexyl)-4-methylpiperazine-1-carboxamide;

(1S,3R)—N-[4-(7-fluoro-3-isopropyl-benzimidazol-5-yl)-5-methyl-2-pyridyl]-3-[(methylsulfonimidoyl)amino]cy-clohexanecarboxamide;

(1S,3R)—N1-(4-(4-fluoro-1-isopropyl-1H-benzo[d]imida-zol-6-yl)-5-methylpyridin-2-yl)-N3-methylcyclohexane-1,3-dicarboxamide;

3-cyano-N-(4-(4-fluoro-1-isopropyl-1H-benzo[d]imidazol-6-yl)-5-methylpyridin-2-yl)cyclohexane-1-carboxamide;
(1S,3R)-3-(3,3-dimethylureido)-N-(4-(4-fluoro-1-(1,1,1-trifluoropropan-2-yl)-1H-benzo[d]imidazol-6-yl)-5-methylpyridin-2-yl)cyclohexane-1-carboxamide;
(1S,3R)-3-acetamido-N-(5-chloro-4-(1,1-dimethyl-2,3-dihydro-1H-pyrrolo[1,2-b]indazol-8-yl)pyridin-2-yl)cyclohexane-1-carboxamide;
(1S,3R)-3-acetamido-N-(5-chloro-4-(7-fluoro-3-(1-hydroxypropan-2-yl)-2-methyl-2H-indazol-5-yl)pyridin-2-yl)cyclohexane-1-carboxamide;
(1S,3R)-3-acetamido-N-(5-chloro-4-(7-fluoro-3-(2-hydroxypropan-2-yl)-2-methyl-2H-indazol-5-yl)pyridin-2-yl)cyclohexane-1-carboxamide;
(1S,3R)-3-acetamido-N-(5-chloro-4-(3-cyclopropyl-7-fluoro-2-methyl-2H-indazol-5-yl)pyridin-2-yl)cyclohexane-1-carboxamide;
(1S,3R)-3-acetamido-N-(5-chloro-4-(3-isopropyl-2-methyl-2H-pyrazolo[4,3-b]pyridin-5-yl)pyridin-2-yl)cyclohexane-1-carboxamide;
(1S,3R)-3-acetamido-N-(4-(7-fluoro-3-isopropyl-2-methyl-2H-indazol-5-yl)-5-methylpyridin-2-yl)cyclohexane-1-carboxamide;
(1S,3R)—N-(5-chloro-4-(7-fluoro-3-isopropyl-2-methyl-2H-indazol-5-yl)pyridin-2-yl)-3-(1-fluorocyclopropane-1-carboxamido)cyclohexane-1-carboxamide;
N-((1R,3S)-3-((5-chloro-4-(7-fluoro-3-isopropyl-2-methyl-2H-indazol-5-yl)pyridin-2-yl)carbamoyl)cyclohexyl)-2-methoxynicotinamide;
N-((1R,3S)-3-((5-chloro-4-(7-fluoro-3-isopropyl-2-methyl-2H-indazol-5-yl)pyridin-2-yl)carbamoyl)cyclohexyl)-5-methylisoxazole-3-carboxamide;
N-((1R,3S)-3-((5-chloro-4-(7-fluoro-3-isopropyl-2-methyl-2H-indazol-5-yl)pyridin-2-yl)carbamoyl)cyclohexyl)-6-methylnicotinamide;
(1S,3R)—N-(4-(7-fluoro-3-isopropyl-2-methyl-2H-indazol-5-yl)-5-methylpyridin-2-yl)-3-(2-methoxyacetamido)cyclohexane-1-carboxamide;
(1S,3R)—N-(4-(7-fluoro-3-isopropyl-2-methyl-2H-indazol-5-yl)-5-methylpyridin-2-yl)-3-(2-methoxyacetamido)cyclohexane-1-carboxamide;
N-((1R,3S)-3-((4-(7-fluoro-3-isopropyl-2-methyl-2H-indazol-5-yl)-5-methylpyridin-2-yl)carbamoyl)cyclohexyl)-5-methylisoxazole-3-carboxamide;
N-((1R,3S)-3-((4-(7-fluoro-3-isopropyl-2-methyl-2H-indazol-5-yl)-5-methylpyridin-2-yl)carbamoyl)cyclohexyl)-2-methoxynicotinamide;
(1S,3R)—N-(5-chloro-4-(7-fluoro-3-isopropyl-2-methyl-2H-indazol-5-yl)pyridin-2-yl)-3-(2-cyanoacetamido)cyclohexane-1-carboxamide;
(1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide;
N-((1R,3S)-3-((4-(7-fluoro-3-isopropyl-2-methyl-2H-indazol-5-yl)-5-methylpyridin-2-yl)carbamoyl)cyclohexyl)morpholine-4-carboxamide;
(1S,3R)-3-(3-ethylureido)-N-(4-(7-fluoro-3-isopropyl-2-methyl-2H-indazol-5-yl)pyridin-2-yl)cyclohexane-1-carboxamide;
N-((1R,3S)-3-((4-(7-fluoro-3-isopropyl-2-methyl-2H-indazol-5-yl)pyridin-2-yl)carbamoyl)cyclohexyl)azetidine-1-carboxamide;
methyl ((1R,3S)-3-((5-chloro-4-(7-fluoro-3-isopropyl-2-methyl-2H-indazol-5-yl)pyridin-2-yl)carbamoyl)cyclohexyl)carbamate;
tetrahydro-2H-pyran-4-yl ((1R,3S)-3-((5-chloro-4-(7-fluoro-3-isopropyl-2-methyl-2H-indazol-5-yl)pyridin-2-yl)carbamoyl)cyclohexyl)carbamate;
(1-methyl-1H-pyrazol-3-yl)methyl ((1R,3S)-3-((5-chloro-4-(7-fluoro-3-isopropyl-2-methyl-2H-indazol-5-yl)pyridin-2-yl)carbamoyl)cyclohexyl)carbamate;
(2,2-difluorocyclopropyl)methyl ((1R,3S)-3-((5-chloro-4-(7-fluoro-3-isopropyl-2-methyl-2H-indazol-5-yl)pyridin-2-yl)carbamoyl)cyclohexyl)carbamate;
(1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide;
(1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide;
(1S,3R)-3-(2-cyanoacetamido)-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide (P1);
(1S,3R)-3-(2-cyanoacetamido)-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide (P2);
(1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide;
(1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide;
(1S,3R)—N-(5-chloro-4-(3-(1,1-difluoro-2-hydroxypropan-2-yl)-7-fluoro-2-methyl-2H-indazol-5-yl)pyridin-2-yl)-3-(2-cyanoacetamido)cyclohexane-1-carboxamide;
(1S,3R)-3-(2-cyanoacetamido)-N-(4-(4-fluoro-1-isopropyl-1H-benzo[d]imidazol-6-yl)-5-methylpyridin-2-yl)cyclohexane-1-carboxamide;
(1S,3R)-3-acetamido-N-(4-(4-fluoro-1-isopropyl-1H-benzo[d]imidazol-6-yl)-5-methoxypyridin-2-yl)cyclohexane-1-carboxamide;
N-((1R,3S)-3-((5-chloro-4-(7-fluoro-3-isopropyl-2-methyl-2H-indazol-5-yl)pyridin-2-yl)carbamoyl)cyclohexyl)bicyclo[1.1.1]pentane-1-carboxamide;
(1S,3R)-3-acetamido-N-(5-chloro-4-(4-fluoro-1-isopropyl-1H-benzo[d][1,2,3]triazol-6-yl)pyridin-2-yl)cyclohexane-1-carboxamide;
(1S,3R)-3-Acetamido-N-(5-chloro-4-(3-isopropyl-3H-imidazo[4,5-b]pyridin-5-yl)pyridin-2-yl)cyclohexane-1-carboxamide;
(1S,3R)—N-(5-chloro-4-(9-fluoro-4,4-dimethyl-3,4-dihydro-1H-benzo[4,5]imidazo[2,1-c][1,4]oxazin-7-yl)pyridin-2-yl)-3-(2-cyanoacetamido)cyclohexane-1-carboxamide;
(1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide;
(1S,3R)-3-acetamido-N-(5-chloro-4-(4-fluoro-1-isopropyl-1H-benzo[d]imidazol-6-yl)pyridin-2-yl)cyclohexane-1-carboxamide;
(1S,3R)-3-acetamido-N-(4-(4-fluoro-1-isopropyl-1H-benzo[d]imidazol-6-yl)pyridin-2-yl)cyclohexane-1-carboxamide; and pharmaceutically acceptable salts thereof.

163. A pharmaceutical composition comprising a compound according to any one of embodiments 1 to 162, or a pharmaceutically acceptable salt or solvate thereof, and optionally a pharmaceutically acceptable excipient.

164. The pharmaceutical composition of embodiment 163, wherein the pharmaceutical composition comprises an enantiomeric excess of at least 90% of one enantiomer of the compound, or a pharmaceutically acceptable salt or solvate thereof.

165. The pharmaceutical composition of embodiment 163, wherein the pharmaceutical composition comprises an enantiomeric excess of at least 95% of one enantiomer of the compound, or a pharmaceutically acceptable salt or solvate thereof.

166. The pharmaceutical composition of embodiment 163, wherein the pharmaceutical composition comprises an enantiomeric excess of at least 98% of one enantiomer of the compound, or a pharmaceutically acceptable salt or solvate thereof.

167. The pharmaceutical composition of embodiment 163, wherein the pharmaceutical composition comprises an enantiomeric excess of at least 99% of one enantiomer of the compound, or a pharmaceutically acceptable salt or solvate thereof.

168. A method of inhibiting a CDK enzyme comprising: contacting the CDK enzyme with an effective amount of a compound of any one of embodiments 1 to 162, or a pharmaceutically acceptable salt or solvate thereof, or a pharmaceutical composition of any one of embodiments 163-167.

169. The method of embodiment 168, wherein the CDK enzyme is CDK9.

170. A method of treating a disease or disorder associated with aberrant CDK activity in a subject or a subject in need thereof comprising administering to the subject, a compound of any one of embodiments 1 to 162, or a pharmaceutically acceptable salt or solvate thereof, or a pharmaceutical composition of any one of embodiments 163-167.

171. The method of embodiment 170, wherein the disease or disorder associated with aberrant CDK activity is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

172. A method of treating cancer in a subject or a subject in need thereof comprising administering to the subject, a compound of any one of embodiments 1 to 162, or a pharmaceutically acceptable salt or solvate thereof.

173. The method of embodiment 172, wherein the cancer is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

174. A compound of any one of embodiments 1 to 162 in use for inhibiting a CDK enzyme in a subject, wherein the use comprises administering to the subject an effective amount of the compound of any one of embodiments 1 to 162, or a pharmaceutically acceptable salt, a solvate, a pharmaceutical composition, or a prodrug thereof.

175. A pharmaceutical composition of any one of embodiments 163-167 in use for inhibiting a CDK enzyme in a subject, wherein the use comprises administering to the subject an effective amount of the pharmaceutical composition of any one of embodiments 163-167.

176. Use of a compound of any one of embodiments 1 to 162 in the manufacture of a formulation inhibiting a CDK enzyme in a subject, wherein the use comprises administering to the subject an effective amount of the compound of any one of embodiments 1 to 162, or a pharmaceutically acceptable salt, a solvate, a pharmaceutical composition, or a prodrug thereof.

177. Use of a pharmaceutical composition of any one of embodiments 163-167 for inhibiting a CDK enzyme in a subject, wherein the use comprises administering to the subject an effective amount of the pharmaceutical composition of any one of embodiments 163-167.

178. The use of any one of embodiments 174-177, wherein the CDK enzyme is CDK9.

179. A compound of any one of embodiments 1 to 162 in use for treating a disease or disorder associated with aberrant CDK activity in a subject or a subject in need thereof, wherein the use comprises administering to the subject an effective amount of the compound of any one of embodiments 1 to 162, or a pharmaceutically acceptable salt, a solvate, a pharmaceutical composition, or a prodrug thereof.

180. A pharmaceutical composition of any one of embodiments 163-167 in use for treating a disease or disorder associated with aberrant CDK activity in a subject or a subject in need thereof, wherein the use comprises administering to the subject an effective amount of the pharmaceutical composition of any one of embodiments 163-167.

181. Use of a compound of any one of embodiments 1 to 162 in the manufacture of a formulation treating a disease or disorder associated with aberrant CDK activity in a subject or a subject in need thereof, wherein the use comprises administering to the subject an effective amount of the compound of any one of embodiments 1 to 162, or a pharmaceutically acceptable salt, a solvate, a pharmaceutical composition, or a prodrug thereof.

182. Use of a pharmaceutical composition of any one of embodiments 163-167 for treating a disease or disorder associated with aberrant CDK activity in a subject or a subject in need thereof, wherein the use comprises administering to the subject an effective amount of the pharmaceutical composition of any one of embodiments 163-167.

183. The use of any one of embodiments 179-182, wherein the disease or disorder associated with aberrant CDK activity is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

184. A compound of any one of embodiments 1 to 162 in use for treating cancer in a subject or a subject in need thereof, wherein the use comprises administering to the subject an effective amount of the compound of any one of embodiments 1 to 162, or a pharmaceutically acceptable salt, a solvate, a pharmaceutical composition, or a prodrug thereof.

185. A pharmaceutical composition of any one of embodiments 163-167 in use for treating cancer in a subject or a subject in need thereof, wherein the use comprises administering to the subject an effective amount of the pharmaceutical composition of any one of embodiments 163-167.

186. Use of a compound of any one of embodiments 1 to 162 in the manufacture of a formulation treating cancer in a subject or a subject in need thereof, wherein the use comprises administering to the subject an effective amount of the compound of any one of embodiments 1 to 162, or a pharmaceutically acceptable salt, a solvate, a pharmaceutical composition, or a prodrug thereof.

187. Use of a pharmaceutical composition of any one of embodiments 163-167 for treating cancer in a subject or a subject in need thereof, wherein the use comprises administering to the subject an effective amount of the pharmaceutical composition of any one of embodiments 163-167.

188. The use of any one of embodiments 183-187, wherein the cancer is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

The following examples are illustrative, but not limiting, of the methods and compositions described herein. Other suitable modifications and adaptations of the variety of conditions and parameters normally encountered in therapy, synthesis, and other embodiments disclosed herein are within the spirit and scope of the embodiments.

Compounds provided for herein include, for example, Examples 1-88, which have been either exemplified or identified in Table A and Tables 1-8. In some embodiments, compounds described herein can be made in trifluoroacetice acid ("TFA") salt forms but the TFA salt form is just a non-limiting example of salt form and the compounds can also be made in other salt forms. For example, Examples 1-27, 43-46, 48, 50-75, 76-1, 76-2, 77-79, and 81-88 are prepared in TFA salt forms.

TABLE A

| Ex. | Structure | Chemical Name |
|---|---|---|
| 1 | 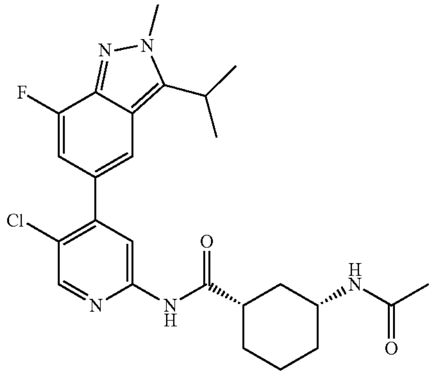 [SMILES: CC(=O)N[C@@H]1CCC[C@H](C(=O)Nc2cc(-c3cc(F)c4nn(C)c(C(C)C)c4c3)c(Cl)cn2)C1] | (1S,3R)-3-acetamido-N-[5-chloro-4-(7-fluoro-3-isopropyl-2-methyl-indazol-5-yl)-2-pyridyl]cyclohexanecarboxamide |
| 2 | 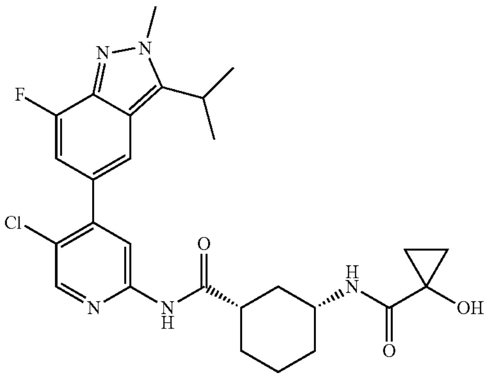 [SMILES: CC(C)c1c2cc(-c3cc(NC(=O)[C@H]4CCC[C@@H](NC(=O)C5(O)CC5)C4)ncc3Cl)cc(F)c2nn1C] | (1S,3R)-N-[5-chloro-4-(7-fluoro-3-isopropyl-2-methyl-indazol-5-yl)-2-pyridyl]-3-[(1-hydroxycyclopropanecarbonyl)amino]-cyclohexanecarboxamide |
| 3 | 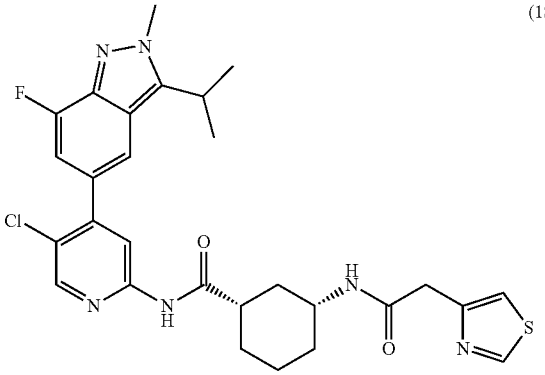 | (1S,3R)-N-(5-chloro-4-(7-fluoro-3-isopropyl-2-methyl-2H-indazol-5-yl)pyridin-2-yl)-3-(2-(thiazol-4-yl)acetamido)cyclohexane-1-carboxamide |

TABLE A-continued

| Ex. | Structure | Chemical Name |
| --- | --- | --- |
| 4 | 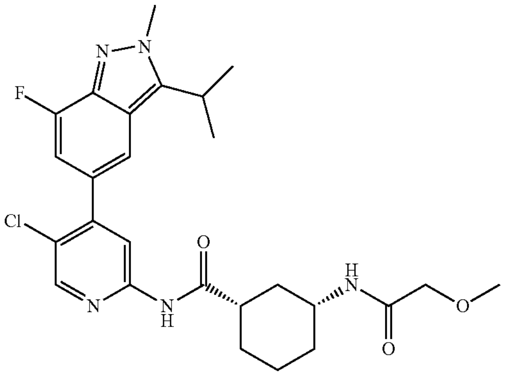 [SMILES: COCC(=O)N[C@@H]1CCC[C@H](C(=O)Nc2cc(-c3cc(F)c4nn(C)c(C(C)C)c4c3)c(Cl)cn2)C1] | (1S,3R)-N-(5-chloro-4-(7-fluoro-3-isopropyl-2-methyl-2H-indazol-5-yl)pyridin-2-yl)-3-(2-methoxyacctamido)cyclohexane-1-carboxamide |
| 5 | 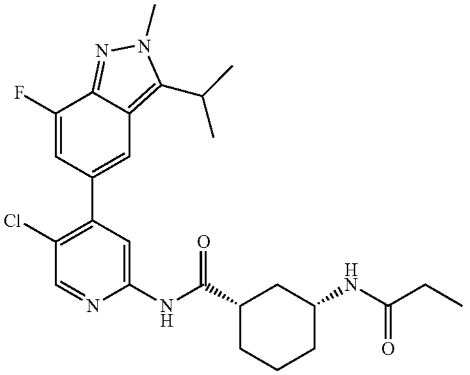 [SMILES: CCC(=O)N[C@@H]1CCC[C@H](C(=O)Nc2cc(-c3cc(F)c4nn(C)c(C(C)C)c4c3)c(Cl)cn2)C1] | (1S,3R)-N-(5-chloro-4-(7-fluoro-3-isopropyl-2-methyl-2H-indazol-5-yl)pyridin-2-yl)-3-propionamido-cyclohexane-1-carboxamide |
| 6 | 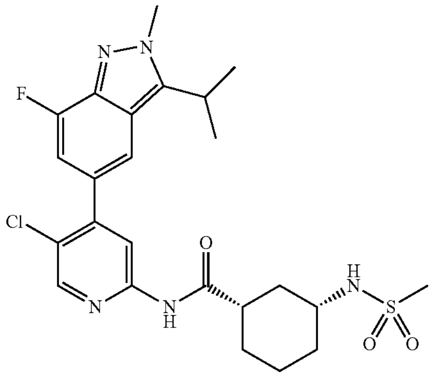 [SMILES: CC(C)c1c2cc(-c3cc(NC(=O)[C@H]4CCC[C@@H](NS(C)(=O)=O)C4)ncc3Cl)cc(F)c2nn1C] | (1S,3R)-N-[5-chloro-4-(7-fluoro-3-isopropyl-2-methyl-indazol-5-yl)-2-pyridyl]-3-(methanesulfonamido)cyclohexanecarboxamide |
| 7 | 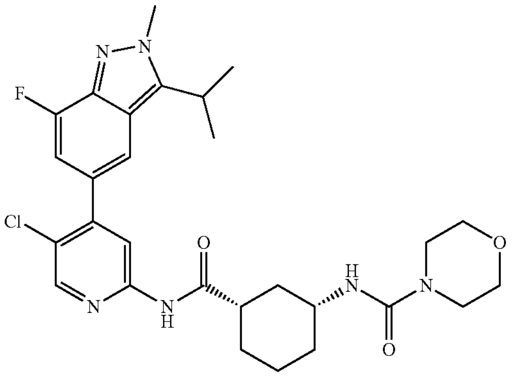 [SMILES: CC(C)c1c2cc(-c3cc(NC(=O)[C@H]4CCC[C@@H](NC(=O)N5CCOCC5)C4)ncc3Cl)cc(F)c2nn1C] | N-[(1R,3S)-3-[[5-chloro-4-(7-fluoro-3-isopropyl-2-methyl-indazol-5-yl)-2-pyridyl]carbamoyl]cyclohcxyl]morpholine-4-carboxamide |

TABLE A-continued

| Ex. | Structure | Chemical Name |
|---|---|---|
| 8 | 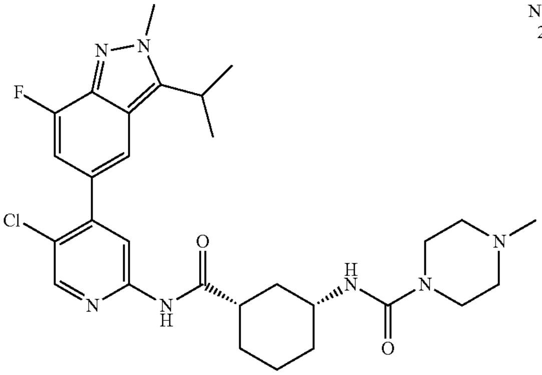 [SMILES: CC(C)c1c2cc(-c3cc(NC(=O)[C@H]4CCC[C@@H](NC(=O)N5CCN(C)CC5)C4)ncc3Cl)cc(F)c2nn1C] | N-((1R,3S)-3-((5-chloro-4-(7-fluoro-3-isopropyl-2-methyl-2H-indazol-5-yl)pyridin-2-yl)carbamoyl)-cyclohexyl)-4-methylpiperazine-1-carboxamide |
| 9 | 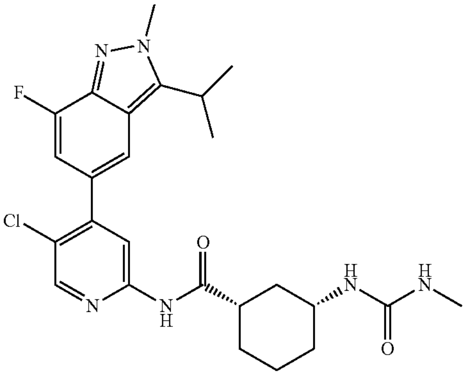 [SMILES: CNC(=O)N[C@@H]1CCC[C@H](C(=O)Nc2cc(-c3cc(F)c4nn(C)c(C(C)C)c4c3)c(Cl)cn2)C1] | (1S,3R)-N-(5-chloro-4-(7-fluoro-3-isopropyl-2-methyl-2H-indazol-5-yl)pyridin-2-yl)-3-(3-methylureido)cyclohexane-1-carboxamide |
| 10 | 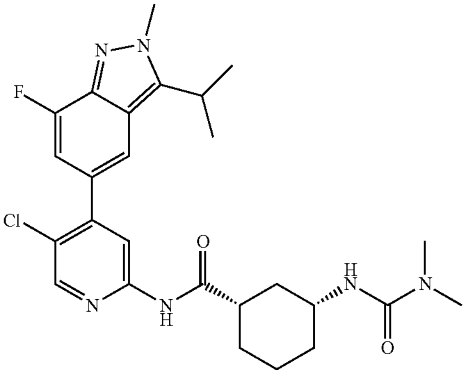 [SMILES: CC(C)c1c2cc(-c3cc(NC(=O)[C@H]4CCC[C@@H](NC(=O)N(C)C)C4)ncc3Cl)cc(F)c2nn1C] | (1S,3R)-N-(5-chloro-4-(7-fluoro-3-isopropyl-2-methyl-2H-indazol-5-yl)pyridin-2-yl)-3-(3,3-dimethylureido)cyclohexane-1-carboxamide |
| 11 | 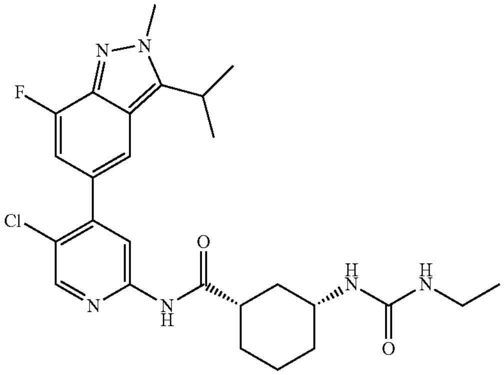 [SMILES: CCNC(=O)N[C@@H]1CCC[C@H](C(=O)Nc2cc(-c3cc(F)c4nn(C)c(C(C)C)c4c3)c(Cl)cn2)C1] | (1S,3R)-N-(5-chloro-4-(7-fluoro-3-isopropyl-2-methyl-2H-indazol-5-yl)pyridin-2-yl)-3-(3-ethylureido)cyclohexane-1-carboxamide |

TABLE A-continued

| Ex. | Structure | Chemical Name |
| --- | --- | --- |
| 12 | 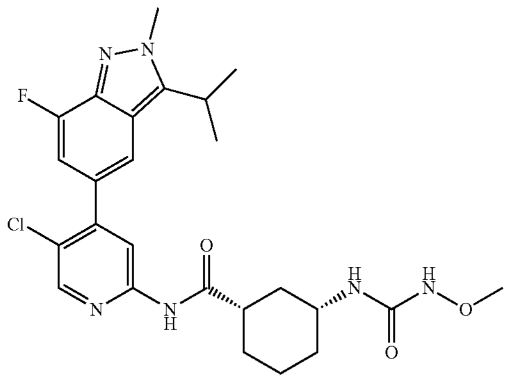 | (1S,3R)-N-(5-chloro-4-(7-fluoro-3-isopropyl-2-methyl-2H-indazol-5-yl)pyridin-2-yl)-3-(3-methoxyureido)cyclohexane-1-carboxamide |
| 13 | 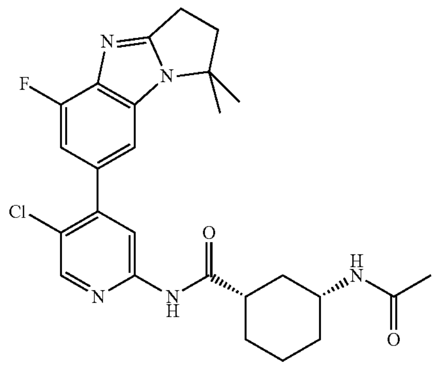 [SMILES: CC(=O)N[C@@H]1CCC[C@H](C(=O)Nc2cc(-c3cc(F)c4nc5n(c4c3)C(C)(C)CC5)c(Cl)cn2)C1] | (1S,3R)-3-acetamido-N-[5-chloro-4-(5-fluoro-1,1-dimethyl-2,3-dihydropyrrolo[1,2-a]benzimidazol-7-yl)-2-pyridyl]cyclohexanecarboxamide |
| 14 | 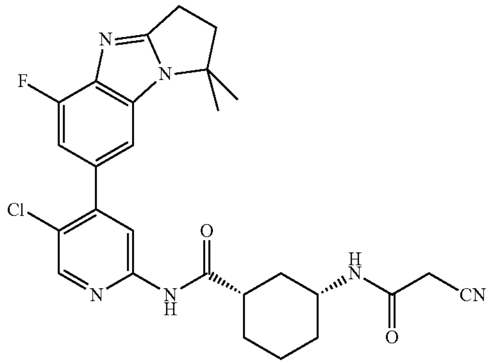 [SMILES: CC1(C)CCc2nc3c(F)cc(-c4cc(NC(=O)[C@H]5CCC[C@@H](NC(=O)CC#N)C5)ncc4Cl)cc3n21] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(2-cyanoacetamido)cyclohexane-1-carboxamide |
| 15 | 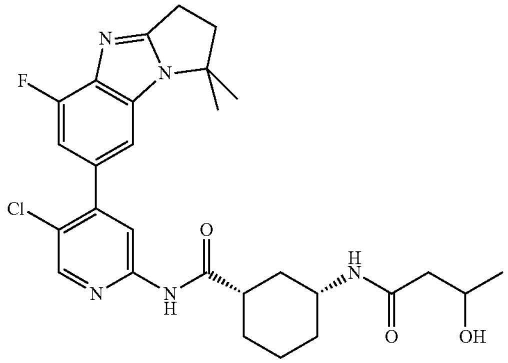 [SMILES: CC(O)CC(=O)N[C@@H]1CCC[C@H](C(=O)Nc2cc(-c3cc(F)c4nc5n(c4c3)C(C)(C)CC5)c(Cl)cn2)C1] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(3-hydroxybutanamido)cyclohexane-1-carboxamide |

TABLE A-continued

| Ex. | Structure | Chemical Name |
|---|---|---|
| 16 | 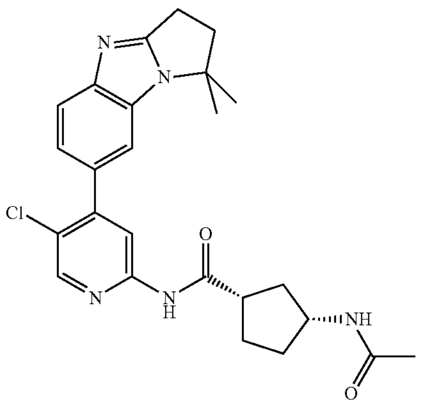 [SMILES: CC(=O)N[C@@H]1CC[C@H](C(=O)Nc2cc(-c3ccc4nc5n(c4c3)C(C)(C)CC5)c(Cl)cn2)C1] | (1S,3R)-3-acetamido-N-(5-chloro-4-(1,1-dimethyl-2,3-dihydro-1H-benzo[d]pyrrolo[1,2-a]imidazol-7-yl)pyridin-2-yl)cyclopentane-1-carboxamide |
| 17 | 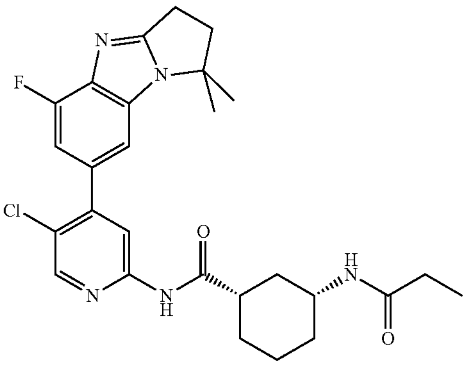 [SMILES: CCC(=O)N[C@@H]1CCC[C@H](C(=O)Nc2cc(-c3cc(F)c4nc5n(c4c3)C(C)(C)CC5)c(Cl)cn2)C1] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-propionamidocyclohexane-1-carboxamide |
| 18 | 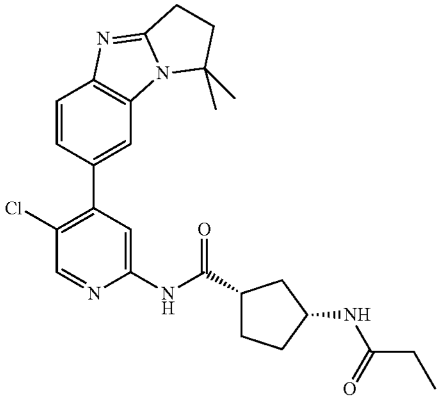 [SMILES: CCC(=O)N[C@@H]1CC[C@H](C(=O)Nc2cc(-c3ccc4nc5n(c4c3)C(C)(C)CC5)c(Cl)cn2)C1] | (1S,3R)-N-(5-chloro-4-(1,1-dimethyl-2,3-dihydro-1H-benzo[d]pyrrolo[1,2-a]imidazol-7-yl)pyridin-2-yl)-3-propionamidocyclopentane-1-carboxamide |
| 19 | 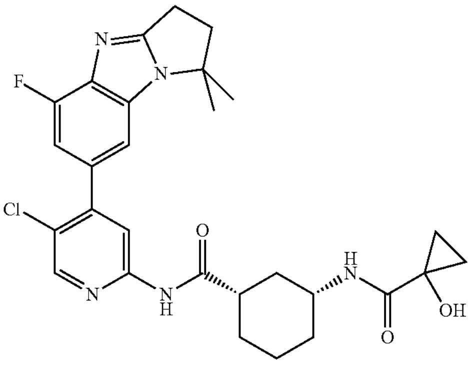 [SMILES: CC1(C)CCc2nc3c(F)cc(-c4cc(NC(=O)[C@H]5CCC[C@@H](NC(=O)C6(O)CC6)C5)ncc4Cl)cc3n21] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(1-hydroxycyclopropane-1-carboxamido)cyclohexane-1-carboxamide |

TABLE A-continued

| Ex. | Structure | Chemical Name |
|---|---|---|
| 20 | 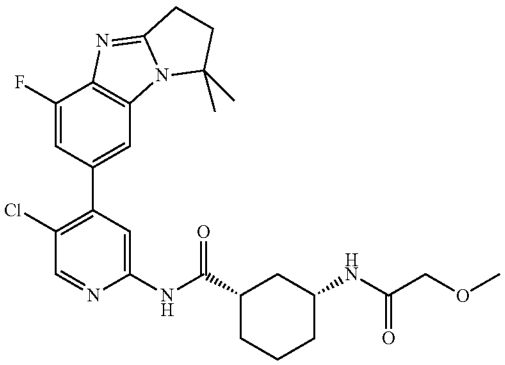 [SMILES: COCC(=O)N[C@@H]1CCC[C@H](C(=O)Nc2cc(-c3cc(F)c4nc5n(c4c3)C(C)(C)CC5)c(Cl)cn2)C1] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(2-methoxyacetamido)cyclohexane-1-carboxamide |
| 21 | 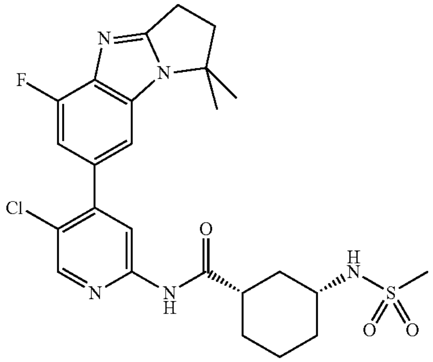 [SMILES: CC1(C)CCc2nc3c(F)cc(-c4cc(NC(=O)[C@H]5CCC[C@@H](NS(C)(=O)=O)C5)ncc4Cl)cc3n21] | (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(methylsulfonamido)cyclohexane-1-carboxamide |
| 22 | 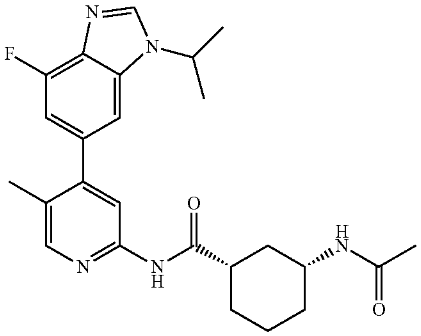 [SMILES: CC(=O)N[C@@H]1CCC[C@H](C(=O)Nc2cc(-c3cc(F)c4ncn(C(C)C)c4c3)c(C)cn2)C1] | (1S,3R)-3-acetamido-N-(4-(4-fluoro-1-isopropyl-1H-benzo[d]imidazol-6-yl)-5-methylpyridin-2-yl)cyclohexane-1-carboxamide |
| 23 | 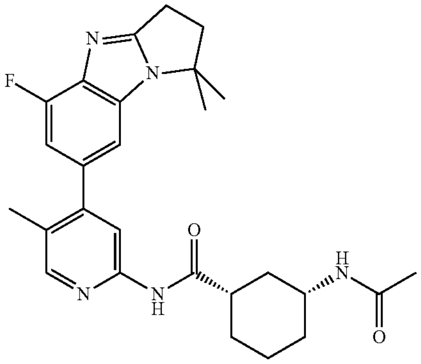 [SMILES: CC(=O)N[C@@H]1CCC[C@H](C(=O)Nc2cc(-c3cc(F)c4nc5n(c4c3)C(C)(C)CC5)c(C)cn2)C1] | (1S,3R)-3-acetamido-N-(4-(5-fluoro-1,1-dimethyl-2,3-dihydro-1H-benzo[d]pyrrolo[1,2-a]imidazol-7-yl)-5-methylpyridin-2-yl)cyclohexane-1-carboxamide |

TABLE A-continued

| Ex. | Structure | Chemical Name |
| --- | --- | --- |
| 24 | 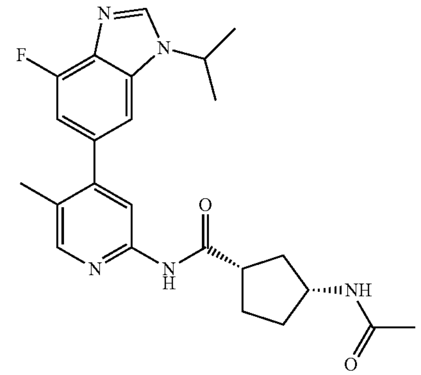 [SMILES: CC(=O)N[C@@H]1CC[C@H](C(=O)Nc2cc(-c3cc(F)c4ncn(C(C)C)c4c3)c(C)cn2)C1] | (1S,3R)-3-acetamido-N-(4-(4-fluoro-1-isopropyl-1H-benzo[d]imidazol-6-yl)-5-methylpyridin-2-yl)cyclopentane-1-carboxamide |
| 25 | 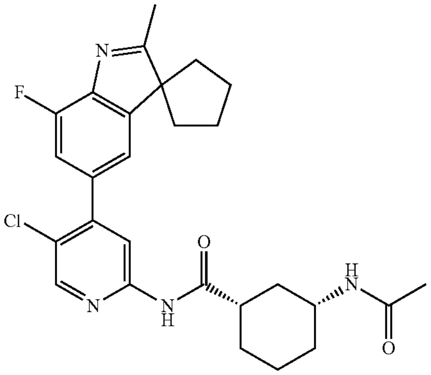 [SMILES: CC(=O)N[C@@H]1CCC[C@H](C(=O)Nc2cc(-c3cc(F)c4c(c3)C3(CCCC3)C(C)=N4)c(Cl)cn2)C1] | (1S,3R)-3-acetamido-N-(5-chloro-4-(7'-fluoro-2'-methylspiro[cyclopentane-1,3'-indol]-5'-yl)pyridin-2-yl)cyclohexane-1-carboxamide |
| 26 | 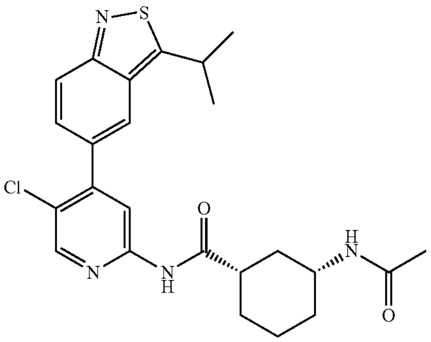 [SMILES: CC(=O)N[C@@H]1CCC[C@H](C(=O)Nc2cc(-c3ccc4nsc(C(C)C)c4c3)c(Cl)cn2)C1] | (1S,3R)-3-acetamido-N-(5-chloro-4-(3-isopropylbenzo[c]isothiazol-5-yl)pyridin-2-yl)cyclohexane-1-carboxamide |
| 27 | 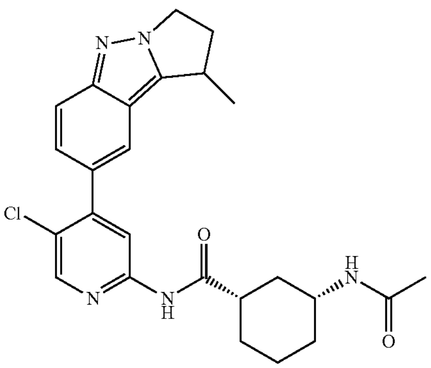 [SMILES: CC(=O)N[C@@H]1CCC[C@H](C(=O)Nc2cc(-c3ccc4nn5c(c4c3)C(C)CC5)c(Cl)cn2)C1] | (1S,3R)-3-acetamido-N-(5-chloro-4-(1-methyl-2,3-dihydro-1H-pyrrolo[1,2-b]indazol-8-yl)pyridin-2-yl)cyclohexane-1-carboxamide |

Synthesis

Compounds of the disclosure, including salts thereof, can be prepared using known organic synthesis techniques and can be synthesized according to any of numerous possible synthetic routes.

The reactions for preparing compounds of the disclosure can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures, which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography ("HPLC") or thin layer chromatography.

The expressions, "ambient temperature," "room temperature" "RT," and "r.t." as used herein, are understood in the art, and refer generally to a temperature, e.g. a reaction temperature, that is about the temperature of the room in which the reaction is carried out, for example, a temperature from about 20° C. to about 30° C.

Compounds of the disclosure can be prepared using numerous preparatory reactions known in the literature. The Schemes below provide general guidance in connection with preparing the compounds provided herein. One skilled in the art would understand that the preparations shown in the Schemes can be modified or optimized using general knowledge of organic chemistry to prepare various compounds. Example synthetic methods for preparing compounds are provided in the Schemes below.

General Schemes

Scheme I

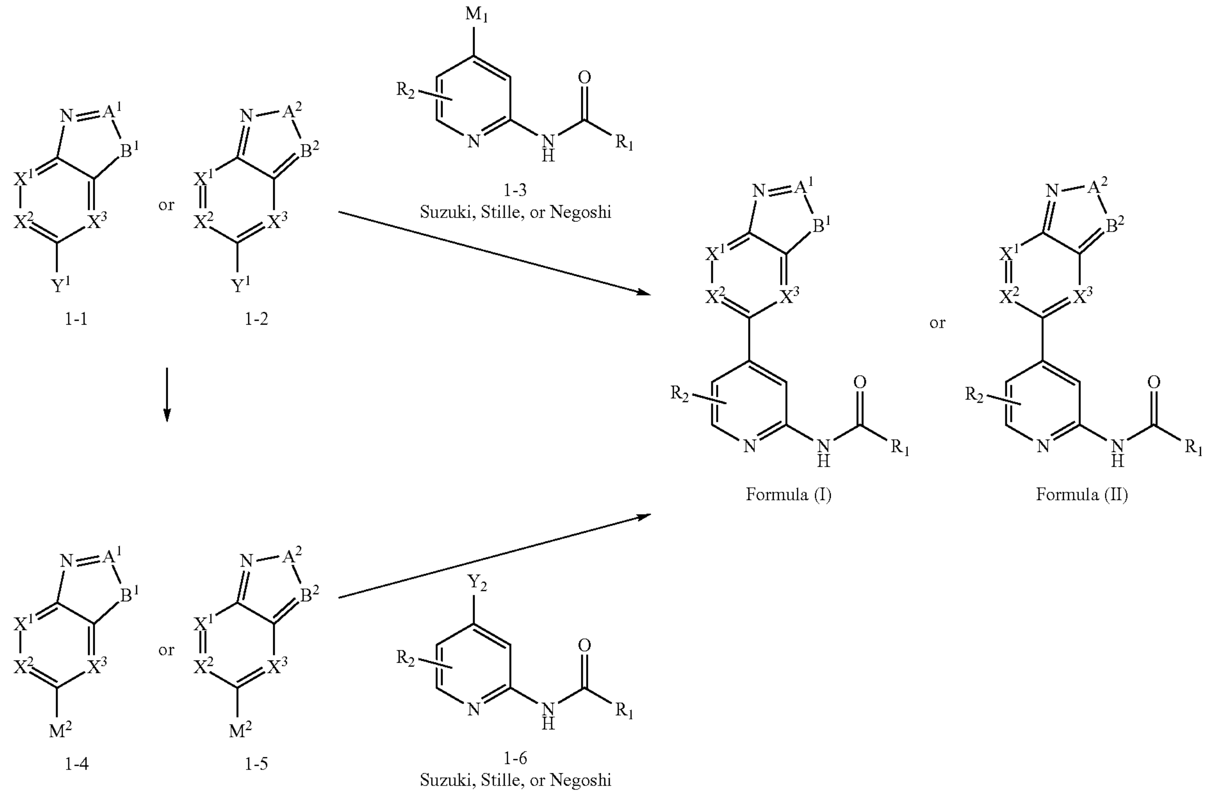

1-1 or 1-2; 1-3; Formula (I) or Formula (II); 1-4 or 1-5; 1-6

Compounds of Formula (I) or Formula (II) can be prepared from optionally protected bicycles or tricycles 1-1 or 1-2 where $Y^1$ is halogen (e.g., Cl, Br, or I) or pseudohalogen (e.g., OTf or OMs) as shown in Scheme I.1-1 or 1-2 can be coupled with 1-3, where $M^1$ is a boronic acid, boronate ester, potassium trifluoroborane, or an appropriately substituted metal, such as $Sn(Bu)_3$ or Zn, tinder standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis (triphenylphosphine)palladium(0) or [1,1'-bis (diphenylphosphino)ferrocene]dichloropalladium (II)), to give compounds of Formula (I) or Formula (II)

Alternatively, the 1-1 or 1-2 can be converted to an appropriate 1-4 or 1-5 (e.g., $M^2$ is $B(OH)_2$, Bpin, $BF_3K$, $Sn(Bu)_3$, or Zn) and then coupled to 1-6 where $Y^2$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base)) or standard Stille conditions (e.g., in the presence of a palladium(0) catalyst, such as tetrakis (triphenylphosphine)palladium(0)) or standard Negishi conditions (e.g., in the presence of a palladium(0) catalyst, such as tetrakis(triphenylphosphine)palladium(0) or [1,1'-bis(diphenylphosphino)ferrocene]dichloropalladium (II) to give to give compounds of Formula (I) or Formula (II).

Some intermediates for synthesizing compounds can be prepared as shown in Scheme II. Optionally substituted 2-aminopyridine 2-1, where $Y^2$ is a halogen (e.g., Cl, Br, or I), or pseudohalogen (e.g., OTf or OMs) can be coupled with Boc-protected amino acid 2-2 under standard amide formation conditions (e.g. treatment with an appropriate base, such as DIPEA or trimethylamine and in the presence of coupling agents, such as HATU. HOBt, or PyBOP). The $Y^2$ halo (e.g., Cl, Br, or I) or pseudohalo group (e.g., OTf or OMs) of 2-3 can be converted to an appropriate substituted metal 2-4 (e.g., $M^2$ is B(OH)z, Bpin, $BF_3K$, $Sn(Bu)_3$, or Zn) under standard conditions (e.g., in the presence of a diboron reagent, such as bis(pinacolato)diboron, a palladium catalyst, such as dichioro[bis(triphenyl phosphoranyl)]palladium or bis(diphenylphosphino)ferrocene]dichloropalladium(II), complex with dichloromethane, and a base, such as potassium acetate). Compounds 2-5 or 2-6 can be synthesized from intermediates 2-4 using the methods described in Scheme I. The Boc protecting groups on 2-5 or 2-6 can be removed under acidic conditions (e.g. TFA or HCl) to afford intermediates 2-7 or 2-8

Scheme II

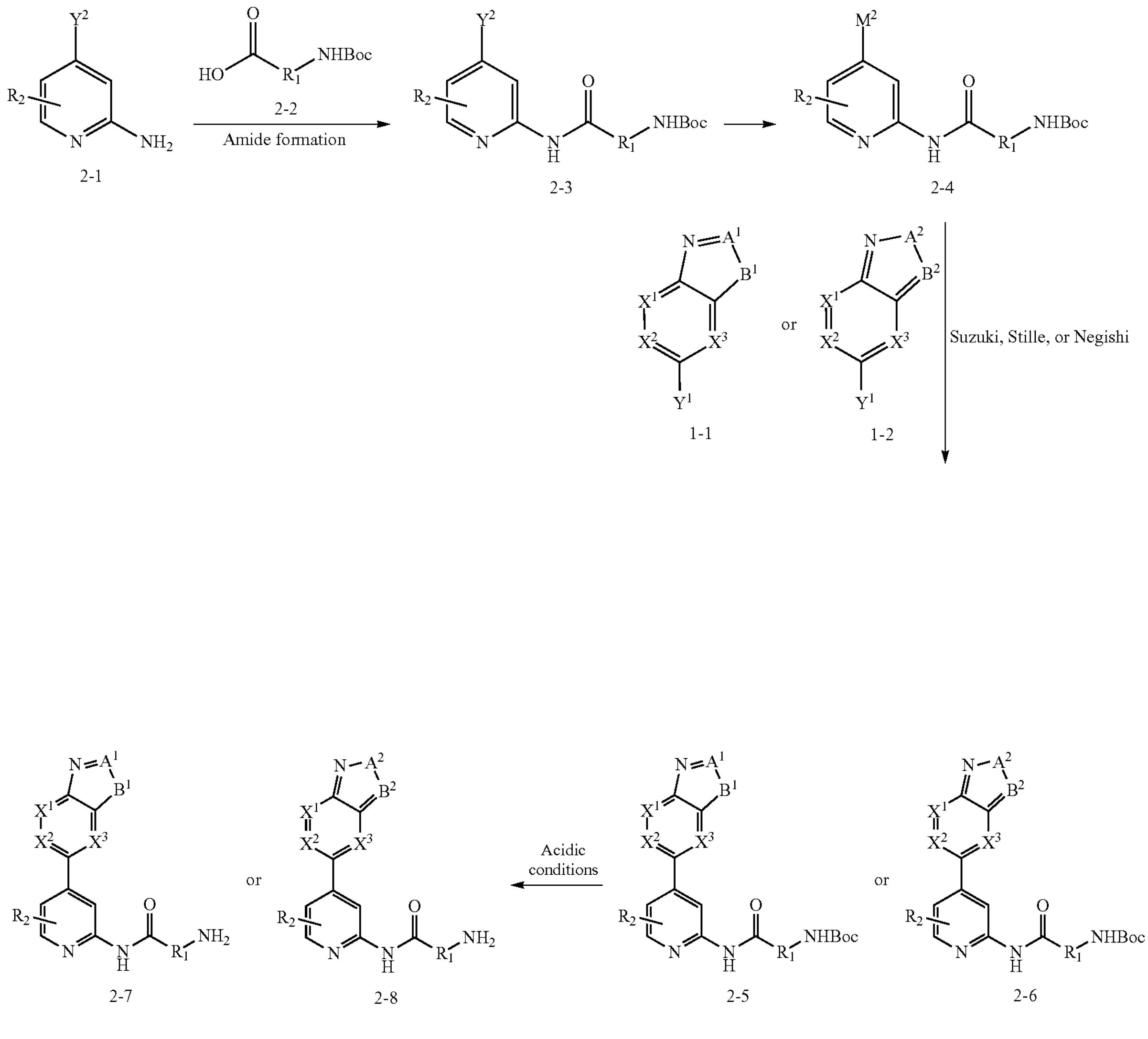

2-1, 2-2, 2-3, 2-4, 1-1 or 1-2, 2-7 or 2-8, 2-5 or 2-6

Scheme III

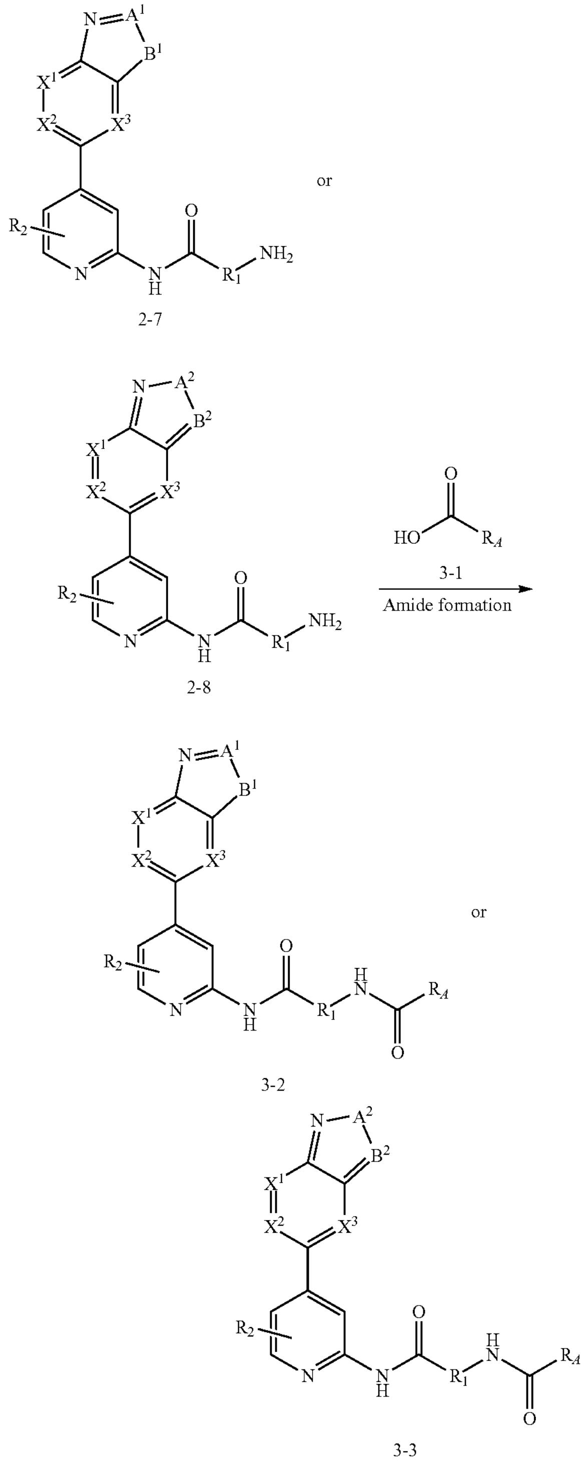

2-7 or 2-8

3-2 or 3-3

Some compounds of Formula (I) or Formula (II) can be prepared as shown in Scheme III. Intermediates 2-7 or 2-8 can be coupled with carboxylic acid 3-1 under standard amide formation conditions (e.g. treatment with an appropriate base, such as DIPEA or trimethylamine and in the presence of coupling agents, such as HATU, HOBt, or PyBOP) to afford compounds 3-2 or 3-3.

Scheme IV

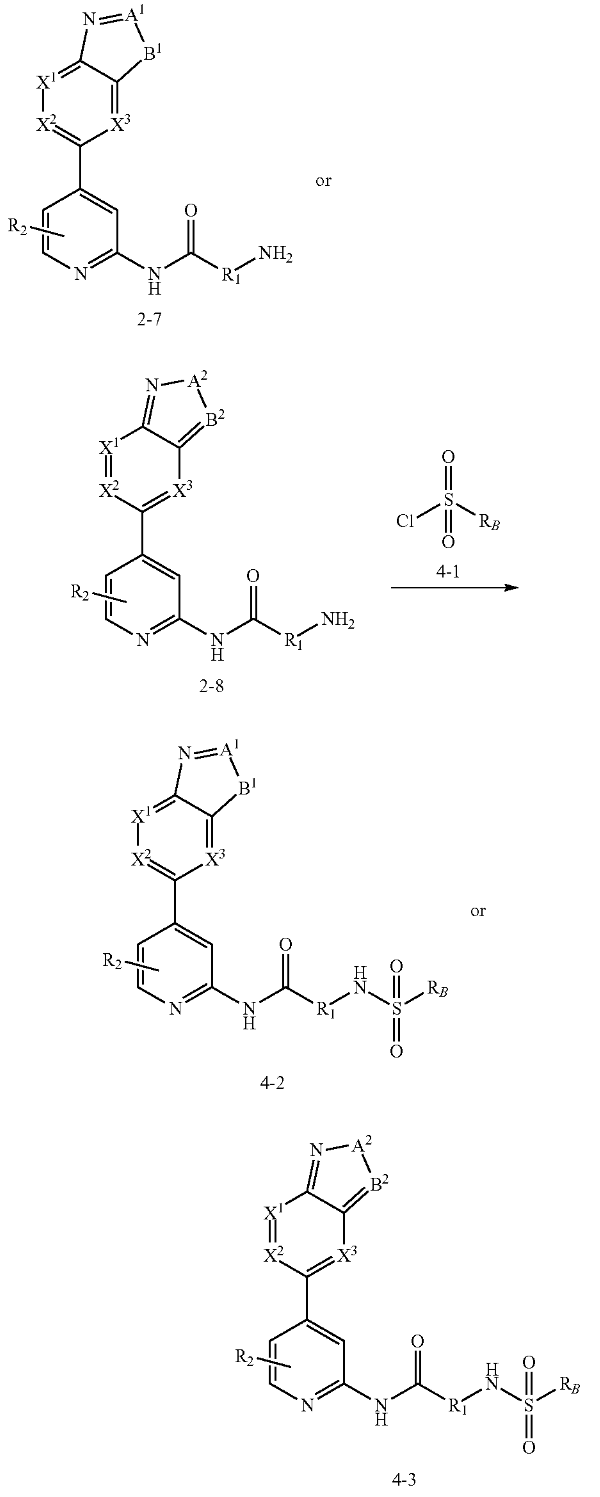

2-7 or 2-8

4-2 or 4-3

Some compounds of Formula (I) or Formula (II) can be prepared as shown in Scheme IV. Amine 2-7 or 2-8 can be coupled sulfonyl chloride 4-1 by various methods (e.g. treatment with an appropriate base, such as pyridine or trimethylamine and optionally with a catalyst such as 4-dimethylaminopyridine) to afford compounds 4-2 or 4-3.

Scheme V

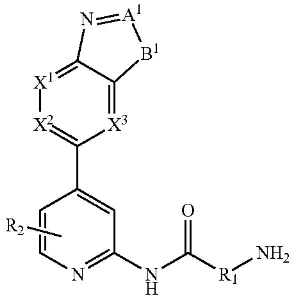

2-7 or

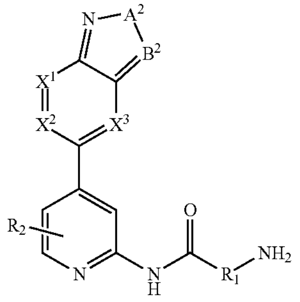

2-8

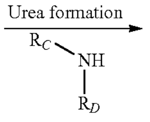

5-1

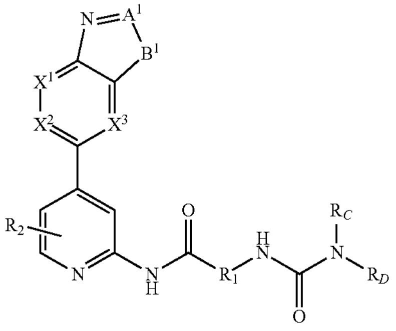

5-2 or

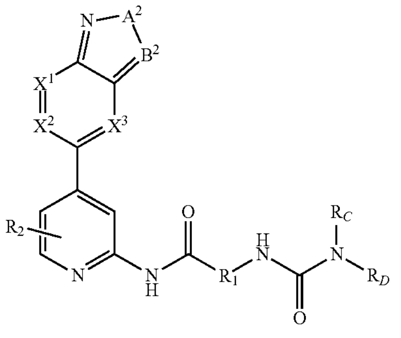

5-3

Some compounds of Formula (I) or Formula (II) can be prepared as shown in Scheme V. Intermediates 2-7 or 2-8 can be coupled with amine 5-1 under standard urea formation conditions (e.g. treatment of amine 2-7 or 2-8 with an appropriate base, such as DIPEA or trimethylamine and in the presence of coupling agents, such as CDI or triphosgene, followed by the addition of amine 5-1) to afford compounds 3-2 or 3-3.

Scheme VI

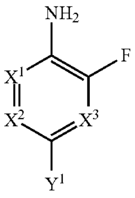

6-1

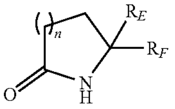

6-2

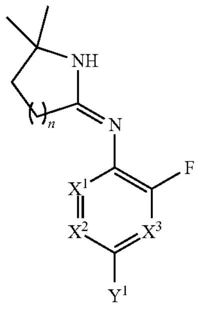

6-3

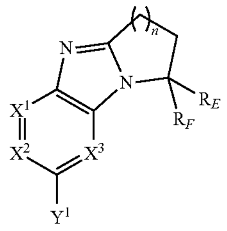

6-4

Some intermediates for making compounds can be prepared as shown in Scheme VI Optionally substituted aniline 6-1, where $Y^1$ is a halogen (e.g., Cl, Br, or I), or pseudohalogen (e.g., OTf or OMs) can be coupled with lactam 6-2 under the treatment with triethylamine and $POCl_3$ to afford compound 6-3. In the presence of a base, such as $Cs_2CO_3$, and $CuSO_4$, compound 6-3 can be converted to tricyclic product 6-4.

Scheme VII

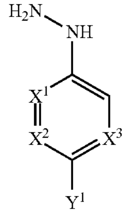

7-1

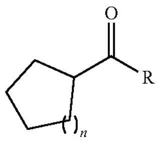

7-2

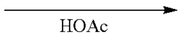

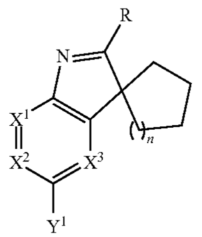

7-3

As is shown in scheme VII, intermediate 7-3 can be prepared by the coupling of hydrazine 7-1, where $Y^1$ is a halogen (e.g., Cl, Br, or I), or pseudohalogen (e.g., OTf or OMs), and ketone 7-2 under acidic conditions (e.g., HOAC as solvent).

Scheme VIII

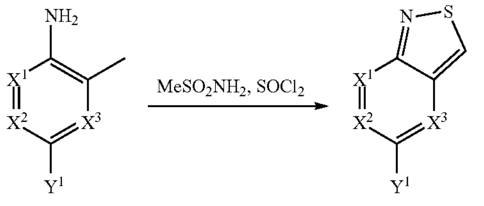

8-1 8-2

As is shown in scheme VIII, intermediate 8-2 can be prepared using aniline 8-1, where $Y^1$ is a halogen (e.g., Cl, Br, or I), or pseudohalogen (e.g., OTf or OMs), and ketone 7-2 under the treatment with $MeSO_2NH_2$ and $SOCl_2$.

Some intermediates for making compounds can be prepared as shown in Scheme IX. Halogenation of compound 9-1 with suitable reagents, such as N-chlorosuccinimide, N-bromosuccinimide, $Br_2$, or N-iodosuccinimide can give halide 9-2. The coupling between 9-2 and boronic ester 9-3 under standard Suzuki conditions (e.g., in the presence of a palladium catalyst, such as tetrakis(triphenylphosphine)palladium(0) or [1,1'-bis(diphenylphosphino)ferrocene]dichloropalladium (II), complex with dichloromethane and a base (e.g., a carbonate base) can give compound 9-4. The double bond in compound 9-4 can be reduced under standard hydrogenation conditions (e.g., in the presence of a catalyst, such as $PtO_2$ and 1-12) to afford compound 9-5.

Scheme IX

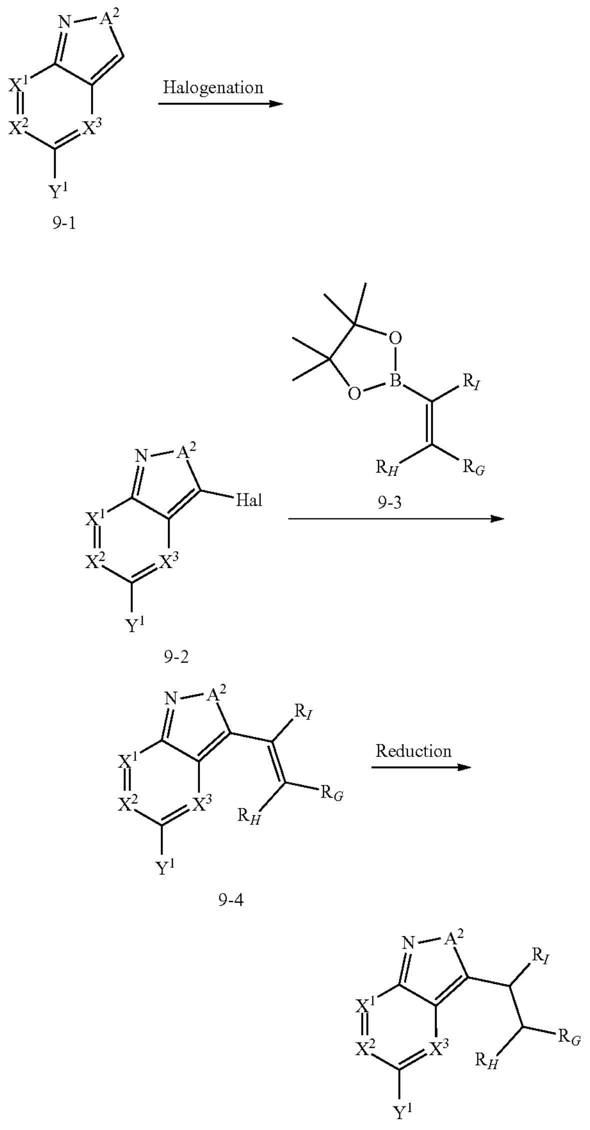

9-1 9-2 9-3 9-4 9-5

Scheme X

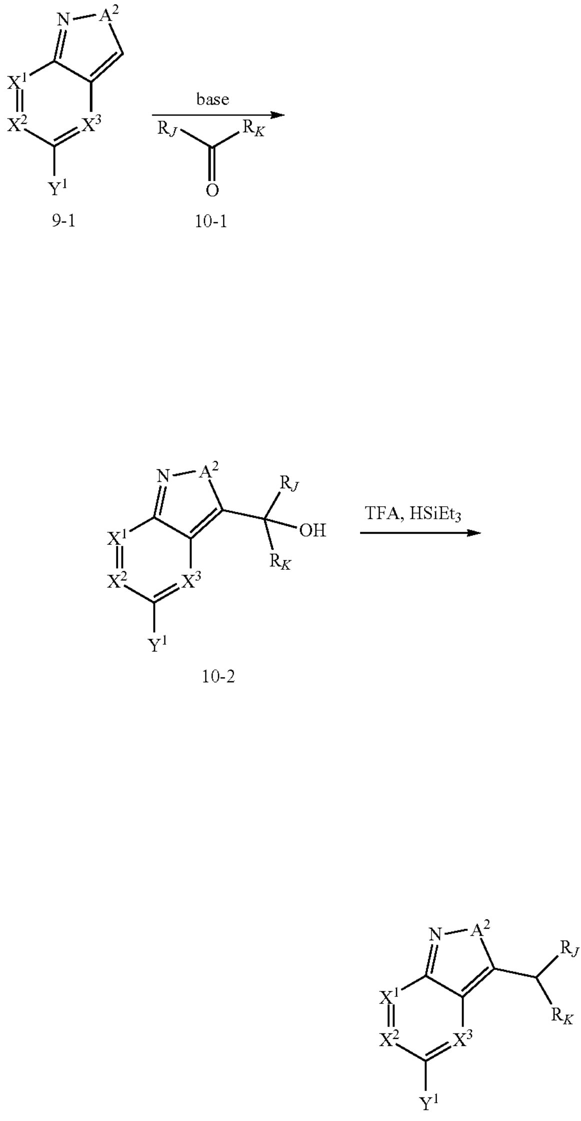

9-1 10-1 10-2 10-3

Some intermediates for making compounds can be prepared as shown in Scheme X. Coupling of compound 9-1 with ketone 10-1 in the presence of a suitable base, such as LDA can give alcohol 10-2. Deoxygenation of 10-2 using trifluoroacetice acid/triethylsilane can yield compound 10-3

Scheme XI

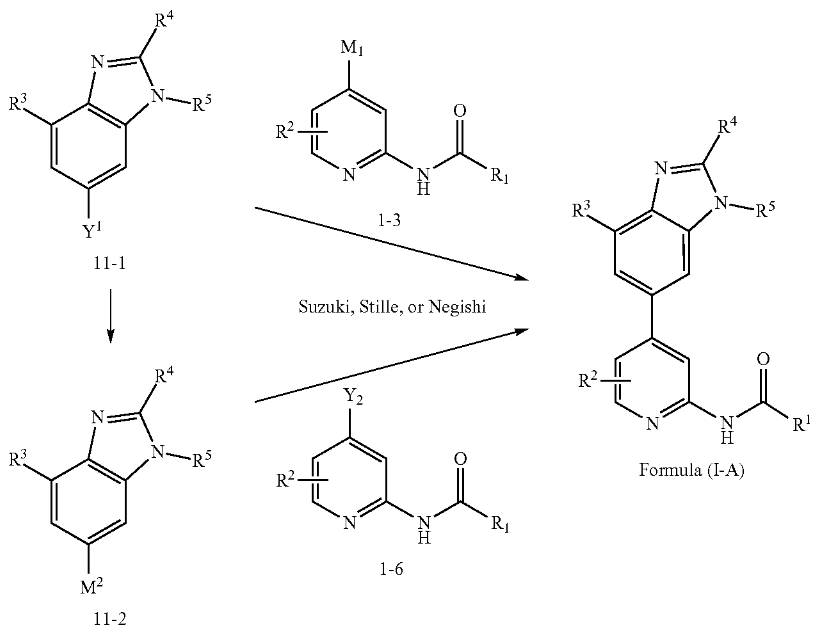

Compounds of Formula (I-A) can be prepared from optionally protected bicycles or tricycles 11-1 where $Y^1$ is halogen (e.g., Cl, Br, or I) or pseudohalogen (e.g., OTf or OMs) as shown in Scheme I. Compound 11-1 can be coupled with 1-3, where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]-dichloropalladium (11), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphe nylphosphine)palladium(0) or [1,1'-bis(diphenylphosphino) ferrocene]dichloropalladium (II)), to give compounds of Formula (I-A).

Alternatively, compound 11-1 can be converted to an appropriate compound 11-2 (e.g., $M^2$ is $B(OH)_2$, Bpin, $BF_3K$, $Sn(Bu)_3$, or Zn) and then coupled to 1-6 where $Y^2$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0) or [1,1'-bis(diphenylphosphino)ferrocene]dichloropalladium (11), complex with dichloro methane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine) palladium(O) or [1,1'-bis(diphenylphosphino)ferrocene]dichloropalladium (II)) to give to give compounds of Formula (I-A).

Scheme XII

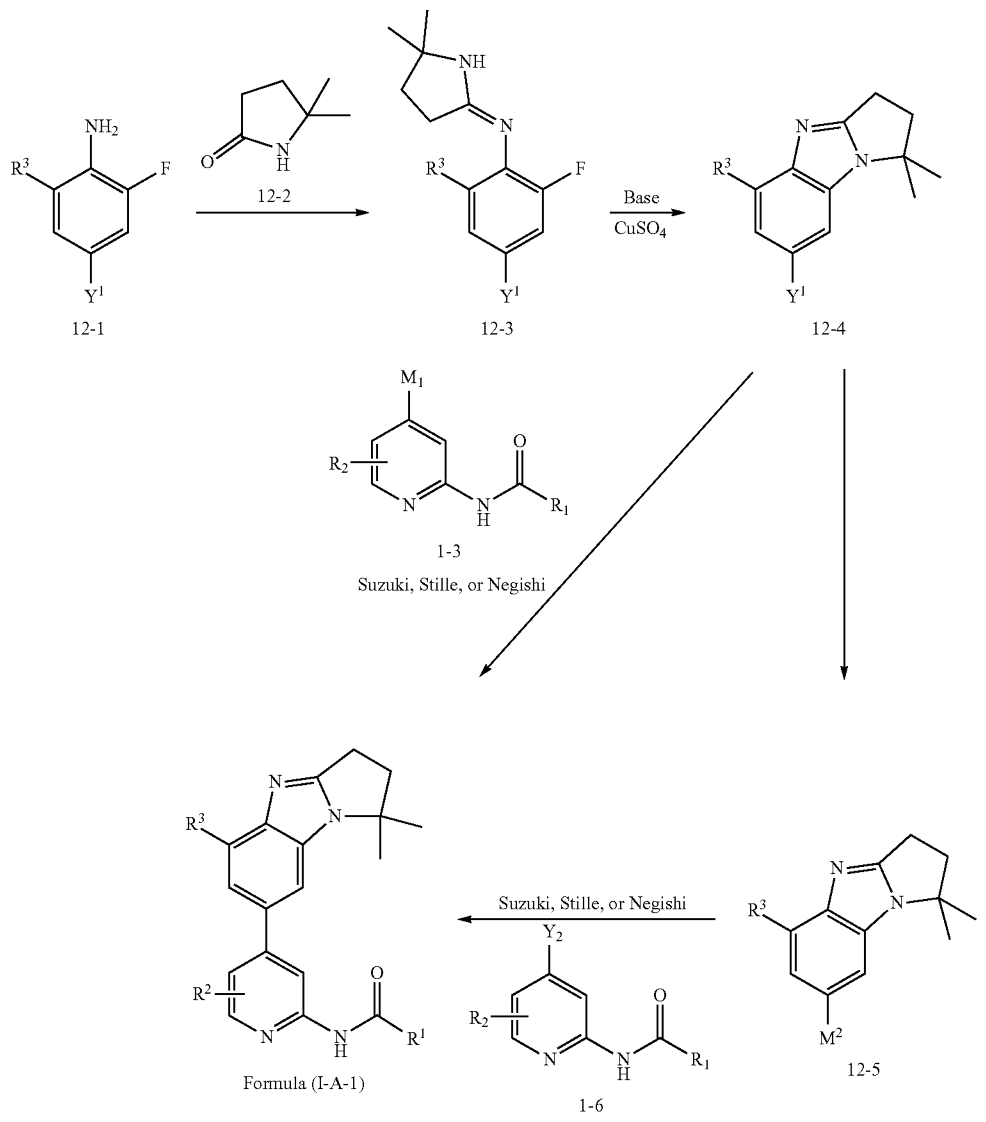

12-2, 12-1, 12-3, 12-4, 1-3, Formula (I-A-1), 1-6, 12-5

Compounds of Formula (XIII) can be prepared from compound 12-4 where $Y^1$ is halogen (e.g., Cl, Br, or 1) or pseudohalogen (e.g., OTf or OMs) as shown in Scheme XII. Optionally substituted aniline 12-1, where $Y^1$ is a halogen (e.g., Cl, Br, or I), or pseudohalogen (e.g., OTf or OMs) can be coupled with lactam 12-2 under the treatment with triethylamine and $POC_3$ to afford compound 12-3. In the presence of a base, such as $Cs_2CO_3$, and $CuSO_4$, compound 12-3 can be converted to tricyclic product 12-4. Compound 12-4 can be coupled with 1-3, where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]-dichloropalladium (II), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (II)), to give compounds of Formula (XIII).

Alternatively, compound 12-4 can be converted to an appropriate compound 12-5 (e.g., $M^2$ is $B(OH)_2$, Bpin, $BF_3K$, $Sn(Bu)_3$, or Zn) and then coupled to 1-6 where $Y^2$ is halogen (e.g., Cl, Br, or I) or pseudohalogen (e.g., OTf or OMs) under standard Suzuki conditions (e.g., in the presence of a Spalladium catalyst, such as tetrakis(triphenylphosphine)palladium(0) or [1,1'-bis(diphenylphosphino)ferrocene]dichloropalladium (11), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine)palladium(O) or [1,1'-bis(diphenylphosphino)ferrocene]dichloropalladium (II)) to give to give compounds of Formula (XIII).

Scheme XIII

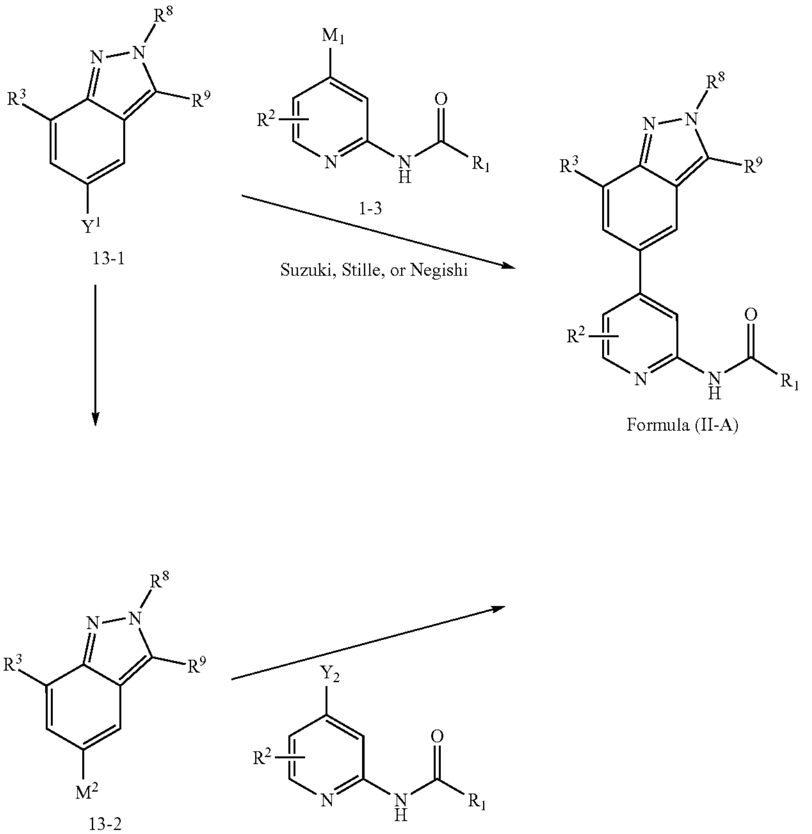

13-1

1-3

Formula (II-A)

13-2

1-6

Compounds of Formula (II-A) can be prepared from optionally protected bicycles or tricycles 13-1 where $Y^1$ is halogen (e.g., Cl, Br, or I) or pseudohalogen (e.g., OTf or OMs) as shown in Scheme I. Compound 13-1 can be coupled with 1-3, where $M^1$ is a boronic acid, boronate ester, potassium trifluoroborate, or an appropriately substituted metal, such as $Sn(Bu)_3$ or Zn, under standard Suzuki conditions (e.g., in the presence of a palladium catalyst, such as tetrakis(triphenylphosphine)palladium(0) or [1,1'-bis(diphenylphosphino)ferrocene]-dichloropalladium (I), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium (H)), to give compounds of Formula (H-A).

Alternatively, compound 13-1 can be converted to an appropriate compound 13-2 (e.g., $M^2$ is $B(OH)_2$, Bpin, $BF_3K$, $Sn(Bu)_3$, or Zn) and then coupled to 1-6 where $Y^2$ is halogen (e.g., Cl, Br, or I) or pseudohalogen (e.g., OTf or OMs) under standard Suzuki conditions (e.g., in the presence of a palladium catalyst, such as tetrakis(triphenylphosphine)palladium(0) or [1,1'-bis(diphenylphosphino)ferrocene]dichloropalladium (H), complex with dichloromethane and a base (e.g., a carbonate base)) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis(triphenylphosphine)palladium (O) or [1,1'-bis(diphenylphosphino)ferrocene]dichloropalladium (II)) to give to give compounds of Formula (II-A).

EXAMPLE COMPOUNDS

Example 1: (1S,3R)-3-acetamido-N-[5-chloro-4-(7-fluoro-3-isopropyl-2-methyl-indazol-5-yl)-2-pyridyl] cyclohexanecarboxamide

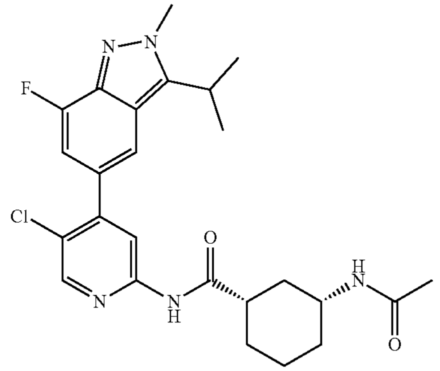 [SMILES: CC(=O)N[C@@H]1CCC[C@H](C(=O)Nc2cc(-c3cc(F)c4nn(C)c(C(C)C)c4c3)c(Cl)cn2)C1]

Step 1: 5-bromo-7-fluoro-3-iodo-2-methyl-indazole

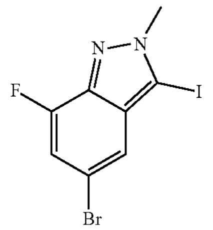

A 4 mL vial with septum containing a solution of 5-bromo-7-fluoro-2-methyl-2H-indazole (102 mg, 0.45 mmol) in dichloromethane ("DCM") (1 mL) under nitrogen ("$N_2$") was charged with pyridine (54 μL, 0.67 mmol) followed by (diacetoxyiodo)benzene (172 mg, 0.53 mmol). The reaction mixture was stirred at 30° C. for 30 min. The reaction mixture was charged with iodine (136 mg, 0.53 mmol) and stirred at 30° C. for 20 h. The reaction mixture was charged with additional pyridine (25 uL, 0.31 mmol) and (diacetoxyiodo)benzene (72 mg, 0.22 mmol), and stirred at 30° C. for 10 min. The mixture was then charged with iodine (56 mg, 0.22 mmol) and stirred at 30° C. for 2 h. The reaction mixture was diluted with water (30 mL), sat. $Na_2SO_3$ (5 mL), sat. $NaHCO_3$ (5 mL), and extracted with DCM (2×30 mL). The organic layer was dried over $Na_2SO_4$, filtered, concentrated under reduced pressure. The crude solids were rinsed with DCM (2×2 mL) and the liquid was purified by flash column chromatography ("FCC") (12 g $SiO_2$, 0→20% EtOAc in hexanes, wet-loaded in DCM). Fractions containing desired product were combined with leftover solids to yield 5-bromo-7-fluoro-3-iodo-2-methyl-indazole (146 mg, 0.41 mmol, 92% yield) as an off-white solid. Liquid chromatography-mass spectrometry ("LCMS") m/z calcd for $C_8H_6BrFIN_2$ $(M+H)^+$: 354.87/356.87; found: 354.9/356.9.

Step 2: 5-bromo-7-fluoro-3-isopropenyl-2-methyl-indazole

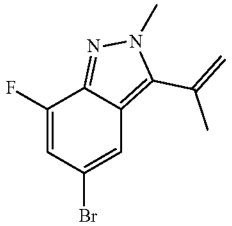

A 50 mL round-bottom flask ("RBF") with septum containing a mixture of 5-bromo-7-fluoro-3-iodo-2-methyl-indazole (720 mg, 2.03 mmol), 1,1'-bis(diphenylphosphino)ferrocene dichloropalladium (150 mg, 0.21 mmol), and potassium carbonate (727 mg, 5.26 mmol) under $N_2$ was charged with tetrahydrofuran ("THF") (12 mL) and water (6 mL). The reaction mixture was sparged with $N_2$ for 2 min, charged with 2-isopropenyl-4,4,5,5-tetramethyl-1,3,2-dioxaborolane (450 μL, 2.4 mmol), then stirred at 45° C. for 1 h. The reaction mixture was charged with additional 2-isopropenyl-4,4,5,5-tetramethyl-1,3,2-dioxaborolane (50 μL, 0.27 mmol) and 1,1'-bis(diphenylphosphino)ferrocene dichloropalladium (30 mg, 0.041 mmol), and was stirred at 45° C. for an additional 1 h. The reaction mixture was diluted with ethyl acetate ("EtOAc") (100 mL), and then washed with sat. $NaHCO_3$ (30 mL) and water (40 mL), water (70 mL), and brine (50 mL). The organic layer was dried over $Na_2SO_4$, filtered, concentrated under reduced pressure, and purified by FCC (40 g $SiO_2$, 0→20% EtOAc in hexanes, wet-loaded in DCM+hexanes). Fractions containing desired product were combined and concentrated under reduced pressure to yield 5-bromo-7-fluoro-3-isopropenyl-2-methyl-indazole (483 mg, 1.8 mmol, 88% yield) as a clear yellow/orange oil. LCMS m/z calcd for $C_{11}H_{11}BrFN_2$ $(M+H)^+$: 269.01/271.01; found: 269.0/271.0.

Step 3: 5-bromo-7-fluoro-3-isopropyl-2-methyl-indazole

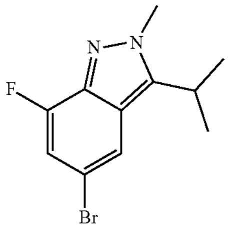

A 20 mL vial with septum containing a mixture of 5-bromo-7-fluoro-3-isopropenyl-2-methyl-indazole (472 mg, 1.75 mmol) and platinum(IV) oxide, anhydrous (14.4 mg, 0.063 mmol) under $N_2$ was charged with ethyl acetate (11 mL). The reaction mixture was sparged with $H_2$ for 1 min., kept under an $H_2$ balloon, and stirred at room temperature ("RT") for 2 h. The reaction mixture was filtered through 0.45 um Pefe filter ("PTFE") and concentrated to dryness. The product, 5-bromo-7-fluoro-3-isopropyl-2-methyl-indazole (1.75 mmol, 100% yield) was assumed to be 100% yield and used crude in subsequent reactions as a stock solution in dioxane. LCMS m/z calcd for $C_{11}H_{13}BrFN_2$ $(M+H)^+$: 271.02/273.02; found: 271.0/273.0.

Step 4: tert-butyl N-[(1R,3S)-3-[(4-bromo-5-chloro-2-pyridyl)carbamoyl]cyclohexyl]carbamate

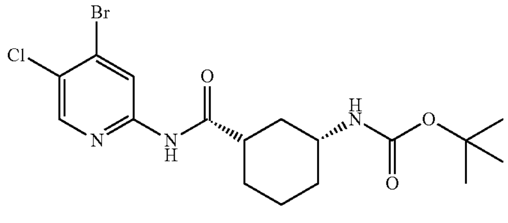

To a mixture of (1S,3R)-3-(tert-butoxycarbonylamino)cyclohexanecarboxylic acid (4.2 g, 17 mmol) in 120 mL of dry DCM at 0° C. was added 1-chloro-N,N,2-trimethylprop-1-en-1-amine (2.77 g, 20.7 mmol) dropwise. The mixture was stirred at room temperature for 1.5 h. Then 4-bromo-5-chloro-pyridin-2-amine (3.58 g, 17.3 mmol) and pyridine (1.68 mL, 20.7 mmol) were added sequentially. The resulting mixture was stirred at room temperature for 12 h. The volatiles were removed under reduced pressure, and the residue was dissolved in 150 mL ethyl acetate, washed with water (50 mL). The organic layer was dried over $Na_2SO_4$ and concentrated. The residue was purified on reverse phase high pressure liquid chromatography ("HPLC") (0.1% ammonia in water and methanol) to get tert-butyl N-[(1R,3 S)-3-[(4-bromo-5-chloro-2-pyridyl)carbamoyl]cyclohexyl] carbamate (4.8 g, 10.6 mmol, 61.6% yield) as a white solid. LCMS calcd. for $C_{13}H_{16}BrClN_3O_3[M+H-tBu]^+$ m/z=376.0; found: 376.0. Proton nuclear magnetic resonance ("$^1H$ NMR") (400 MHz, DMSO-$d_6$) δ 1.03-1.13 (m, 1H), 1.22-1.32 (m, 3H), 1.37 (s, 9H), 1.68-1.80 (m, 3H), 1.88 (d, J=12.0 Hz, 1H), 2.54-2.61 (m, 1H), 3.21-3.29 (m, 1H), 6.81 (d, J=8.0 Hz, 1H), 8.48 (s, 1H), 8.50 (s, 1H), 10.81 (s, 1H).

Step 5: (1S,3R)-3-amino-N-(4-bromo-5-chloropyridin-2-yl)cyclohexane-1-carboxamide

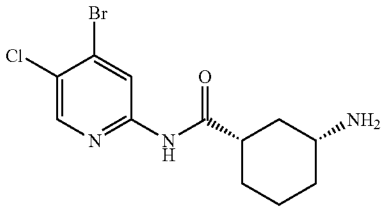 [SMILES: N[C@@H]1CCC[C@H](C(=O)Nc2cc(Br)c(Cl)cn2)C1]

To a mixture of tert-butyl N-[(1R,3 S)-3-[(4-bromo-5-chloro-2-pyridyl)carbamoyl]cyclohexyl]carbamate (500 mg, 1.16 mmol) in 10 mL of DCM was added TFA (0.88 mL, 11.55 mmol). The mixture was stirred at room temperature for 5 h. The volatiles were removed under reduced pressure to afford (1S,3R)-3-amino-N-(4-bromo-5-chloropyridin-2-yl)cyclohexane-1-carboxamide as its TFA salt (518 mg, 1.16 mmol, 100% yield). LCMS calcd. for $C_{12}H_{16}BrClN_3O$ $[M+H]^+$ m/z=332.01; found: 332.0.

Step 6: (1S,3R)-3-acetamido-N-(4-bromo-5-chloro-pyridin-2-yl)cyclohexane-1-carboxamide

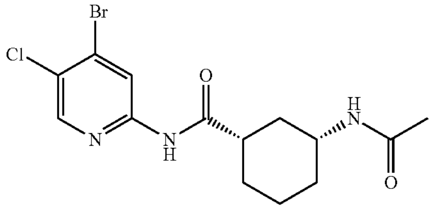 [SMILES: CC(=O)N[C@@H]1CCC[C@H](C(=O)Nc2cc(Br)c(Cl)cn2)C1]

To a mixture of (1S,3R)-3-amino-N-(4-bromo-5-chloro-2-pyridyl)cyclohexanecarboxamide; 2,2,2-trifluoroacetic acid (518 mg, 1.16 mmol) in 15 mL of dry DCM at 0° C. was added triethylamine (587 mg, 5.8 mmol), followed by acetic anhydride (142 mg, 1.39 mmol) dropwise. The mixture was stirred at 0° C. for 1 h. The volatiles were removed, and the residue was dissolved in 60 mL of ethyl acetate, washed with water (20 mL). The organic layer was dried over $Na_2SO_4$ and concentrated. The residue was purified on reverse phase HPLC (0.1% ammonia in water and methanol) to afford (1S,3R)-3-acetamido-N-(4-bromo-5-chloro-2-pyridyl)cyclohexanecarboxamide (361 mg, 0.96 mmol, 83% yield) as a white solid. LCMS calcd. for $C_{14}H_{18}BrClN_3O_2[M+H]^+$ m/z=374.02; found: 374.0. $^1H$ NMR (400 MHz, DMSO-$d_6$) δ 1.04-1.12 (m, 1H), 1.21-1.32 (m, 3H), 1.71-1.77 (m, 6H), 1.84-1.93 (m, 1H), 2.56-2.63 (m, 1H), 3.51-3.62 (m, 1H), 7.78 (d, J=7.6 Hz, 1H), 8.49 (s, 1H), 8.50 (s, 1H), 10.83 (s, 1H).

Step 7: [2-[[(1S,3R)-3-acetamidocyclohexanecarbonyl]amino]-5-chloro-4-pyridyl]boronic acid

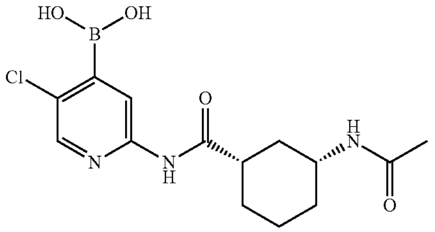 [SMILES: CC(=O)N[C@@H]1CCC[C@H](C(=O)Nc2cc(B(O)O)c(Cl)cn2)C1]

A 20 mL microwave vial with septum containing a mixture of (1S,3R)-3-acetamido-N-(4-bromo-5-chloro-2-pyridyl)cyclohexanecarboxamide (180 mg, 0.48 mmol), bis(pinacolato)diboron (128 mg, 0.50 mmol), [1,1'-bis(diphenylphosphino)ferrocene]dichloropalladium(II), complexed with dichloromethane (39 mg, 0.05 mmol), and potassium acetate (90 mg, 0.92 mmol) was charged with 1,4-dioxane (4.8 mL) and sparged with $N_2$ for 2 min. The reaction mixture was microwaved at 90° C. for 10 h. The black mixture was used crude and estimated as a 0.086 M solution of [2-[[(1S,3R)-3-acetamidocyclohexanecarbonyl]amino]-5-chloro-4-pyridyl]boronic acid (5 mL, 0.43 mmol, 90% yield). LCMS calcd for $C_{14}H_{20}BClN_3O_4(M+H)^+$ m/z: 340.12/342.12; found: 340.2/342.2.

Step 8: (1S,3R)-3-acetamido-N-[5-chloro-4-(7-fluoro-3-isopropyl-2-methyl-indazol-5-yl)-2-pyridyl] cyclohexanecarboxamide A 5 mL microwave vial with septum containing a mixture of sodium carbonate (42.0 mg, 0.40 mmol) and [1,1'-bis(diphenylphosphino)ferrocene]dichloropalladium(II), complex with dichloromethane (17 mg, 0.02 mmol) was charged with a stock solution of crude 5-bromo-7-fluoro-3-isopropyl-2-methyl-indazole (55 mg, 0.20 mmol) in 1,4-dioxane (350 μL), followed by a crude solution of [2-[[(1S,3R)-3-acetamidocyclohexanecarbonyl]amino]-5-chloro-4-pyridyl] boronic acid (2.5 mL, 0.23 mmol); 0.086 M in dioxane (2.5 mL, 0.215 mmol) and then water (850 μL). The reaction mixture was sparged with $N_2$ for 2 min, and then stirred at 90° C. for 2 h. The reaction mixture was concentrated to dryness under reduced pressure. The residue was extracted with acetonitrile (~7-8 mL total) with sonication, filtered through 0.45 um PTFE, and purified directly by prep-LCMS (5 m 10×3 cm Luna C18, 38→54% acetonitrile ("MeCN") in $H_2O$ (0.1% TFA), wet-loaded in MeCN). Fractions containing pure desired product were combined, partially concentrated under reduced pressure, and lyophilized to yield 98.2% pure desired product. This material was further purified by prep-HPLCMS (5 m 10×3 cm Luna C18, 38→54% MeCN in $H_2O$ (0.1% TFA), wet-loaded in MeCN). Fractions containing pure product were combined and lyophilized to yield (1S,3R)-3-acetamido-N-[5-chloro-4-(7-fluoro-3-isopropyl-2-methyl-indazol-5-yl)-2-pyridyl] cyclohexanecarboxamide as its TFA salt (38 mg, 0.053 mmol, 26% yield). LCMS calcd. for $C_{25}H_{30}ClFN_5O_2(M+H)^+$ m/z: 486.21/488.20; found: 486.3/488.3; $^1H$ NMR (500 MHz, DMSO-$d_6$) δ 10.69 (s, 1H), 8.45 (s, 1H), 8.22 (s, 1H), 7.80-7.71 (m, 2H), 7.11 (dd, J=1.3, 12.3 Hz, 1H), 4.17 (s, 3H), 3.64-3.49 (m, 2H), 2.69-2.56 (m, 1H), 1.89 (d, J=12.3 Hz, 1H), 1.83-1.69 (m, 6H), 1.45 (d, J=7.0 Hz, 6H), 1.34-1.22 (m, 3H), 1.13-1.02 (m, 1H);

Example 2: (1S,3R)—N-[5-chloro-4-(7-fluoro-3-isopropyl-2-methyl-indazol-5-yl)-2-pyridyl]-3-[(1-hydroxycyclopropanecarbonyl)amino]cyclohexan-ecarboxamide

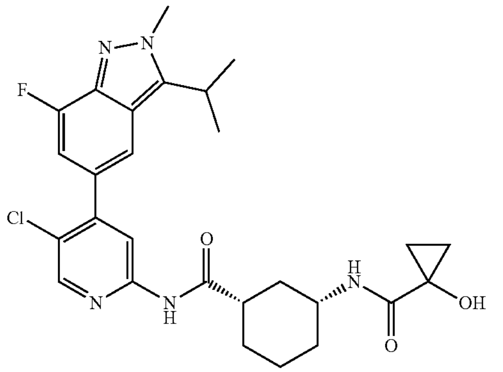 [SMILES: CC(C)c1c2cc(-c3cc(NC(=O)[C@H]4CCC[C@@H](NC(=O)C5(O)CC5)C4)ncc3Cl)cc(F)c2nn1C]

Step 1: [2-[[(1S,3R)-3-(tert-butoxycarbonylamino) cyclohexanecarbonyl]amino]-5-chloro-4-pyridyl] boronic acid

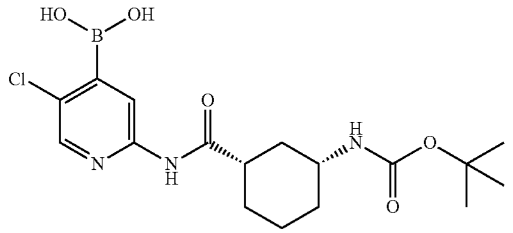 [SMILES: CC(C)(C)OC(=O)N[C@@H]1CCC[C@H](C(=O)Nc2cc(B(O)O)c(Cl)cn2)C1]

A heat-dried 20 mL microwave vial with septum containing a mixture of tert-butyl N-[(1R,3S)-3-[(4-bromo-5-chloro-2-pyridyl)carbamoyl]cyclohexyl]carbamate (prepared as in Example 1, Step 4, 500 mg, 1.16 mmol), bis(pinacolato)diboron (300 mg, 1.18 mmol), potassium acetate (224 mg, 2.28 mmol), and [1,1'-bis(diphenylphosphino)ferrocene]dichloropalladium(II), complex with dichloromethane (94 mg, 0.12 mmol) under $N_2$ was charged with 1,4-dioxane (11.4 mL) and sparged with $N_2$ for 2 min. The reaction mixture was stirred at 93° C. for 9.5 h. LCMS analysis shows consumption of SM, -90% formation of the desired boronic acid, with minor formation of proto-deborylation product. The black mixture was used crude and estimated as a 0.086 M solution of [2-[[(1S,3R)-3-(tert-butoxycarbonylamino)cyclohexanecarbonyl]amino]-5-chloro-4-pyridyl]boronic acid (12 mL, 1.03 mmol, 89% yield). LCMS calcd for $C_{17}H_{26}BClN_3O_5(M+H)^+$ m/z: 398.16/400.16; found: 398.3/400.3.

Step 2: tert-butyl N-[(1R,3S)-3-[[5-chloro-4-(7-fluoro-3-isopropyl-2-methyl-indazol-5-yl)-2-pyridyl] carbamoyl]cyclohexyl]carbamate

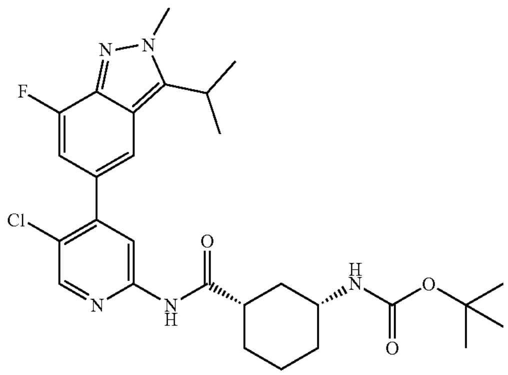 [SMILES: CC(C)c1c2cc(-c3cc(NC(=O)[C@H]4CCC[C@@H](NC(=O)OC(C)(C)C)C4)ncc3Cl)cc(F)c2nn1C]

A 20 mL microwave vial with septum containing a mixture of sodium carbonate (185 mg, 1.75 mmol) and [1,1'-bis(diphenylphosphino)ferrocene]dichloropalladium (II), complexed with dichloromethane (71 mg, 0.087 mmol) under $N_2$ was charged with a solution of 5-bromo-7-fluoro-3-isopropyl-2-methyl-indazole (prepared as in Example 1, Step 3, 238 mg, 0.88 mmol) in 1,4-dioxane (750 uL), followed by a crude solution of [2-[[(1S,3R)-3-(tert-butoxycarbonylamino)cyclohexanecarbonyl]amino]-5-chloro-4-pyridyl]boronic acid (1.04 mmol) in 1,4-dioxane (11.4 mL), and then water (3.9 mL). The reaction mixture was sparged with $N_2$ for 2 min, then microwaved at 90° C. for 2 h. The reaction mixture was diluted with EtOAc (100 mL), washed with sat. $NaHCO_3$ (30 mL) and water (30 mL), water (30 mL) and brine (30 mL), and brine (2×40 mL). The combined aqueous layers were back-extracted with EtOAc (30 mL), and then washed with brine (20 mL). The organic layers were combined and were dried over $Na_2SO_4$, filtered through cotton, concentrated under reduced pressure, and purified by FCC (40 g $SiO_2$, 0→40% EtOAc in DCM, wet-loaded in DCM, broad/tailing peaks). Fractions containing mostly desired product were combined and concentrated under reduced pressure and heat (~50° C.) to yield tert-butyl N-[(1R,3S)-3-[[5-chloro-4-(7-fluoro-3-isopropyl-2-methyl-indazol-5-yl)-2-pyridyl]carbamoyl]cyclohexyl] carbamate (500 mg, 0.92 mmol, 100% yield) as an orange foam. LCMS calcd for $C_{28}H_{36}ClFN_5O_3(M+H)^+$ m/z: 544.25/546.25; found: 544.3/546.3;

Step 3: (1S,3R)-3-amino-N-[5-chloro-4-(7-fluoro-3-isopropyl-2-methyl-indazol-5-yl)-2-pyridyl]cyclohexanecarboxamide

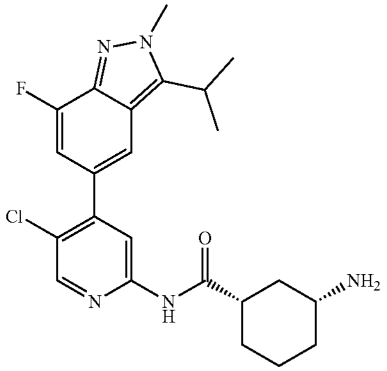 [SMILES: CC(C)c1c2cc(-c3cc(NC(=O)[C@H]4CCC[C@@H](N)C4)ncc3Cl)cc(F)c2nn1C]

A 50 mL round bottom flask with septum containing a solution of tert-butyl N-[(1R,3S)-3-[[5-5chloro-4-(7-fluoro-3-isopropyl-2-methyl-indazol-5-yl)-2-pyridyl]carbamoyl]cyclohexyl]carbamate (500 mg, 0.92 mmol) in ethyl acetate (10 mL) was charged with 12 M $HCl_{(aq)}$ (1.0 mL, 12 mmol). The reaction mixture was stirred at RT for 10 min. The reaction mixture was concentrated under reduced pressure and co-evaporated twice with dioxane to yield crude (1S,3R)-3-amino-N-[5-chloro-4-(7-fluoro-3-isopropyl-2-methyl-indazol-5-yl)-2-pyridyl]cyclohexanecarboxamide as its HCl salt (500 mg, 0.90 mmol, 98% yield). LCMS calcd. for $C_{23}H_{28}ClFN_5O$ $(M+H)^+$ m/z: 444.20/446.19; found: 444.1/446.1.

Step 4: (1S,3R)—N-[5-chloro-4-(7-fluoro-3-isopropyl-2-methyl-indazol-5-yl)-2-pyridyl]-3-[(1-hydroxycyclopropanecarbonyl)amino]cyclohexanecarboxamide A 4 mL vial with septum containing a solution of 1-hydroxy-1-cyclopropanecarboxylic acid (5.0 mg, 0.05 mmol, 3.3 eq) in N,N-dimethylformamide ("DMF") (0.15 mL) was charged with triethylamine (10 μL, 0.07 mmol, 4.8 eq) followed by a stock solution of HATU (17 mg, 0.04 mmol, 3 eq) in DMF (0.15 mL). The reaction mixture was stirred at RT for 15 min. The reaction mixture was then charged with a stock solution of (1S,3R)-3-amino-N-[5-chloro-4-(7-fluoro-3-isopropyl-2-methyl-indazol-5-yl)-2-pyridyl]cyclohexanecarboxamide; trihydrochloride (8.3 mg, 0.02 mmol, 1 eq) and triethylamine (10 μL, 0.07 mmol, 4.8 eq) in DMF, and stirred at RT for 3 h. The reaction mixture was diluted with water and MeOH, filtered through 0.45 um PTFE, and purified by prep-LCMS (5 m 10×3 cm Luna C18, 40→55% MeCN in $H_2O$ (0.1% TFA), wet-loaded). Fractions containing pure product were combined and lyophilized to yield (1S,3R)—N-[5-chloro-4-(7-fluoro-3-isopropyl-2-methyl-indazol-5-yl)-2-pyridyl]-3-[(1-hydroxycyclopropanecarbonyl)amino]cyclohexanecarboxamide as its TFA salt (4.1 mg, 0.0054 mmol, 36% yield). LCMS calcd. for $C_{27}H_{32}ClFN_5O_3$ $(M+H)^+$ m/z: 528.22/530.21; found: 528.4/530.3.

Examples in Table 1 were prepared using the procedure described in the synthesis of Example 2.

TABLE 1

| Example | Structure/Name | Calcd. $(M + H)^+$ m/z | Found $(M + H)^+$ m/z |
|---|---|---|---|
| 3 | 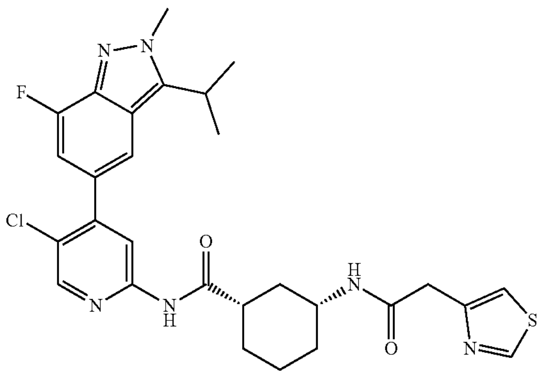 (1S,3R)-N-(5-chloro-4-(7-fluoro-3-isopropyl-2-methyl-2H-indazol-5-yl)pyridin-2-yl)-3-(2-(thiazol-4-yl)acetamido)cyclohexane-1-carboxamide | 569.2/571.2 | 569.3/571.3 |

TABLE 1-continued
| Example | Structure/Name | Calcd. (M + H)+ m/z | Found (M + H)+ m/z |
|---|---|---|---|
| 4 | 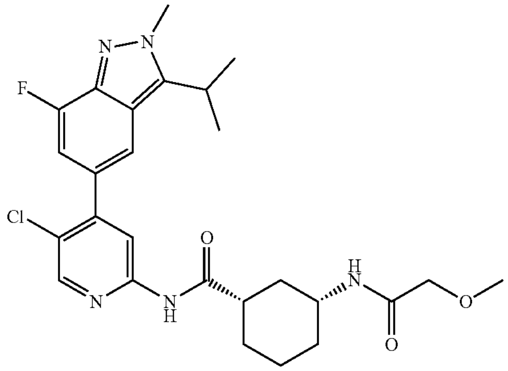 (1S,3R)-N-(5-chloro-4-(7-fluoro-3-isopropyl-2-methyl-2H-indazol-5-yl)pyridin-2-yl)-3-(2-methoxyacetamido)cyclohexane-1-carboxamide | 516.2/518.2 | 516.3/518.3 |
| 5 | 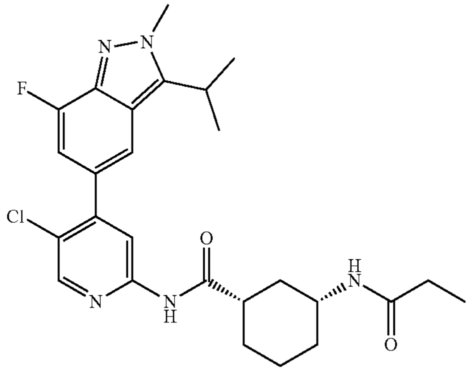 (1S,3R)-N-(5-chloro-4-(7-fluoro-3-isopropyl-2-methyl-2H-indazol-5-yl)pyridin-2-yl)-3-propionamido-cyclohexane-1-carboxamide | 500.2/502.2 | 500.4/502.3 |

Example 6: (1S,3R)—N-[5-chloro-4-(7-fluoro-3-isopropyl-2-methyl-indazol-5-yl)-2-pyridyl]-3-(methanesulfonamido)cyclohexanecarboxamide

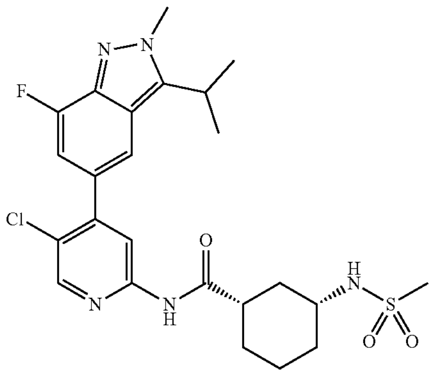 [SMILES: CC(C)c1c2cc(-c3cc(NC(=O)[C@H]4CCC[C@@H](NS(C)(=O)=O)C4)ncc3Cl)cc(F)c2nn1C]

A 4 mL vial with septum containing a solution of (1S,3R)-3-amino-N-[5-chloro-4-(7-fluoro-3-isopropyl-2-methyl-indazol-5-yl)-2-pyridyl]cyclohexanecarboxamide; trihydrochloride (prepared as in Example 2, Step 3, 8.2 mg, 0.01 mmol) in DMIF (0.15 mL) was charged with triethylamine (12 μL, 0.09 mmol) followed by a methanesulfonyl chloride (1.5 μL, 0.02 mmol). The reaction mixture was stirred at RT for 18 h. The reaction mixture was diluted with water and MeCN, filtered through 0.45 um PTFE, and purified by prep-HPLCMS (5 m 10×3 cm Luna C18, 40→55% MeCN in $H_2O$ (0.1% TFA), wet-loaded) to yield 99.3% pure (1S,3R)—N-[5-chloro-4-(7-fluoro-3-isopropyl-2-methyl-indazol-5-yl)-2-pyridyl]-3-(methanesulfonamido)cyclohexanecarboxamide as its TFA salt (5.9 mg, 0.0078 mmol, 53% yield). LCMS calcd for $C_{24}H_{30}ClFN_5O_3S$ $(M+H)^+$ m/z: 522.17/524.17; found: 522.1/524.1.

Example 7: N-[(1R,3S)-3-[[5-chloro-4-(7-fluoro-3-isopropyl-2-methyl-indazol-5-yl)-2-pyridyl]carbamoyl]cyclohexyl]morpholine-4-carboxamide

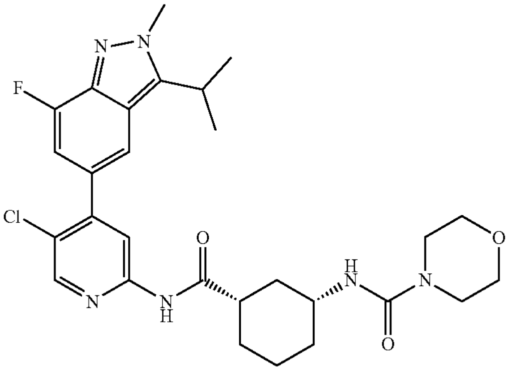 [SMILES: CC(C)c1c2cc(-c3cc(NC(=O)[C@H]4CCC[C@@H](NC(=O)N5CCOCC5)C4)ncc3Cl)cc(F)c2nn1C]

Step 1: N-[(1R,3S)-3-[[5-chloro-4-(7-fluoro-3-isopropyl-2-methyl-indazol-5-yl)-2-pyridyl]carbamoyl]cyclohexyl]imidazole-1-carboxamide

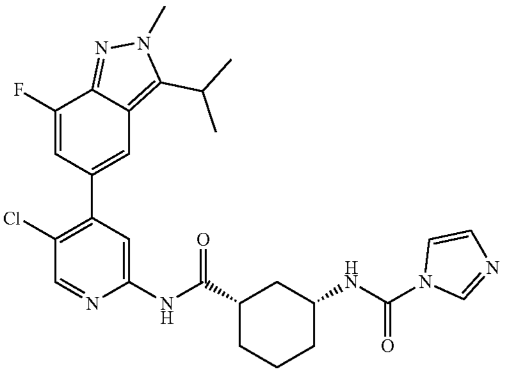 [SMILES: CC(C)c1c2cc(-c3cc(NC(=O)[C@H]4CCC[C@@H](NC(=O)n5ccnc5)C4)ncc3Cl)cc(F)c2nn1C]

A 4 mL vial with septum containing a solution of (1S,3R)-3-amino-N-[5-chloro-4-(7-fluoro-3-isopropyl-2-methyl-indazol-5-yl)-2-pyridyl]cyclohexanecarboxamide; trihydrochloride (prepared as in Example 2, Step 3, 42 mg, 0.08 mmol) in DMF (880 μL) charged with 1,1'-carbonyldiimidazole (25 mg, 0.15 mmol) followed by triethylamine (70 μL, 0.50 mmol). The reaction mixture was stirred at RT for 18 h. The reaction mixture was used as a crude solution of N-[(1R,3S)-3-[[5-chloro-4-(7-fluoro-3-isopropyl-2-methyl-indazol-5-yl)-2-pyridyl]carbamoyl]cyclohexyl]imidazole-1-carboxamide (40.838 mg, 100% yield) in DMF for subsequent reactions, assumed at 100% yield. LCMS calcd for $C_{27}H_{30}ClFN_7O_2$ $(M+H)^+$ m/z: 538.21/540.21; found: 538.2/540.2. HCH Step 2: N-[(1R,3S)-3-[[5-chloro-4-(7-fluoro-3-isopropyl-2-methyl-indazol-5-yl)-2-pyridyl]carbamoyl]cyclohexyl]morpholine-4-carboxamide A 4 mL vial with septum containing a crude solution N-[(1R,3S)-3-[[5-chloro-4-(7-fluoro-3-isopropyl-2-methyl-indazol-5-yl)-2-pyridyl]carbamoyl]cyclohexyl]imidazole-1-carboxamide (6.2 mg, 0.01 mmol, 1 equivalent ("eq") in DMF (200 μL) was charged with morpholine (10 μL, 0.12 mmol, 10 eq) and stirred at 40° C. for 2 h. The reaction mixture was diluted with water and MeCN, filtered through 0.45 um PTFE, and purified by prep-LCMS (5 m 10×3 cm Luna C18, 38→54% MeCN in $H_2O$ (0.1% TFA), wet-loaded) to yield N-[(1R,3S)-3-[[5-chloro-4-(7-fluoro-3-isopropyl-2-methyl-indazol-5-yl)-2-pyridyl]carbamoyl]cyclohexyl]morpholine-4-carboxamide as its TFA salt (4.9 mg, 0.0062 mmol, 54% yield). LCMS calcd. for $C_{28}H_{35}ClFN_6O_3(M+H)^+$ m/z: 557.24/559.24; found: 557.3/559.2.

Examples in Table 2 were prepared using the procedure described in the synthesis of Example 7.

TABLE 2

| Example | Structure/Name | Calcd. (M + H)+ m/z | Found (M + H)+ m/z |
|---|---|---|---|
| 8 | 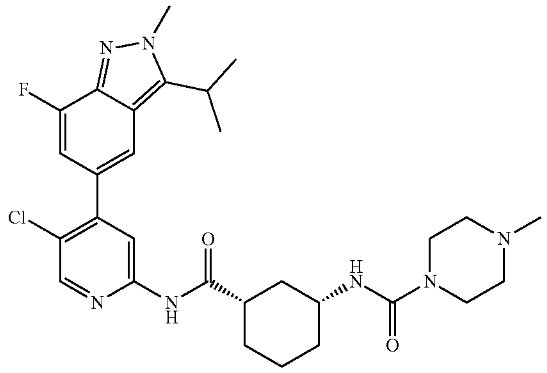 N-((1R,3S)-3-((5-chloro-4-(7-fluoro-3-isopropyl-2-methyl-2H-indazol-5-yl)pyridin-2-yl)carbamoyl)-cyclohexyl)-4-methylpiperazine-1-carboxamide | 570.3/572.3 | 570.3/572.3 |
| 9 | 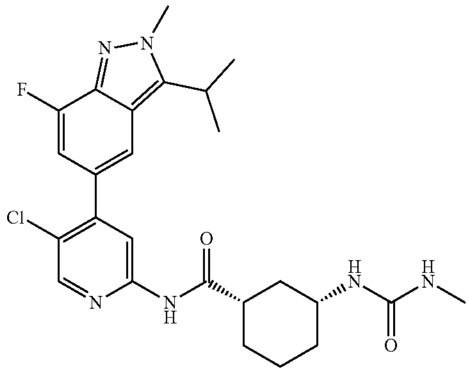 (1S,3R)-N-(5-chloro-4-(7-fluoro-3-isopropyl-2-methyl-2H-indazol-5-yl)pyridin-2-yl)-3-(3-methylureido) cyclohexane-1-carboxamide | 501.2/503.2 | 501.2/503.2 |
| 10 | 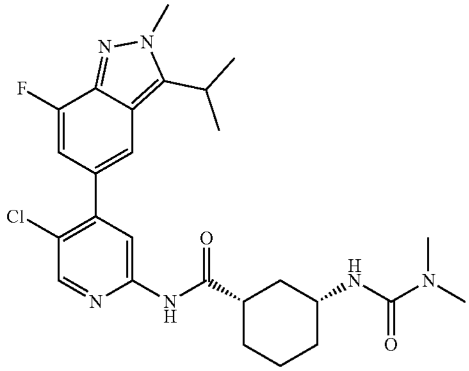 (1S,3R)-N-(5-chloro-4-(7-fluoro-3-isopropyl-2-methyl-2H-indazol-5-yl)pyridin-2-yl)-3-(3,3-dimethylureido) cyclohexane-1-carboxamide | 515.2/517.2 | 515.2/517.2 |

TABLE 2-continued

| Example | Structure/Name | Calcd. (M + H)+ m/z | Found (M + H)+ m/z |
| --- | --- | --- | --- |
| 11 | 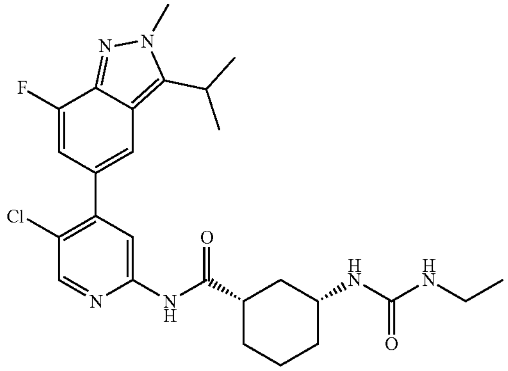 (1S,3R)-N-(5-chloro-4-(7-fluoro-3-isopropyl-2-methyl-2H-indazol-5-yl)pyridin-2-yl)-3-(3-ethylureido)cyclohexane-1-carboxamide | 515.2/517.2 | 515.2/517.2 |
| 12 | 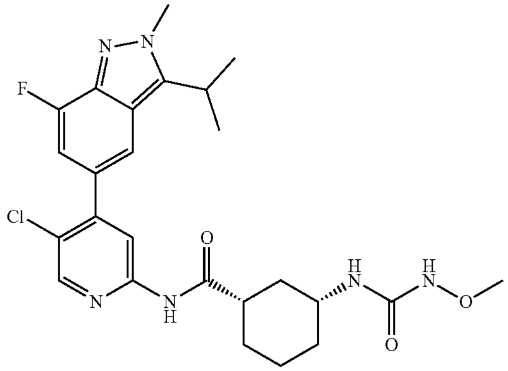 (1S,3R)-N-(5-chloro-4-(7-fluoro-3-isopropyl-2-methyl-2H-indazol-5-yl)pyridin-2-yl)-3-(3-methoxyureido)cyclohexane-1-carboxamide | 517.2/519.2 | 517.2/519.2 |

Example 13: (1S,3R)-3-acetamido-N-[5-chloro-4-(5-fluoro-1,1-dimethyl-2,3-dihydropyrrolo[1,2-a]benzimidazol-7-yl)-2-pyridyl]cyclohexanecarboxamide

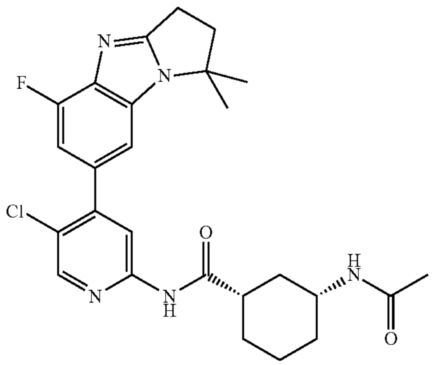 [SMILES: CC(=O)N[C@@H]1CCC[C@H](C(=O)Nc2cc(-c3cc(F)c4nc5n(c4c3)C(C)(C)CC5)c(Cl)cn2)C1]

Step 1: N-(4-bromo-2,6-difluoro-phenyl)-5,5-dimethyl-pyrrolidin-2-imine

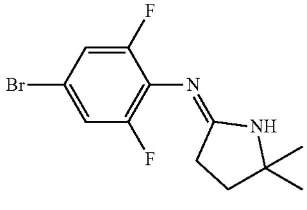 [SMILES: CC1(C)CC/C(=N\c2c(F)cc(Br)cc2F)N1]

To a solution of 4-bromo-2,6-difluoro-aniline (1.8 g, 8.65 mmol) and 5,5-dimethylpyrrolidin-2-one (1.08 g, 9.52 mmol) in Toluene (20 mL) was added triethyl amine ("TEA") (2.14 mL, 13 mmol) and $POCl_3$ (1.21 mL, 13 mmol), the mixture was stirred at 120° C. for 3 h under $N_2$. LCMS showed the reaction was completed. The reaction was concentrated in vacuum to dryness and the residue was extracted with DCM (3×100 ml). The combined organic layers were washed with water (2×100 mL), then brine (100 mL), dried over $MgSO_4$ and filtered. The filtrate was concentrated in vacuum to give crude product which was purified by column chromatography on silica gel eluting with MeOH in DCM from 1% to 5% to give N-(4-bromo- 2,6-difluoro-phenyl)-5,5-dimethyl-pyrrolidin-2-imine (2.0 g, 6.60 mmol, 76.2% yield) as a yellow oil. LCMS calcd. for $C_{12}H_{14}BrF_2N_2(M+H)^+$ m/z: 303.0/305.0; found: 303.0/305.0.

Step 2: 7-bromo-5-fluoro-1,1-dimethyl-2,3-dihydro-pyrrolo[1,2-a]benzimidazole

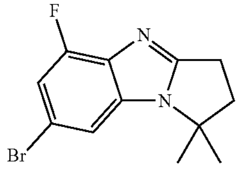 [SMILES: CC1(C)CCc2nc3c(F)cc(Br)cc3n21]

To a solution of N-(4-bromo-2,6-difluoro-phenyl)-5,5-dimethyl-pyrrolidin-2-imine (2.0 g, 6.6 mmol) in DMA (20 ml) was added $CuSO_4$ (1.05 g, 6.6 mmol) and $Cs_2CO_3$ (4.3 g, 13.2 mmol). The mixture was stirred at 210° C. for 10 h under $N_2$. The reaction was concentrated in vacuum to dryness and the residue was extracted with EtOAc (3×100 mL). The combined organic layers were washed with water (2×100 mL), then saturated brine solution (100 mL), dried with $MgSO_4$ and filtered. The filtrate was concentrated in vacuum to give crude product which was purified by column chromatography on silica gel eluting MeOH in DCM from 1% to 5% to give 7-bromo-5-fluoro-1,1-dimethyl-2,3-dihydropyrrolo[1,2-a]benzimidazole (1.32 g, 4.15 mmol, 62.9% yield) as a brown solid. LCMS calcd. for $C_{12}H_{13}BrFN_2$ (M+H)$^+$ m/z: 283.0/285.0; found: 283.0/285.0. $^1$H NMR (400 MHz, DMSO-$d_6$) δ 7.76 (d, J=1.6 Hz, 1H), 7.26-7.23 (m, 1H), 3.04-3.00 (m, 2H), 2.51-2.49 (m, 2H), 1.60 (s, 6H).

Step 3: 5-fluoro-1,1-dimethyl-7-(4,4,5,5-tetramethyl-1,3,2-dioxaborolan-2-yl)-2,3-dihydropyrrolo[1,2-a]benzimidazole

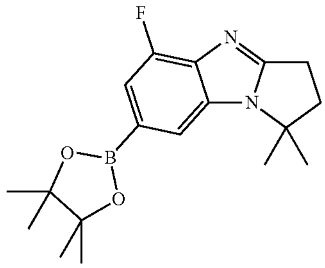 [SMILES: CC1(C)CCc2nc3c(F)cc(B4OC(C)(C)C(C)(C)O4)cc3n21]

To a mixture of 7-bromo-5-fluoro-1,1-dimethyl-2,3-dihydropyrrolo[1,2-a]benzimidazole (300 mg, 1.06 mmol) in 1,4-dioxane (10 mL) was added bis(pinacolato)diboron (430 mg, 1.7 mmol), KOAc (311 mg, 3.18 mmol) and Pd(dppf)$Cl_2$ (138 mg, 0.21 mmol) at rt, the mixture was stirred at 100° C. under $N_2$ for 16 h. The reaction was concentrated to dryness and the residue was taken up in EtOAc (30 mL). The organic layer was washed with water (2×10 mL) and brine (1×10 mL), dried over $MgSO_4$ and concentrated to dryness. The crude residue was then purified by flash column chromatography, eluting with 10~30% EtOAc in isohexanes to give 5-fluoro-1,1-dimethyl-7-(4,4,5,5-tetramethyl-1,3,2-dioxaborolan-2-yl)-2,3-dihydropyrrolo[1,2-a]benzimidazole (235 mg, 0.67 mmol, 63% yield) as a white solid. LCMS calcd. for $C_{18}H_{25}BFN_2O_2(M+H)^+$ m/z: 331.2; found: 331.2. $^1$H NMR (400 MHz, DMSO-$d_6$) δ 7.61 (s, 1H), 7.17-7.15 (m, 1H), 3.07-3.04 (m, 2H), 2.54-2.51 (m, 2H), 1.6-1.60 (m, 6H), 1.32 (s, 12H).

Step 4: (1S,3R)-3-acetamido-N-[5-chloro-4-(5-fluoro-1,1-dimethyl-2,3-dihydropyrrolo[1,2-a]benzimidazol-7-yl)-2-pyridyl]cyclohexanecarboxamide A microwave tube containing tetrakis(triphenylphosphine)palladium(0) (3.7 mg, 3.2 μmol) in 1,4-dioxane (1 mL) and water (0.25 mL) was charged with (1S,3R)-3-acetamido-N-(4-bromo-5-chloro-2-pyridyl)cyclohexanecarboxamide (prepared as in Example 1, Step 6, 12.0 mg, 0.03 mmol) and 1,1-dimethyl-7-(4,4,5,5-tetramethyl-1,3,2-dioxaborolan-2-yl)-2,3-dihydropyrrolo[1,2-a]benzimidazole (10.0 mg, 0.03 mmol). The reaction mixture was sparged with nitrogen for 10 mins. The reaction was charged with sodium carbonate (6.8 mg, 0.06 mmol) and sparged with nitrogen for additional 5 mins. The reaction tube was capped and heated in the microwave reactor for 1 h. The reaction mixture was filtered through Celite, concentrated under reduced pressure, and the crude residue was purified by C-18 reverse phase chromatography using 5-95% ACN in water using 0.1% TFA as modifier to give (1S,3R)-3-acetamido-N-[5-chloro-4-(1,1-dimethyl-2,3-dihydropyrrolo[1,2-a]benzimidazol-7-yl)-2-pyridyl]cyclohexanecarboxamide; 2,2,2-trifluoroacetic acid (8 mg, 0.013 mmol, 42% yield)). LCMS calcd. for $C_{26}H_{30}ClFN_5O_2(M+H)^+$ m/z: 498.2; found: 498.3. $^1$H NMR (500 MHz, Acetonitrile-$d_3$) δ 8.95 (s, 1H), 8.45 (s, 1H), 8.31 (s, 1H), 7.79 (s, 1H), 7.44 (dd, J=1.2, 11.0 Hz, 1H), 6.65 (d, J=8.1 Hz, 1H), 3.76 (dt, J=3.8, 7.8 Hz, 1H), 3.45 (t, J=7.6 Hz, 2H), 2.77 (t, J=7.6 Hz, 2H), 2.61 (s, 1H), 2.15-2.05 (m, 1H), 1.92 (s, 6H), 1.78 (s, 6H), 1.52-1.28 (m, 3H), 1.20 (m, 1H).

Example 14: (1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(2-cyanoacetamido)cyclohexane-1-carboxamide

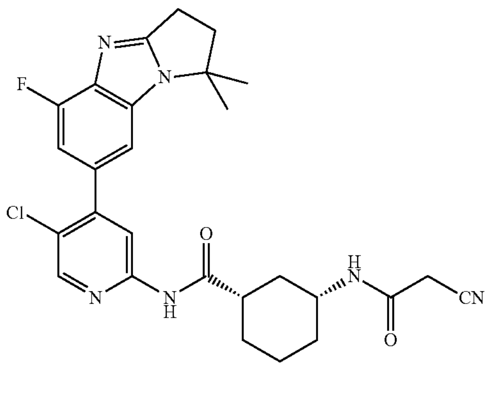 [SMILES: CC1(C)CCc2nc3c(F)cc(-c4cc(NC(=O)[C@H]5CCC[C@@H](NC(=O)CC#N)C5)ncc4Cl)cc3n21]

Step 1: (1S,3R)-3-amino-N-(5-chloro-4-(5-fluoro-1,1-dimethyl-2,3-dihydro-1H-benzo[d]pyrrolo[1,2-a]imidazol-7-yl)pyridin-2-yl)cyclohexane-1-carboxamide

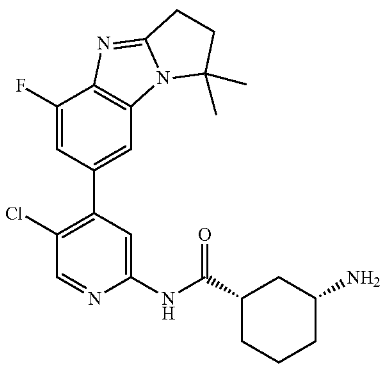 [SMILES: CC1(C)CCc2nc3c(F)cc(-c4cc(NC(=O)[C@H]5CCC[C@@H](N)C5)ncc4Cl)cc3n21]

A microwave tube containing sodium carbonate (27.9 mg, 0.26 mmol)) in 1,4-dioxane (4 mL) and water (0.50 mL) was charged with tert-butyl N-[3-[(4-bromo-5-chloro-2-pyridyl)carbamoyl]cyclohexyl]carbamate (prepared as in Example 1, Step 4, (114 mg, 0.26 mmol)), and 5-fluoro-1,1-dimethyl-7-(4,4,5,5-tetramethyl-1,3,2-dioxaborolan-2-yl)-2,3-dihydropyrrolo[1,2-a]benzimidazole (prepared as in Example 13, Step 3, (87 mg, 0.26 mmol). The reaction mixture was sparged with nitrogen for 10 mins. The reaction mixture was charged with dichloro-1,1'-bisdiphenylphosphino)ferrocene palladium (II) dichloromethane (216 mg, 0.26 mmol) and sparged with $N_2$ for additional 5 mins. The reaction tube was capped and heated in a microwave reactor for 1 h at 50° C. The reaction mixture was filtered through Celite®, concentrated, and the crude residue was purified by silica gel chromatography using 0-30% EtOAc in DCM to give the Boc protected amine. The product was dissolved in ethyl acetate (2 mL) and treated with 0.5 mL of conc HCl. The reaction mixture was stirred at RT for 30 mins, and concentrated under vacuum, azeotroped with 1,4-dioxane to give (1S,3R)-3-amino-N-(5-chloro-4-(5-fluoro-1,1-dimethyl-2,3-dihydro-1H-benzo[d]pyrrolo[1,2-a]imidazol-7-yl)pyridin-2-yl)cyclohexane-1-carboxamide as its HCl salt (110 mg, 0.22 mmol, 85% yield). LCMS calcd. for $C_{24}H_{28}ClFN_5O$ $(M+H)^+$ m/z: 456.2; found:456.2.

Step 2: (1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(2-cyanoacetamido)cyclohexane-1-carboxamide The title compound was prepared using procedures analogous to those described for Example 2, Step 4, using appropriate starting materials. LCMS calcd. for $C_{27}H_{29}ClFN_6O_2$ $(M+H)^+$ m/z: 523.2; found: 523.3.

Examples in Table 3 were prepared using the procedure described in the synthesis of Example 14.

TABLE 3

| Example | Structure/Name | Calcd. $(M + H)^+$ m/z | Found $(M + H)^+$ m/z |
|---|---|---|---|
| 15 | 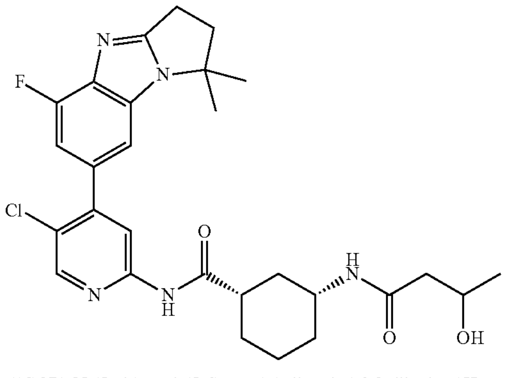 (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(3-hydroxybutanamido)cyclohexane-1-carboxamide | 542.2 | 542.3 |

TABLE 3-continued

| Example | Structure/Name | Calcd. (M + H)+ m/z | Found (M + H)+ m/z |
|---|---|---|---|
| 16 | 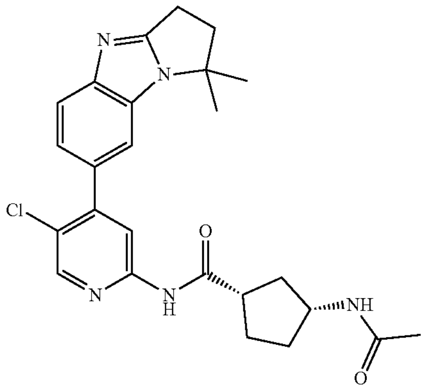 (1S,3R)-3-acetamido-N-(5-chloro-4-(1,1-dimethyl-2,3-dihydro-1H-benzo[d]pyrrolo[1,2-a]imidazol-7-yl) pyridin-2-yl)cyclopentane-1-carboxamide | 466.2 | 466.3 |
| 17 | 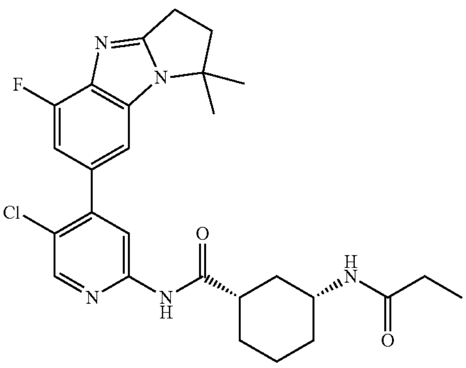 (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-propionamidocyclohexane-1-carboxamide | 512.2 | 512.3 |
| 18 | 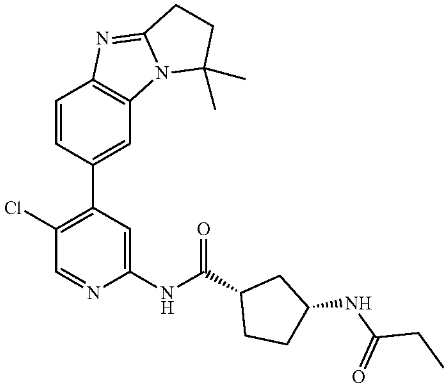 (1S,3R)-N-(5-chloro-4-(1,1-dimethyl-2,3-dihydro-1H-benzo[d]pyrrolo[1,2-a]imidazol-7-yl)pyridin-2-yl)-3-propionamidocyclopentane-1-carboxamide | 480.2 | 480.3 |

TABLE 3-continued

| Example | Structure/Name | Calcd. (M + H)$^+$ m/z | Found (M + H)$^+$ m/z |
|---|---|---|---|
| 19 | 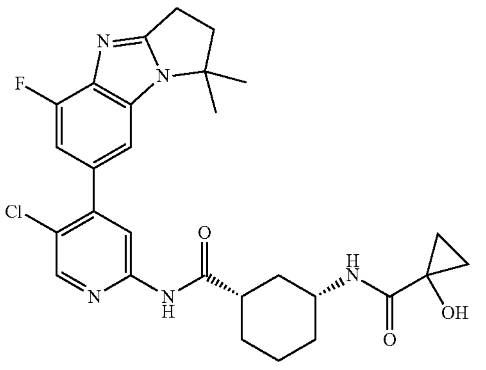 (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(1-hydroxycyclopropane-1-carboxamido)cyclohexane-1-carboxamide | 540.2 | 540.3 |
| 20 | 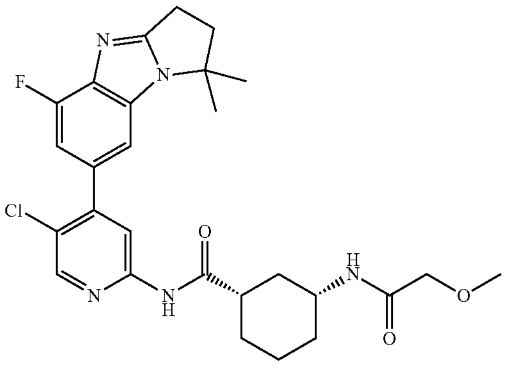 (1S,3R)-N-(5-chloro-4-(5-fluoro-1,1-dimethyl-2,3-dihydro-1H-benzo[d]pyrrolo[1,2-a]imidazol-7-yl)pyridin-2-yl)-3-(2-methoxyacetamido)cyclohexane-1-carboxamide | 528.2 | 528.3 |

Example 21: (1S,3R)—N-(5-chloro-4-(5-fluoro-1,1-dimethyl-2,3-dihydro-1H-benzo[d]pyrrolo[1,2-a]imidazol-7-yl)pyridin-2-yl)-3-(methylsulfonamido)cyclohexane-1-carboxamide

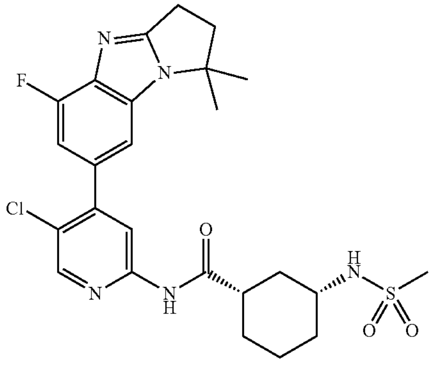 [SMILES: CC1(C)CCc2nc3c(F)cc(-c4cc(NC(=O)[C@H]5CCC[C@@H](NS(C)(=O)=O)C5)ncc4Cl)cc3n21]

The title compound was prepared using procedures analogous to those described for Example 6, with appropriate starting materials. LCMS calcd. for $C_{25}H_{30}ClFN_5O_3S$ (M+H)$^+$ m/z=534.2; found: 534.3.

Example 22: (1S,3R)-3-acetamido-N-(4-(4-fluoro-1-isopropyl-1H-benzo[d]imidazol-6-yl)-5-methylpyridin-2-yl)cyclohexane-1-carboxamide

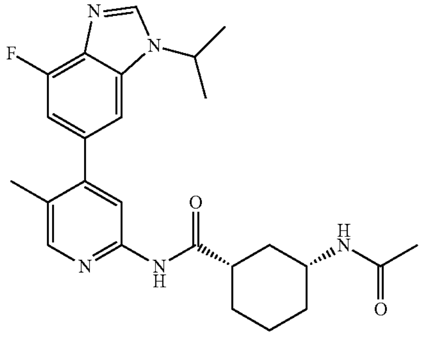 [SMILES: CC(=O)N[C@@H]1CCC[C@H](C(=O)Nc2cc(-c3cc(F)c4ncn(C(C)C)c4c3)c(C)cn2)C1]

Step 1:
5-Bromo-3-fluoro-N-isopropyl-2-nitro-aniline

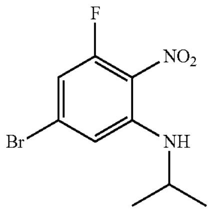

To a mixture of 5-bromo-1,3-difluoro-2-nitro-benzene (11.0 g, 46.2 mmol, 1.0 eq) and $K_2CO_3$ (8.05 mL, 46.2 mmol, 1.0 eq) in DMF (50 mL) at 0° C. was slowly added isopropylamine (5.5 g, 92.4 mmol, 2.0 eq). After stirring for another 30 mins, the cooling bath was removed. The reaction vessel was warmed up to room temperature and stirred at RT for 1 h. The mixture was quenched with sat. aqueous $Na_2CO_3$ solution, extracted with EtOAc (3×100 mL). The combined organic layers were washed with brine, dried over anhydrous $Na_2SO_4$, and filtered. The filtrate was concentrated and the residue was purified by column chromatography on a silica gel column (100-200 mesh size, petroleum ether: ethyl acetate=20/1) to give 5-bromo-3-fluoro-N-isopropyl-2-nitro-aniline (7.0 g, 55% yield) as a yellow solid. $^1$H NMR (400 MHz, $CDCl_3$) δ 6.76 (t, J=1.6 Hz, 1H), 6.57 (dd, J=10.8, 2.0 Hz, 1H), 3.68-3.76 (m, 1H), 1.30 (dd, J=9.6, 4.4 Hz, 6H).

Step 2:
5-Bromo-3-fluoro-N1-isopropyl-benzene-1,2-diamine

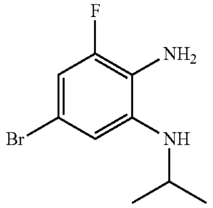

To a solution of 5-bromo-3-fluoro-N-isopropyl-2-nitro-aniline (11.0 g, 39.7 mmol, 1.0 eq) in methanol (50 mL) and water (6 mL) were added iron powder (22.2 g, 397 mmol, 10.0 eq) and ammonium chloride ("$NH_4Cl$") (21.0 g, 397 mmol, 10.0 eq). The reaction mixture was stirred at 80° C. for 1 h. The reaction mixture was cooled to r.t., filtered, and washed with MeOH (100 mL). The filtrate was concentrated and purified by column chromatography on a silica gel column (100-200 mesh size, petroleum ether: ethyl acetate=1/1) to afford 5-bromo-3-fluoro-N1-isopropyl-benzene-1,2-diamine (7.00 g, 71.3% yield). $^1$H NMR (400 MHz, DMSO-$d^6$) δ 6.55 (dd, J=10.4, 2.0 Hz, 1H), 6.36 (s, 1H), 4.80 (br.s, 1H), 4.63 (br.s, 2H), 3.53-3.56 (m, 1H), 1.15 (d, J=6.4 Hz, 6H).

Step 3:
6-Bromo-4-fluoro-1-isopropyl-benzimidazole

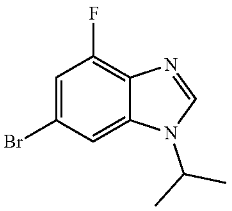

To a solution of 5-bromo-3-fluoro-N1-isopropyl-benzene-1,2-diamine (3.00 g, 12.1 mmol, 1 eq) and trimethyl orthoformate (38.6 g, 364 mmol, 30 eq) was added formic acid (60.0 mg, 1.21 mmol, 0.10 eq). The reaction mixture was stirred at 85° C. for 2 h. The reaction mixture was concentrated and purified by column chromatography on a silica gel column (100-200 mesh size, petroleum ether: ethyl acetate=1/1) to afford 6-bromo-4-fluoro-1-isopropyl-benzimidazole (2.50 g, 80.1% yield). LCMS calcd. for $C_{10}H_{11}BrFN_2(M+H)^+$ m/z=257.0; found:256.8.

Step 4: 4-Fluoro-1-isopropyl-6-(4,4,5,5-tetramethyl-1,3,2-dioxaborolan-2-yl)benzimidazole

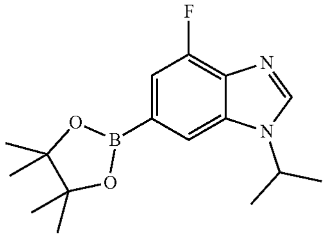 [SMILES: CC(C)n1cnc2c(F)cc(B3OC(C)(C)C(C)(C)O3)cc21]

To a solution of 6-bromo-4-fluoro-1-isopropyl-benzimidazole (1.00 g, 3.89 mmol, 1.0 eq) and bis(pinacolato) diboron (1.48 g, 5.83 mmol, 1.5 eq) in DMSO (10 mL) were added potassium acetate (1.14 g, 11.7 mmol, 3.0 eq), tricyclohexylphosphane (218 mg, 0.780 mmol, 0.20 eq) and palladium (II) acetate (43.7 mg, 0.190 mmol, 0.050 eq) at room temperature. The reaction mixture was de-gassed under reduced pressure and recharged with $N_2$. The reaction was stirred at 90° C. for 1 h. Then the reaction mixture was diluted with water (50 mL), filtered, and extracted with EtOAc (3×50 mL). The combined organic layers were washed with brine, dried over anhydrous $Na_2SO_4$, and filtered. The filtrate was concentrated and the residue was purified by column chromatography on a silica gel column (100-200 mesh size, petroleum ether: ethyl acetate=5/1) to afford 4-fluoro-1-isopropyl-6-(4,4,5,5-tetramethyl-1,3,2-dioxaborolan-2-yl)benzimidazole (500 mg, 42.3% yield). LCMS calcd. for $C_{16}H_{23}BFN_2O_2(M+H)^+$ m/z=305.2; found:305.0.

Step 5: tert-butyl ((1R,3S)-3-((4-iodo-5-methylpyridin-2-yl)carbamoyl)cyclohexyl)carbamate

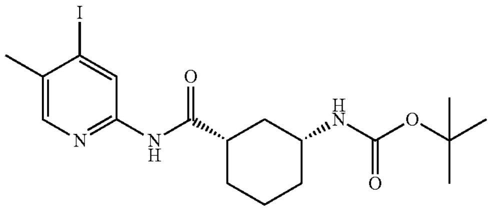 [SMILES: Cc1cnc(NC(=O)[C@H]2CCC[C@@H](NC(=O)OC(C)(C)C)C2)cc1I]

To a mixture of (1S,3R)-3-(tert-butoxycarbonylamino) cyclohexanecarboxylic acid (260 mg, 1.07 mmol, 1.0 eq) in DCM (20 mL) was added 1-chloro-N,N,2-trimethylprop-1-en-1-amine (171 mg, 1.28 mmol, 1.2 eq) at OC. The mixture was stirred at room temperature for 1.5 h. Then 4-iodo-5-methyl-pyridin-2-amine (250 mg, 1.07 mmol, 1.0 eq) and pyridine (101 mg, 1.28 mmol, 1.2 eq) were added. The mixture was stirred at room temperature for 12 h. Then the reaction mixture was concentrated and purified by prep-HPLC on a $C_{18}$ column (20-35 μM, 100 A, 80 g) with mobile phase: $H_2O$ (0.1% TFA)/MeOH at flow rate: 50 mL/min to give tert-butyl ((1R,3S)-3-((4-iodo-5-methylpyridin-2-yl) carbamoyl)cyclohexyl)carbamate (230 mg, 46.9% yield). LCMS calcd. for $C_{16}H_{27}IN_3O_3$ $(M+H)^+$ m/z=460.1; found: 460.0.

Step 6: (1S,3R)-3-amino-N-(4-iodo-5-methylpyridin-2-yl)cyclohexane-1-carboxamide

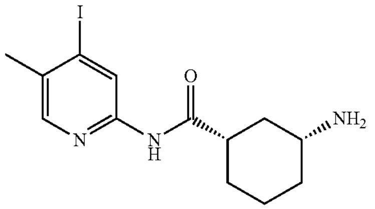 [SMILES: Cc1cnc(NC(=O)[C@H]2CCC[C@@H](N)C2)cc1I]

To a mixture of tert-butyl ((1R,3S)-3-((4-iodo-5-methylpyridin-2-yl)carbamoyl)cyclohexyl)carbamate (230 mg, 0.500 mmol, 1.0 eq) in DCM (5 mL) was added TFA (5.0 mL). The mixture was stirred at room temperature for 5 h. The mixture was concentrated under reduced pressure and dried in vacuo to afford (1S,3R)-3-amino-N-(4-iodo-5-methylpyridin-2-yl)cyclohexane-1-carboxamide as its TFA salt (237 mg, 0.500 mmol, 100% yield). LCMS calcd. for $C_{13}H_{19}1N_3O$ $(M+H)^+$ m/z=360.1; found: 360.0.

Step 7: (1S,3R)-3-acetamido-N-(4-iodo-5-methylpyridin-2-yl)cyclohexane-1-carboxamide

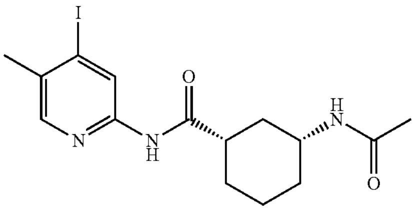 [SMILES: CC(=O)N[C@@H]1CCC[C@H](C(=O)Nc2cc(I)c(C)cn2)C1]

To a mixture of (1S,3R)-3-amino-N-(4-iodo-5-methylpyridin-2-yl)cyclohexane-1-carboxamide (237 mg, 0.500 mmol, 1.0 eq, TFA salt) in DCM (10 mL) at 0° C. was added TEA (0.410 mL, 2.50 mmol, 2.5 eq), followed by acetic anhydride (0.05 mL, 0.550 mmol, 1.1 eq) dropwise. The mixture was stirred at 0° C. for 1 h. The mixture was concentrated and purified by prep-HPLC on a $C_{18}$ column (20-35 μM, 100 A, 80 g) with mobile phase: $H_2O$ (0.1% TFA)/MeOH at flow rate: 50 mL/min to give (1S,3R)-3-acetamido-N-(4-iodo-5-methylpyridin-2-yl)cyclohexane-1-carboxamide as its TFA salt (121 mg, 0.300 mmol, 59.6% yield). LCMS calcd. for $C_{15}H_{21}IN_3O_2(M+H)^+$ m/z=402.1; found: 402.0. $^1H$ NMR (400 MHz, DMSO-$d_6$) δ 10.48 (s, 1H), 8.60 (s, 1H), 8.15 (s, 1H), 7.78 (d, J=7.6 Hz, 1H), 3.51-3.57 (m, 1H), 2.50-2.60 (m, 1H), 2.28 (s, 3H), 1.74-1.87 (m, 7H), 1.22-1.31 (m, 3H), 1.03-1.11 (m, 1H).

Step 8: (1S,3R)-3-acetamido-N-(4-(4-fluoro-1-isopropyl-1H-benzo[d]imidazol-6-yl)-5-methylpyridin-2-yl)cyclohexane-1-carboxamide To a solution of 4-fluoro-1-isopropyl-6-(4,4,5,5-tetramethyl-1,3,2-dioxaborolan-2-yl)benzimidazole (60.0 mg, 0.200 mmol, 1.0 eq) and (1S,3R)-3-acetamido-N-(4-iodo-5-methylpyridin-2-yl)cyclohexane-1-carboxamide (0.08 g, 0.200 mmol, 1.0 eq, TFA salt) in 1,4-dioxane (10 mL) and water (2 mL) were added $Na_2CO_3$ (0.130 g, 0.590 mmol, 3.0 eq) and tetrakis(triphenylphosphine)palladium (22.8 mg, 0.02 mmol, 0.10 eq) at rt. The reaction mixture was degassed under reduced pressure and recharged with $N_2$. Then the reaction was stirred at 90° C. for 14 h. The reaction mixture was diluted with water (30 mL), filtered, extracted with EtOAc (3×30 mL). The combined organic layers were washed with brine, dried over anhydrous $Na_2SO_4$, and filtered. The filtrate was concentrated and the residue was purified by Prep-HPLC on a $C_{18}$ column (5 μM, 50×150 mm) with mobile phase:$H_2O$ (0.1% TFA)/MeOH at flow rate:50 mL/min to give rac-(1S,3R)-3-acetamido-N-[4-(7-fluoro-3-isopropyl-benzimidazol-5-yl)-5-methyl-2-pyridyl] cyclohexanecarboxamide (24.0 mg, 25.6% yield). LCMS calcd. for $C_{25}H_{31}FN_5O_2(M+H)^+$ m/z=452.2; found: 452.0. $^1H$ NMR (400 MHz, $CD_3OD$) δ 8.38 (s, 1H), 8.22 (s, 1H), 8.02 (s, 1H), 7.47 (d, J=1.2 Hz, 1H), 7.06 (dd, J=11.2, 1.2 Hz, 1H), 3.70-3.76 (m, 1H), 3.20-3.27 (m, 1H), 2.56-2.62 (m, 1H), 2.27 (s, 3H), 2.06 (d, J=13.6 Hz, 1H), 1.90 (d, J=10.4 Hz, 6H), 1.59-1.68 (m, 6H), 1.43 (m, 3H), 1.20 (m, 1H).

Example 23: (1S,3R)-3-acetamido-N-(4-(5-fluoro-1,1-dimethyl-2,3-dihydro-1H-benzo[d]pyrrolo[1,2-a]imidazol-7-yl)-5-methylpyridin-2-yl)cyclohexane-1-carboxamide

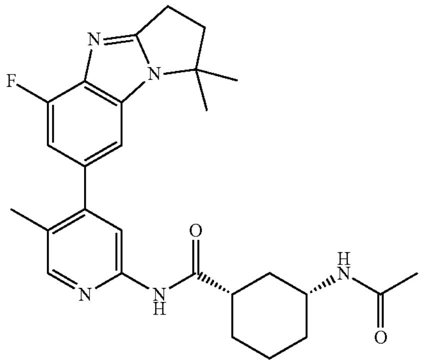 [SMILES: CC(=O)N[C@@H]1CCC[C@H](C(=O)Nc2cc(-c3cc(F)c4nc5n(c4c3)C(C)(C)CC5)c(C)cn2)C1]

The title compound was prepared using procedures analogous to those described for Example 22, Step 8, with 5-fluoro-1,1-dimethyl-7-(4,4,5,5-tetramethyl-1,3,2-dioxaborolan-2-yl)-2,3-dihydropyrrolo[1,2-a]benzimidazole replacing 4-fluoro-1-isopropyl-6-(4,4,5,5-tetramethyl-1,3,2-dioxaborolan-2-yl)benzimidazole. LCMS calcd. for $C_{27}H_{33}FN_5O_2$ $(M+H)^+$ m/z=478.3; found: 478.3.

Example 24: (1S,3R)-3-acetamido-N-(4-(4-fluoro-1-isopropyl-1H-benzo[d]imidazol-6-yl)-5-methylpyridin-2-yl)cyclopentane-1-carboxamide

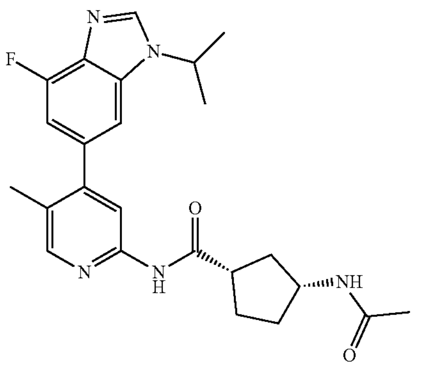 [SMILES: CC(=O)N[C@@H]1CC[C@H](C(=O)Nc2cc(-c3cc(F)c4ncn(C(C)C)c4c3)c(C)cn2)C1]

The title compound was prepared using procedures analogous to those described for Example 22, with (1S,3R)-(+)-3-(Boc-amino)cyclopentanecarboxylic acid replacing (1S,3R)-3-(tert-butoxycarbonylamino)cyclohexanecarboxylic acid in Step 5. LCMS calcd. for $C_{24}H_{29}FN_5O_2$ $(M+H)^+$ m/z=438.2; found: 438.2. $^1H$ NMR (400 MHz, $CD_3OD$) δ 9.00 (s, 1H), 8.31 (s, 1H), 7.78 (d, J=1.2 Hz, 1H), 7.67 (s, 1H), 7.35 (dd, J=10.8, 1.2 Hz, 1H), 4.93-5.00 (m, 1H), 4.16-4.26 (m, 1H), 3.05-3.12 (m, 1H), 2.31-2.40 (m, 4H), 2.00-2.01 (m, 3H), 1.94 (s, 3H), 1.82-1.85 (m, 1H), 1.63-1.71 (m, 7H).

Example 25: (1S,3R)-3-acetamido-N-(5-chloro-4-(7'-fluoro-2'-methylspiro[cyclopentane-1,3'-indol]-5'-yl)pyridin-2-yl)cyclohexane-1-carboxamide

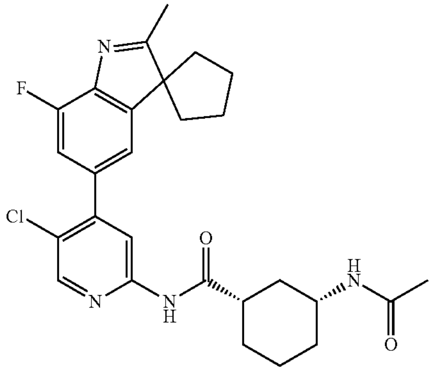 [SMILES: CC(=O)N[C@@H]1CCC[C@H](C(=O)Nc2cc(-c3cc(F)c4c(c3)C3(CCCC3)C(C)=N4)c(Cl)cn2)C1]

Step 1: 5'-Bromo-7'-fluoro-2'-methylspiro[cyclopentane-1,3'-indole]

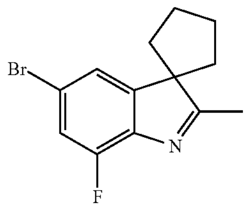 [SMILES: CC1=Nc2c(F)cc(Br)cc2C12CCCC2]

1-Cyclopentylethanone (6.00 g, 53.5 mmol, 1.0 eq was added to a solution of 2-(4-bromo-2-fluorophenyl)hydrazin-1-ium chloride (12.9 g, 53.5 mmol, 1.0 eq) in acetic acid (40 mL). The mixture was refluxed for 5 h. After that, AcOH was removed in vacuum. The residue was diluted with water (20 mL) and extracted with ethyl acetate (3×20 mL). The combined organic layers were washed with brine (25 mL), dried over anhydrous $Na_2SO_4$, filtered, and concentrated under vacuum. The residue was purified by silica gel column chromatography (EA/PE=1:50 to 1:25) to obtain 5'-bromo-7'-fluoro-2'-methyl-spiro[cyclopentane-1,3'-indole] (5.40 g, 35.8% yield) as a yellow solid. $^1H$ NMR: (400 MHz, $CDCl_3$) δ 7.18-7.22 (m, 2H), 2.30 (s, 3H), 1.99-2.07 (m, 6H), 1.78-1.82 (m, 2H).

Step 2: 7'-Fluoro-2'-methyl-5'-(4,4,5,5-tetramethyl-1,3,2-dioxaborolan-2-yl)spiro[cyclopentane-1,3'-indole]

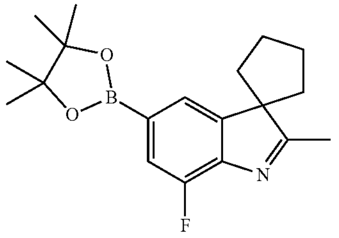

$Pd(dppf)Cl_2$ (2.49 g, 3.83 mmol, 0.20 eq) was added to a mixture of 5'-bromo-7'-fluoro-2'-methyl-spiro[cyclopentane-1,3'-indole] (5.40 g, 19.1 mmol, 1.0 eq), bis(pinacolato) diboron (5.35 g, 21.0 mmol, 1.1 eq) and potassium acetate ("KOAc") (3.75 g, 38.3 mmol, 2.0 eq) in 1,4-dioxane (100 mL). The mixture was degassed and recharged with $N_2$. Then the reaction was heated to 90° C. and stirred overnight. The mixture was cooled to room temperature, filtered, diluted with water (100 mL), and extracted with EtOAc (100 mL×3). The combined organic layers were washed with brine (100 mL), dried over anhydrous $Na_2SO_4$, concentrated under vacuum, and purified by silica gel column chromatography (DCM/MeOH=50/1~30/1) to obtain 7'-fluoro-2'-methyl-5'-(4,4,5,5-tetramethyl-1,3,2-dioxaborolan-2-yl) spiro[cyclopentane-1,3'-indole] (5.60 g, 88.9% yield) as a yellow oil. $^1H$ NMR: (400 MHz, $CDCl_3$) δ 7.48 (s, 1H), 7.45 (d, J=10.0 Hz, 1H), 2.33 (s, 3H), 2.09-2.14 (m, 2H), 1.95-2.03 (m, 4H), 1.82-1.89 (m, 2H), 1.34 (s, 12H).

Step 3: (1S,3R)-3-acetamido-N-(5-chloro-4-(7'-fluoro-2'-methylspiro[cyclopentane-1,3'-indol]-5'-yl) pyridin-2-yl)cyclohexane-1-carboxamide The title compound was prepared using procedures analogous to those described for Example 13, Step 4, with 7'-fluoro-2'-methyl-5'-(4,4,5,5-tetramethyl-1,3,2-dioxaborolan-2-yl)spiro[cyclopentane-1,3'-indole] replacing 1,1-dimethyl-7-(4,4,5,5-tetramethyl-1,3,2-dioxaborolan-2-yl)-2,3-dihydropyrrolo[1,2-a]benzimidazole. LCMS calcd. for $C_{27}H_{31}ClFN_4O_2$ $(M+H)^+$ m/z=497.2; found: 497.3.

Example 26: (1S,3R)-3-acetamido-N-(5-chloro-4-(3-isopropylbenzo[c]isothiazol-5-yl)pyridin-2-yl) cyclohexane-1-carboxamide

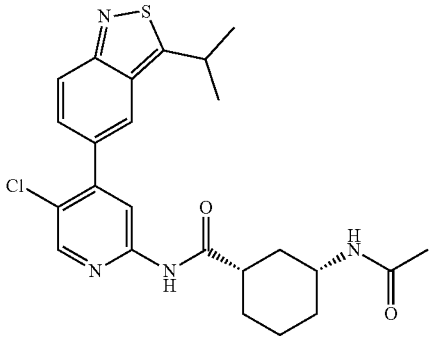 [SMILES: CC(=O)N[C@@H]1CCC[C@H](C(=O)Nc2cc(-c3ccc4nsc(C(C)C)c4c3)c(Cl)cn2)C1]

Step 1: 5-bromo-2, 1-benzothiazole

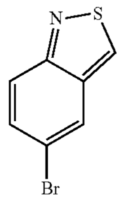

A mixture of methanesulfonamide (7.2 g, 75.3 mmol), thionyl chloride (8.0 mL, 110 mmol) and toluene (10 mL) was stirred at 120° C. for 18 hours under $N_2$. After cooling to rt, toluene was removed under reduced pressure and the residue was used directly in the next step. To a solution of 4-bromo-2-methyl-aniline (2.0 g, 10.8 mmol) in toluene (40 mL) was added Thionyl chloride (1.4 g, 11.8 mmol) drop wise at 0° C. After the addition was complete, the reaction mixture was heated at 120° C. for 18 hours. Pyridine (1.0 mL, 12.3 mmol) and the crude residue from the above reaction were added to the mixture. The resulted solution was then stirred at 120° C. for 18 h. The reaction mixture was concentrated under reduced pressure, dissolved in EtOAc (100 mL), and washed with water (2×100 mL). The organic layer was washed with brine (100 mL), dried with $Na_2SO_4$ and concentrated in vacuum to give the crude product which was purified by column chromatography on silica gel (EA:PE=1:10) to give 5-bromo-2, 1-benzothiazole (800 mg, 3.74 mmol, 35% yield) as a yellow solid. LCMS calcd. for $C_7H_5BrNS$ $(M+H)^+$ m/z=214.0/216.0; found: 214.1/216.2.

Step 2: 2-(5-bromobenzo[c]isothiazol-3-yl)propan-2-ol

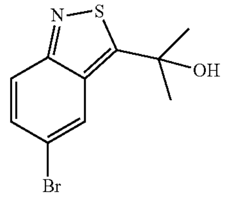

To a solution of 5-bromo-2, 1-benzothiazole (0.92 g, 4.3 mmol) in THF (5 mL) was added LDA (1.16 mL, 21.5 mmol) at −78° C. The mixture was stirred at 0° C. for 10 min, then cooled to −78° C. To the solution dry acetone (3.18 mL, 43 mmol) was added. The resulting solution was stirred at 25° C. for 12 h. The reaction was then quenched with 20 mL of aqueous sodium bicarbonate. The resulting solution was extracted with ethyl acetate (3×30 mL). The organic layers were combined, dried over anhydrous $Na_2SO_4$, filtered and concentrated in vacuum. The residue was purified by column chromatography on silica gel (petroleum ether: ethyl acetate=10:1 to 2 1) to give 2-(5-bromo-2, 1-benzothiazol-3-yl) propan-2-ol (610 mg, 2.24 mmol, 52% yield). LCMS calcd. for $C_{10}H_{11}BrNSO$ $(M+H)^+$ m/z=272.0/274.0; found: 271.9/274.0.

Step 3: 5-bromo-3-isopropylbenzo[c]isothiazole

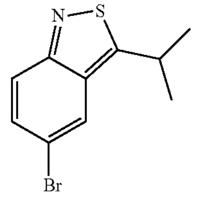

To a solution of 2-(5-bromo-2,1-benzothiazol-3-yl)propan-2-ol (610 mg, 2.24 mmol) in DCM (2 mL) was added triethylsilane (3.6 mL, 22 mmol) and TFA (1.7 mL, 22 mmol). The reaction was stirred 25° C. for 18 h. The resulting mixture was concentrated in vacuum. The solution was adjusted to pH 8 with 2 M aqueous sodium bicarbonate. The resulted solution was extracted with ethyl acetate (3×20 mL), and the organic layers were combined and washed with 30 mL of brine.

The mixture was dried over anhydrous $Na_2SO_4$, filtered, and concentrated in vacuum. The residue was purified by column chromatography on silica gel (petroleum ether: ethyl acetate=10:1) to give 5-bromo-3-isopropyl-2, 1-benzothiazole (420 mg, 1.64 mmol, 73% yield). LCMS calcd. for $C_{10}H_{11}BrNS$ $(M+H)^+$ m/z=256.0/258.0; found: 256.0/258.0.

Step 4: 3-isopropyl-5-(4,4,5,5-tetramethyl-1, 3,2-dioxaborolan-2-yl)benzo[c]isothiazole

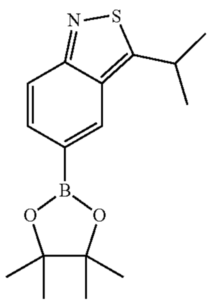 [SMILES: CC(C)c1snc2ccc(B3OC(C)(C)C(C)(C)O3)cc12]

To a solution of 5-bromo-3-isopropyl-2,1-benzothiazole (100 mg, 0.39 mmol) in 1,4-dioxane (5 mL) was added bis(pinacolato)diboron (0.16 mL, 0.47 mmol), potassium acetate (76.62 mg, 0.78 mmol) and [1,1'-bis(diphenylphosphino)ferrocene]dichloropalladium(II) (28.6 mg, 0.04 mmol). The resulting solution was stirred for 12 h at 90° C. under $N_2$, and then cooled to room temperature and concentrated in vacuum. The residue was purified by column chromatography on silica gel (petroleum ether: ethyl acetate=10:1) to give 3-isopropyl-5-(4,4,5,5-tetramethyl-1, 3,2-dioxaborolan-2-yl)-2,1-benzothiazole (60 mg, 0.20 mmol, 51% yield) as a white solid. LCMS calcd. for $C_{16}H_{23}BNO_2S$ $(M+H)^+$ m/z=304.2; found:304.2.

Step 5: (1S,3R)-3-acetamido-N-(5-chloro-4-(3-isopropylbenzo[c]isothiazol-5-yl)pyridin-2-yl)cyclohexane-1-carboxamide The title compound was prepared using procedures analogous to those described for Example 13, Step 4, with 3-isopropyl-5-(4,4,5,5-tetramethyl-1,3,2-dioxaborolan-2-yl)-2,1-benzothiazole replacing 1,1-dimethyl-7-(4,4,5,5-tetramethyl-1,3,2-dioxaborolan-2-yl)-2,3-dihydropyrrolo[1,2-a]benzimidazole. LCMS calcd. for $C_{24}H_{28}Cl\ N_4O_2S$ $(M+H)^+$ m/z=471.1; found:471.0. $^1H$ NMR (400 MHz, DMSO-$d_6$) 10.76 (s, 1H), 8.50 (s, 1H), 8.27 (s, 1H), 8.01 (s, 1H), 7.84-7.78 (m, 2H), 7.56-7.54 (m, 1H), 3.96-3.91 (m, 1H), 3.55-3.50 (m, 1H), 2.67-2.60 (m, 1H), 1.90-1.86 (m, 1H), 1.81-1.69 (m, 6H), 1.50-1.48 (m, 6H), 1.31-1.22 (m, 3H), 1.11-1.04 (m, 1H).

Example 27: (1S,3R)-3-acetamido-N-(5-chloro-4-(1-methyl-2,3-dihydro-1H-pyrrolo[1,2-b]indazol-8-yl)pyridin-2-yl)cyclohexane-1-carboxamide

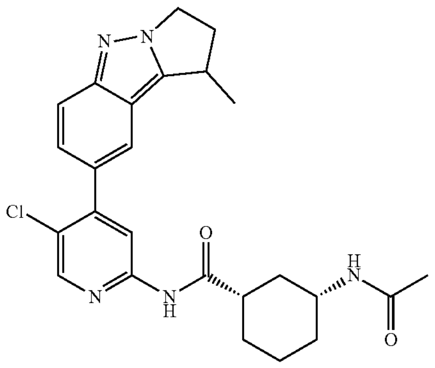 [SMILES: CC(=O)N[C@@H]1CCC[C@H](C(=O)Nc2cc(-c3ccc4nn5c(c4c3)C(C)CC5)c(Cl)cn2)C1]

Step 1: 5-bromo-N-methoxy-N-methyl-1H-indazole-3-carboxamide

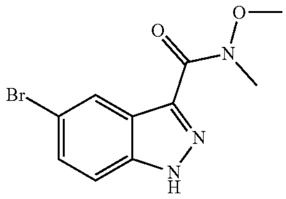 [SMILES: CON(C)C(=O)c1n[nH]c2ccc(Br)cc12]

To a stirred solution of 5-bromo-1H-indazole-3-carboxylic acid (4.5 g, 18.7 mmol), 1-Ethyl-3-(3-dimethylaminopropyl)carbodiimide ("EDCI") (5.01 mg, 26.1 mmol), and N,N-dimethylaminopyridine ("DMAP") (3.4 g, 28 mmol) in DMF (15 mL) was added N,O-dimethylhydroxylamine hydrochloride (1.7 g, 28 mmol) at rt. After 16 h, the mixture was added water (50 mL) and white solid precipitates out. The solids were filtrated to get the product 5-bromo-N-methoxy-N-methyl-1H-indazole-3-carboxamide (5.3 g, 18.7 mmol, 99.9% yield). LCMS calcd. for $C_{10}H_{11}BrN_3O_2$[M+H]$^+$ m/z=284.0/286.0; found: 284.0/286.0.

Step 2: 1-(5-bromo-1H-indazol-3-yl)ethan-1-one

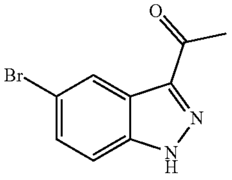

To a stirred solution of 5-bromo-N-methoxy-N-methyl-1H-indazole-3-carboxamide (12.0 g, 42.2 mmol) in THE (250 mL) was added methylmagnesium bromide (1 M in $Et_2O$, 211 mL, 211 mmol) at 0° C. After 3 h, the reaction mixture was quenched with aq. $NH_4Cl$ (50 ml) and diluted with EtOAc (500 mL). The organic layer was washed with water (2×200 mL) and brine (1×200 mL). The organics were separated, dried over $MgSO_4$ and filtered. The filtrate was concentrated. The crude residue was purified by flash column chromatography eluting with 10% EtOAc in isohexane and get the product 1-(5-bromo-1H-indazol-3-yl)ethanone (11.4 g, 40.1 mmol, 95% yield) as a yellow solid. LCMS calcd. for $C_9H_8BrN_2O$ $[M+H]^+$ m/z=239.0/241.0; found: 239.0/241.0.

Step 3: 1-(5-bromo-1-((2-(trimethylsilyl)ethoxy)methyl)-1H-indazol-3-yl)ethan-1-one

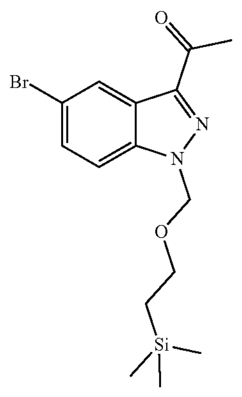 [SMILES: CC(=O)c1nn(COCC[Si](C)(C)C)c2ccc(Br)cc12]

To a stirred solution of 1-(5-bromo-1H-indazol-3-yl)ethanone (10 g, 41.8 mmol) in DMF (200 mL) was added sodium hydride (2.5 g, 62.7 mmol) at 0° C. After 1 h, 2-(chloromethoxy)ethyl-trimethyl-silane (8.4 g, 50.2 mmol) was added. The resulted solution was stirred at 0° C. for additional 2 h. The mixture was taken up in EtOAc (100 mL) and washed with water (2×100 mL) then saturated brine (1×100 mL). The organics were separated, dried over $MgSO_4$, and filtered. The filtrate was concentrated to dryness under reduced pressure. The crude was then purified by flash column chromatography, eluting with 10% EtOAc in isohexane, to give 1-(5-bromo-1-((2-(trimethylsilyl)ethoxy)methyl)-1H-indazol-3-yl)ethan-1-one (24.5 g, 59.7 mmol, 71% yield) as a yellow oil. LCMS calcd. for $C_{15}H_{22}BrN_2O_2Si$ $[M+H]^+$ m/z=369.1/371.1; found: 369.1/371.1.

Step 4: ethyl 3-(5-bromo-1-((2-(trimethylsilyl)ethoxy)methyl)-1H-indazol-3-yl)but-2-enoate

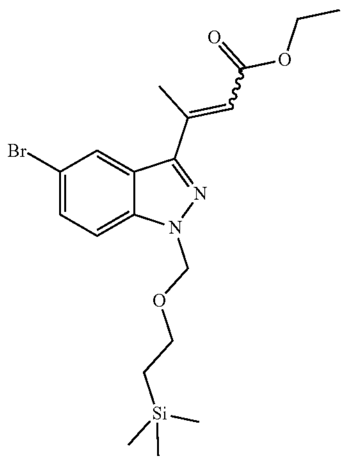 [SMILES: CCOC(=O)C=C(C)c1nn(COCC[Si](C)(C)C)c2ccc(Br)cc12]

To a stirred solution of NaH (2.0 g, 51 mmol) in THE (100 mL) was added ethyl 2-(diethoxyphosphoryl)acetate (11.4 g, 50.9 mmol) at 0° C. A solution of 1-[5-bromo-1-(2-trimethylsilylethoxymethyl)indazol-3-yl]ethanone (7.5 g, 20.3 mmol) in THE (20 mL) was then added dropwise at rt. After 6 h, the reaction was quenched with saturated aq. $NH_4Cl$ and extracted with EtOAc. The organic layers were combined, dried over $Na_2SO_4$, filtered and concentrated under vacuum. The residue was purified by flash column, eluting with petroleum ether: ethyl acetate=10:1, to give ethyl 3-[5-bromo-1-(2-trimethylsilylethoxymethyl)indazol-3-yl]but-2-enoate (6 g, 13.7 mmol, 67.2% yield) as a yellow oil. LCMS calcd. for $C_{19}H_{28}BrN_2O_3Si$ $[M+H]^+$ m/z=439.1/441.1; found: 439.1/441.1.

Step 5: 3-(5-bromo-1H-indazol-3-yl)but-2-enoate

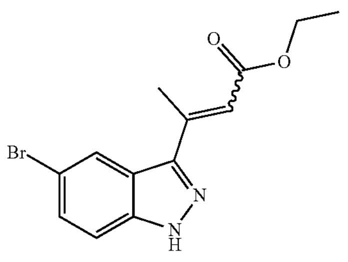 [SMILES: CCOC(=O)C=C(C)c1n[nH]c2ccc(Br)cc12]

To a stirred solution of ethyl 3-[5-bromo-1-(2-trimethylsilylethoxymethyl)indazol-3-yl]but-2-enoate (500 mg, 1.14 mmol) in THF (10 mL) was added TBAF(1 M in THF, 2.28 mL, 2.28 mmol) at rt. The resulted mixture was heated at 80° C. for 5 h. The reaction mixture was diluted with EtOAc (30 mL), then washed with $H_2O$ and brine. The organics were separated, dried over $Na_2SO_4$, and filtered. The filtrate was concentrated to dryness under reduced pressure. The crude residue was then purified by flash column chromatography, eluting with 17% EtOAc in isohexane, to give ethyl 3-(5-bromo-1H-indazol-3-yl)but-2-enoate (130 mg, 0.42 mmol, 37% yield) as a light yellow solid. LCMS calcd. for $C_{13}H_{14}BrN_2O_2[M+H]^+$ m/z=309.0/311.0; found: 309.0/311.0.

Step 6: ethyl 3-(5-bromo-1H-indazol-3-yl)butanoate

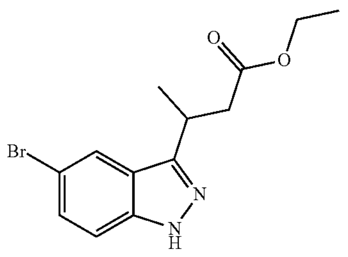 [SMILES: CCOC(=O)CC(C)c1n[nH]c2ccc(Br)cc12]

To a stirred solution of ethyl 3-(5-bromo-1H-indazol-3-yl)but-2-enoate (105 mg, 0.34 mmol) in THE (6 mL)/water (6 mL) were added 4-methylbenzenesulfonicacidhydrazide (632 mg, 3.4 mmol) and sodium acetate trihydrate (693 mg, 5.1 mmol) at rt. The resulted mixture was heated at 90° C. for 16 h. The reaction mixture was diluted with EtOAc and washed with $H_2O$. The organic layer was dried over $Na_2SO_4$, filtered and concentrated under vacuum. The residue was purified by flash column chromatography, eluting with petroleum ether: ethyl acetate=7:1 to petroleum ether: ethyl acetate=4:1, to give ethyl 3-(5-bromo-1H-indazol-3-yl)butanoate (50 mg, 0.16068 mmol, 47.3% yield) as an colorless oil. LCMS calcd. for $C_{13}H_{16}BrN_2O_2[M+H]^+$ m/z=311.0/313.0; found: 311.0/313.0.

Step 7: 3-(5-bromo-1H-indazol-3-yl)butan-1-ol

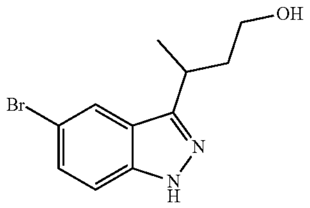

To a solution of ethyl 3-(5-bromo-1H-indazol-3-yl)butanoate (4.8 g, 15.4 mmol) in THE (50 mL) was added $LiAlH_4$ (875 mg, 23.1 mmol) at 0° C. The resulted mixture was stirred at 0° C. for 1 h. The reaction was quenched with saturated aq. $NH_4Cl$ and extracted with EtOAc. The organic layers were combined, dried over $Na_2SO_4$, filtered and concentrated under vacuum. The residue was purified by flash column chromatography, eluting with DCM: MeOH=20:1, to give 3-(5-bromo-1H-indazol-3-yl)butan-1-ol (3.3 g, 12.3 mmol, 79.5% yield). LCMS calcd. for $C_{11}H_{14}BrN_2O$ $[M+H]^+$ m/z=269.0/271.0; found: 269.0/271.0.

Step 8: 5-bromo-3-(4-chlorobutan-2-yl)-1H-indazole

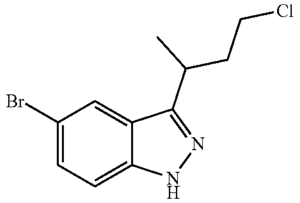

To a solution of 3-(5-bromo-1H-indazol-3-yl)butan-1-ol (3.3 g, 12.3 mmol) in MeCN (15 mL) and chloroform (15 mL) was added $SOCl_2$ (8.81 mL, 123 mmol). The resulted mixture was stirred at 70° C. for 2 h. The volatiles were removed under reduced pressure and the residue was used in the next step without further purification. LCMS calcd. for $C_{11}H_{13}BrClN_2$ $[M+H]^+$ m/z=287.0/289.0; found: 287.0/289.0.

Step 9: 8-bromo-1-methyl-2,3-dihydro-1H-pyrrolo [1,2-b]indazole

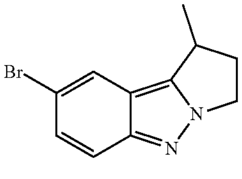

To a solution of 5-bromo-3-(3-chloro-1-methyl-propyl)-1H-indazole (3.0 g, 10.4 mmol) in and DMSO (10 mL) was added triethylamine (0.07 mL, 31.3 mmol). The resulted mixture was stirred at 90° C. for 16 h. The volatiles were removed under reduced pressure and the residue was purified on flash column chromatography, eluting with petroleum ether: ethyl acetate=2:1, to give 8-bromo-1-methyl-2,3-dihydro-1H-pyrrolo[1,2-b]indazole (1.95 g, 7.77 mmol, 74.4% yield). LCMS calcd. for $C_{11}H_2BrN_2$ $[M+H]^+$ m/z=251.0/253.0; found: 251.0/253.0.

Step 10: 1-methyl-8-(4,4,5,5-tetramethyl-1, 3, 2-dioxaborolan-2-yl)-2,3-dihydro-1H-pyrrolo[1,2-b] indazole

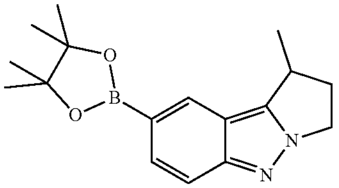 [SMILES: CC1CCn2nc3ccc(B4OC(C)(C)C(C)(C)O4)cc3c21]

To a solution of 8-bromo-1-methyl-2,3-dihydro-1H-pyrrolo[1,2-b]indazole (600 mg, 2.39 mmol) in DMSO (10 mL) was added bis(pinacolato)diboron (971 mg, 3.82 mmol), tricyclohexylphosphane (134 mg, 0.48 mmol), KOAc (702 mg, 7.17 mmol) and palladium (II) acetate (54 mg, 0.24 mmol) at rt. The resulted mixture was stirred at 90° C. under $N_2$ for 1 h. The reaction was poured into $H_2O$ (30 mL) and extracted with EtOAc (20×2 mL). The organic layers were combined, washed with brine, dried with $Na_2SO_4$, and filtered. The filtrate was concentrated in vacuum to give crude product which was purified by reversed phase column, eluting with $H_2O$/ACN=90/10-5/95, to give 1-methyl-8-(4,4,5,5-tetramethyl-1,3,2-dioxaborolan-2-yl)-2,3-dihydro-1H-pyrrolo[1,2-b]indazole (565 mg, 1.89 mmol, 79% yield) as a white solid. LCMS calcd. for $C_{17}H_{24}BN_2O_2[M+H]^+$ m/z=299.2; found: 299.2. $^1H$ NMR (400 MHz, DMSO-$d_6$) δ 8.10 (s, 1H), 7.51-7.42 (m, 2H), 4.50-4.32 (m, 2H), 3.71-3.66 (m, 1H), 2.95-2.86 (m, 1H), 2.33-2.22 (m, 1H), 1.45-1.43 (m, 3H), 1.31-1.30 (m, 12H).

Step 11: (1S,3R)-3-acetamido-N-(5-chloro-4-(1-methyl-2,3-dihydro-1H-pyrrolo[1,2-b]indazol-8-yl) pyridin-2-yl)cyclohexane-1-carboxamide The title compound was prepared using procedures analogous to those described for Example 13, Step 4, with 1-methyl-8-(4,4,5,5-tetramethyl-1,3,2-dioxaborolan-2-yl)-2,3-dihydro-1H-pyrrolo[1,2-b]indazole replacing 1,1-dimethyl-7-(4,4,5,5-tetramethyl-1,3,2-dioxaborolan-2-yl)-2,3-dihydropyrrolo[1,2-a]benzimidazole. LCMS calcd. for $C_{25}H_{29}ClN_5O_2(M+H)^+$ m/z=466.2; found:466.4.

Example 28: (1S,3R)-3-(3,3-dimethylureido)-N-(4-(4-fluoro-1-isopropyl-1H-benzo[d]imidazol-6-yl)-5-methylpyridin-2-yl)cyclohexane-1-carboxamide

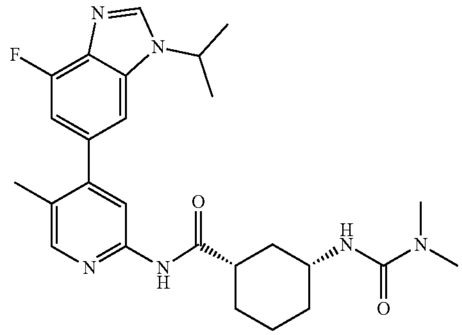 [SMILES: Cc1cnc(NC(=O)[C@H]2CCC[C@@H](NC(=O)N(C)C)C2)cc1-c1cc(F)c2ncn(C(C)C)c2c1]

Step 1: 4-(7-Fluoro-3-isopropyl-benzimidazol-5-yl)-5-methyl-pyridin-2-amine

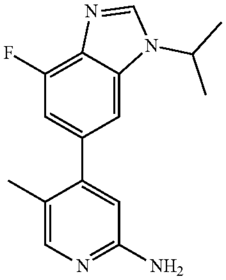 [SMILES: Cc1cnc(N)cc1-c1cc(F)c2ncn(C(C)C)c2c1]

To a solution of 4-iodo-5-methyl-pyridin-2-amine (22.5 g, 96.1 mmol, 1.0 eq) and 4-fluoro-1-isopropyl-6-(4,4,5,5-tetramethyl-1,3,2-dioxaborolan-2-yl)benzimidazole (Step 4, Example 22, 40.9 g, 135 mmol, 1.4 eq) in DMSO (250 mL) and water (50 mL) was added $Na_2CO_3$ (40.8 g, 192 mmol, 2.0 eq) and Pd(dppf)$Cl_2$ (6.26 mg, 9.61 mmol, 0.1 eq) at room temperature. The reaction mixture was de-gassed under reduced pressure and recharged with $N_2$ for three times. The resulted mixture was heated at 110° C. for 3 h. The reaction mixture was diluted with water (600 mL), filtered, and extracted with EA (3×200 mL). The combined organic layers were washed with brine, dried over anhydrous $Na_2SO_4$, and filtered. The filtrate was concentrated and the residue was purified by chromatography (eluting with DCM/MeOH=30/1) to afford 4-(7-fluoro-3-isopropyl-benzimidazol-5-yl)-5-methyl-pyridin-2-amine (22.0 g, 77.4 mmol, 80.5% yield) as a yellow solid. $^1H$ NMR (400 MHz, $CDCl_3$) δ 8.00-8.02 (m, 2H), 7.14 (d, J=1.2 Hz, 1H), 6.93 (dd, J=11.2, 1.2 Hz, 1H), 6.47 (s, 1 HI), 4.63-4.65 (rn, $1H_1$) 4.39 (br.s, 2H), 2.14 (s, $3H_1$), 1.65 (d, J=6.8 Hz, 6H).

Step 2: tert-Butyl N-[(1R,3S)-3-[[4-(7-fluoro-3-isopropyl-benzimidazol-5-yl)-5-methyl-2-pyridyl]carbamoyl]cyclohexyl]carbamate

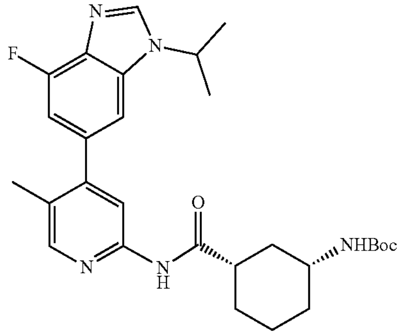 [SMILES: Cc1cnc(NC(=O)[C@H]2CCC[C@@H](NC(=O)OC(C)(C)C)C2)cc1-c1cc(F)c2ncn(C(C)C)c2c1]

To a stirred solution of (1S,3R)-3-(tert-butoxycarbonylamino)cyclohexanecarboxylic acid (8.56 g, 35.2 mmol, 1.0 eq) in DCM (50.0 mL), [chloro(dimethylamino)methylene]-dimethyl-ammonium; hexafluorophosphate (11.8 g, 42.2 mmol, 1.2 eq) was added at 0° C. The mixture was stirred at room temperature for 1 h, and then 4-(7-fluoro-3-isopropyl-benzimidazol-5-yl)-5-methyl-pyridin-2-amine (10.0 g, 35.2 mmol, 1.0 eq) and 1-methyl-1H-imidazole (9.45 mL, 123 mmol, 3.5 eq) were added. After another 14 h, the reaction mixture was diluted with water (50 mL), filtered, and extracted with DCM (3×50 mL). The combined organic layers were washed with brine, dried over anhydrous $Na_2SO_4$, and filtered. The filtrate was concentrated and the residue was purified by column chromatography on a silica gel column (eluting with petroleum ether/ethyl acetate=5/1) to afford tert-butyl N-[(1R,3S)-3-[[4-(7-fluoro-3-isopropyl-benzimidazol-5-yl)-5-methyl-2-pyridyl]carbamoyl]cyclohexyl]carbamate (17.0 g, 33.3 mmol, 94.8% yield). LCMS calcd. for $C_{28}H_{37}FN_5O_3(M+H)^+$ m/z=510.3; found:510.2.

Step 3: (1S,3R)-3-Amino-N-[4-(7-fluoro-3-isopropyl-benzimidazol-5-yl)-5-methyl-2-pyridyl]cyclohexanecarboxamide

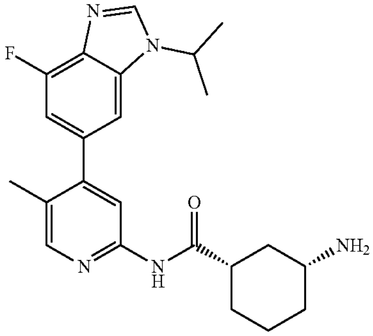 [SMILES: Cc1cnc(NC(=O)[C@H]2CCC[C@@H](N)C2)cc1-c1cc(F)c2ncn(C(C)C)c2c1]

To a mixture of tert-butyl N-[(1R,3S)-3-[[4-(7-fluoro-3-isopropyl-benzimidazol-5-yl)-5-methyl-2-pyridyl]carbamoyl]cyclohexyl]carbamate (29.0 g, 56.9 mmol, 1.0 eq) in DCM (200 mL) was added TFA (43.5 mL, 569 mmol, 10.0 eq). The resulted mixture was stirred at room temperature for 1 h. The volatiles were removed under reduced pressure and the brown oily residue was diluted with water (500 mL).

The aqueous solution was basified with $Na_2CO_3$ to pH>10, and the basified water phase was extracted with DCM (3×500 mL). The combined organic layers were dried over anhydrous $Na_2SO_4$, and filtered. The filtrate was concentrated to afford (1S,3R)-3-amino-N-[4-(7-fluoro-3-isopropyl-benzimidazol-5-yl)-5-methyl-2-pyridyl]cyclohexanecarboxamide (19.0 g, 46.4 mmol, 81.5% yield). LCMS calcd. for $C_{23}H_{29}FN_5O$ $(M+H)^+$ m/z=410.2; found:410.2. $^1H$ NMR (400 MHz, DMSO-$d_6$) δ 10.37 (s, 1H), 8.48 (s, 1H), 8.24 (s, 1H), 8.06 (s, 1H), 7.53 (d, J=1.2 Hz, 1H), 7.07 (dd, J=11.6, 0.8 Hz, 1H), 4.82-4.87 (m, 1H), 4.03 (br.s, 1H), 2.64-2.70 (m, 1H), 2.22 (s, 3H), 1.86 (d, J=12.0 Hz, 1H), 1.71-1.76 (m, 3H), 1.53 (d, J=10.8 Hz, 6H), 1.22-1.27 (m, 3H), 1.16-1.19 (m, 1H).

Step 4: (1S,3R)-3-(Dimethylcarbamoylamino)-N-[4-(7-fluoro-3-isopropyl-benzimidazol-5-yl)-5-methyl-2-pyridyl]cyclohexanecarboxamide Diisopropylethylamine ("DIPEA") (30.2 mL, 183 mmol, 5.0 eq) and (1S,3R)-3-amino-N-[4-(7-fluoro-3-isopropyl-benzimidazol-5-yl)-5-methyl-2-pyridyl]cyclohexanecarboxamide (15.0 g, 36.6 mmol, 1.0 eq) were successively added to a solution of dimethylcarbamoyl chloride (5.91 g, 55.0 mmol, 1.5 eq) in dry DCM (300 mL) at 0° C. The reaction was stirred at room temperature overnight. Then the mixture was diluted with water (500 mL), filtered, and extracted with DCM (3×500 mL). The combined organic layers were washed with brine, dried over anhydrous $Na_2SO_4$, and filtered. The filtrate was concentrated and the residue was purified by column chromatography on a silica gel column (100-200 mesh size, DCM/MeOH=5/1) to afford 16.0 g crude product. The crude product was added to 50 mL MeOH, stirred and filtered. The solid was dried in vacuum to give (1S,3R)-3-(dimethylcarbamoylamino)-N-[4-(7-fluoro-3-isopropyl-benzimidazol-5-yl)-5-methyl-2-pyridyl]cyclohexanecarboxamide (8.90 g, 18.5 mmol, 50.6% yield). LCMS calcd. for $C_{26}H_{34}FN_6O_2$[M+1]+m/z=481.3, found for:481.3 $^1H$ NMR (400 MHz, $CD_3OD$) δ 8.38 (s, 1H), 8.21 (s, 1H), 8.04 (s, 1H), 7.47 (d, J=0.8 Hz, 1H), 7.05 (dd, J=11.2, 0.8 Hz, 1H), 6.06 (d, J=8.0 Hz, 1H), 4.79-4.84 (m, 1H), 3.61-3.68 (m, 1H), 2.87 (s, 6H), 2.55-2.61 (m, 1H), 2.26 (s, 3H), 2.06 (d, J=12.4 Hz, 1H), 1.88-1.90 (m, 3H), 1.64 (d, J=6.8 Hz, 6H), 1.41-1.51 (m, 3H), 1.21-1.30 (m, 1H).

Examples in Table 4 were prepared using the procedure described in the synthesis of Example 28 using appropriate starting materials.

TABLE 4

| Example | Structure/Name | Calcd. $(M + H)^+$ m/z | Found $(M + H)^+$ m/z |
|---|---|---|---|
| 29 | 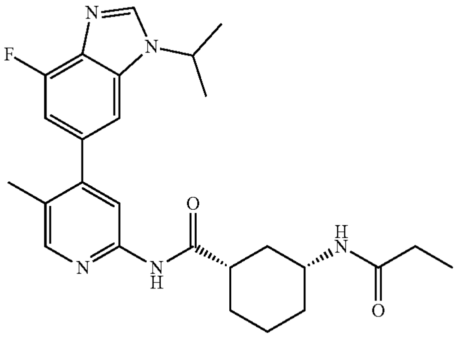 (1S,3R)-N-(4-(4-fluoro-1-isopropyl-1H-benzo[d]imidazol-6-yl)-5-methylpyridin-2-yl)-3-propionamidocyclohexane-1-carboxamide | 466.2 | 466.2 |
| 30 | 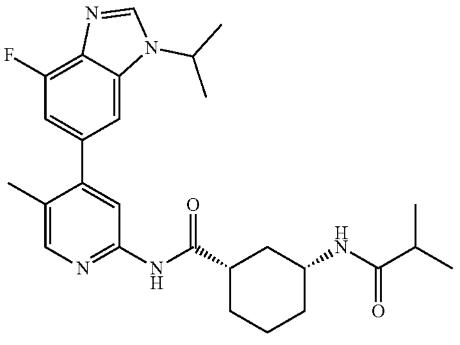 (1S,3R)-N-(4-(4-fluoro-1-isopropyl-1H-benzo[d]imidazol-6-yl)-5-methylpyridin-2-yl)-3-isobutyramidocyclohexane-1-carboxamide | 480.2 | 480.3 |

TABLE 4-continued

| Example | Structure/Name | Calcd. (M + H)+ m/z | Found (M + H)+ m/z |
|---|---|---|---|
| 31 | 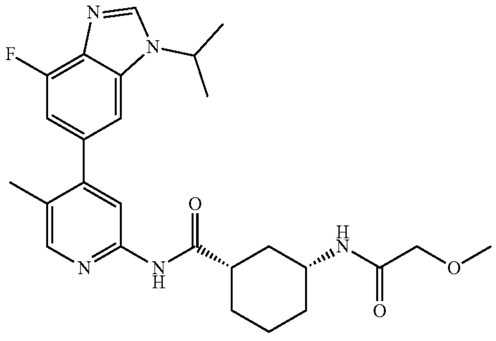 (1S,3R)-N-(4-(4-fluoro-1-isopropyl-1H-benzo[d]imidazol-6-yl)-5-methylpyridin-2-yl)-3-(2-methoxyacetamido)cyclohexane-1-carboxamide | 482.2 | 482.2 |
| 32 | 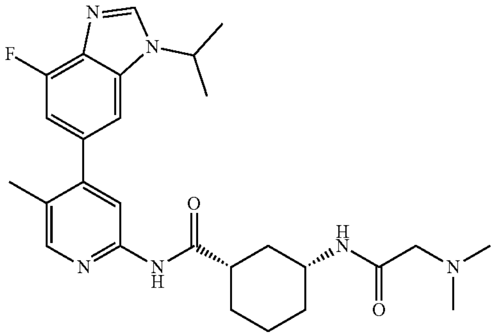 (1S,3R)-3-(2-(dimethylamino)acetamido)-N-(4-(4-fluoro-1-isopropyl-1H-benzo[d]imidazol-6-yl)-5-methylpyridin-2-yl) cyclohexane-1-carboxamide | 495.2 | 495.3 |
| 33 | 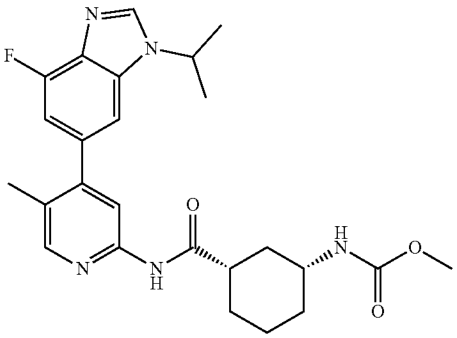 methyl ((1R,3S)-3-((4-(4-fluoro-1-isopropyl-1H-benzo[d] imidazol-6-yl)-5-methylpyridin-2-yl)carbamoyl) cylcohexyl)carbamate | 468.2 | 468.1 |

TABLE 4-continued

| Example | Structure/Name | Calcd. (M + H)+ m/z | Found (M + H)+ m/z |
|---|---|---|---|
| 34 | 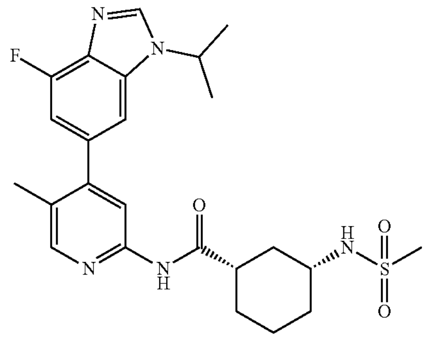 (1S,3R)-N-(4-(4-fluoro-1-isopropyl-1H-benzo[d]imidazol-6-yl)-5-methylpyridin-2-yl)-3-(methylsulfonamido) cyclohexane-1-carboxamide | 488.2 | 488.2 |
| 35 | 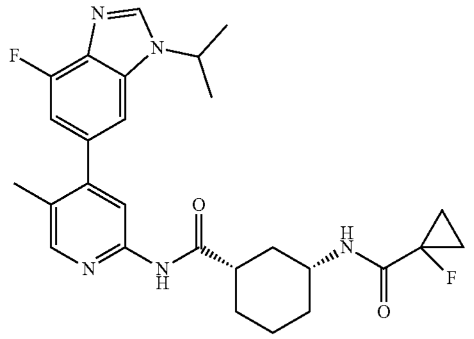 (1S,3R)-N-(4-(4-fluoro-1-isopropyl-1H-benzo[d]imidazol-6-yl)-5-methylpyridin-2-yl)-3-(1-fluorocyclopropane-1-carboxamido)cyclohexane-1-carboxamide | 496.2 | 496.2 |
| 36 | 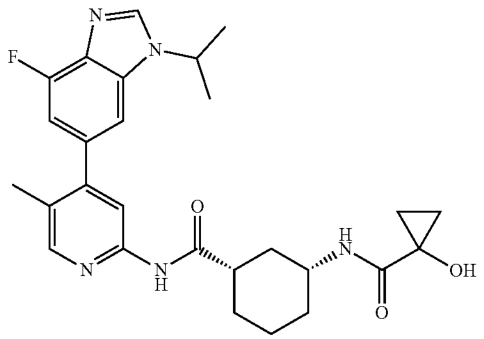 (1S,3R)-N-(4-(4-fluoro-1-isopropyl-1H-benzo[d]imidazol-6-yl)-5-methylpyridin-2-yl)-3-(1-hydroxycyclopropane-1-carboxamido)cyclohexane-1-carboxamide | 494.2 | 494.2 |

TABLE 4-continued

| Example | Structure/Name | Calcd. (M + H)+ m/z | Found (M + H)+ m/z |
|---|---|---|---|
| 37 | 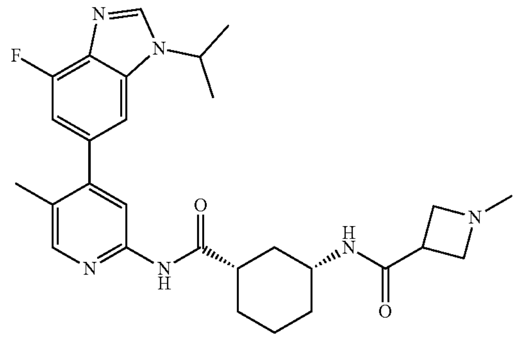 N-((1R,3S)-3-((4-(4-fluoro-1-isopropyl-1H-benzo[d]imidazol-6-yl)-5-methylpyridin-2-yl)carbamoyl)cyclohexyl)-1-methylazetidine-3-carboxamide | 507.2 | 507.3 |
| 38 | 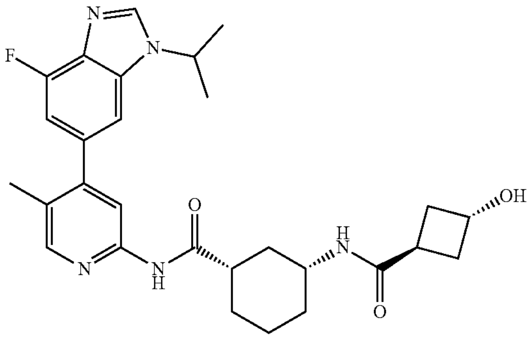 (1S,3R)-N-(4-(4-fluoro-1-isopropyl-1H-benzo[d]imidazol-6-yl)-5-methylpyridin-2-yl)-3-((1r,3R)-3-hydroxycyclobutane-1-carboxamido)cyclohexane-1-carboxamide | 508.3 | 508.2 |
| 39 | 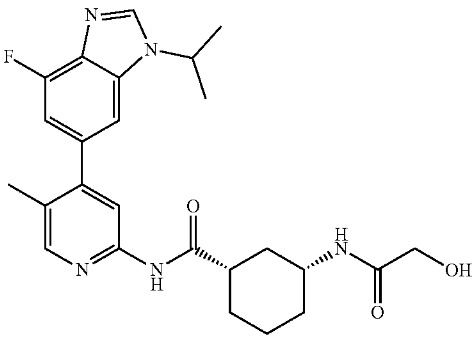 (1S,3R)-N-(4-(4-fluoro-1-isopropyl-1H-benzo[d]imidazol-6-yl)-5-methylpyridin-2-yl)-3-(2-hydroxyacetamido) cyclohexane-1-carboxamide | 468.2 | 468.2 |

TABLE 4-continued

| Example | Structure/Name | Calcd. (M + H)+ m/z | Found (M + H)+ m/z |
|---|---|---|---|
| 40 | 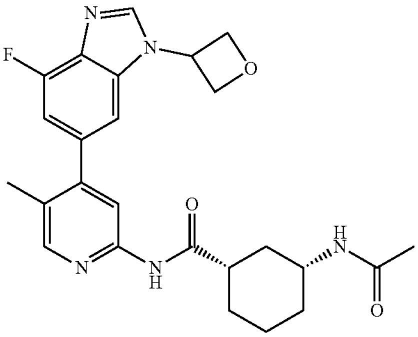 (1S,3R)-3-acetamido-N-(4-(4-fluoro-1-(oxetan-3-yl)-1H-benzo[d]imidazol-6-yl)-5-methylpyridin-2-yl) cyclohexane-1-carboxamide | 466.2 | 466.1 |
| 41 | 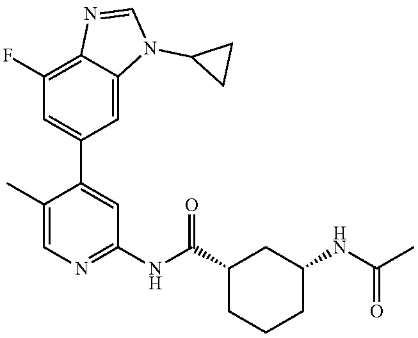 (1S,3R)-3-acetamido-N-(4-(1-cyclopropyl-4-fluoro-1H-benzo[d]imidazol-6-yl)-5-methylpyridin-2-yl)cyclohexane-1-carboxamide | 450.2 | 450.2 |
| 42 | 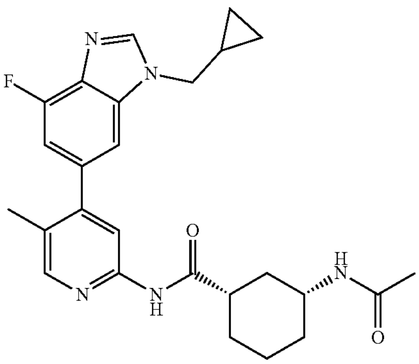 (1S,3R)-3-acetamido-N-(4-(1-(cyclopropylmethyl)-4-fluoro-1H-benzo[d]imidazol-6-yl)-5-methylpyridin-2-yl)cyclohexane-1-carboxamide | 464.2 | 464.2 |

Example 43: (S)—N-((1R,3S)-3-((4-(4-fluoro-1-isopropyl-1H-benzo[d]imidazol-6-yl)-5-methylpyridin-2-yl)carbamoyl)cyclohexyl)-3-hydroxypyrrolidine-1-carboxamide

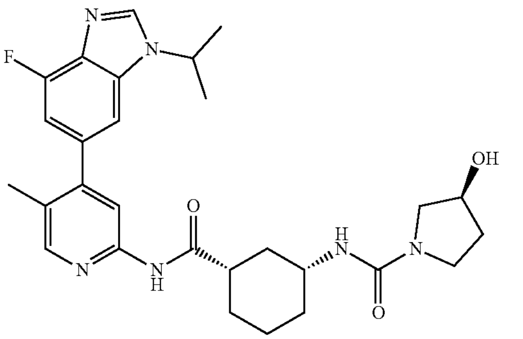 [SMILES: Cc1cnc(NC(=O)[C@H]2CCC[C@@H](NC(=O)N3CC[C@H](O)C3)C2)cc1-c1cc(F)c2ncn(C(C)C)c2c1]

To a stirred solution of (1S,3R)-3-amino-N-[4-(7-fluoro-3-isopropyl-benzimidazol-5-yl)-5-methyl-2-pyridyl]cyclohexanecarboxamide (Step 3, Example 28, 50.0 mg, 0.120 mmol, 1.0 eq) in DCM (10 mL) was added TEA (0.0500 mL, 0.370 mmol, 3.0 eq), followed by triphosgene (18.1 mg, 0.0600 mmol, 0.5 eq) in one portion in ice-bath. The reaction mixture was stirred at room temperature for 30 mins. (S)-pyrrolidin-3-ol (0.0300 mL, 0.610 mmol, 5.0 eq) was added and the resulted mixture was stirred at room temperature for another 18 h. The volatiles were removed and the residue was purified by reverse phase chromatography to get desired product (S)—N-((1R,3S)-3-((4-(4-fluoro-1-isopropyl-1H-benzo[d]imidazol-6-yl)-5-methylpyridin-2-yl)carbamoyl)cyclohexyl)-3-hydroxypyrrolidine-1-carboxamide (35.0 mg, 0.0670 mmol, 54.8% yield) as a white solid. LCMS calcd. for $C_{28}H_{36}FN_6O_3$ $[M+1]^+$ m/z=523.3, found for: 523.3.

Examples in Table 5 were prepared using the procedure described in the synthesis of Example 43 using appropriate starting materials.

TABLE 5

| Example | Structure/Name | Calcd. $(M + H)^+$ m/z | Found $(M + H)^+$ m/z |
| --- | --- | --- | --- |
| 44 | 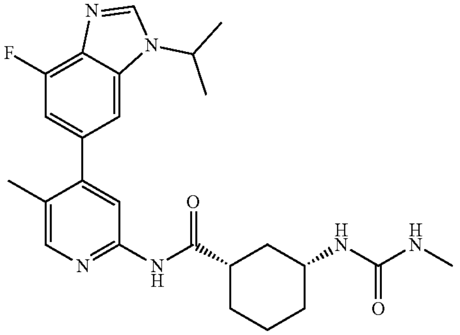 (1S,3R)-N-(4-(4-fluoro-1-isopropyl-1H-benzo[d]imidazol-6-yl)-5-methylpyridin-2-yl)-3-(3-methylureido)cyclohexane-1-carboxamide | 467.2 | 467.2 |
| 45 | 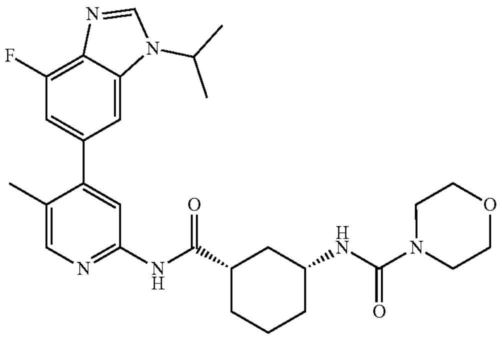 N-((1R,3S)-3-((4-(4-fluoro-1-isopropyl-1H-benzo[d]imidazol-6-yl)-5-methylpyridin-2-yl)carbamoyl)cyclohexyl)morpholine-4-carboxamide | 523.3 | 523.3 |

TABLE 5-continued

| Example | Structure/Name | Calcd. (M + H)+ m/z | Found (M + H)+ m/z |
|---|---|---|---|
| 46 | 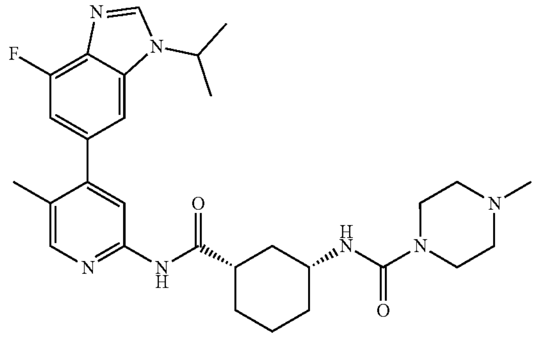 N-((1R,3S)-3-((4-(4-fluoro-1-isopropyl-1H-benzo[d]imidazol-6-yl)-5-methylpyridin-2-yl)carbamoyl)cyclohexyl)-4-methylpiperazine-1-carboxamide | 536.3 | 536.3 |

Example 47: (1S,3R)—N-[4-(7-fluoro-3-isopropyl-benzimidazol-5-yl)-5-methyl-2-pyridyl]-3-[(methyl-sulfonimidoyl)amino]cyclohexanecarboxamide

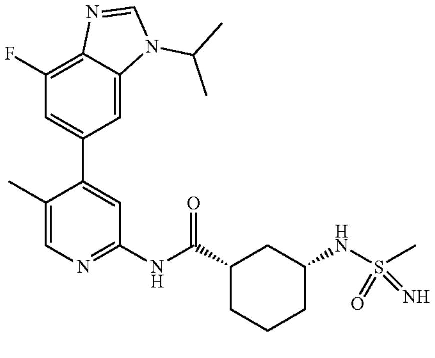 [SMILES: Cc1cnc(NC(=O)[C@H]2CCC[C@@H](NS(C)(=N)=O)C2)cc1-c1cc(F)c2ncn(C(C)C)c2c1]

Step 1: N-(tert-Butyldimethylsilyl)methanesulfonamide

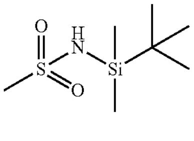

To a stirred solution of methanesulfonamide (10.0 g, 105 mmol, 1.0 eq) and tert-butyl dimethylchlorosilane (23.8 g, 158 mmol, 1.5 eq) in chloroform (150 mL) was added triethylamine (22.0 mL, 158 mmol, 1.5 eq) at 0° C. After stirred at room temperature overnight, the mixture was concentrated under reduced pressure. The residue was diluted with water (200 mL) and extracted with ethyl acetate (2×100 mL). The combined organic layers were washed with brine, dried over sodium sulfate and filtered. The filtrate was concentrated under reduced pressure to give N-[tert-butyl(dimethyl)silyl]methanesulfonamide (17.8 g, 84.7 mmol, 80.6% yield) as a white solid. LCMS calcd. for $C_7H_{20}NO_2SSi$ $(M+H)^+$ m/z=210.1; found: 210.0. $^1H$ NMR (400 MHz, DMSO-$d_6$) δ 6.88 (s, 1H), 2.74 (s, 3H), 0.72 (s, 9H), 0.00 (s, 6H).

Step 2: 2: (1S,3R)-3-[[N-[tert-Butyl(dimethyl)silyl]-methyl-sulfonimidoyl]amino]-N-[4-(7-fluoro-3-iso-propyl-benzimidazol-5-yl)-5-methyl-2-pyridyl]cy-clohexanecarboxamide

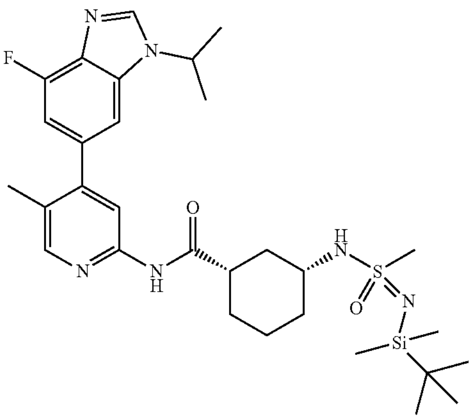 [SMILES: Cc1cnc(NC(=O)[C@H]2CCC[C@@H](NS(C)(=O)=N[Si](C)(C)C(C)(C)C)C2)cc1-c1cc(F)c2ncn(C(C)C)c2c1]

To a solution of triphenylphosphine dichloride (55.3 mg, 0.170 mmol, 1.0 eq) in dichloromethane (2.0 mL), was added triethylamine (0.06 mL, 0.520 mmol, 3.0 eq) and stirred at room temperature for 10 mins. A solution of N-[tert-butyl(dimethyl)silyl]methanesulfonamide (34.8 mg, 0.170 mmol, 1.0 eq) in dichloromethane (2.0 mL) was added at 0° C., the mixture was stirred at 0° C. for 20 mins. A solution of (1S,3R)-3-amino-N-[4-(7-fluoro-3-isopropyl-benzimidazol-5-yl)-5-methyl-2-pyridyl]cyclohexanecar-boxamide (Step 3, Example 28, 20.0 mg, 0.05 mmol, 0.3 eq) was added at 0° C. The mixture was stirred at 0° C. for 30 mins and warmed to room temperature overnight. The obtained mixture was concentrated and purified by flash chromatography to afford the desired product (20.0 mg, 0.0300 mmol, 60.0% yield). $^1H$ NMR (400 MHz, $CD_3OD$) δ 8.38 (s, 1H), 8.22 (s, 1H), 8.03 (s, 1H), 7.47 (d, J=0.8 Hz, 1H), 7.06 (d, J=10.8 Hz, 1H), 4.68-4.80 (m, 1H), 3.30-3.31 (m, 1H), 2.97 (d, J=1.2 Hz, 3H), 2.54-2.61 (m, 1H), 2.27 (s, 3H), 2.13-2.20 (m, 1H), 1.99-2.06 (m, 1H), 1.84-1.92 (m, 2H), 1.64 (d, J=6.4 Hz, 6H), 1.36-1.52 (m, 3H), 1.22-1.30 (m, 1H), 0.90 (s, 9H), 0.09 (s, 3H), 0.08 (s, 3H).

Step 3: (1S,3R)—N-[4-(7-Fluoro-3-isopropyl-benzimidazol-5-yl)-5-methyl-2-pyridyl]-3-[(methylsulfonimidoyl)amino]cyclohexanecarboxamide To a solution of (1S,3R)-3-[[N-[tert-butyl(dimethyl)silyl]-S-methyl-sulfonimidoyl]amino]-N-[4-(7-fluoro-3-isopropyl-benzimidazol-5-yl)-5-methyl-2-pyridyl]cyclohexanecarboxamide (20.0 mg, 0.03 mmol, 1.0 eq) in methanol (2.0 mL) was added 4 N HCl solution in methanol (0.5 mL, 2.00 mmol, 60.0 eq). The reaction mixture was stirred at room temperature for 1 h. The reaction was quenched with ammonia solution, concentrated and purified by flash column chromatography to afford (1S,3R)—N-[4-(7-fluoro-3-isopropyl-benzimidazol-5-yl)-5-methyl-2-pyridyl]-3-[(methylsulfonimidoyl)amino]cyclohexanecarboxamide (3.9 mg, 0.007 mmol, 23.1% yield) as a yellow solid. LCMS calcd. for $C_{24}H_{32}FN_6O_2S$ $[M+H]^+$ m/z=487.2; found: 487.1. $^1H$ NMR (400 MHz, $CD_3OD$) δ 8.38 (s, 1H), 8.22 (s, 1H), 8.03 (s, 1H), 7.47 (s, 1H), 7.06 (d, J=11.2 Hz, 1H), 4.68-4.80 (m, 1H), 3.30-3.31 (m, 1H), 3.02 (s, 3H), 2.55-2.61 (m, 1H), 2.27 (s, 3H), 2.15-2.20 (m, 1H), 1.96-2.04 (m, 1H), 1.85-1.91 (m, 2H), 1.64 (d, J=6.8 Hz, 6H), 1.38-1.52 (m, 3H), 1.26-1.29 (m, 1H).

Example 48: (1S,3R)—N1-(4-(4-fluoro-1-isopropyl-1H-benzo[d]imidazol-6-yl)-5-methylpyridin-2-yl)-N3-methylcyclohexane-1,3-dicarboxamide

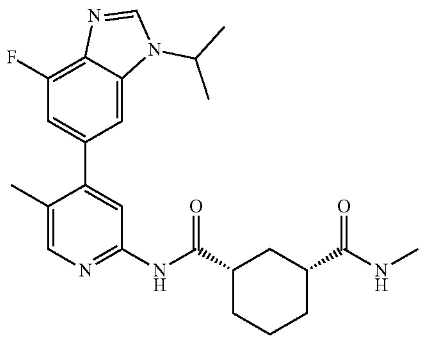 [SMILES: CNC(=O)[C@@H]1CCC[C@H](C(=O)Nc2cc(-c3cc(F)c4ncn(C(C)C)c4c3)c(C)cn2)C1]

Step 1: Ethyl (1R,3S)-3-[(4-iodo-5-methyl-2-pyridyl)carbamoyl]cyclohexanecarboxylate

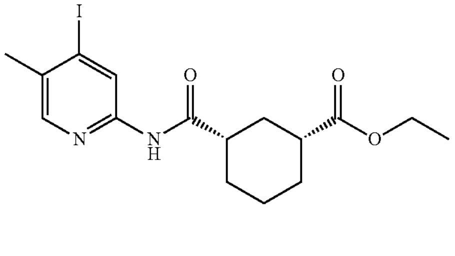 [SMILES: CCOC(=O)[C@@H]1CCC[C@H](C(=O)Nc2cc(I)c(C)cn2)C1]

To a mixture of (1S,3R)-3-ethoxycarbonylcyclohexanecarboxylic acid (0.470 g, 2.35 mmol, 1.0 eq) in DCM (25 mL) were added N-(chloro(dimethylamino)methylene)-N-methylmethanaminium hexafluorophosphate(V) (0.720 g, 2.56 mmol, 1.1 eq) and 1-methyl-1H-imidazole (0.590 g, 7.48 mmol, 3.2 eq) at 0° C. The mixture was stirred at room temperature for 20 mins. Then 4-iodo-5-methyl-pyridin-2-amine (0.500 g, 2.14 mmol, 0.91 eq) was added. After another 18 h, the volatiles were removed under reduced pressure and the residue was purified by chromatography (eluting with DCM/MeOH=20/1) to give ethyl (1R,3S)-3-[(4-iodo-5-methyl-2-pyridyl)carbamoyl]cyclohexanecarboxylate (0.800 g, 1.92 mmol, 89.9% yield). LCMS calcd. for $C_{16}H_{22}1N_2O_3(M+H)^+$ m/z=417.1; found:417.0.

Step 2: (1S,3R)—N1-(4-Iodo-5-methylpyridin-2-yl)-N3-methylcyclohexane-1,3-dicarboxamide

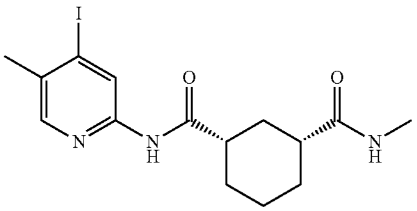

The mixture of ethyl (1R,3S)-3-[(4-iodo-5-methyl-2-pyridyl)carbamoyl]cyclohexanecarboxylate (300.0 mg, 0.72 mmol, 1.0 eq) in methylamine ethanol solution (3 M, 7.19 mL, 21.6 mmol, 30.0 eq) was heated to 100° C. under microwave conditions with stirring for 3 h. The mixture was concentrated and purified by chromatography (eluting with DCM/MeOH=30/1) to afford (1S,3R)—N1-(4-iodo-5-methyl-2-pyridyl)-N3-methyl-cyclohexane-1,3-dicarboxamide (92.0 mg, 0.229 mmol, 31.8% yield) as a white solid. LCMS calcd. for $C_{15}H_{211}N_3O_2$ $(M+H)^+$ m/z=402.1; found: 402.0.

Step 3: (1S,3R)—N1-(4-(4-Fluoro-1-isopropyl-H-benzo[d]imidazol-6-yl)-5-methylpyridin-2-yl)-N3-methylcyclohexane-1,3-dicarboxamide The title compound was prepared using procedure analogous to that described for Example 22, step 8 with (1S,3R)—N1-(4-iodo-5-methyl-2-pyridyl)-N3-methyl-cyclohexane-1,3-dicarboxamide replacing (1S,3R)-3-acetamido-N-(4-iodo-5-methylpyridin-2-yl)cyclohexane-1-carboxamide. LCMS calcd. for $C_{25}H_{31}FN_5O_2(M+H)^+$ m/z=452.2; found:452.2. $^1H$ NMR (400 MHz, $CD_3OD$) δ 8.38 (s, 1H), 8.21 (s, 1H), 8.03 (s, 1H), 7.47 (d, J=1.2 Hz, 1H), 7.05 (dd, J=11.2, 1.2 Hz, 1H), 4.73-4.89 (m, 1H), 2.70 (s, 3H), 2.52 (t, J=8.0 Hz, 1H), 2.28-2.31 (m, 1H), 2.26 (s, 3H), 1.92-1.96 (m, 3H), 1.82-1.84 (m, 1H), 1.68-1.78 (m, 1H), 1.64 (d, J=6.8 Hz, 6H), 1.41-1.53 (m, 3H).

Example 49: 3-cyano-N-(4-(4-fluoro-1-isopropyl-1H-benzo[d]imidazol-6-yl)-5-methylpyridin-2-yl)cyclohexane-1-carboxamide

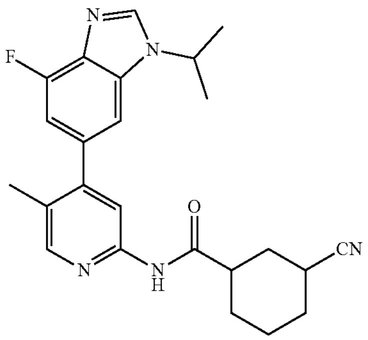 [SMILES: Cc1cnc(NC(=O)C2CCCC(C#N)C2)cc1-c1cc(F)c2ncn(C(C)C)c2c1]

Step 1: Methyl 3-carbamoylcyclohexane-1-carboxylate

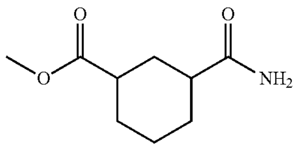

A solution of 3-methoxycarbonylcyclohexane-1-carboxylic acid (1.00 g, 5.37 mmol, 1.0 eq) in thionyl chloride (3.00 mL, 41.7 mmol, 7.8 eq) was stirred at room temperature overnight. The mixture was concentrated in vacuum. Then the residue was dissolved in ether and cooled to 0° C. Ammonia solution (1.00 mL) was added dropwise. After another 2 h, the reaction mixture was filtered. The solid was dissolved in DCM, washed with brine, dried over anhydrous magnesium sulfate, and filtered. The filtrate was concentrated to give methyl 3-carbamoylcyclohexane-1-carboxylate (627 mg, 3.38 mmol, 63% yield). LCMS calcd. for $C_9H_{16}NO_3$ $(M+H)^+$ m/z=186.1; found: 186.2.

Step 2: Methyl 3-cyanocyclohexane-1-carboxylate

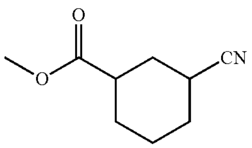

To a solution of methyl 3-carbamoylcyclohexane-1-carboxylate (185 mg, 1.00 mmol, 1.0 eq) in tetrahydrofuran (3.0 mL) was added Burgess reagent (384 mg, 1.50 mmol, 1.5 eq) at room temperature. The reaction mixture was stirred at room temperature overnight. The mixture was diluted with water (10 mL) and extracted with ethyl acetate (3×10 mL). The combined organic layers were washed with brine, dried over anhydrous sodium sulfate, and filtered. The filtrate was concentrated to give crude methyl 3-cyanocyclohexane-1-carboxylate (169 mg, 0.960 mmol, 96.1% yield), which was used in the next step without further purification. LCMS calcd. for $C_9H_{14}NO_2$ $(M+H)^+$ m/z=168.1; found: 168.2.

Step 3: 3-Cyanocyclohexane-1-carboxylic acid

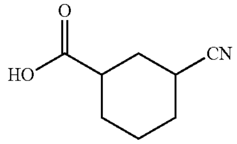 [SMILES: N#CC1CCCC(C(=O)O)C1]

Lithium hydroxide (58.1 mg, 2.43 mmol, 2.4 eq) was added to a solution of methyl 3-cyanocyclohexane-1-carboxylate (169 mg, 1.01 mmol, 1.0 eq) in a mixed solvent of tetrahydrofuran (4.0 mL), methanol (1.0 mL), and water (1.0 mL) at room temperature. The reaction mixture was stirred at room temperature overnight. The mixture was adjusted to pH 5-6 with 1 N HCl solution and extracted with ethyl acetate (3×10 mL). The combined organic layers were washed with brine, dried over anhydrous sodium sulfate, and filtered. The filtrate was concentrated to give 3-cyanocyclohexane-1-carboxylic acid (119 mg, 0.780 mmol, 76.9% yield). LCMS calcd. for $C_8H_{12}NO_2$ $(M+H)^+$ m/z=154.1; found: 154.2.

Step 4: 3-Cyano-N-(4-(4-fluoro-1-isopropyl-1H-benzo[d]imidazol-6-yl)-5-methylpyridin-2-yl)cyclohexane-1-carboxamide The title compound was prepared using procedure analogous to that described for Example 28, Step 2 with 3-cyanocyclohexane-1-carboxylic acid replacing (1S,3R)-3-(tert-butoxycarbonylamino)cyclohexanecarboxylic acid. LCMS calcd. for $C_{24}H_{27}FN_5O$ $(M+H)^+$ m/z=420.2; found: 420.2. $^1H$ NMR (400 MHz, $CD_3OD$) δ 10.46 (s, 1H), 8.48 (s, 1H), 8.25 (s, 1H), 8.04 (s, 1H), 7.53 (d, J=1.2 Hz, 1H), 7.06 (d, J=1.2, 11.2 Hz, 1H), 4.81-4.88 (m, 1H), 2.67-2.74 (m, 1H), 2.49-2.55 (m, 1H), 2.27 (s, 3H), 2.22-2.25 (m, 1H), 2.08-2.11 (m, 1H), 1.90-1.96 (m, 2H), 1.68-1.80 (m, 1H), 1.64 (d, J=6.8 Hz, 6H), 1.41-1.58 (m, 3H).

Example 50: (1S,3R)-3-(3,3-dimethylureido)-N-(4-(4-fluoro-1-(1,1,1-trifluoropropan-2-yl)-1H-benzo[d]imidazol-6-yl)-5-methylpyridin-2-yl)cyclohexane-1-carboxamide

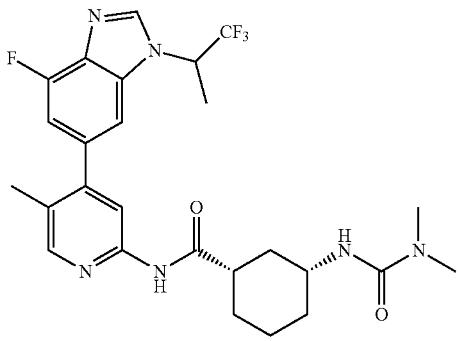 [SMILES: Cc1cnc(NC(=O)[C@H]2CCC[C@@H](NC(=O)N(C)C)C2)cc1-c1cc(F)c2ncn(C(C)C(F)(F)F)c2c1]

Step 1: 5-Bromo-3-fluoro-2-nitro-N-(1,1,1-trifluoropropan-2-yl)aniline

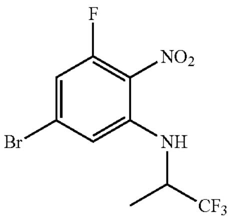 [SMILES: CC(Nc1cc(Br)cc(F)c1[N+](=O)[O-])C(F)(F)F]

To a solution of 5-bromo-1,3-difluoro-2-nitro-benzene (200 mg, 0.840 mmol, 1.0 eq) and in THF (10.0 mL) at 0° C. was slowly added TEA (0.490 mL, 4.20 mmol, 5.0 eq) and 2-amino-1,1,1-trifluoropropane hydrochloride (126 mg, 0.840 mmol, 1.0 eq). After stirred for further 30 mins, the cooling bath was removed and the reaction was stirred at 110° C. in seal tube for 3 days. The reaction mixture was concentrated and purified by reverse phase chromatography to give 5-bromo-3-fluoro-2-nitro-N-(1,1,1-trifluoropropan-2-yl)aniline (1.80 g, 5.43 mmol, 64.8% yield). 1H NMR (400 MHz, $CD_3OD$) δ 7.20 (s, 1H), 6.89 (dd, J=10.8, 2.0 Hz, 1H), 4.59-4.64 (m, 1H), 1.45 (d, J=6.8 Hz, 3H).

Step 2 to Step 8: (1S,3R)-3-(3,3-Dimethylureido)-N-(4-(4-fluoro-1-(1,1,1-trifluoropropan-2-yl)-1H-benzo[d]imidazol-6-yl)-5-methylpyridin-2-yl)cyclohexane-1-carboxamide

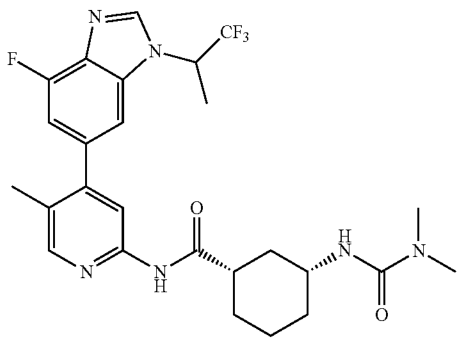 [SMILES: Cc1cnc(NC(=O)[C@H]2CCC[C@@H](NC(=O)N(C)C)C2)cc1-c1cc(F)c2ncn(C(C)C(F)(F)F)c2c1]

The title compound was prepared using procedures analogous to those described for Example 22, Step 2 to Step 8, using appropriate starting materials. LCMS calcd. for $C_{26}H_{31}F_4N_6O_2$ $(M+H)^+$ m/z=535.2; found: 535.2. $^1H$ NMR (400 MHz, $CD_3OD$) δ 8.54 (s, 1H), 8.23 (s, 1H), 8.03 (s, 1H), 7.55 (s, 1H), 7.14 (dd, J=10.8, 1.2 Hz, 1H), 6.05-6.07 (m, 1H), 5.57-5.61 (m, 1H), 3.62-3.66 (m, 1H), 2.92 (s, 6H), 2.56-2.58 (m, 1H), 2.26 (s, 3H), 2.06 (d, J=12.0 Hz, 1H), 1.88-1.93 (m, 6H), 1.41-1.54 (m, 3H), 1.24-1.28 (m, 1H).

Example 51: (1S,3R)-3-acetamido-N-(5-chloro-4-(1,1-dimethyl-2,3-dihydro-1H-pyrrolo[1,2-b]indazol-8-yl)pyridin-2-yl)cyclohexane-1-carboxamide

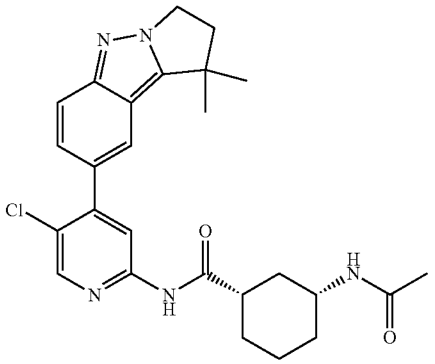 [SMILES: CC(=O)N[C@@H]1CCC[C@H](C(=O)Nc2cc(-c3ccc4nn5c(c4c3)C(C)(C)CC5)c(Cl)cn2)C1]

Step 1: 3,3-Dimethyl-1-nitrosopyrrolidine-2-carboxylic acid

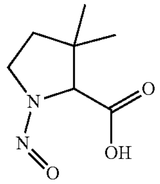

3,3-Dimethylpyrrolidine-2-carboxylic acid (500 mg, 3.49 mmol, 1.0 eq), water (1.0 mL) and sodium nitrite (342.24 mg, 4.89 mmol, 1.4 eq) were added to a 5 mL vial, dissolved, and cooled to 0° C. 12 N HCl solution (0.580 mL, 6.98 mmol) was added dropwise. The mixture was stirred at room temperature for 16 h. The mixture was diluted with water (3 mL) and extracted with ethyl acetate (3×5 mL). The organic phase was washed with brine, dried over anhydrous sodium sulfate, and concentrated to afford 3,3-dimethyl-1-nitrosopyrrolidine-2-carboxylic acid (374 mg, 2.17 mmol, 62.2% yield). LCMS calcd. for $C_7H_{13}N_2O_3$ $(M+H)^+$ m/z=173.1; found: 173.2.

Step 2: 4,4-dimethyl-5, 6-dihydro-4H-pyrrolo[1,2-c][1,2,3]oxadiazol-7-ium-3-olate

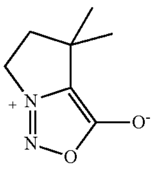

To a stirred solution of 3,3-dimethyl-1-nitrosopyrrolidine-2-carboxylic acid (374 mg, 2.17 mmol, 1.0 eq) in acetonitrile (3.0 mL) was slowly added trifluoroacetic anhydride (0.390 mL, 2.82 mmol, 1.3 eq). The mixture was stirred at room temperature for 18 h. Potassium carbonate (405 mg, 2.93 mmol, 1.35 eq) was added and the mixture was stirred at room temperature for 1 h. The obtained mixture was diluted with water (5 mL) and extracted with ethyl acetate (3×5 mL). The combined organic phase was washed with brine, dried over anhydrous sodium sulfate, and concentrated to afford the desired product (371 mg, 2.13 mmol, 97.9% yield). LCMS calcd. for $C_7H_{11}N_2O_2^+$ $(M)^+$ m/z=155.1; found: 155.2. $^1H$ NMR (400 MHz, DMSO-$d_6$) δ 4.54-4.58 (m, 2H), 2.44-2.51 (m, 2H), 1.30 (s, 6H).

Step 3: 1,1-Dimethyl-2,3-dihydro-JH-pyrrolo[1,2-b]indazole

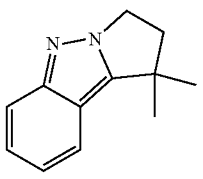

To a solution of 4,4-dimethyl-3-oxo-3a,4,5,6-tetrahydro-3H-pyrrolo[1,2-c][1,2,3]oxadiazol-7-ium (100 mg, 0.570 mmol, 1.0 eq) and (2-trimethylsilylphenyl) trifluoromethanesulfonate (204 mg, 0.680 mmol, 1.2 eq) in tetrahydrofuran (5.0 mL) was added tetrabutylammonium fluoride (239 mg, 0.910 mmol, 1.3 eq). The mixture was stirred at room temperature for 18 h. The obtained mixture was diluted with ethyl acetate (10 mL) and washed with saturated aqueous solution of ammonium chloride (3×5 mL). The organic phase was washed with brine, dried over anhydrous sodium sulfate, concentrated and purified by prepared TLC (eluting with light petroleum ether/ethyl acetate=3/1) to afford 1,1-dimethyl-2,3-dihydropyrrolo[1,2-b]indazole (66.0 mg, 0.350 mmol, 62.2% yield). LCMS calcd. for $C_{12}H_{15}N_2$ $(M+H)^+$ m/z=187.1; found: 187.2. $^1H$ NMR (400 MHz, DMSO-$d_6$) δ 7.71-7.74 (m, 1H), 7.51-7.54 (m, 1H), 7.17-7.20 (m, 1H), 6.94-6.98 (m, 1H), 4.42-4.45 (m, 2H), 2.49-2.52 (m, 2H), 1.47 (s, 6H).

Step 4: 8-Bromo-1,1-dimethyl-2,3-dihydro-1H-pyrrolo[1,2-b]indazole

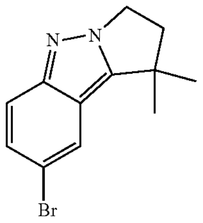

To a solution of 1,1-dimethyl-2,3-dihydropyrrolo[1,2-b]indazole (66.0 mg, 0.350 mmol, 1.0 eq) in acetic acid (2.0 mL) was slowly added bromine (56.6 mg, 0.350 mmol, 1.0 eq). The mixture was heated at 65° C. overnight. The mixture was quenched with aqueous solution of sodium sulfite, alkalized with sodium bicarbonate to pH 8 and extracted with ethyl acetate (3×10 mL). The combined organic phase was washed with brine, dried over anhydrous sodium sulfate, concentrated and purified by prepared TLC (light petroleum ether/ethyl acetate=3/1) to afford 8-bromo-1,1-dimethyl-2,3-dihydropyrrolo[1,2-b]indazole (44.0 mg, 0.160 mmol, 46.8% yield). LCMS calcd. for $C_{12}H_{14}BrN_2$ $(M+H)^+$ m/z=265.0, 267.0; found: 265.1, 267.1. $^1H$ NMR (400 MHz, $CDCl_3$) δ 7.78 (d, J=1.2 Hz, 1H), 7.55 (d, J=9.2 Hz, 1H), 7.32 (dd, J=9.2, 1.2 Hz, 1H), 4.48 (t, J=7.2 Hz, 2H), 2.56 (t, J=7.2 Hz, 2H), 1.53 (s, 6H).

Step 5: 1,1-Dimethyl-8-(4,4,5,5-tetramethyl-1, 3,2-dioxaborolan-2-yl)-2,3-dihydro-1H-pyrrolo[1,2-b]indazole

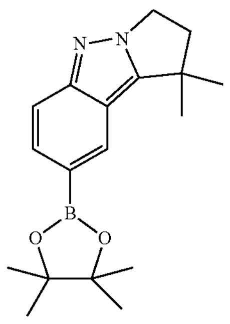

A mixture of 8-bromo-1,1-dimethyl-2,3-dihydropyrrolo[1,2-b]indazole (44.0 mg, 0.170 mmol, 1.0 eq), bis(pinacolato)diboron (63.2 mg, 0.250 mmol, 1.5 eq), and potassium acetate (32.5 mg, 0.330 mmol, 2.0 eq) in 1,4-dioxane (1.0 mL) was bubbled with nitrogen for 5 mins. 1,1'-Bis(diphenylphosphino)ferrocene palladium(II)dichloride (12.1 mg, 0.0200 mmol, 0.11 eq) was added. The mixture was stirred at 100° C. for 3 h. The reaction mixture was diluted with ethyl acetate (10 mL) and washed with water (3×10 mL). The organic layer was washed with brine, dried over anhydrous sodium sulfate, and filtered. The filtrate was concentrated to give 1,1-dimethyl-8-(4,4,5,5-tetramethyl-1,3,2-dioxaborolan-2-yl)-2,3-dihydropyrrolo[1,2-b]indazole (50.0 mg, 0.160 mmol, 96.5% yield). LCMS calcd. for $C_{18}H_{26}BN_2O_2(M+H)^+$ m/z=313.2; found: 313.2.

Step 6 to Step 9: (1S,3R)-3-Acetamido-N-(5-chloro-4-(1,1-dimethyl-2, 3-dihydro-1H-pyrrolo[1,2-b]indazol-8-yl)pyridin-2-yl)cyclohexane-1-carboxamide The title compound was prepared using procedures analogous to those described for Example 22, Step 5 to Step 8, using appropriate starting material. LCMS calcd. for $C_{26}H_{31}Cl N_5O_2$ $(M+H)^+$ m/z=480.2; found: 480.3. $^1H$ NMR (400 MHz, $CD_3OD$) δ 8.36 (s, 1H), 8.22 (s, 1H), 7.87 (s, 1H), 7.64 (d, J=9.2 Hz, 1H), 7.42 (dd, J=9.2, 1.6 Hz, 1H), 4.52 (t, J=7.2 Hz, 2H), 3.70-3.76 (m, 1H), 2.65 (t, J=3.6 Hz, 2H), 2.57-2.64 (m, 1H), 2.04-2.07 (m, 1H), 1.91 (s, 3H), 1.86-1.92 (m, 3H), 1.58 (s, 6H), 1.36-1.49 (m, 3H), 1.15-1.28 (m, 1H).

Example 52: (1S,3R)-3-acetamido-N-(5-chloro-4-(7-fluoro-3-(1-hydroxypropan-2-yl)-2-methyl-2H-indazol-5-yl)pyridin-2-yl)cyclohexane-1-carboxamide

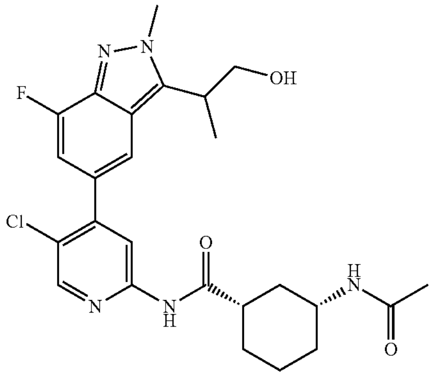 [SMILES: CC(=O)N[C@@H]1CCC[C@H](C(=O)Nc2cc(-c3cc(F)c4nn(C)c(C(C)CO)c4c3)c(Cl)cn2)C1]

Step 1: 2-(5-bromo-7-fluoro-2-methyl-2H-indazol-3-yl)propan-1-ol and 2-(5-bromo-7-fluoro-2-methylindazol-3-yl)propan-2-ol

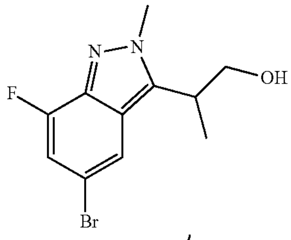

and

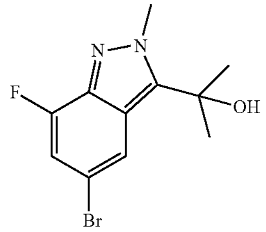

A 4 mL vial with septum containing a solution of 5-bromo-7-fluoro-2-methyl-3-prop-1-en-2-ylindazole (Step 2, Example 1, 70 mg, 0.26 mmol) in THE (1.3 mL) under $N_2$ was charged with borane; 1 M in tetrahydrofuran (300 µL 0.30 mmol) at 0° C. over 1 min. The reaction mixture was stirred at 0° C. for 1 h. The reaction was stirred at RT for 1 d. The reaction mixture was charged with additional borane; 1 M in tetrahydrofuran (310 µL, 0.31 mmol) and stirred at RT for 1 d. The reaction mixture was charged with additional borane; 1 M in tetrahydrofuran (170 µL, 0.17 mmol) and stirred at RT for 4 h. The reaction mixture was charged with a solution of sodium hydroxide; 15 wt % (800 µL, 3 mmol) and stirred at 40° C. for 15 min. The reaction mixture was then cooled to 0° C., charged with hydrogen peroxide, 35 wt % in water (500 µL, 5.84 mmol), and stirred at RT for 20 min. The reaction mixture was quenched with sat. $NH_4Cl$ (15 mL) and water (15 mL), and extracted with EtOAc (50 mL), washed with brine (15 mL). The aqueous layers were combined and back-extracted with EtOAc (50 mL). The organic layers were combined, dried over $Na_2SO_4$, filtered, concentrated under reduced pressure, and purified by FCC (12 g $SiO_2$, 10-80% EtOAc in hexanes, wet-loaded in DCM). Fractions containing the separated isomeric products were separately combined and concentrated under reduced pressure and heat (~40° C.) to yield 2-(5-bromo-7-fluoro-2-methylindazol-3-yl)propan-1-ol (18.7 mg, 0.065 mmol, 25% yield) as a clear/white solid after scratching. LCMS calcd. for $C_{11}H_{13}BrFN_2O(M+H)^+$ m/z: 287.0/289.0; found: 286.9/288.9; $R_f$=0.04 (2:1 hexanes:EtOAc). $^1H$ NMR (500 MHz, $CDCl_3$) δ 7.73 (d, J=1.4 Hz, 1H), 7.03 (dd, J=1.4, 10.0 Hz, 1H), 4.44 (s, 3H), 2.17 (s, 1H), 1.87 (s, 6H) From the same reaction, 2-(5-bromo-7-fluoro-2-methylindazol-3-yl) propan-2-ol (21 mg, 0.072 mmol, 28% yield) was also isolated as a white solid. LCMS calcd. for $C_{11}H_{13}BrFN_2O$ $(M+H)^+$ m/z: 287.0/289.0; found: 286.9/288.9; $R_f$=0.15 (2:1 hexanes:EtOAc). $^1H$ NMR (500 MHz, $CDCl_3$) δ 7.67 (d, J=1.4 Hz, 1H), 7.07 (dd, J=1.4, 10.1 Hz, 1H), 4.24 (s, 3H), 3.98 (d, J=7.0 Hz, 2H), 3.53 (h, J=6.8 Hz, 1H), 1.51 (d, J=7.2 Hz, 3H).

Step 2: (1S,3R)-3-acetamido-N-(5-chloro-4-(7-fluoro-3-(I-hydroxypropan-2-yl)-2-methyl-2H-indazol-5-yl)pyridin-2-yl)cyclohexane-1-carboxamide The title compound was prepared using procedure analogous to that described for Example 1, Step 8, with 2-(5-bromo-7-fluoro-2-methylindazol-3-yl)propan-1-ol replacing 5-bromo-7-fluoro-3-isopropyl-2-methyl-indazole. LCMS calcd. for $C_{25}H_{30}ClFN_5O_3(M+H)^+$ m/z: 502.2; found 502.0.

Example 53: (1S,3R)-3-acetamido-N-(5-chloro-4-(7-fluoro-3-(2-hydroxypropan-2-yl)-2-methyl-2H-indazol-5-yl)pyridin-2-yl)cyclohexane-1-carboxamide

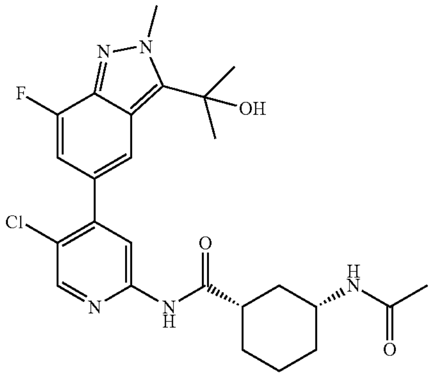 [SMILES: CC(=O)N[C@@H]1CCC[C@H](C(=O)Nc2cc(-c3cc(F)c4nn(C)c(C(C)(C)O)c4c3)c(Cl)cn2)C1]

The title compound was prepared using procedure analogous to that described for Example 1, Step 8, with 2-(5-bromo-7-fluoro-2-methylindazol-3-yl)propan-2-ol replacing 5-bromo-7-fluoro-3-isopropyl-2-methyl-indazole. LCMS calcd. for $C_{25}H_{30}ClFN_5O_3(M+H)^+$ m/z: 502.2; found 502.0. $^1H$ NMR (500 MHz, Acetonitrile-d3) δ 8.78 (s, 1H), 8.34 (s, 1H), 8.24 (s, 1H), 7.80 (d, J=1.3 Hz, 1H), 7.05 (dd, J=1.3, 12.2 Hz, 1H), 6.30 (d, J=8.1 Hz, 1H), 4.38 (s, 3H), 3.78 (s, 1H), 3.69 (tdt, J=4.0, 8.1, 11.7 Hz, 1H), 2.55 (tt, J=3.1, 11.5 Hz, 1H), 2.04 (d, J=12.5 Hz, 1H), 1.89-1.82 (m, 3H), 1.81 (s, 3H), 1.80 (s, 6H), 1.48-1.26 (m, 3H), 1.13 (qd, J=3.7, 12.6, 13.2 Hz, 1H).

Example 54: (1S,3R)-3-acetamido-N-(5-chloro-4-(3-cyclopropyl-7-fluoro-2-methyl-2H-indazol-5-yl)pyridin-2-yl)cyclohexane-1-carboxamide

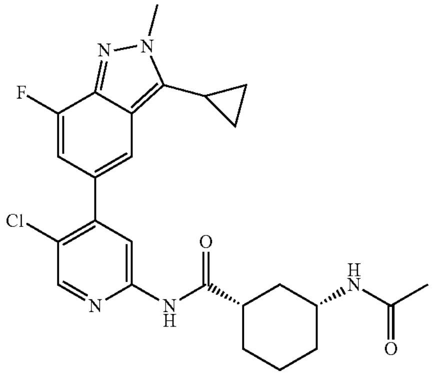 [SMILES: CC(=O)N[C@@H]1CCC[C@H](C(=O)Nc2cc(-c3cc(F)c4nn(C)c(C5CC5)c4c3)c(Cl)cn2)C1]

Step 1: 5-bromo-3-cyclopropyl-7-fluoro-2-methyl-2H-indazole

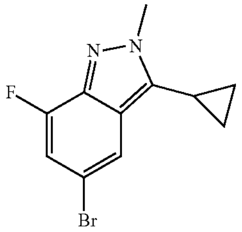

A 4 mL vial with septum containing a mixture of 5-bromo-7-fluoro-3-iodo-2-methyl-indazole (Step 1, Example 1, 41.0 mg, 0.12 mmol), sodium carbonate (25.0 mg, 0.24 mmol), [1,1'-bis(diphenylphosphino)ferrocene]dichloropalladium(II), complex with dichloromethane (9.0 mg, 0.01 mmol), and cyclopropylboronic acid (13.0 mg, 0.15 mmol) was evacuated and backfilled with $N_2$. The reaction mixture was charged with 1,4-dioxane (800 μL), sparged with $N_2$ for 1 min, charged with water (200 μL), sparged with $N_2$ for an additional minute, and then stirred at 50° C. for 1 h. The reaction mixture was charged with additional cyclopropylboronic acid (17.0 mg, 0.20 mmol), [1,1'-bis(diphenylphosphino)ferrocene]dichloropalladium (II), complex with dichloromethane (15.0 mg, 0.02 mmol), and 1,4-dioxane (100 μL), sparged with $N_2$ for 1 min, and stirred at 80° C. for 2 h. The reaction mixture was diluted with EtOAc (30 mL), sat. $NH_4Cl$ (15 mL) and water (15 mL), and filtered through a polypropylene frit. The organic layer was separated and washed with brine (30 mL). The aqueous layers were combined and back-extracted with EtOAc (30 mL). The organic fractions were combined, dried over $Na_2SO_4$, filtered, concentrated under reduced pressure, and purified by FCC (24 g $SiO_2$, 5-30% EtOAc in hexanes, wet-loaded in DCM). Fractions containing desired product were combined and concentrated under reduced pressure and heat (~50° C.) to yield 5-bromo-3-cyclopropyl-7-fluoro-2-methyl-indazole (11.7 mg, 0.04348 mmol, 37.639% yield) as an off-white solid. LCMS calcd. for $C_{11}H_{11}BrFN_2$ $(M+H)^+$ m/z: 269.0/271.0; found: 268.9/270.9.

Step 2: (1S,3R)-3-acetamido-N-(5-chloro-4-(3-cyclopropyl-7-fluoro-2-methyl-2H-indazol-5-yl)pyridin-2-yl)cyclohexane-1-carboxamide The title compound was prepared using procedure analogous to that described for Example 1, Step 8, with 5-bromo-3-cyclopropyl-7-fluoro-2-methyl-2H-indazole replacing 5-bromo-7-fluoro-3-isopropyl-2-methyl-indazole. LCMS calcd. for $C_{25}H_{28}ClFN_5O_2(M+H)^+$ m/z: 484.2; found 484.0.

Example 55: (1S,3R)-3-acetamido-N-(5-chloro-4-(3-isopropyl-2-methyl-2H-pyrazolo[4,3-b]pyridin-5-yl)pyridin-2-yl)cyclohexane-1-carboxamide

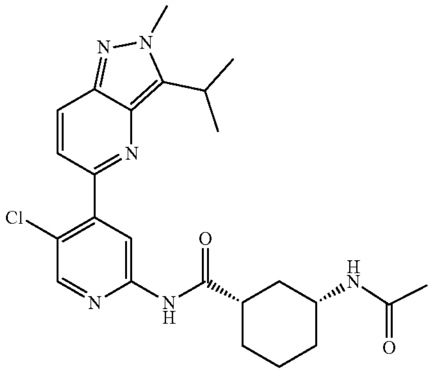 [SMILES: CC(=O)N[C@@H]1CCC[C@H](C(=O)Nc2cc(-c3ccc4nn(C)c(C(C)C)c4n3)c(Cl)cn2)C1]

Step 1: 1-(3-fluoropyridin-2-yl)-2-methylpropan-1-one

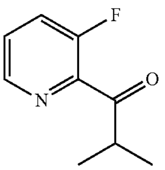

A 4 mL heat-dried vial with septum containing a solution of 2-bromo-3-fluoropyridine (505 mg, 2.87 mmol) in THF (14.5 mL) under N2 at −78° C. was charged with n-Butyllithium (1.9 mL, 3.0 mmol) slowly over 2 min (light→deep yellow color formation during addition). The reaction mixture was stirred at −78° C. for 10-15 min, then charged with a solution of N-methoxy-N,2-dimethyl-propanamide (454 μL, 3.12 mmol) in THF (500 μL) over 2 min. The solution was stirred at −78° C. for an additional 15 min, then quenched with sat. $NH_4Cl$ (5 mL). The reaction mixture was diluted with EtOAc (100 mL), washed with sat. $NH_4Cl$ (50 mL), and brine (50 mL). The organic layer was dried over $Na_2SO_4$, filtered, concentrated under reduced pressure, and purified by FCC (40 g $SiO_2$, 0→15% EtOAc in hexanes, wet-loaded in DCM). Fractions containing desired product were combined and concentrated under reduced pressure and heat (~50° C.) to yield 1-(3-fluoro-2-pyridyl)-2-methyl-propan-1-one (154 mg, 0.92 mmol, 32% yield) as a clear oil. LCMS calcd. for $C_9H_{11}FNO$ $(M+H)^+$ m/z: 168.1; found: 168.0.

Step 2: 3-isopropyl-2H-pyrazolo[4,3-b]pyridine

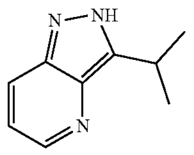

A 2 mL microwave vial with septum containing a mixture of 1-(3-fluoro-2-pyridyl)-2-methyl-propan-1-one (154 mg, 0.92 mmol) in hydrazine monohydrate (1.0 mL, 20.6 mmol) and pyridine (1 mL) was heated in a microwave reactor at 120° C. for 5.5 h. The reaction mixture was concentrated under reduced pressure, and coevaporated with dioxane (2×10 mL) to yield crude 3-isopropyl-1H-pyrazolo[4,3-b]pyridine (143 mg, 0.89 mmol, 96% yield) as a clear/yellow oil which solidified to a white solid. LCMS calcd. for $C_9H_{12}N_3$ $(M+H)^+$ m/z: 162.1; found: 162.1.

Step 3: 3-isopropyl-2-methyl-2H-pyrazolo[4,3-b]pyridine

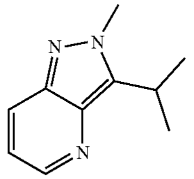

A 100 mL RBF with septum containing a solution of 3-isopropyl-1H-pyrazolo[4,3-b]pyridine (143 mg, 0.89 mmol) in ethyl acetate (5 mL) under $N_2$ was charged with trimethyloxonium tetrafluoroborate (214 mg, 1.45 mmol) in 2 portions over 2 h at RT. After 3 h total. the reaction mixture was charged with additional trimethyloxonium tetrafluoroborate (150 mg, 1.01 mmol) in 4 portions over 1 h. The reaction mixture was diluted with EtOAc (50 mL), and then quenched with sat. $NaHCO_3$ (20 mL) and water (20 mL). The organic layer was separated and washed with water (30 mL), and brine (20 mL). The organic layer was dried over $Na_2SO_4$, filtered, concentrated under reduced pressure, and purified by FCC (24 g $SiO_2$, 0-70% EtOAc in hexanes, wet-loaded in DCM). Fractions containing desired product were combined and concentrated under reduced pressure and heat (~50° C.) to yield the desired product (11 mg, 0.063 mmol, 7.1% yield) as a white solid. LCMS calcd. for $C_{10}H_{14}N_3(M+H)^+$ m/z: 176.1; found: 176.0.

Step 4: 5-bromo-3-isopropyl-2-methyl-2H-pyrazolo[4,3-b]pyridine

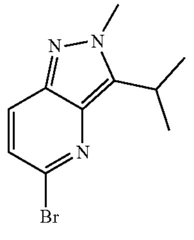

A 20 mL vial containing a solution of 3-isopropyl-2-methyl-pyrazolo[4,3-b]pyridine (11 mg, 0.06 mmol) in DCM (1.6 mL) was charged with 1% v/v bromine in DCM (1.6 mL, 0.31 mmol) and stirred at RT for 1 h. The reaction mixture was then stirred at 50° C. for 1 d. The reaction mixture was charged with additional 1% v/v bromine in DCM (500 μL, 0.10 mmol) and stirred at 50° C. for 1 d. The crude reaction mixture was purified directly by FCC (12 g $SiO_2$, 0→40% EtOAc in hexanes, wet-loaded in DCM). Fractions containing desired product were combined and concentrated under reduced pressure to yield the desired product (4.4 mg, 0.017 mmol, 28% yield) as a clear film. LCMS calcd. for $C_{10}H_{13}BrN_3$ $(M+H)^+$ m/z: 254.0/256.0; found: 253.9/255.9; $^1H$ NMR (500 MHz, Chloroform-d): δ 7.78 (d, J=8.9 Hz, 1H), 7.26 (d, J=9.0 Hz, 1H), 4.17 (s, 3H), 3.51 (hept, J=7.1 Hz, 1H), 1.57 (d, J=7.1 Hz, 6H).

Step 5: (1S,3R)-3-acetamido-N-(5-chloro-4-(3-isopropyl-2-methyl-2H-pyrazolo[4,3-b]pyridin-5-yl)pyridin-2-yl)cyclohexane-1-carboxamide The title compound was prepared using procedure analogous to that described for Example 1, Step 8, with 5-bromo-3-isopropyl-2-methyl-2H-pyrazolo[4,3-b]pyridine replacing 5-bromo-7-fluoro-3-isopropyl-2-methyl-indazole. LCMS calcd. for $C_{24}H_{30}Cl\ N_6O_2(M+H)^+$ m/z: 469.2; found 469.0.

Example 56: (1S,3R)-3-acetamido-N-(4-(7-fluoro-3-isopropyl-2-methyl-2H-indazol-5-yl)-5-methylpyridin-2-yl)cyclohexane-1-carboxamide

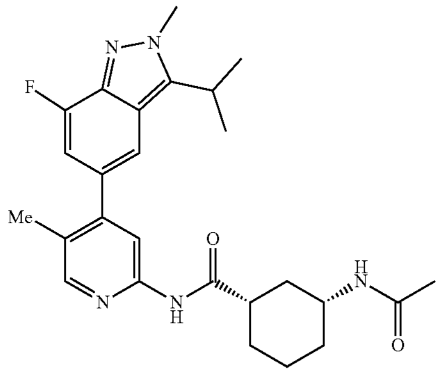 [SMILES: CC(=O)N[C@@H]1CCC[C@H](C(=O)Nc2cc(-c3cc(F)c4nn(C)c(C(C)C)c4c3)c(C)cn2)C1]

Step 1: 7-fluoro-3-isopropyl-2-methyl-5-(4,4,5,5-tetramethyl-1, 3,2-dioxaborolan-2-yl)-2H-indazole

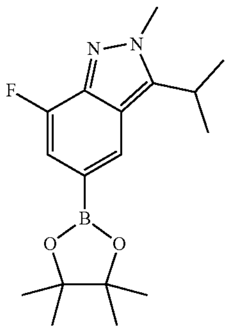 [SMILES: CC(C)c1c2cc(B3OC(C)(C)C(C)(C)O3)cc(F)c2nn1C]

A heat-dried 20 mL microwave vial containing a mixture of 5-bromo-7-fluoro-3-isopropyl-2-methyl-indazole (297 mg, 1.1 mmol), bis(pinacolato)diboron (285 mg, 1.12 mmol), and [1,1'-bis(diphenylphosphino)ferrocene]dichloropalladium(II), complex with dichloromethane (72 mg, 0.09 mmol) was charged with potassium acetate (215 mg, 2.19 mmol), crimped with a septum cap, and evacuated and backfilled with $N_2$ (3×). The vial was then charged with 1,4-dioxane (10 mL) and sparged with $N_2$ for 1 min. The reaction mixture was microwaved at 90° C. for 3.5 h. The reaction mixture was treated as a 0.1 M mixture of 7-fluoro-3-isopropyl-2-methyl-5-(4,4,5,5-tetramethyl-1,3,2-dioxaborolan-2-yl)indazole (349 mg, 1.03 mmol, 94% yield) in dioxane and used as is. LCMS calcd. for $C_{17}H_{25}BFN_2O_2$ $(M+H)^+$ m/z: 319.2; found: 319.0.

Step 2: tert-butyl ((1R,3S)-3-((4-(7-fluoro-3-isopropyl-2-methyl-2H-indazol-5-yl)-5-methylpyridin-2-yl)carbamoyl)cyclohexyl)carbamate

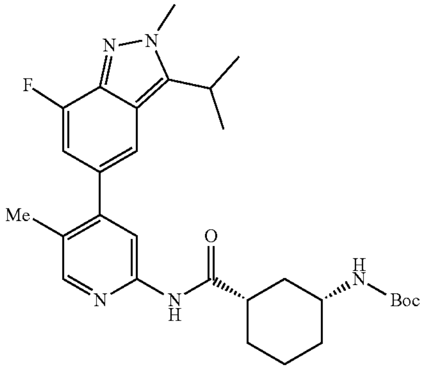 [SMILES: Cc1cnc(NC(=O)[C@H]2CCC[C@@H](NC(=O)OC(C)(C)C)C2)cc1-c1cc(F)c2nn(C)c(C(C)C)c2c1]

A 20 mL microwave vial with septum containing a crude reaction mixture of 7-fluoro-3-isopropyl-2-methyl-5-(4,4,5,5-tetramethyl-1,3,2-dioxaborolan-2-yl)indazole (318 mg, 1 mmol) in 1,4-dioxane (10 mL) was charged with sodium carbonate (194 mg, 1.83 mmol), [1,1'-bis(diphenylphosphino)ferrocene]dichloropalladium(II), complex with dichloromethane (60 mg, 0.07 mmol) and tert-butyl N-[(1R,3S)-3-[(4-iodo-5-methyl-2-pyridyl)carbamoyl]cyclohexyl] carbamate (Step 5, Example 22, 418 mg, 0.91 mmol), and sparged with $N_2$ for 1 min. The vial was then charged with water (2.5 mL), sparged with $N_2$ for 2 min, sonicated for 10 s, and microwaved at 90° C. for 2 h. The combined mixture was diluted with ethyl acetate ("EtOAc") (100 mL), sat. $NaHCO_3$ (30 mL) and water (30 mL), and vacuum filtered through a polypropylene frit. The organic layer was separated and washed with brine (50 mL). The aqueous layers were combined and extracted with DCM (2×50 mL). The organic layers were combined, dried over $Na_2SO_4$, filtered, concentrated under reduced pressure, and purified by FCC (40 g $SiO_2$, 10-45% EtOAc in DCM, wet-loaded in DCM). Fractions containing mostly desired product were combined and concentrated under reduced pressure and heat (~40° C.) to yield the desired product (535 mg, 1.02 mmol, 112% yield) as an orange-tan foam. The product likely contains pinacolborane-related by-products. LCMS calcd. for $C_{29}H_{39}FN_5O_3(M+H)^+$ m/z: 524.3; found: 524.2.

Step 3: (1S,3R)-3-amino-N-(4-(7-fluoro-3-isopropyl-2-methyl-2H-indazol-5-yl)-5-methylpyridin-2-yl)cyclohexane-1-carboxamide

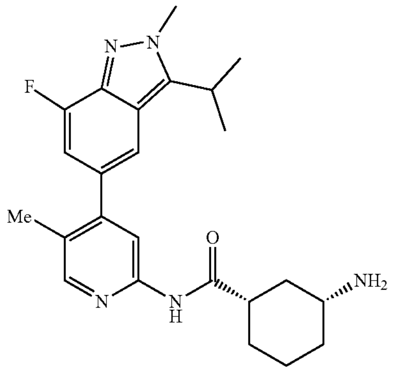 [SMILES: Cc1cnc(NC(=O)[C@H]2CCC[C@@H](N)C2)cc1-c1cc(F)c2nn(C)c(C(C)C)c2c1]

A 20 mL vial with septum containing a solution of tert-butyl ((1R,3S)-3-((4-(7-fluoro-3-isopropyl-2-methyl-2H-indazol-5-yl)-5-methylpyridin-2-yl)carbamoyl)cyclohexyl)carbamate (535.0 mg, 1.02 mmol) in ethyl acetate (11 mL) was charged with 6 M HCl (aq) (2.5 mL, 15 mmol) (caution: gas evolution). The reaction mixture was stirred vigorously at RT for 15 min. The reaction mixture was concentrated under reduced pressure, co-evaporated twice with dioxane and methanol, and dried under high vacuum and heat (~50° C.) to yield (1S,3R)-3-amino-N-(4-(7-fluoro-3-isopropyl-2-methyl-2H-indazol-5-yl)-5-methylpyridin-2-yl)cyclohexane-1-carboxamide as its HCl salt (489 mg, 0.917 mmol, 90% yield) as a pale yellow powder after scratching. LCMS calcd. for $C_{24}H_{31}FN_5O$ $(M+H)^+$ m/z: 424.3; found: 424.1.

Step 5: (1S,3R)-3-acetamido-N-(4-(7-fluoro-3-isopropyl-2-methyl-2H-indazol-5-yl)-5-methylpyridin-2-yl)cyclohexane-1-carboxamide A 4 mL vial with septum containing (1S,3R)-3-amino-N-[4-(7-fluoro-3-isopropyl-2-methyl-indazol-5-yl)-5-methyl-2-pyridyl]cyclohexanecarboxamide; trihydrochloride (4.8 mg, 0.01 mmol) in DMF (200 μL) and triethylamine (8 μL, 0.06 mmol) was charged with acetic anhydride (2 uL, 0.02 mmol). The reaction mixture was stirred at 40° C. for 1 h. The reaction mixture was concentrated under vacuum to remove excess $Et_3N$, diluted with water and MeOH, filtered through 0.45 um PTFE, and purified by prep-HPLCMS (5 μm 10×3 cm Luna C18, 25→37% MeCN in $H_2O$ (0.100 TFA), wet-loaded). Fractions containing pure product were combined and lyophilized to yield 99.600 pure (1S,3R)-3-acetamido-N-(4-(7-fluoro-3-isopropyl-2-methyl-2H-indazol-5-yl)-5-methylpyridin-2-yl)cyclohexane-1-carboxamide as its TFA salt (3.7 mg, 0.0053 mmol, 59% yield), as a light-yellow lyophilate. LCMS calcd. for $C_{26}H_{33}FN_5O_2(M+H)^+$ m/z: 466.3; found: 466.2.

Examples in Table 6 were prepared using the procedure described in the synthesis of Example 2, using appropriate starting materials.

TABLE 6

| Example | Structure/Name | Calcd. (M + H)+ m/z | Found (M + H)+ m/z |
|---|---|---|---|
| 57 | 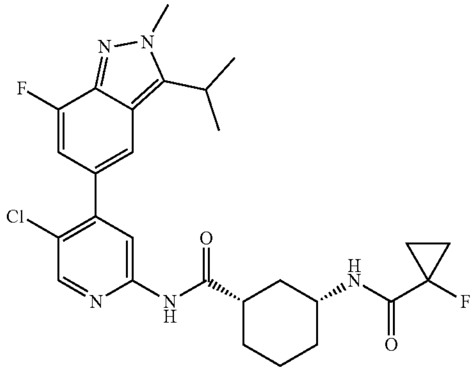 (1S,3R)-N-(5-chloro-4-(7-fluoro-3-isopropyl-2-methyl-2H-indazol-5-yl)pyridin-2-yl)-3-(1-fluorocyclopropane-1-carboxamido)cyclohexane-1-carboxamide | 530.2/532.2 | 530.1/532.1 |
| 58 | 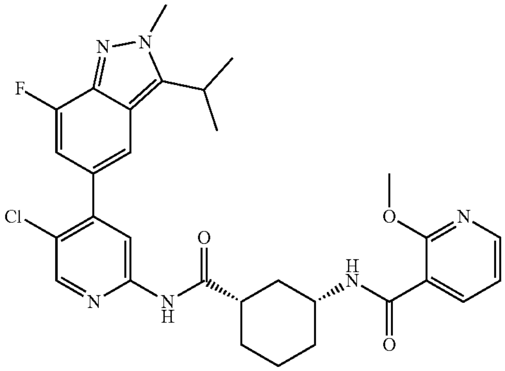 N-((1R,3S)-3-((5-chloro-4-(7-fluoro-3-isopropyl-2-methyl-2H-indazol-5-yl)pyridin-2-yl)carbamoyl)cyclohexyl)-2-methoxynicotinamide | 579.2 | 579.1 |
| 59 | 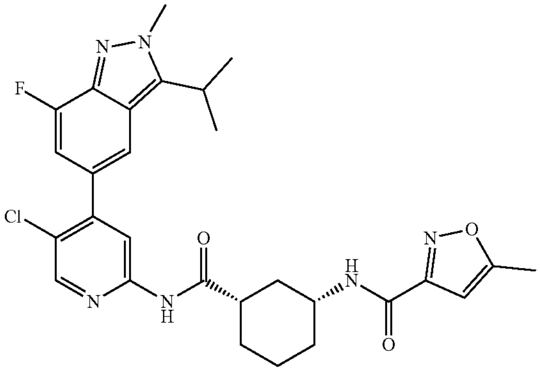 N-((1R,3S)-3-((5-chloro-4-(7-fluoro-3-isopropyl-2-methyl-2H-indazol-5-yl)pyridin-2-yl)carbamoyl)cyclohexyl)-5-methylisoxazole-3-carboxamide | 553.2/555.2 | 553.0/555.0 |

TABLE 6-continued

| Example | Structure/Name | Calcd. (M + H)+ m/z | Found (M + H)+ m/z |
|---|---|---|---|
| 60 | 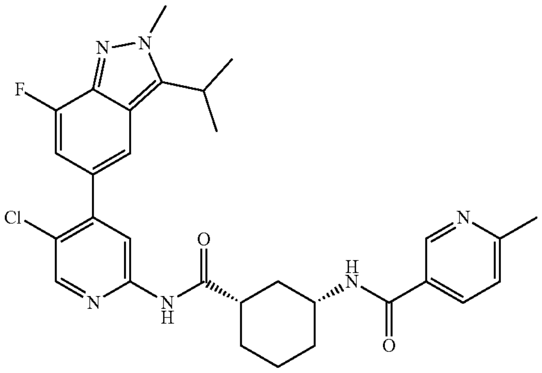 N-((1R,3S)-3-((5-chloro-4-(7-fluoro-3-isopropyl-2-methyl-2H-indazol-5-yl)pyridin-2-yl)carbamoyl)cyclohexyl)-6-methylnicotinamide | 563.2 | 563.1 |
| 61 | 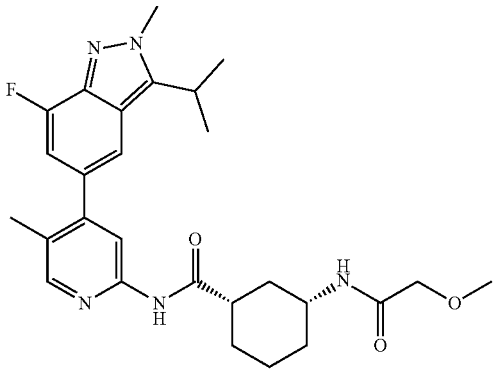 (1S,3R)-N-(4-(7-fluoro-3-isopropyl-2-methyl-2H-indazol-5-yl)-5-methylpyridin-2-yl)-3-(2-methoxyacetamido)cyclohexane-1-carboxamide | 496.3 | 496.2 |
| 62 | 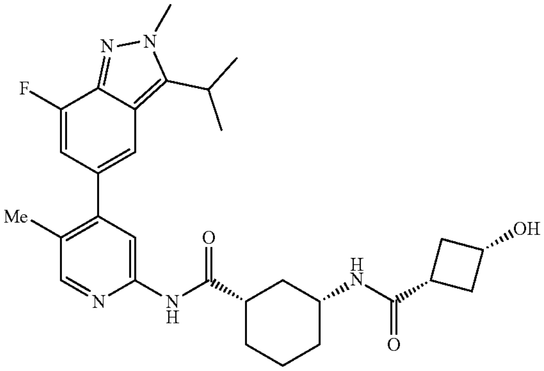 (1S,3R)-N-(4-(7-fluoro-3-isopropyl-2-methyl-2H-indazol-5-yl)-5-methylpyridin-2-yl)-3-((1s,3S)-3-hydroxycyclobutane-1-carboxamido)cyclohexane-1-carboxamide | 522.3 | 522.3 |

TABLE 6-continued

| Example | Structure/Name | Calcd. (M + H)+ m/z | Found (M + H)+ m/z |
| --- | --- | --- | --- |
| 63 | 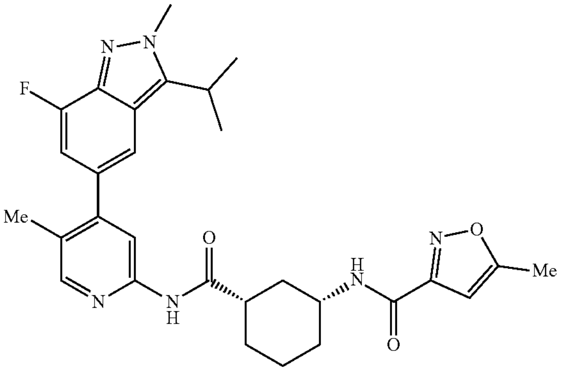 N-((1R,3S)-3-((4-(7-fluoro-3-isopropyl-2-methyl-2H-indazol-5-yl)-5-methylpyridin-2-yl)carbamoyl)cyclohexyl)-5-methylisoxazole-3-carboxamide | 533.3 | 533.1 |
| 64 | 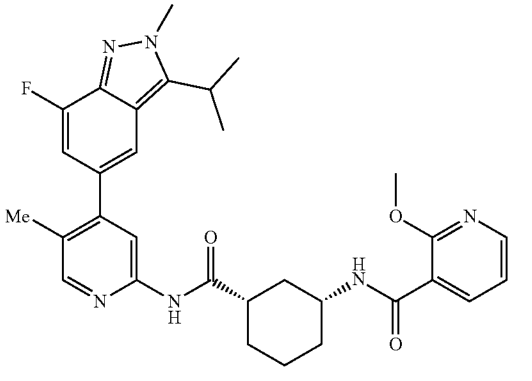 N-((1R,3S)-3-((4-(7-fluoro-3-isopropyl-2-methyl-2H-indazol-5-yl)-5-methylpyridin-2-yl)carbamoyl)cyclohexyl)-2-methoxynicotinamide | 559.3 | 559.1 |

Example 65: (1S,3R)—N-(5-chloro-4-(7-fluoro-3-isopropyl-2-methyl-2H-indazol-5-yl)pyridin-2-yl)-3-(2-cyanoacetamido)cyclohexane-1-carboxamide

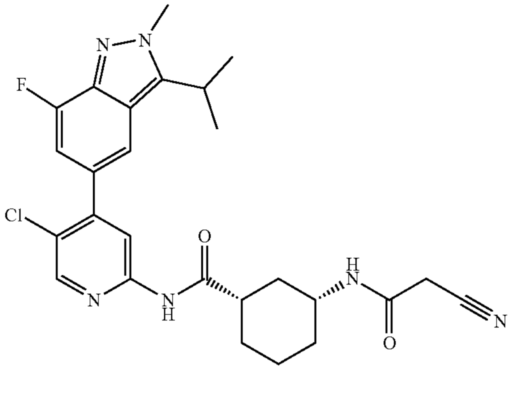 [SMILES: CC(C)c1c2cc(-c3cc(NC(=O)[C@H]4CCC[C@@H](NC(=O)CC#N)C4)ncc3Cl)cc(F)c2nn1C]

A 4 mL vial containing a solution of (1S,3R)-3-amino-N-(5-chloro-4-(7-fluoro-3-isopropyl-2-methyl-2H-indazol-5-yl)pyridin-2-yl)cyclohexane-1-carboxamide as its HCl salt (Step 3, Example 2, 7.0 mg, 0.01 mmol) in DMF (200 uL) was charged with triethylamine (9.0 uL, 0.06 mmol) followed by cyanoacetic acid N-hydroxysuccinimide ester (3.2 mg, 0.02 mmol) in one portion. The mixture was stirred at RT for 1 h, charged with additional cyanoacetic acid N-hydroxysuccinimide ester (1.5 mg, 0.01 mmol) and triethylamine (3.0 μL, 0.02 mmol), and stirred at RT for 1 additional 1 h. The reaction mixture was placed under high vacuum to remove excess triethylamine, then diluted with water and MeOH, filtered through 0.45 pm PTFE, and purified by prep-HPLCMS (5 μm 10×3 cm Luna C18, 42→62% MeCN in $H_2O$ (0.1% TFA), wet-loaded in MeOH+water). Fractions containing the desired product were combined and lyophilized to yield (1S,3R)—N-(5-chloro-4-(7-fluoro-3-isopropyl-2-methyl-2H-indazol-5-yl)pyridin-2-yl)-3-(2-cyanoacetamido)cyclohexane-1-carboxamide as its TFA salt (5.7 mg, 0.0077 mmol, 61% yield) as a yellow lyophilate. LCMS calcd. for $C_{26}H_{29}ClFN_6O_2(M+H)^+$ m/z: 511.2/513.2; found: 511.1/513.1.

Example 66: (1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide

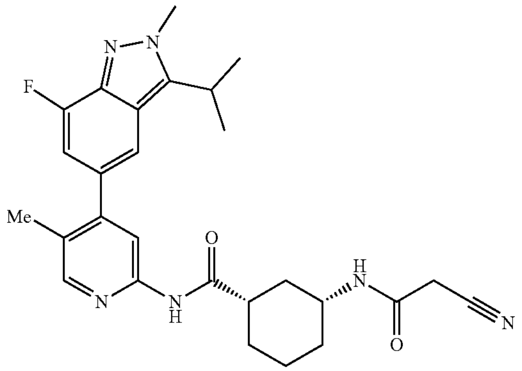 [SMILES: Cc1cnc(NC(=O)[C@H]2CCC[C@@H](NC(=O)CC#N)C2)cc1-c1cc(F)c2nn(C)c(C(C)C)c2c1]

The title compound was prepared using procedures analogous to those described for Example 65, using appropriate starting materials. LCMS calcd. for $C/H_{32}FN_6O_2$ (M+H) m/z: 491.3; found: 491.2.

Examples in Table 7 were prepared using the procedure described in the synthesis of Example 7, using appropriate starting materials.

TABLE 7

| Example | Structure/Name | Calcd. (M + H)$^+$ m/z | Found (M + H)$^+$ m/z |
|---|---|---|---|
| 67 | 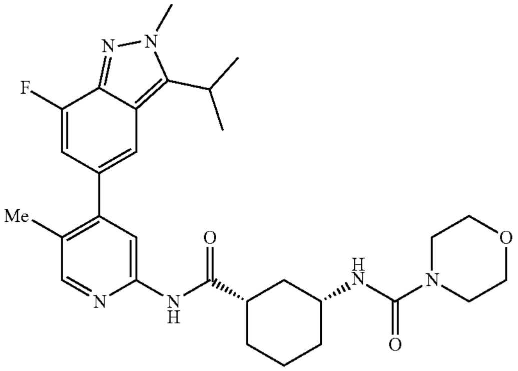 N-((1R,3S)-3-((4-(7-fluoro-3-isopropyl-2-methyl-2H-indazol-5-yl)-5-methylpyridin-2-yl)carbamoyl)cyclohexyl)morpholine-4-carboxamide <br> $^1$H NMR (500 MHz, Acetonitrile-d3) δ 8.64 (s, 1H), 8.16 (s, 1H), 8.05 (s, 1H), 7.58 (d, J = 1.3 Hz, 1H), 6.93 (dd, J = 1.3, 12.5 Hz, 1H), 5.10 (d, J = 7.9 Hz, 1H), 4.15 (s, 3H), 3.63 (tdt, J = 3.8, 7.8, 11.7 Hz, 1H), 3.56 (t, J = 4.9 Hz, 4H), 3.55-3.49 (m, 1H), 3.23 (t, J = 4.9 Hz, 4H), 2.53 (tt, J = 3.5, 11.7 Hz, 1H), 2.22 (s, 3H), 2.06 (dp, J = 2.6, 12.7 Hz, 1H), 1.91-1.80 (m, 3H), 1.47 (d, J = 7.0 Hz, 6H, 1.44-1.33 (m, 3H), 1.17 (qd, J = 3.9, 13.1, 13.6 Hz, 1H). | 537.3 | 537.3 |

TABLE 7-continued

| Example | Structure/Name | Calcd. (M + H)+ m/z | Found (M + H)+ m/z |
|---|---|---|---|
| 68 | 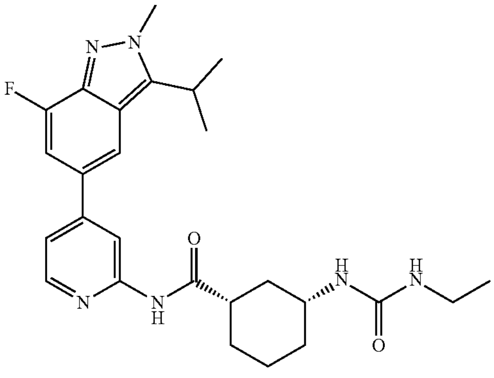 (1S,3R)-3-(3-ethylureido)-N-(4-(7-fluoro-3-isopropyl-2-methyl-2H-indazol-5-yl)pyridin-2-yl)cyclohexane-1-carboxamide | 481.3 | 481.1 |
| 69 | 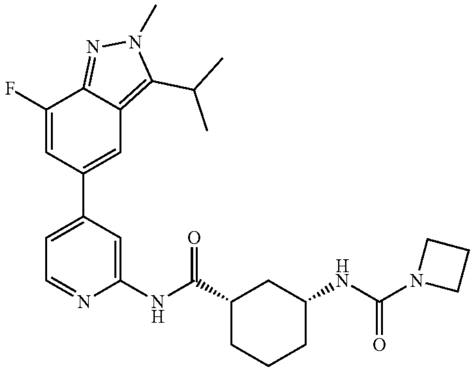 N-((1R,3S)-3-((4-(7-fluoro-3-isopropyl-2-methyl-2H-indazol-5-yl)pyridin-2-yl)carbamoyl)cyclohexyl)azetidine-1-carboxamide | 493.3 | 493.1 |
| 70 | 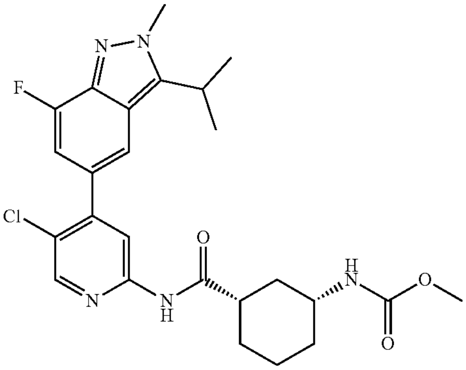 methyl ((1R,3S)-3-((5-chloro-4-(7-fluoro-3-isopropyl-2-methyl-2H-indazol-5-yl)pyridin-2-yl)carbamoyl)cyclohexyl) carbamate | 502.2/504.2 | 502.0/504.0 |

TABLE 7-continued

| Example | Structure/Name | Calcd. (M + H)+ m/z | Found (M + H)+ m/z |
| --- | --- | --- | --- |
| 71 | 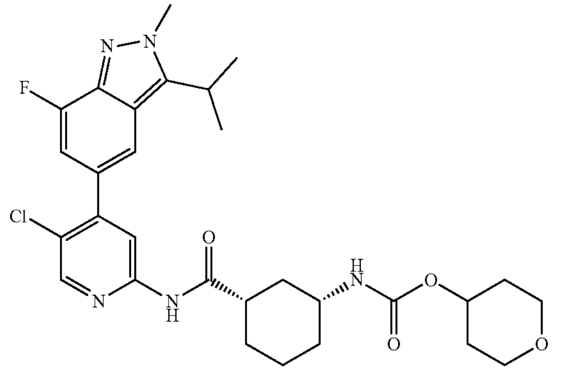 tetrahydro-2H-pyran-4-yl ((1R,3S)-3-((5-chloro-4-(7-fluoro-3-isopropyl-2-methyl-2H-indazol-5-yl)pyridin-2-yl)carbamoyl) cyclohexyl)carbamate | 572.2/574.2 | 572.1/574.0 |
| 72 | 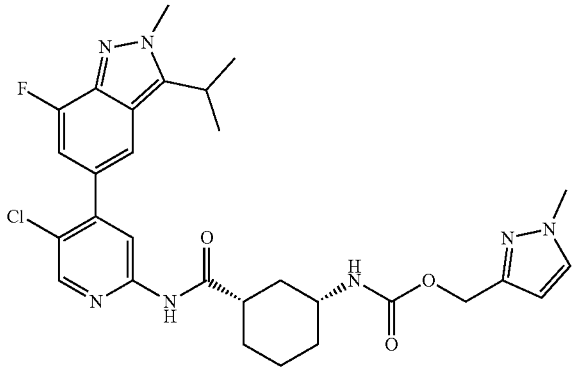 (1-methyl-1H-pyrazol-3-yl)methyl ((1R,3S)-3-((5-chloro-4-(7-fluoro-3-isopropyl-2-methyl-2H-indazol-5-yl)pyridin-2-yl) carbamoyl)cyclohexyl)carbamate | 582.2/584.2 | 582.1/584.1 |
| 73 | 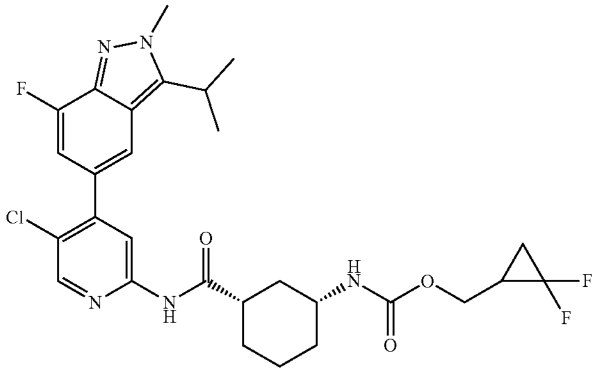 (2,2-difluorocyclopropyl)methyl ((1R,3S)-3-((5-chloro-4-(7-fluoro-3-isopropyl-2-methyl-2H-indazol-5-yl)pyridin-2-yl)carbamoyl) cyclohexyl)carbamate | 578.2/580.2 | 578.0/580.0 |

Example 74: (1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide (Mixture of 2 Diastereomers)

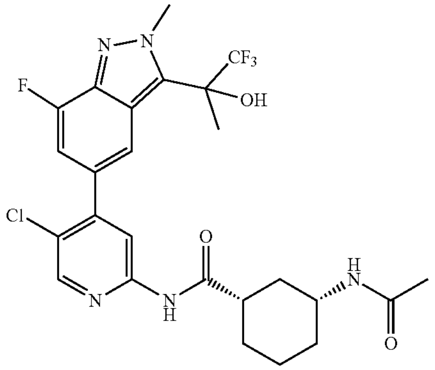 [SMILES: CC(=O)N[C@@H]1CCC[C@H](C(=O)Nc2cc(-c3cc(F)c4nn(C)c(C(C)(O)C(F)(F)F)c4c3)c(Cl)cn2)C1]

Step 1: 1-(5-bromo-7-fluoro-2-methyl-2H-indazol-3-yl)ethan-1-one

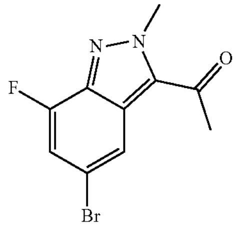

To a flame-dried 100 mL round bottom flask containing a solution of 5-bromo-7-fluoro-3-iodo-2-methyl-2H-indazole (prepared as in Example 1, Step 1) (588 mg, 1.66 mmol) in THE (11 mL) at −78° C. was added a 2 M Magnesium chloride propan-2-ide in THF (0.9 mL, 1.8 mmol) dropwise over two minutes and was stirred at same temperature for 15 minutes. Acetyl chloride (0.35 mL, 4.9 mmol) was added dropwise and left to stir for 5 hours at −78° C. The reaction mixture was diluted with sat. $NH_4Cl$ (aq) and washed with DCM 2× then once with EtOAc. The organic layers were combined, dried with sodium sulfate, and filtered. Volatiles were removed under reduced pressure and the residue was purified with FCC (40 g, $SiO_2$, 0→25% EtOAc in hexane) to give 1-(5-bromo-7-fluoro-2-methyl-2H-indazol-3-yl)ethan-1-one (289.5 mg, 0.875 mmol, 52.9% yield) as a white solid. LCMS calcd. for $C_{10}H_9BrFN_2O$+$[M+H]^+$ m/z=270.9; found: 270.8.

Step 2: 2-(5-bromo-7-fluoro-2-methyl-2H-indazol-3-yl)-1,1,1-trifluoropropan-2-ol

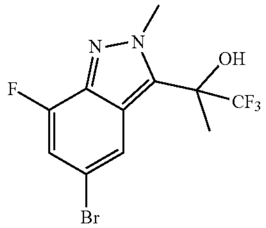 [SMILES: Cn1nc2c(F)cc(Br)cc2c1C(C)(O)C(F)(F)F]

To a 50 mL vial containing 1-(5-bromo-7-fluoro-2-methyl-2H-indazol-3-yl)ethan-1-one (243 mg, 0.74 mmol) in THE (2.5 mL) at 0° C. was added trimethyl(trifluoromethyl)silane (TCI) (320 μL, 2.16 mmol) and stirred for 30 minutes at 0° C. The reaction was then treated with 1 M Tetrabutylammonium fluoride solution in THE (110 μL, 0.11 mmol) at 0° C. and stirred at room temperature for 1 hour. Next, 1 M Tetrabutylammonium fluoride solution in THE (735 μL, 0.74 mmol) was added and left to stir for 1.5 hours at RT. The reaction was diluted with sat. $NH_4Cl$ (aq) and extracted with DCM (2×) and once with EtOAc. The organic layer was dried with sodium sulfate and filtered. Volatiles were removed under reduced pressure and the residue was purified with FCC (24 g, $SiO_2$, 0→40% EtOAc in hexane) to give racemic 2-(5-bromo-7-fluoro-2-methyl-2H-indazol-3-yl)-1,1,1-trifluoropropan-2-ol (160.8 mg, 0.471 mmol, 64.1% yield) as a tan powder. LCMS calcd. for $C_{11}H_{10}BrF_4N_2O$+ $[M+H]^+$ m/z=340.9; found: 340.8.

Step 3: (1S,3R)-3-acetamido-N-(5-chloro-4-(7-fluoro-2-methyl-3-(1,1,1-trifluoro-2-hydroxypropan-2-yl)-2H-indazol-5-yl)pyridin-2-yl)cyclohexane-1-carboxamide (Mixture of 2 Diastereomers)

The title compound was prepared using procedure analogous to that described for Example 1, Step 8, with 2-(5-bromo-7-fluoro-2-methyl-2H-indazol-3-yl)-1,1,1-trifluoropropan-2-ol replacing 5-bromo-7-fluoro-3-isopropyl-2-methyl-indazole. LCMS calcd. for $C_{25}H_{27}ClF_4N_5O_3$ $(M+H)^+$ m/z: 556.2; found 556.0.

Example 75: (1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide (Mixture of 2 Diastereomers)

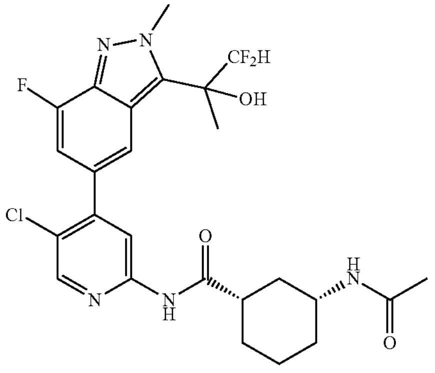 [SMILES: CC(=O)N[C@@H]1CCC[C@H](C(=O)Nc2cc(-c3cc(F)c4nn(C)c(C(C)(O)C(F)F)c4c3)c(Cl)cn2)C1]

Step 1: 2-(5-bromo-7-fluoro-2-methyl-2H-indazol-3-yl)-1,1-difluoropropan-2-ol

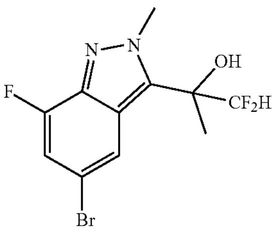 [SMILES: Cn1nc2c(F)cc(Br)cc2c1C(C)(O)C(F)F]

To a 20 mL vial containing 1-(5-bromo-7-fluoro-2-methyl-2H-indazol-3-yl)ethan-1-one (prepared as in Example 74, Step 1) (106 mg, 0.32 mmol) in THE (1 mL) was added (Difluoromethyl)trimethylsilane (TCI) (200 μL, 1.46 mmol) on ice. The reaction stirred for 35 min at 0° C. The reaction was then treated with 1 M Tetrabutylammonium fluoride solution in THE (100 uL, 0.10 mmol) and left to react at room temperature. After 1 hour, 1 M tetrabutylammonium fluoride solution in THF (200 μL, 0.20 mmol) was added. Reaction stirred for 1 hour at RT then was diluted with sat. $NH_4Cl$ (aq) (20 mL) and 1 N HCl (5 mL). The water layer was washed with EtOAc (3×). The organic layer was dried with sodium sulfate and filtered. Volatiles were removed under reduced pressure and the residue was purified with FCC (12 g, $SiO_2$, 0→50% EtOAc in hexane) to give racemic 2-(5-bromo-7-fluoro-2-methyl-2H-indazol-3-yl)-1,1-difluoropropan-2-ol (60.3 mg, 0.136 mmol, 42% yield) as a translucent yellow oil. LCMS calcd. for $C_{11}H_{11}BrF_3N_{20}+[M+H]^+$ m/z=323.0/324.9; found: 322.8/324.8.

Step 2: (1S,3R)-3-acetamido-N-(5-chloro-4-(3-(1,1-difluoro-2-hydroxypropan-2-yl)-7-fluoro-2-methyl-2H-indazol-5-yl)pyridin-2-yl)cyclohexane-1-carboxamide (Mixture of 2 Diastereomers)

The title compound was prepared using procedure analogous to that described for Example 1, Step 8, with 2-(5-bromo-7-fluoro-2-methyl-2H-indazol-3-yl)-1,1-difluoropropan-2-ol replacing 5-bromo-7-fluoro-3-isopropyl-2-methyl-indazole. LCMS calcd. for $C_{25}H_{28}ClF_3N_5O_3$ $(M+H)^+$ m/z: 538.2; found 538.0.

Example 76-1: (1S,3R)-3-(2-cyanoacetamido)-N-(4-(7-fluoro-2-methyl-3-((R)-1,1,1-trifluoro-2-hydroxypropan-2-yl)-2H-indazol-5-yl)-5-methylpyridin-2-yl)cyclohexane-1-carboxamide

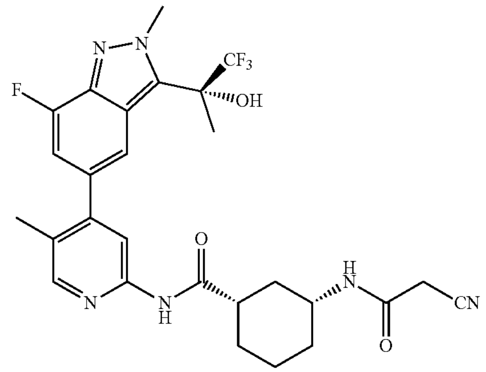 [SMILES: Cc1cnc(NC(=O)[C@H]2CCC[C@@H](NC(=O)CC#N)C2)cc1-c1cc(F)c2nn(C)c([C@@](C)(O)C(F)(F)F)c2c1]

Step 1: SFC separation of racemic 2-(5-bromo-7-fluoro-2-methyl-2H-indazol-3-yl)-1,1,1-trifluoropropan-2-ol

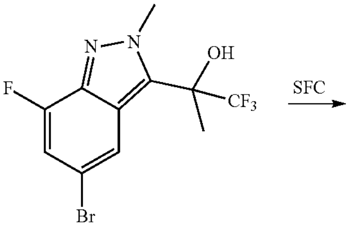

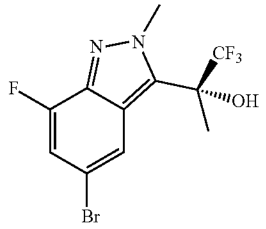

Peak 1

+

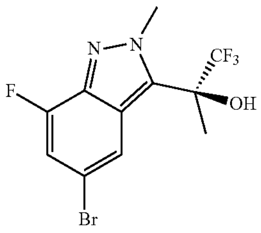

Peak 2

1.34 g of racemic 2-(5-bromo-7-fluoro-2-methyl-2H-indazol-3-yl)-1,1,1-trifluoropropan-2-ol was purified on chiral supercritical fluid chromatography using the following conditions: column: Chiralpak AD-H (2×25 cm); mobile phase: 12% IPA/$CO_2$; pressure: 100 bar; flow rate: 65 mL/min; UV: 220 nM; injection: 0.2 mL, 50 mg/mL in IPA. 550 mg peak 1 ($t_r$=1.88 min) and 560 mg peak 2 ($t_r$=2.19 min) were collected. The absolute (S)-configuration of Peak 2 was determined by an X-ray crystal structure (data as shown in Tables D-I).

Step 2 to step 6: (1S,3R)-3-(2-cyanoacetamido)-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide (P1)

The title compound was prepared according to the procedure analogous to that described for Example 22, Step 4 to step 8, using enantiomerically pure 2-(5-bromo-7-fluoro-2-methyl-2H-indazol-3-yl)-1,1,1-trifluoropropan-2-ol (peak 1) and other appropriate starting materials. LCMS calcd. for $C_{27}H_{29}F_4N_6O_2$ $(M+H)^+$ m/z: 561.2; found: 561.2. $^1$H NMR (500 MHz, dmso) δ 10.43 (s, 1H), 8.22 (s, 1H), 8.19 (d, J=7.7 Hz, 1H), 8.00 (s, 1H), 7.57 (s, 1H), 7.47 (s, 1H), 7.11 (d, J=12.0, 1.2 Hz, 1H), 4.39 (s, 3H), 3.60-3.51 (m, 3H), 2.60 (t, J=11.7 Hz, 1H), 2.18 (s, 3H), 2.05 (s, 3H), 1.89 (d, J=12.3 Hz, 1H), 1.81-1.73 (m, 3H), 1.28 (q, J=12.4 Hz, 3H), 1.09 (q, 1H). $^{19}$F NMR (470 MHz, dmso) 6-79.91 (3.10 F), -129.10 (d, J=12.0 Hz, 1.0 F).

Example 76-2: (1S,3R)-3-(2-cyanoacetamido)-N-(4-(7-fluoro-2-methyl-3-((S)-1,1,1-trifluoro-2-hydroxypropan-2-yl)-2H-indazol-5-yl)-5-methylpyridin-2-yl)cyclohexane-1-carboxamide

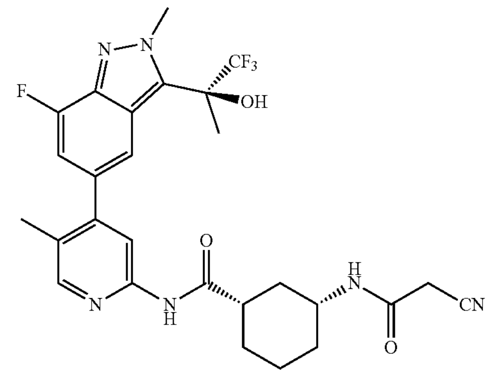 [SMILES: Cc1cnc(NC(=O)[C@H]2CCC[C@@H](NC(=O)CC#N)C2)cc1-c1cc(F)c2nn(C)c([C@](C)(O)C(F)(F)F)c2c1]

The title compound was prepared according to the procedure analogous to that described for Example 22, Step 4 to step 8, using enantiomerically pure 2-(5-bromo-7-fluoro-2-methyl-2H-indazol-3-yl)-1,1,1-trifluoropropan-2-ol (peak 2) and other appropriate starting materials. LCMS calcd. for $C_{27}H_{29}F_4N_6O_2$ $(M+H)^+$ m/z: 561.2; found: 561.2. $^1$H NMR (500 MHz, dmso) δ 10.44 (s, 1H), 8.23 (s, 1H), 8.20 (d, J=7.8 Hz, 1H), 8.01 (s, 1H), 7.58 (s, 1H), 7.48 (s, 1H), 7.12 (d, J=11.9, 1.2 Hz, 1H), 4.40 (s, 3H), 3.61-3.53 (m, 3H), 2.60 (t, J=11.9 Hz, 1H), 2.19 (s, 3H), 2.06 (s, 3H), 1.93-1.87 (m, 1H), 1.79 (d, J=11.1 Hz, 3H), 1.37-1.21 (m, 3H), 1.09 (q, J=11.7 Hz, 1H). $^{19}$F NMR (470 MHz, dmso) 6-79.91 (3.1° F.), -129.10 (d, J=11.9 Hz, 1F).

Examples in Table 8 were prepared using the appropriate Suzuki and amide coupling procedures previously described in the synthesis of Example 56, with appropriate starting materials

TABLE 8

| Example | Structure/Name | Calcd. $(M/ + H)^+$ m/z | Found $(M + H)^+$ m/z |
|---|---|---|---|
| 77 | 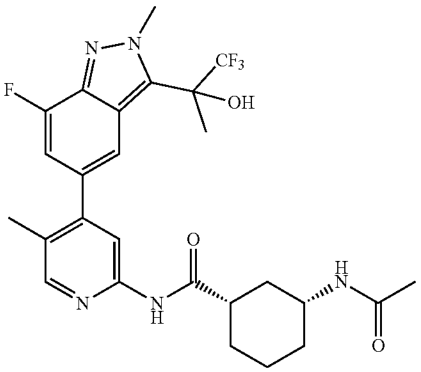 (1S,3R)-3-acetamido-N-(4-(7-fluoro-2-methyl-3-(1,1,1-trifluoro-2-hydroxypropan-2-yl)-2H-indazol-5-yl)-5-methylpyridin-2-yl)cyclohexane-1-carboxamide | 536.2/537.2 | 536.1/537.0 |

TABLE 8-continued

| Example | Structure/Name | Calcd. (M/ + H)$^+$ m/z | Found (M + H)$^+$ m/z |
|---|---|---|---|
| 78 | 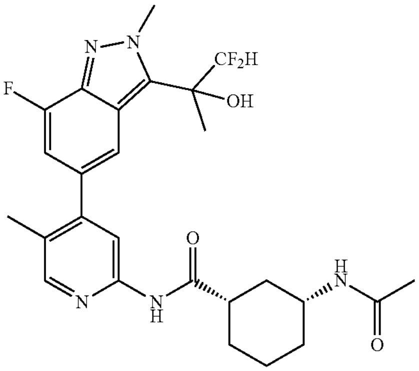 (1S,3R)-3-acetamido-N-(4-(3-(1,1-difluoro-2-hydroxy-propan-2-yl)-7-fluoro-2-methyl-2H-indazol-5-yl)-5-methylpyridin-2-yl)cyclohexane-1-carboxamide | 518.2/519.2 | 518.1/519.1 |
| 79 | 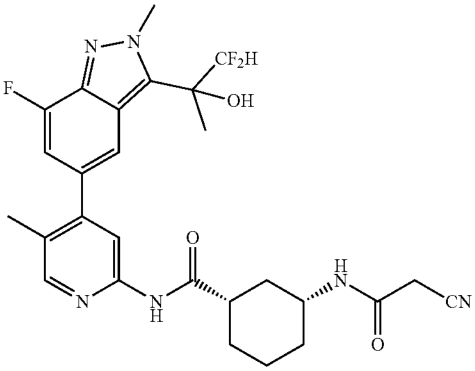 (1S,3R)-3-(2-cyanoacetamido-N-(4-(3-(1,1-difluoro-2-hydroxypropan-2-yl)-7-fluoro-2-methyl-2H-indazol-5-yl)-5-methylpyridin-2-yl)cyclohexane-1-carboxamide | 543.2/544.2 | 543.0/544.0 |

Example 80: (1S,3R)-3-(2-cyanoacetamido)-N-(4-(4-fluoro-1-isopropyl-1H-benzo[d]imidazol-6-yl)-5-methylpyridin-2-yl)cyclohexane-1-carboxamide

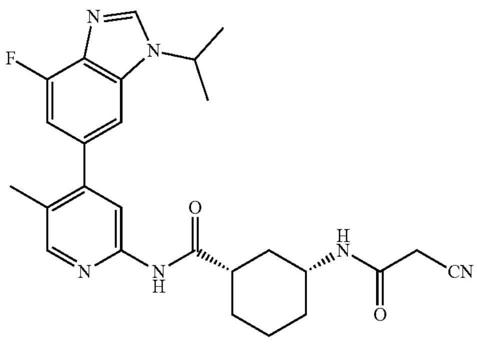 [SMILES: Cc1cnc(NC(=O)[C@H]2CCC[C@@H](NC(=O)CC#N)C2)cc1-c1cc(F)c2ncn(C(C)C)c2c1]

To a stirred solution of cyanoacetic acid N-hydroxysuccinimide ester (267 mg, 1.47 mmol) in DCM (4 mL) was added triethylamine; (272 uL, 1.95 mmol) at RT. After 0.5 hour, (1 S,3R)-3-amino-N-[4-(7-fluoro-3-isopropyl-benzimidazol-5-yl)-5-methyl-2-pyridyl]cyclohexanecarboxamide (Example 28, step 3, 400 mg, 0.98 mmol) was added. The resulted mixture was stirred at RT overnight. The reaction mixture was diluted with DCM (50 mL), washed with water (5 mL) and brine (5 mL), dried over $Na_2SO_4$, and filtered. The filtrate was concentrated under reduced pressure. The residue was purified by a 20 g silica column, eluting with EA/hexanes=0-100%, to give (1S,3R)-3-[(2-cyanoacetyl)amino]-N-[4-(7-fluoro-3-isopropyl-benzimidazol-5-yl)-5-methyl-2-pyridyl]cyclohexanecarboxamide (410 mg, 0.86 mmol, 88% yield) as a white solid. LCMS calcd. for $C_{26}H_{30}FN_6O_2(M+H)^+$ m/z: 477.2; found: 477.1. $^1H$ NMR (500 MHz, DMSO-d6) δ 10.43 (s, 1H), 8.47 (s, 1H), 8.23 (s, 1H), 8.19 (d, J=7.7 Hz, 1H), 8.02 (s, 1H), 7.51 (d, J=1.3 Hz, 1H), 7.05 (dd, J=1.3, 11.5 Hz, 1H), 4.83 (hept, J=6.7 Hz, 1H), 3.56 (s, 3H), 2.63-2.58 (m, 1H), 2.20 (s, 3H), 1.94-1.84 (m, 1H), 1.80-1.72 (m, 3H), 1.53 (d, J=6.7 Hz, 6H), 1.32-1.24 (m, 3H), 1.10-1.06 (m, 1H)

Example 81: (1S,3R)-3-acetamido-N-(4-(4-fluoro-1-isopropyl-1H-benzo[d]imidazol-6-yl)-5-methoxy-pyridin-2-yl)cyclohexane-1-carboxamide

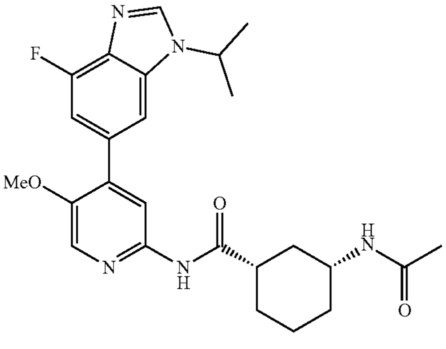 [SMILES: COc1cnc(NC(=O)[C@H]2CCC[C@@H](NC(C)=O)C2)cc1-c1cc(F)c2ncn(C(C)C)c2c1]

Step 1: 4-iodo-5-methoxypyridin-2-amine

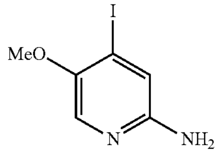

A solution of 2-Fluoro-4-iodo-5-methoxypyridine (100.0 mg, 0.40 mmol) and ammonium hydroxide (1.03 mL, 7.9 mmol) in 1,4-Dioxane (2 mL) was sealed in a 5 mL microwave tube and heated to 160° C. under microwave radiation overnight. After the reaction cooled down, the volatile was removed under vacuum. The residue was purified by a 4 g silica column with 50% EA/Hex to give 4-iodo-5-methoxy-pyridin-2-amine (16 mg, 16% yield) LCMS calcd for $C_6H_{71}N_2O(M+H)^+$ m/z: 251.0; found: 251.1.

Step 2 to step 9: (1S,3R)-3-acetamido-N-(4-(4-fluoro-1-isopropyl-1H-benzo[d]imidazol-6-yl)-5-methoxypyridin-2-yl)cyclohexane-1-carboxamide The title compound was prepared using procedures analogous to those described for Example 22, Step 1 to Step 8, using appropriate starting materials. LCMS calcd. for $C_{25}H_{31}FN_5O_3$ $(M+H)^+$ m/z: 468.2; found: 468.1.

Example 82: N-((1R,3S)-3-((5-chloro-4-(7-fluoro-3-isopropyl-2-methyl-2H-indazol-5-yl)pyridin-2-yl) carbamoyl)cyclohexyl)bicyclo[1.1.1]pentane-1-carboxamide

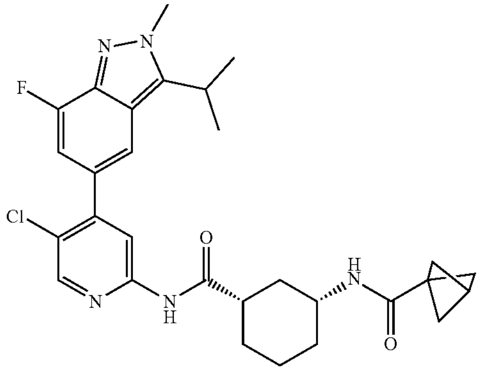 [SMILES: CC(C)c1c2cc(-c3cc(NC(=O)[C@H]4CCC[C@@H](NC(=O)C56CC(C5)C6)C4)ncc3Cl)cc(F)c2nn1C]

The title compound was prepared using procedures analogous to those described for Example 2, using appropriate starting materials. LCMS calcd. for $C_{29}H_{34}ClFN_5O_2(M+H)^+$ m/z=538.2; found: 538.1

Example 83: (1S,3R)-3-acetamido-N-(5-chloro-4-(4-fluoro-1-isopropyl-1H-benzo[d][1,2,3]triazol-6-yl)pyridin-2-yl)cyclohexane-1-carboxamide

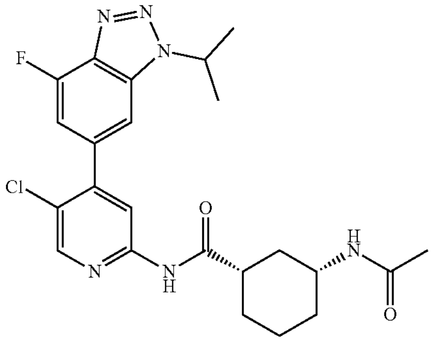 [SMILES: CC(=O)N[C@@H]1CCC[C@H](C(=O)Nc2cc(-c3cc(F)c4nnn(C(C)C)c4c3)c(Cl)cn2)C1]

Step 1: 6-bromo-4-fluoro-1-isopropyl-1H-benzo[d][1,2,3]triazole

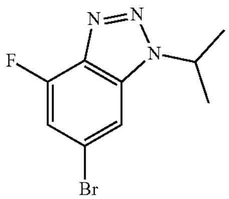

To a 20 mL vial containing 5-bromo-3-fluoro-1-N-propan-2-ylbenzene-1,2-diamine (Step 2, Example 22, 123.0 mg, 0.50 mmol) was added hydrochloric acid 2 N (aq) (1.5 mL, 3 mmol) and acetic acid (0.5 mL, 8.74 mmol). The mixture was cooled to 0° C. and sodium nitrite (37.78 mg, 0.55 mmol) in water (0.2 mL) was charged slowly. The reaction was then stirred at RT overnight. Sodium hydroxide (497 mg, 12.44 mmol) was charged in portions until pH>8. The resulting mixture was extracted with DCM 20 mL×2 and combined organic layers were washed with brine dried over $Na_2SO_4$, concentrated under vacuum. The residue was purified by a 12 g column with 100% DCM to give 6-bromo-4-fluoro-1-propan-2-ylbenzotriazole (111 mg, 86% yield) as a light brown solid. LCMS calcd. for $C_{29}H_{10}BrFN_3$ $(M+H)^+$ m/z=258.0/260.0; found: 257.8/259.8.

Step 2: (1S,3R)-3-acetamido-N-(5-chloro-4-(4-fluoro-1-isopropyl-1H-benzo[d][1,2,3]triazol-6-yl)pyridin-2-yl)cyclohexane-1-carboxamide A solution of [2-[[(1S,3R)-3-acetamidocyclohexanecarbonyl]amino]-5-chloro-4-pyridyl]boronic acid (Step 7, Example 1, 0.086 M, 0.3 mL, 0.03 mmol),6-bromo-4-fluoro-1-propan-2-ylbenzotriazole (7.7 mg, 0.03 mmol), Tetrakis(triphenylphosphine)palladium(0) (3.1 mg, 0.0027 mmol), sodium carbonate (8.59 mg, 0.08 mmol) in 1,4-dioxane (1 mL) and water (0.30 mL) was stirred at 100° C. for 2 h under $N_2$. The reaction was diluted with MeOH, filtered then purified by auto-pure prep-HPLC to give (1S, 3R)-3-acetamido-N-[5-chloro-4-(7-fluoro-3-propan-2-yl-benzotriazol-5-yl)pyridin-2-yl]cyclohexane-1-carboxamide (8 mg, 63% yield) as it's TFA salt. LCMS calcd. for $C_{23}H_{27}ClFN_6O_2$ $(M+H)^+$ m/z=473.2; found: 473.1. $^1H$ NMR (500 MHz, DMSO-$d_6$) δ 10.77 (s, 1H), 8.51 (s, 1H), 8.25 (s, 1H), 7.96 (d, J=1.2 Hz, 1H), 7.76 (d, J=7.9 Hz, 1H), 7.38 (d, J=11.0 Hz, 1H), 5.31 (hept, J=6.7 Hz, 1H), 3.60-3.51 (m, 1H), 2.64-2.59 (m, 1H), 1.87-1.75 (m, 4H), 1.75 (s, 3H), 1.64 (d, J=6.7 Hz, 6H), 1.31-1.22 (m, 3H), 1.07-1.04 (m, 1H).

Example 84: (1S,3R)-3-Acetamido-N-(5-chloro-4-(3-isopropyl-3H-imidazo[4,5-b]pyridin-5-yl)pyridin-2-yl)cyclohexane-1-carboxamide

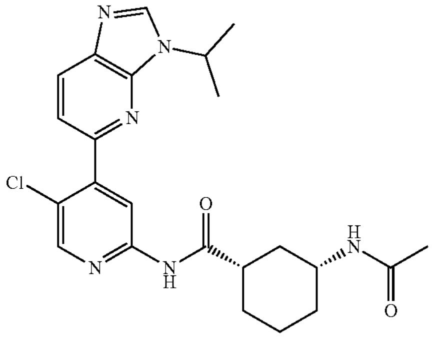 [SMILES: CC(=O)N[C@@H]1CCC[C@H](C(=O)Nc2cc(-c3ccc4ncn(C(C)C)c4n3)c(Cl)cn2)C1]

Step 1: 5-bromo-3-isopropyl-3H-imidazo[4,5-b]pyridine

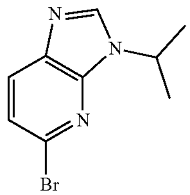

To 5-Bromo-1H-imidazo[4,5-b]pyridine (300 mg, 1.51 mmol) in DMF (3 mL) under nitrogen was added sodium hydride (60% dispersion in mineral oil, 90.8 mg, 2.27 mmol) and the reaction mixture stirred for 30 mins. To the reaction was added the 2-bromopropane (0.28 mL, 3.03 mmol) and stirred for 2 h. The reaction was quenched with water, extracted with ethyl acetate. The combined organic layers was washed with water, brine, dried over sodium sulfate and filtered. The filtrate was concentrated under reduced pressure. The crude was purified by silica gel chromatography, eluting with 0-10% MeOH in DCM, to give 5-bromo-3-isopropyl-imidazo[4,5-b]pyridine (180 mg, 0.75 mmol, 49.5% yield). LCMS calcd. for $C_9H_{11}BrN_3$ $(M+H)^+$ m/z: 240.0; found 240.0.

Step 2: (1S,3R)-3-Acetamido-N-(5-chloro-4-(3-isopropyl-3H-imidazo[4,5-b]pyridin-5-yl)pyridin-2-yl)cyclohexane-1-carboxamide The title compound was prepared using procedure analogous to that described for Example 1, Step 8, with 5-bromo-3-isopropyl-3H-imidazo[4,5-b]pyridine replacing 5-bromo-7-fluoro-3-isopropyl-2-methyl-indazole). LCMS calcd. for $C_{23}H_{28}Cl\ N_6O_2(M+H)^+$ m/z: 455.2; found: 455.1.

Example 85: (1S,3R)—N-(5-chloro-4-(9-fluoro-4,4-dimethyl-3,4-dihydro-1H-benzo[4,5]imidazo[2,1-c][1,4]oxazin-7-yl)pyridin-2-yl)-3-(2-cyanoacetamido)cyclohexane-1-carboxamide

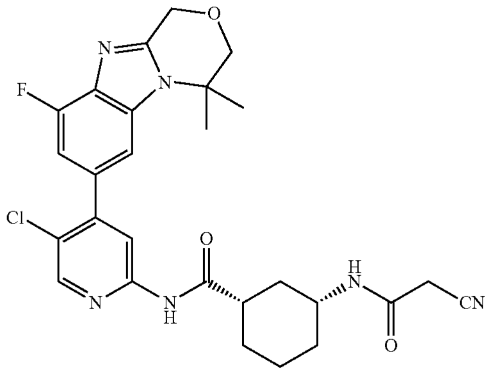 [SMILES: CC1(C)COCc2nc3c(F)cc(-c4cc(NC(=O)[C@H]5CCC[C@@H](NC(=O)CC#N)C5)ncc4Cl)cc3n21]

Step 1: 4-(5-bromo-3-fluoro-2-nitrophenyl)-5,5-dimethylmorpholin-3-one

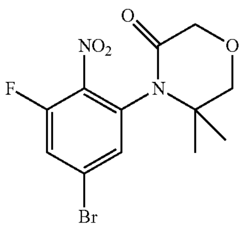 [SMILES: CC1(C)COCC(=O)N1c1cc(Br)cc(F)c1[N+](=O)[O-]]

To a stirred solution of sodium hydride (60% dispersion in mineral oil, 762 mg, 19.0 mmol) in DMF (3 mL) under nitrogen was added the 5,5-Dimethyl-3-morpholinone (1.66 g, 12.8 mmol) and then stirred for 30 mins at room temperature. To the reaction was added the 5-bromo-1,3-difluoro-2-nitro-benzene (3.02 g, 12.7 mmol) as a solution in DMF (0.50 mL) and stirred for 1 h. The reaction was quenched with water (30 mL) extracted ethyl acetate (30 mL×2). The organic layers were combined, washed with brine, dried over $Na_2SO_4$, filtered. The filtrate was concentrated under reduced pressure to give crude 4-(5-bromo-3-fluoro-2-nitrophenyl)-5,5-dimethylmorpholin-3-one, which was used in the next step without further purification. $C_{12}H_{13}BrFN_2O_4(M+H)^+$ m/z: 347.0; found: 346.9.

Step 2: 4-(2-amino-5-bromo-3-fluorophenyl)-5,5-dimethylmorpholin-3-one

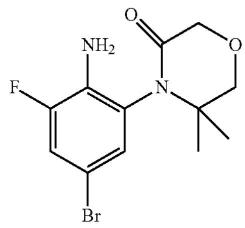 [SMILES: CC1(C)COCC(=O)N1c1cc(Br)cc(F)c1N]

To the solution of crude 4-(5-bromo-3-fluoro-2-nitrophenyl)-3,3-dimethylmorpholine in methanol (15 mL)/water (5 mL) was added ammonium chloride (535 mg, 10 mmol) andiron powder (558 mg, 10 mmol). The reaction mixture was heated at 80° C. for 2 h and was filtered through Celite®, concentrated. The crude was extracted with ethyl acetate, washed with water, brine, dried over sodium sulfate. The ethyl acetate layer was filtered, concentrated and the crude purified by silica gel chromatography using 0-50% EtOAc in hexane to give 4-(2-amino-5-bromo-3-fluorophenyl)-5,5-dimethylmorpholin-3-one (670 mg, 2.1 mmol, 16.6% yield over 2 steps). $C_{12}H_{15}BrFN_2O_2(M+H)^+$ m/z: 317.0; found: 316.9.

Step 3: 7-bromo-9-fluoro-4,4-dimethyl-3, 4-dihydro-1H-benzo[4,5]imidazo[2,1-c][1,4]oxazine

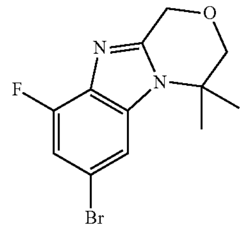 [SMILES: CC1(C)COCc2nc3c(F)cc(Br)cc3n21]

To a stirred solution of 4-(2-amino-5-bromo-3-fluorophenyl)-5,5-dimethylmorpholin-3-one (640 mg, 2.02 mmol) in toluene (25 mL) was added the acetic acid (3.0 mL, 2.02 mmol) at rt. The resulted mixture was heated at 110° C. for 3 h. The volatiles were removed, and the residue was dissolved in ethyl acetate, washed with saturated sodium bicarbonate, dried over sodium sulfate, and filtered. The filtrate was concentrated and the crude was purified by silica gel chromatography using 0-30% EtOAc in hexane to give 7-bromo-9-fluoro-4,4-dimethyl-1,3-dihydro-[1,4]oxazino [4,3-a]benzimidazole (470 mg, 1.57 mmol, 77.8% yield). $C_{12}H_{13}BrFN_2O$ $(M+H)^+$ m/z: 299.0; found: 299.0.

Step 4: (1S,3R)—N-(5-chloro-4-(9-fluoro-4,4-dimethyl-3, 4-dihydro-1H-benzo[4,5]imidazo[2,1-c][1,4]oxazin-7-yl)pyridin-2-yl)-3-(2-cyanoacetamido) cyclohexane-1-carboxamide The title compound was prepared using procedures analogous to those described for Example 65, using appropriate starting materials. LCMS calcd. for $C_{27}H_{29}ClFN_6O_3$ $(M+H)^+$ m/z: 539.2; found: 539.1.

Example 86: (1S,3R)-3-(2-cyanoacetamido)-N-(4-(7-fluoro-3-isopropyl-2-methyl-2H-indazol-5-yl)-5-methylpyridin-2-yl)cyclohexane-1-carboxamide

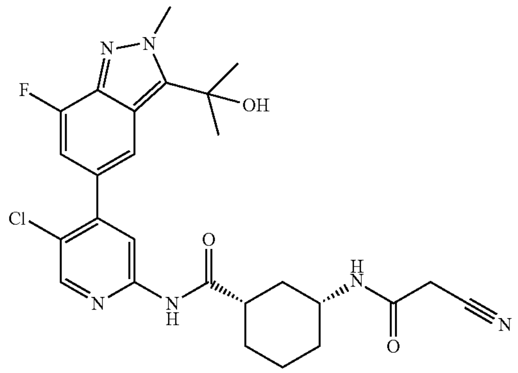 [SMILES: Cn1nc2c(F)cc(-c3cc(NC(=O)[C@H]4CCC[C@@H](NC(=O)CC#N)C4)ncc3Cl)cc2c1C(C)(C)O]

The title compound was prepared using procedures analogous to those described for Example 65, using appropriate starting materials. LCMS calcd. for $C_{26}H_{29}ClFN_6O_3(M+H)^+$ m/z: 527.2; found: 527.2.

Example 87: (1S,3R)-3-acetamido-N-(5-chloro-4-(4-fluoro-1-isopropyl-1H-benzo[d]imidazol-6-yl) pyridin-2-yl)cyclohexane-1-carboxamide

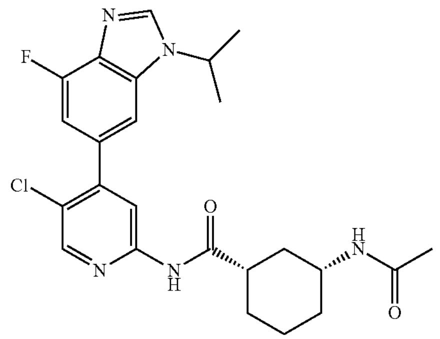 [SMILES: CC(=O)N[C@@H]1CCC[C@H](C(=O)Nc2cc(-c3cc(F)c4ncn(C(C)C)c4c3)c(Cl)cn2)C1]

The title compound was prepared using procedures analogous to those described for Example 22, using appropriate starting materials. LCMS calcd. for $C_{24}H_{28}ClFN_5O_2(M+H)^+$ m/z: 472.2; found: 472.2.

Example 88: (1S,3R)-3-acetamido-N-(4-(4-fluoro-1-isopropyl-1H-benzo[d]imidazol-6-yl)pyridin-2-yl) cyclohexane-1-carboxamide

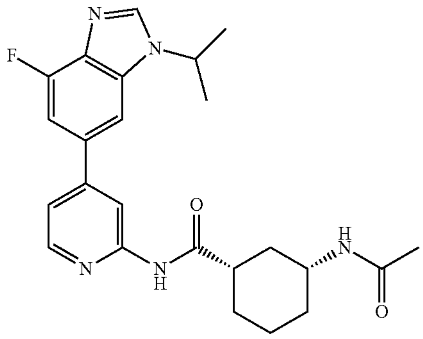 [SMILES: CC(=O)N[C@@H]1CCC[C@H](C(=O)Nc2cc(-c3cc(F)c4ncn(C(C)C)c4c3)ccn2)C1]

The title compound was prepare using procedures analogous to those described for Example 22, using appropriate starting materials. LCMS calcd. for $C_{24}H_{29}FN_5O_2(M+H)^+$ m/z: 438.2; found: 438.2.

Biological Assays

CDK9/CyclinT1 Enzymatic Activity Assay

The inhibitory activity of compounds was evaluated in vitro using TR-FRET assay with white 384-well low volume microplate (Greiner Bio-One). CDK9/Cyclin T1 catalyzed phosphorylation of peptide in the presence and absence of compounds was measured and used in $IC_{50}$ determination. Recombinant protein complex CDK9/Cyclin T1, expressed from insect cell, was purchased from ProQinase. Testing compounds were dissolved in DMSO at 1 mM and tested in 9-dose $IC_{50}$ mode. The reaction mixture was prepared by mixing CDK9/CyclinT1 (1 nM final), ULight-4E-BP1 (50 nM final, Perkinelmer, TRF0128-D), and ATP (1 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E) to make a 9.9 μL of reaction mixture. After 20 minutes preincubation at room temperature, 0.1 μL $MgCl_2$ (10 mM final) was added to initiate the reaction. Following a 45 minutes incubation at 37° C., the reaction was stopped by addition of 2 μL of quenching buffer consisting of Lance detection buffer (Perkinelmer CR97-100C), LANCE Ultra Europium-anti-P-4E-BP1 (Perkinelmer, TRF0216-D), EDTA, and incubate at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software. See Table B (CDK9_T1).

CDK2/CyclinA2 Enzymatic Activity Assay

The inhibitory activity of compounds was evaluated in vitro using TR-FRET assay with white 384-well low volume microplate (Greiner Bio-One). CDK2/Cyclin A2 catalyzed phosphorylation of peptide in the presence and absence of compounds was measured and used in $IC_{50}$ determination. Recombinant protein complex CDK2/Cyclin A2, expressed from insect cell, was purchased from ProQinase. Testing compounds were dissolved in DMSO at 1 mM and tested in 9-dose $IC_{50}$ mode. The reaction mixture was prepared by mixing CDK2/CyclinA2 (1 nM final), ULight-4E-BP1 (50 nM final, Perkinelmer, TRF0128-D), and ATP (1 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E) to make a 9.9 μL of reaction mixture. After 20 minutes preincubation at room temperature, 0.1 μL $MgCl_2$ (10 mM final) was added to initiate the reaction. Following a 45 minutes incubation at 37° C., the reaction was stopped by addition of 2 μL of quenching buffer consisting of Lance detection buffer (Perkinelmer CR97-100C), LANCE Ultra Europium-anti-P-4E-BP1 (Perkinelmer, TRF0216-D), EDTA, and incubate at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software. See Table B (CDK2_A2).

CDK4/CyclinD1 Enzymatic Activity Assay

The inhibitory activity of compounds was evaluated in vitro using TR-FRET assay with white 384-well low volume microplate (Greiner Bio-One). CDK4/Cyclin D1 catalyzed phosphorylation of peptide in the presence and absence of compounds was measured and used in $IC_{50}$ determination. Recombinant protein complex CDK4/Cyclin D1, expressed from insect cell, was purchased from ProQinase. Testing compounds were dissolved in DMSO at 1 mM and tested in 9-dose $IC_{50}$ mode. The reaction mixture was prepared by mixing CDK4/CyclinD1 (1 nM final), ULight-4E-BP1 (100 nM final, Perkinelmer, TRF0128-D), and ATP (2 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E) to make a 9.9 μL of reaction mixture. After 20 minutes preincubation at room temperature, 0.1 μL $MgCl_2$ (10 mM final) was added to initiate the reaction. Following a 45 minutes incubation at 37° C., the reaction was stopped by addition of 2 μL of quenching buffer consisting of Lance detection buffer (Perkinelmer CR97-100C), LANCE Ultra Europium-anti-P-4E-BP1 (Perkinelmer, TRF0216-D), EDTA, and incubate at room temperature for additional 60 minutes in dark. The reaction signal was measured by Envision multimode plate reader (PerkinElmer, 2102-0010). $IC_{50}$ values were determined by fitting the data to the standard 4 parameters with Hill Slope using GraphPad Prism software. See Table B (CDK4_D1).

CellTiter-Glo® Protocol (Proliferation)

Dispense 10 μL aliquot of prepared H929 cells (1:1 ratio of cells:Trypan Blue (#1450013, Bio-Rad)) onto cell counting slide (#145-0011, Bio-Rad) and obtain cell density and cell viability using cell counter (TC20, Bio-Rad). Remove appropriate volume of resuspended cells from culture flask to accommodate 4000 cells/well at 10 μL/well. Transfer H929 cells to 50 mL conical (#430290, Corning). Spin down at 1000 rpm for 5 min. using tabletop centrifuge (SPINCHRON 15, Beckman). Discard supernatant and resuspend cell pellet in modified RPMI 1640 (#10-040-CV, Corning) cell culture media containing 10% FBS (F2422-500ML, Sigma), sodium pyruvate (100 mM) (#25-000-CL, Corning), HEPES buffer (1M) (#25-060-CL, Corning) and glucose (200 g/L) (A24940-01, Gibco) to a cell density of 400,000 cells/mL. Dispense 10 μL of resuspended H929 cells per well in 384-well small volume TC treated plate (#784080, Greiner Bio-one) using standard cassette (#50950372, Thermo Scientific) on Multidrop Combi (#5840310, Thermo Scientific) in laminar flow cabinet. Dispense compounds onto plates using digital liquid dispenser (D300E, Tecan). Incubate plates in humidified tissue culture incubator at 37° C. for 24 hours. Add 10 μL of prepared CellTiTer-Glo® detection buffer (G7570, Promega) to each well of 384-well plate using small tube cassette (#24073295, Thermo Scientific) on Combi multi drop, incubate at RT for 30-60 min. Read plates with microplate reader (PheraStar, BMG Labtech) using 384 well luminescence mode. See Table B (Proliferation_CTG_H929).

TABLE B

| Example | CDK2_A2 $IC_{50}$ (nM) | CDK4_D1 $IC_{50}$ (nM) | CDK9_T1 $IC_{50}$ (nM) | PROLIFERATION_ CTG_H929 $IC_{50}$ (nM) |
|---|---|---|---|---|
| 1 | 83.9 | 54 | 1.61 | 19.7 |
| 2 | 83.1 | 45.7 | 0.477 | 11.9 |
| 3 | 146 | 84.7 | 0.699 | 29.9 |
| 4 | 54 | 36.7 | 0.528 | 11.1 |
| 5 | 114 | 49.2 | 1.04 | 21.3 |
| 6 | 338 | 36.9 | 0.794 | 27.3 |
| 7 | 177 | 41 | 0.76 | 12.7 |
| 8 | 63 | 38 | 0.98 | 20 |
| 9 | 101 | 15.6 | 0.416 | 13 |
| 10 | 125 | 10.8 | 0.455 | 10.1 |
| 11 | 105 | 22.8 | 0.498 | 13.5 |
| 12 | 102 | 19.7 | 0.489 | 11.4 |
| 13 | 183 | 108 | 2.31 | 42.4 |
| 14 | 940 | 341 | 4.61 | 27.8 |
| 15 | 651 | 146 | 3.8 | 47.4 |
| 16 | 77.8 | 115 | 3.99 | 59.7 |
| 17 | 297 | 80.2 | 2.31 | 21.3 |
| 18 | 39.7 | 153 | 3.09 | 74.9 |
| 19 | 837 | 262 | 3.71 | 24 |
| 20 | 398 | 114 | 2.98 | 26.3 |
| 21 | 321 | 137 | 4.15 | 42 |
| 22 | 434 | 590 | 0.694 | 28.6 |
| 23 | 1120 | 822 | 9.18 | 100 |
| 24 | 202 | 237 | 0.539 | 16.8 |
| 25 | 478 | 408 | 2.55 | 30.4 |
| 26 | 129 | 429 | 2.87 | 94.1 |
| 27 | 1170 | 1480 | 34.8 | 134 |
| 28 | 1520 | 787 | 2.23 | 23.9 |
| 29 | 920 | 941 | 1.48 | 22 |
| 30 | 748 | 240 | 1.01 | 27.1 |
| 31 | | 493 | 1.29 | 29.9 |
| 32 | | 707 | 5.02 | 65.9 |
| 33 | | 941 | 1.57 | 21.6 |
| 34 | | 968 | 1.87 | 32.6 |
| 35 | | 468 | 1.04 | 15 |
| 36 | | 1000 | 1.37 | 40.9 |
| 37 | | 1000 | 9.19 | 913 |
| 38 | | 1000 | 3.07 | 75.8 |
| 39 | | 1000 | 4.91 | 95.7 |
| 40 | | 1000 | 18.4 | 572 |
| 41 | | 1000 | 3.92 | 41.1 |
| 42 | | 528 | 2.49 | 21.4 |
| 43 | | 624 | 0.979 | 129 |
| 44 | | 227 | 0.984 | 54.7 |
| 45 | | 587 | 0.743 | 41.3 |
| 46 | | 1000 | 1.39 | 78.5 |
| 47 | | 1000 | 7.22 | 450 |
| 48 | | 1000 | 9.72 | 69.4 |
| 49 | | 1000 | 51.6 | 176 |
| 50 | | 1000 | 2.3 | 22.9 |
| 51 | | 155 | 3.35 | 123 |
| 52 | | 187 | 1.49 | 22.5 |
| 53 | | 78.8 | 0.82 | 15.3 |
| 54 | | 198 | 4.12 | 74.3 |
| 55 | | 805 | 8.56 | 48.7 |
| 56 | | 250 | 1.52 | 51.1 |
| 57 | | 137 | 2.0 | 25 |
| 58 | | 184 | 4.13 | 54 |
| 59 | | 176 | 1.95 | 8.35 |
| 60 | | 90.1 | 2.27 | 9.97 |
| 61 | 1310 | 388 | 1.41 | 53.5 |
| 62 | | 133 | 0.961 | 51.5 |
| 63 | | 584 | 2.93 | 19 |
| 64 | | 1000 | 5.95 | 66.1 |
| 65 | | 55.1 | 0.48 | 13.1 |

TABLE B-continued

| Example | CDK2_A2 $IC_{50}$ (nM) | CDK4_D1 $IC_{50}$ (nM) | CDK9_T1 $IC_{50}$ (nM) | PROLIFERATION_ CTG_H929 $IC_{50}$ (nM) |
|---|---|---|---|---|
| 66 | | 531 | 1.67 | 49.2 |
| 66 | 1350 | 351 | 1.65 | 70.4 |
| 68 | | 163 | 3.29 | 16.9 |
| 69 | 73.7 | 95.7 | 2.43 | 11.6 |
| 70 | | 225 | 3.39 | 41.1 |
| 71 | | 648 | 5.7 | 155 |
| 72 | | 1000 | 5.48 | 92 |
| 73 | | 1000 | 9.27 | 74.2 |
| 74 | | 41.6 | 0.938 | 12.6 |
| 75 | | 31.7 | 1.38 | 7.28 |
| 76-1 | | 109 | 0.78 | 17.4 |
| 76-2 | | 648 | 11.2 | 255 |
| 77 | | 133 | 1.97 | 38.1 |
| 78 | | 343 | 3.05 | 27 |
| 79 | | 414 | 2.51 | 43.4 |
| 80 | 1180 | 640 | 1.09 | 17.4 |
| 81 | | 1000 | 29.2 | 242 |
| 82 | | 41.3 | 1.55 | 12.9 |
| 83 | | 1000 | 35.9 | 176 |
| 84 | 168 | 10000 | 1.42 | 28.5 |
| 85 | | 149 | 2.83 | 29.5 |
| 86 | | 20.4 | 0.406 | 71.5 |
| 87 | 117 | 65 | 0.837 | 8.02 |
| 88 | | 102 | 7.22 | 12.8 |

As shown in Table B, compounds having a formula of either Formula (I) or Formula (II) wherein $R^2$ on the pyridine ring is Me, have demonstrated surprisingly and unexpectedly improved selectivity towards CDK9 over other CDKs, such as CDK4, compared to the corresponding compounds with $R^2$ as Cl or H. A few examples of compounds showing the surprising and unexpected selectivity towards CDK9 over CDK4 are shown in Table C.

TABLE C

| Example | $R^2$ | CDK4 $IC_{50}$:CDK9 $IC_{50}$ |
|---|---|---|
| 1 | Cl | 34:1 |
| 56 | Me | 164:1 |
| 75 | Cl | 23:1 |
| 78 | Me | 112:1 |
| 87 | Cl | 77:1 |
| 88 | H | 14:1 |
| 22 | Me | 855:1 |

X-Ray Crystal Structure Analysis

Peak 2 was used as the precursor for preparation of Example 76-2 as shown in Example 76-2. The absolute (S)-configuration of Peak 2 for preparation of Example 76-2 was determined by an X-ray crystal structure analysis and the representation of the (S)-configuration can be illustrated as shown in the compound of

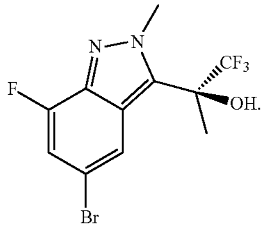 [SMILES: Cn1nc2c(F)cc(Br)cc2c1[C@](C)(O)C(F)(F)F]

The details of the crystal data and parameters for the X-ray crystal structure analysis are as shown in Tables D-I.

TABLE D

| Crystal data | |
|---|---|
| $2(C_{11}H_9BrF_4N_2O)\bullet H_2O$ | $D_x$ = 1.872 Mg m$^{-3}$ |
| $M_r$ = 700.24 | Mo Kα radiation, λ = 0.71073 Å |
| Orthorhombic, $C222_1$ | Cell parameters from 6014 reflections |
| a = 13.4149 (3) Å | θ = 2.3-26.3° |
| b = 41.2066 (12) Å | μ = 3.36 mm$^{-1}$ |
| c = 17.9748 (5) Å | T = 170K |
| V = 9936.2 (5) Å$^3$ | Block, colourless |
| Z = 16 | 0.16 × 0.12 × 0.08 mm |
| F(000) = 5536 | |

TABLE E

| Data collection | |
|---|---|
| D8 VENTURE diffractometer | 6984 reflections with I > 2σ(I) |
| ϕ and ω scans | $R_{int}$ = 0.047 |
| Absorption correction: multi-scan SADABS2016/2 (Bruker, 2016/2) was used for absorption correction. wR2(int) was 0.0980 before and 0.0617 after correction. The Ratio of minimum to maximum transmission is 0.7718. The λ/2 correction factor is Not present. | $\theta_{max}$ = 26.4°, $\theta_{min}$ = 2.0° |
| $T_{min}$ = 0.575, $T_{max}$ = 0.745 | h = −16 → 15 |
| 30334 measured reflections | k = −48 → 51 |
| 10112 independent reflections | l = −20 → 22 |

TABLE F

| Refinement | |
|---|---|
| Refinement on F$^2$ | Hydrogen site location: mixed |
| Least-squares matrix: full | H-atom parameters constrained |
| | w = 1/[$\sigma^2(F_o^2)$ + $(0.0123P)^2$ + 10.3169P] |
| R[F$^2$ > 2σ(F$^2$)] = 0.039 | where P = ($F_o^2$ + $2F_c^2$)/3 |
| wR(F$^2$) = 0.096 | $(\Delta/\sigma)_{max}$ = 0.001 |
| S = 1.01 | $\Delta\rangle_{max}$ = 0.37 e Å$^{-3}$ |
| 10112 reflections | $\Delta\rangle_{max}$ = −0.61 e Å$^{-3}$ |
| 721 parameters | Absolute structure: Flack x determined using 2473 quotients [(I+) − (I−)]/[(I+) + (I−)] (Parsons, Flack and Wagner, Acta Cryst. B69 (2013) 249-259). |
| 0 restraints | Absolute structure parameter: 0.003 (6) |
| Primary atom site location: dual | |

TABLE G

| parameters (Å$^2$) for (xx) | | | | |
|---|---|---|---|---|
| | x | y | z | $U_{iso}$*/$U_{eq}$ |
| Br2 | 0.60863 (5) | 0.69965 (2) | 0.65090 (4) | 0.0362 (2) |
| Br3 | 0.36474 (6) | 0.55209 (2) | 0.33773 (4) | 0.0341 (2) |
| Br1 | 0.86366 (6) | 0.69463 (2) | 0.83409 (4) | 0.03643 (19) |
| Br4 | 0.88388 (7) | 0.55540 (2) | 0.34068 (4) | 0.0423 (2) |
| F15 | 0.3891 (3) | 0.63774 (10) | 0.12756 (18) | 0.0354 (10) |
| F5 | 0.6383 (3) | 0.61414 (10) | 0.86118 (19) | 0.0347 (9) |
| F8 | 1.0049 (3) | 0.71877 (10) | 0.4686 (2) | 0.0428 (11) |
| F13 | 0.3682 (3) | 0.68792 (9) | 0.56370 (18) | 0.0385 (10) |
| F12 | 0.4612 (3) | 0.66099 (11) | 0.4875 (2) | 0.0410 (11) |
| F4 | 0.8713 (3) | 0.60814 (11) | 0.62517 (19) | 0.0440 (11) |
| F2 | 0.7757 (3) | 0.58700 (11) | 0.9859 (2) | 0.0459 (12) |
| F00C | 0.8819 (3) | 0.64463 (11) | 0.13765 (19) | 0.0433 (11) |
| F6 | 0.9953 (3) | 0.66736 (10) | 0.4916 (2) | 0.0414 (11) |
| F14 | 0.3058 (3) | 0.64855 (10) | 0.5011 (2) | 0.0438 (11) |
| F9 | 0.7491 (3) | 0.53269 (11) | 0.5436 (3) | 0.0502 (12) |
| F10 | 0.7344 (3) | 0.58236 (11) | 0.5068 (2) | 0.0457 (12) |
| F1 | 0.8681 (4) | 0.56090 (10) | 1.06350 (19) | 0.0453 (11) |
| F7 | 0.9339 (3) | 0.70225 (11) | 0.5691 (2) | 0.0428 (11) |

TABLE G-continued

| parameters (Å$^2$) for (xx) | | | | |
|---|---|---|---|---|
| | x | y | z | $U_{iso}$*/$U_{eq}$ |
| O3 | 0.4079 (3) | 0.72443 (10) | 0.4476 (2) | 0.0266 (10) |
| H3 | 0.380582 | 0.737990 | 0.475878 | 0.040* |
| O4 | 0.6232 (3) | 0.72601 (12) | 0.4040 (2) | 0.0322 (11) |
| H4D | 0.564199 | 0.728179 | 0.423574 | 0.048* |
| H4E | 0.620980 | 0.711553 | 0.368829 | 0.048* |
| F3 | 0.9318 (4) | 0.59978 (10) | 0.9998 (2) | 0.0478 (12) |
| O6 | 0.5443 (3) | 0.52544 (11) | 0.5506 (3) | 0.0289 (11) |
| H6 | 0.482746 | 0.527050 | 0.542940 | 0.043* |
| O2 | 0.8057 (3) | 0.72563 (10) | 0.4667 (3) | 0.0266 (11) |
| H2 | 0.746148 | 0.725996 | 0.452171 | 0.040* |
| O1 | 0.8298 (4) | 0.52359 (11) | 0.9466 (3) | 0.0333 (12) |
| H1 | 0.837485 | 0.515874 | 0.989439 | 0.050* |
| F11 | 0.6737 (3) | 0.54351 (11) | 0.4401 (2) | 0.0505 (13) |
| O5 | 0.3559 (5) | 0.52544 (14) | 0.6142 (3) | 0.0449 (14) |
| H5A | 0.313097 | 0.528943 | 0.578668 | 0.067* |
| H5B | 0.413523 | 0.525466 | 0.591992 | 0.067* |
| N8 | 0.3777 (4) | 0.68995 (13) | 0.2332 (3) | 0.0263 (13) |
| N3 | 0.6264 (4) | 0.56186 (13) | 0.7552 (3) | 0.0248 (12) |
| N2 | 0.8755 (5) | 0.55673 (13) | 0.7326 (3) | 0.0277 (13) |
| N7 | 0.3690 (4) | 0.70496 (12) | 0.2999 (3) | 0.0219 (12) |
| N5 | 0.8731 (4) | 0.69507 (14) | 0.2502 (3) | 0.0288 (13) |
| N4 | 0.6169 (4) | 0.54686 (13) | 0.6882 (3) | 0.0248 (13) |
| N1 | 0.8795 (4) | 0.54211 (13) | 0.7999 (3) | 0.0254 (13) |
| C16 | 0.6144 (5) | 0.65582 (15) | 0.6846 (3) | 0.0238 (14) |
| C15 | 0.6072 (4) | 0.63114 (15) | 0.6328 (3) | 0.0224 (14) |
| H15 | 0.600396 | 0.635443 | 0.581083 | 0.027* |
| N6 | 0.8669 (4) | 0.70836 (13) | 0.3194 (3) | 0.0283 (13) |
| C18 | 0.6051 (4) | 0.56752 (15) | 0.6303 (3) | 0.0187 (14) |
| C012 | 0.8766 (5) | 0.59956 (16) | 0.3110 (3) | 0.0265 (15) |
| C6 | 0.8776 (5) | 0.59441 (16) | 0.8268 (3) | 0.0246 (14) |
| C28 | 0.3613 (4) | 0.68411 (14) | 0.3589 (3) | 0.0172 (13) |
| C015 | 0.8601 (5) | 0.68580 (15) | 0.3747 (3) | 0.0215 (14) |
| C25 | 0.3757 (5) | 0.65854 (15) | 0.2500 (3) | 0.0229 (14) |
| C5 | 0.8812 (5) | 0.56351 (14) | 0.8582 (3) | 0.0207 (13) |
| C7 | 0.8746 (5) | 0.58816 (15) | 0.7486 (3) | 0.0220 (14) |
| C23 | 0.3639 (5) | 0.62053 (14) | 0.3549 (3) | 0.0223 (14) |
| H23 | 0.358652 | 0.616221 | 0.406650 | 0.027* |
| C24 | 0.3667 (4) | 0.65245 (15) | 0.3280 (3) | 0.0191 (13) |
| C14 | 0.6227 (5) | 0.59344 (16) | 0.7387 (3) | 0.0241 (15) |
| C12 | 0.6245 (5) | 0.65108 (16) | 0.7617 (3) | 0.0281 (15) |
| H12 | 0.628621 | 0.668959 | 0.794912 | 0.034* |
| C01D | 0.8665 (4) | 0.65565 (15) | 0.3407 (3) | 0.0220 (14) |
| C22 | 0.3688 (5) | 0.59570 (16) | 0.3042 (3) | 0.0249 (15) |
| C01F | 0.8722 (5) | 0.66321 (17) | 0.2623 (3) | 0.0265 (15) |
| C8 | 0.8741 (5) | 0.62679 (14) | 0.8524 (3) | 0.0225 (14) |
| H8 | 0.873914 | 0.631557 | 0.904098 | 0.027* |
| C27 | 0.3768 (5) | 0.60087 (16) | 0.2265 (3) | 0.0267 (16) |
| H27 | 0.378994 | 0.583108 | 0.192879 | 0.032* |
| C17 | 0.6104(4) | 0.59916 (15) | 0.6610 (3) | 0.0220 (14) |
| C01J | 0.8786 (5) | 0.60620 (17) | 0.2332 (4) | 0.0298 (16) |
| H01J | 0.880871 | 0.589056 | 0.197931 | 0.036* |
| C13 | 0.6283 (5) | 0.62004 (17) | 0.7870 (3) | 0.0270 (16) |
| C01L | 0.8772 (5) | 0.63743 (19) | 0.2110 (3) | 0.0310 (17) |
| C01M | 0.8703 (5) | 0.62303 (14) | 0.3644 (3) | 0.0234 (14) |
| H01M | 0.868534 | 0.617592 | 0.415750 | 0.028* |
| C9 | 0.8710 (5) | 0.65089 (16) | 0.8011 (3) | 0.0251 (15) |
| C11 | 0.8721 (6) | 0.61464 (19) | 0.6987 (3) | 0.0293 (17) |
| C26 | 0.3813 (5) | 0.63176 (17) | 0.2016 (3) | 0.0246 (15) |
| C3 | 1.0031 (5) | 0.53980 (18) | 0.9499 (4) | 0.0361 (18) |
| H3A | 1.010706 | 0.532225 | 1.001277 | 0.054* |
| H3B | 1.047359 | 0.558360 | 0.941372 | 0.054* |
| H3C | 1.020601 | 0.522226 | 0.915563 | 0.054* |
| C30 | 0.2328 (4) | 0.70738 (17) | 0.4455 (4) | 0.0311 (16) |
| H30A | 0.221528 | 0.715019 | 0.496480 | 0.047* |
| H30B | 0.190411 | 0.688504 | 0.435713 | 0.047* |
| H30C | 0.216472 | 0.724755 | 0.410374 | 0.047* |
| C10 | 0.8714 (5) | 0.64554 (17) | 0.7231 (3) | 0.0300 (16) |
| H10 | 0.871186 | 0.663208 | 0.689107 | 0.036* |
| C1 | 0.8948 (5) | 0.55010 (15) | 0.9366 (3) | 0.0230 (15) |
| C20 | 0.5236 (5) | 0.58072 (18) | 0.5073 (4) | 0.0353 (18) |
| H20A | 0.506638 | 0.571539 | 0.458672 | 0.053* |
| H20B | 0.560243 | 0.601072 | 0.500416 | 0.053* |
| H20C | 0.462333 | 0.584963 | 0.535394 | 0.053* |
| C29 | 0.3427 (4) | 0.69777 (15) | 0.4362 (3) | 0.0202 (14) |
| C01W | 0.8449 (5) | 0.69405 (16) | 0.4573 (3) | 0.0225 (15) |
| C32 | 0.3719 (5) | 0.67315 (16) | 0.4967 (3) | 0.0281 (15) |

TABLE G-continued

| parameters (Å$^2$) for (xx) | | | | |
|---|---|---|---|---|
| | x | y | z | $U_{iso}$*/$U_{eq}$ |
| C01Y | 0.7801 (5) | 0.66906 (17) | 0.4963 (4) | 0.0306 (17) |
| H01A | 0.765605 | 0.676428 | 0.547041 | 0.046* |
| H01B | 0.815386 | 0.648249 | 0.498325 | 0.046* |
| H01C | 0.717545 | 0.666380 | 0.468877 | 0.046* |
| C31 | 0.3661 (6) | 0.74024 (16) | 0.2982 (4) | 0.0354 (18) |
| H31A | 0.421898 | 0.748916 | 0.327321 | 0.053* |
| H31B | 0.303100 | 0.747830 | 0.319597 | 0.053* |
| H31C | 0.371517 | 0.747755 | 0.246662 | 0.053* |
| C020 | 0.6239 (7) | 0.51158 (15) | 0.6893 (4) | 0.0397 (19) |
| H02A | 0.648547 | 0.504438 | 0.737926 | 0.060* |
| H02B | 0.669939 | 0.504368 | 0.650337 | 0.060* |
| H02C | 0.557823 | 0.502192 | 0.680344 | 0.060* |
| C19 | 0.5881 (5) | 0.55683 (16) | 0.5501 (4) | 0.0251 (15) |

TABLE G-continued

| parameters (Å$^2$) for (xx) | | | | |
|---|---|---|---|---|
| | x | y | z | $U_{iso}$*/$U_{eq}$ |
| C022 | 0.9450 (5) | 0.69552 (17) | 0.4964 (4) | 0.0309 (16) |
| C2 | 0.8671 (6) | 0.57517 (16) | 0.9958 (3) | 0.0324 (16) |
| C4 | 0.8814 (6) | 0.50657 (17) | 0.7992 (4) | 0.041 (2) |
| H4A | 0.821541 | 0.498217 | 0.823913 | 0.062* |
| H4B | 0.940796 | 0.498879 | 0.825653 | 0.062* |
| H4C | 0.883173 | 0.498833 | 0.747696 | 0.062* |
| C025 | 0.8719 (6) | 0.74371 (15) | 0.3235 (4) | 0.0401 (18) |
| H02D | 0.891954 | 0.752413 | 0.274998 | 0.060* |
| H02E | 0.920864 | 0.750084 | 0.361211 | 0.060* |
| H02F | 0.806290 | 0.752349 | 0.336960 | 0.060* |
| C21 | 0.6869 (6) | 0.55369 (19) | 0.5106 (4) | 0.0372 (19) |

TABLE H

| Atomic displacement parameters (Å$^2$) for (xx) | | | | | | |
|---|---|---|---|---|---|---|
| | $U^{11}$ | $U^{22}$ | $U^{33}$ | $U^{12}$ | $U^{13}$ | $U^{23}$ |
| Br2 | 0.0449 (4) | 0.0220 (4) | 0.0418 (4) | 0.0002 (3) | 0.0051 (4) | −0.0079 (3) |
| Br3 | 0.0445 (4) | 0.0195 (4) | 0.0384 (5) | −0.0002 (4) | −0.0054 (4) | −0.0066 (3) |
| Br1 | 0.0396 (4) | 0.0210 (4) | 0.0487 (4) | −0.0007 (4) | −0.0051 (4) | 0.0116 (3) |
| Br4 | 0.0538 (5) | 0.0238 (4) | 0.0492 (6) | 0.0022 (4) | 0.0052 (5) | −0.0127 (3) |
| F15 | 0.038 (2) | 0.051 (3) | 0.017 (2) | 0.005 (2) | 0.0011 (18) | −0.0054 (17) |
| F5 | 0.033 (2) | 0.054 (3) | 0.0165 (19) | −0.002 (2) | −0.0023 (18) | −0.0039 (18) |
| F8 | 0.025 (2) | 0.043 (3) | 0.060 (3) | −0.001 (2) | −0.008 (2) | −0.005 (2) |
| F13 | 0.065 (3) | 0.032 (2) | 0.0186 (19) | 0.003 (2) | −0.003 (2) | −0.0091 (16) |
| F12 | 0.052 (3) | 0.041 (3) | 0.030 (2) | 0.022 (2) | −0.0116 (19) | −0.003 (2) |
| F4 | 0.047 (3) | 0.065 (3) | 0.019 (2) | 0.005 (3) | −0.001 (2) | 0.0064 (19) |
| F2 | 0.058 (3) | 0.048 (3) | 0.032 (2) | 0.024 (2) | 0.013 (2) | 0.003 (2) |
| F00C | 0.040 (2) | 0.073 (3) | 0.017 (2) | 0.014 (3) | 0.0002 (19) | −0.001 (2) |
| F6 | 0.044 (2) | 0.035 (3) | 0.046 (3) | 0.022 (2) | −0.012 (2) | −0.011 (2) |
| F14 | 0.078 (3) | 0.026 (2) | 0.027 (2) | −0.014 (2) | 0.009 (2) | 0.0038 (19) |
| F9 | 0.035 (2) | 0.050 (3) | 0.066 (3) | 0.010 (2) | 0.011 (2) | −0.002 (3) |
| F10 | 0.051 (3) | 0.045 (3) | 0.041 (3) | −0.025 (2) | 0.016 (2) | −0.009 (2) |
| F1 | 0.077 (3) | 0.041 (2) | 0.018 (2) | 0.011 (3) | 0.004 (2) | 0.0107 (17) |
| F7 | 0.054 (3) | 0.047 (3) | 0.027 (2) | 0.017 (2) | −0.0125 (18) | −0.015 (2) |
| O3 | 0.028 (2) | 0.020 (2) | 0.032 (3) | −0.006 (2) | 0.007 (2) | −0.009 (2) |
| O4 | 0.023 (2) | 0.038 (3) | 0.035 (3) | 0.006 (2) | 0.000 (2) | −0.013 (2) |
| F3 | 0.083 (3) | 0.030 (3) | 0.030 (2) | −0.014 (2) | −0.013 (2) | −0.004 (2) |
| O6 | 0.029 (2) | 0.024 (3) | 0.033 (3) | −0.006 (2) | −0.002 (2) | −0.005 (2) |
| O2 | 0.028 (2) | 0.016 (2) | 0.036 (3) | 0.003 (2) | −0.004 (2) | −0.007 (2) |
| O1 | 0.045 (3) | 0.025 (3) | 0.030 (3) | −0.008 (2) | −0.001 (2) | 0.008 (2) |
| F11 | 0.060 (3) | 0.060 (3) | 0.032 (2) | −0.021 (2) | 0.019 (2) | −0.026 (2) |
| O5 | 0.063 (4) | 0.040 (3) | 0.032 (3) | −0.002 (3) | 0.002 (3) | −0.007 (2) |
| N8 | 0.029 (3) | 0.031 (3) | 0.019 (3) | 0.002 (3) | 0.003 (3) | 0.004 (2) |
| N3 | 0.026 (3) | 0.030 (3) | 0.019 (3) | −0.005 (3) | 0.002 (3) | 0.000 (2) |
| N2 | 0.025 (3) | 0.038 (4) | 0.020 (3) | 0.000 (3) | 0.000 (3) | −0.004 (3) |
| N7 | 0.027 (3) | 0.017 (3) | 0.021 (3) | 0.002 (3) | 0.001 (2) | 0.002 (2) |
| N5 | 0.029 (3) | 0.032 (3) | 0.026 (3) | 0.001 (3) | −0.001 (3) | 0.008 (3) |
| N4 | 0.030 (3) | 0.024 (3) | 0.020 (3) | 0.000 (3) | 0.004 (3) | −0.002 (2) |
| N1 | 0.028 (3) | 0.022 (3) | 0.026 (3) | 0.002 (3) | 0.004 (3) | −0.006 (2) |
| C16 | 0.022 (3) | 0.020 (3) | 0.029 (4) | 0.003 (3) | −0.001 (3) | −0.001 (3) |
| C15 | 0.021 (3) | 0.030 (4) | 0.016 (3) | 0.000 (3) | −0.001 (3) | −0.005 (3) |
| N6 | 0.026 (3) | 0.030 (3) | 0.029 (3) | 0.000 (3) | −0.001 (3) | 0.002 (2) |
| C18 | 0.022 (3) | 0.018 (3) | 0.017 (3) | −0.001 (3) | 0.000 (3) | −0.003 (2) |
| C012 | 0.021 (3) | 0.027 (4) | 0.031 (4) | 0.000 (3) | 0.002 (3) | −0.009 (3) |
| C6 | 0.019 (3) | 0.034 (4) | 0.021 (3) | 0.000 (3) | −0.001 (3) | 0.004 (3) |
| C28 | 0.022 (3) | 0.015 (3) | 0.014 (3) | 0.001 (3) | 0.002 (3) | 0.002 (2) |
| C015 | 0.022 (3) | 0.019 (3) | 0.024 (3) | 0.000 (3) | 0.001 (3) | 0.001 (3) |
| C25 | 0.019 (3) | 0.028 (4) | 0.021 (3) | 0.002 (3) | −0.001 (3) | −0.002 (3) |
| C5 | 0.022 (3) | 0.019 (3) | 0.021 (3) | 0.000 (3) | 0.001 (3) | 0.005 (3) |
| C7 | 0.017 (3) | 0.030 (4) | 0.019 (3) | 0.005 (3) | 0.003 (3) | −0.004 (3) |
| C23 | 0.021 (3) | 0.024 (3) | 0.022 (3) | 0.003 (3) | 0.004 (3) | 0.000 (3) |
| C24 | 0.014 (3) | 0.029 (3) | 0.014 (3) | −0.003 (3) | 0.002 (3) | 0.003 (3) |
| C14 | 0.015 (3) | 0.037 (4) | 0.020 (3) | −0.003 (3) | 0.000 (3) | 0.002 (3) |
| C12 | 0.024 (3) | 0.030 (4) | 0.030 (4) | 0.000 (4) | −0.003 (3) | −0.013 (3) |
| C01D | 0.015 (3) | 0.032 (4) | 0.018 (3) | −0.001 (3) | −0.001 (3) | 0.000 (3) |
| C22 | 0.022 (3) | 0.025 (4) | 0.027 (4) | −0.002 (3) | −0.006 (3) | −0.009 (3) |
| C01F | 0.016 (3) | 0.041 (4) | 0.023 (3) | 0.000 (4) | −0.001 (3) | 0.000 (3) |
| C8 | 0.025 (3) | 0.022 (3) | 0.021 (3) | 0.001 (3) | 0.001 (3) | 0.000 (3) |
| C27 | 0.018 (3) | 0.032 (4) | 0.031 (4) | −0.002 (3) | −0.001 (3) | −0.024 (3) |
| C17 | 0.017 (3) | 0.029 (4) | 0.019 (3) | −0.001 (3) | −0.004 (3) | 0.002 (3) |

TABLE H-continued

| Atomic displacement parameters (Å²) for (xx) | | | | | | |
|---|---|---|---|---|---|---|
| | U¹¹ | U²² | U³³ | U¹² | U¹³ | U²³ |
| C01J | 0.020 (3) | 0.041 (4) | 0.029 (4) | 0.004 (4) | 0.002 (3) | −0.014 (3) |
| C13 | 0.024 (3) | 0.041 (4) | 0.016 (3) | −0.001 (4) | 0.000 (3) | −0.007 (3) |
| C01L | 0.019 (3) | 0.056 (5) | 0.018 (3) | 0.008 (4) | −0.001 (3) | −0.013 (3) |
| C01M | 0.023 (3) | 0.027 (4) | 0.020 (3) | 0.003 (3) | 0.000 (3) | −0.004 (3) |
| C9 | 0.016 (3) | 0.025 (4) | 0.034 (4) | 0.002 (3) | −0.003 (3) | 0.007 (3) |
| C11 | 0.025 (4) | 0.049 (5) | 0.014 (3) | 0.007 (4) | 0.003 (3) | 0.007 (3) |
| C26 | 0.021 (4) | 0.035 (4) | 0.018 (3) | 0.000 (3) | 0.002 (3) | −0.001 (3) |
| C3 | 0.028 (4) | 0.039 (5) | 0.041 (5) | −0.005 (3) | −0.002 (3) | 0.012 (4) |
| C30 | 0.023 (3) | 0.033 (4) | 0.038 (4) | −0.007 (3) | 0.002 (3) | −0.006 (3) |
| C10 | 0.023 (3) | 0.038 (4) | 0.029 (4) | 0.003 (4) | −0.005 (3) | 0.021 (3) |
| C1 | 0.030 (4) | 0.014 (3) | 0.024 (3) | −0.003 (3) | 0.000 (3) | 0.006 (3) |
| C20 | 0.045 (4) | 0.036 (5) | 0.025 (4) | 0.001 (4) | −0.011 (3) | −0.008 (4) |
| C29 | 0.020 (3) | 0.015 (3) | 0.026 (3) | −0.002 (3) | 0.002 (3) | −0.004 (3) |
| C01W | 0.023 (3) | 0.020 (4) | 0.025 (3) | 0.009 (3) | 0.000 (3) | −0.005 (3) |
| C32 | 0.038 (4) | 0.025 (4) | 0.021 (3) | −0.007 (4) | −0.003 (3) | 0.000 (3) |
| C01Y | 0.040 (4) | 0.027 (4) | 0.025 (4) | −0.010 (3) | 0.004 (3) | −0.010 (3) |
| C31 | 0.050 (5) | 0.027 (4) | 0.030 (4) | −0.002 (4) | 0.003 (4) | 0.013 (3) |
| C020 | 0.060 (5) | 0.025 (4) | 0.034 (4) | 0.010 (4) | −0.011 (4) | 0.010 (3) |
| C19 | 0.029 (4) | 0.020 (4) | 0.026 (4) | 0.000 (3) | −0.001 (3) | 0.002 (3) |
| C022 | 0.029 (4) | 0.026 (4) | 0.037 (4) | 0.002 (3) | −0.002 (3) | −0.005 (4) |
| C2 | 0.050 (5) | 0.027 (4) | 0.020 (3) | 0.002 (4) | 0.004 (4) | 0.001 (3) |
| C4 | 0.048 (5) | 0.031 (4) | 0.045 (5) | −0.004 (4) | 0.005 (4) | −0.012 (3) |
| C025 | 0.056 (5) | 0.022 (4) | 0.042 (4) | −0.009 (4) | 0.012 (4) | 0.007 (3) |
| C21 | 0.042 (4) | 0.036 (5) | 0.034 (4) | −0.013 (4) | 0.002 (4) | −0.006 (4) |

TABLE I

| Geometric parameters (Å, °) for (xx) | | | |
|---|---|---|---|
| Br2-C16 | 1.906 (6) | C15-C17 | 1.413 (8) |
| Br3-C22 | 1.896 (7) | N6-C015 | 1.364 (8) |
| Br1-C9 | 1.900 (6) | N6-C025 | 1.460 (8) |
| Br4-C012 | 1.899 (7) | C18-C17 | 1.417 (8) |
| F15-C26 | 1.358 (7) | C18-C19 | 1.525 (8) |
| F5-C13 | 1.362 (7) | C012-C01J | 1.425 (9) |
| F8-C022 | 1.346 (8) | C012-C01M | 1.366 (8) |
| F13-C32 | 1.351 (7) | C6-C5 | 1.393 (8) |
| F12-C32 | 1.309 (8) | C6-C7 | 1.430 (8) |
| F4-C11 | 1.349 (7) | C6-C8 | 1.412 (8) |
| F2-C2 | 1.332 (8) | C28-C24 | 1.420 (8) |
| F00C-C01L | 1.354 (7) | C28-C29 | 1.520 (8) |
| F6-C022 | 1.345 (8) | C015-C01D | 1.388 (8) |
| F14-C32 | 1.349 (7) | C015-C01W | 1.536 (8) |
| F9-C21 | 1.340 (8) | C25-C24 | 1.430 (8) |
| F10-C21 | 1.344 (8) | C25-C26 | 1.407 (8) |
| F1-C2 | 1.352 (7) | C5-C1 | 1.526 (8) |
| F7-C022 | 1.344 (7) | C7-C11 | 1.412 (9) |
| O3-C29 | 1.418 (7) | C23-C24 | 1.402 (8) |
| F3-C2 | 1.337 (8) | C23-C22 | 1.372 (8) |
| O6-C19 | 1.421 (8) | C14-C17 | 1.427 (8) |
| O2-C01W | 1.414 (7) | C14-C13 | 1.400 (9) |
| O1-C1 | 1.410 (7) | C12-C13 | 1.359 (9) |
| F11-C21 | 1.346 (8) | C01D-C01F | 1.446 (8) |
| N8-N7 | 1.355 (6) | C01D-C01M | 1.411 (8) |
| N8-C25 | 1.330 (8) | C22-C27 | 1.416 (8) |
| N3-N4 | 1.359 (7) | C01F-C01L | 1.407 (9) |
| N3-C14 | 1.335 (8) | C8-C9 | 1.356 (8) |
| N2-N1 | 1.352 (7) | C27-C26 | 1.350 (9) |
| N2-C7 | 1.326 (8) | C01J-C01L | 1.347 (10) |
| N7-C28 | 1.369 (7) | C9-C10 | 1.419 (8) |
| N7-C31 | 1.455 (8) | C11-C10 | 1.346 (10) |
| N5-N6 | 1.362 (7) | C3-C1 | 1.532 (9) |
| N5-C01F | 1.331 (8) | C30-C29 | 1.536 (8) |
| N4-C18 | 1.354 (7) | C1-C2 | 1.528 (9) |
| N4-C020 | 1.457 (8) | C20-C19 | 1.519 (9) |
| N1-C5 | 1.369 (7) | C29-C32 | 1.537 (9) |
| N1-C4 | 1.465 (8) | C01W-C01Y | 1.520 (9) |
| C16-C15 | 1.383 (8) | C01W-C022 | 1.517 (8) |
| C16-C12 | 1.406 (8) | C19-C21 | 1.509 (10) |
| C25-N8-N7 | 104.0 (5) | C01L-C01J-C012 | 118.3 (6) |
| C14-N3-N4 | 104.1 (5) | F5-C13-C14 | 118.2 (6) |
| C7-N2-N1 | 104.0 (5) | C12-C13-F5 | 120.0 (6) |
| N8-N7-C28 | 114.0 (5) | C12-C13-C14 | 121.8 (6) |

TABLE I-continued

| Geometric parameters (Å, °) for (xx) | | | |
|---|---|---|---|
| N8-N7-C31 | 116.1 (5) | F00C-C01L-C01F | 118.3 (7) |
| C28-N7-C31 | 129.9 (5) | C01J-C01L-F00C | 119.8 (6) |
| C01F-N5-N6 | 104.3 (5) | C01J-C01L-C01F | 121.9 (6) |
| N3-N4-C020 | 115.8 (5) | C012-C01M-C01D | 117.7 (6) |
| C18-N4-N3 | 113.9 (5) | C8-C9-Br1 | 118.9 (5) |
| C18-N4-C020 | 130.2 (5) | C8-C9-C10 | 123.9 (6) |
| N2-N1-C5 | 113.4 (5) | C10-C9-Br1 | 117.1 (5) |
| N2-N1-C4 | 116.0 (5) | F4-C11-C7 | 117.9 (6) |
| C5-N1-C4 | 130.5 (5) | C10-C11-F4 | 120.4 (6) |
| C15-C16-Br2 | 118.7 (5) | C10-C11-C7 | 121.7 (6) |
| C15-C16-C12 | 124.7 (6) | F15-C26-C25 | 117.9 (6) |
| C12-C16-Br2 | 116.7 (5) | C27-C26-F15 | 120.0 (6) |
| C16-C15-C17 | 116.2 (6) | C27-C26-C25 | 122.1 (6) |
| N5-N6-C015 | 113.3 (5) | C11-C10-C9 | 117.9 (6) |
| N5-N6-C025 | 116.4 (5) | O1-C1-C5 | 108.9 (5) |
| C015-N6-C025 | 130.3 (6) | O1-C1-C3 | 110.6 (5) |
| N4-C18-C17 | 105.9 (5) | O1-C1-C2 | 106.6 (5) |
| N4-C18-C19 | 124.2 (5) | C5-C1-C3 | 111.0 (5) |
| C17-C18-C19 | 129.9 (5) | C5-C1-C2 | 111.7 (5) |
| C01J-C012-Br4 | 117.3 (5) | C2-C1-C3 | 108.0 (6) |
| C01M-C012-Br4 | 119.0 (5) | O3-C29-C28 | 108.5 (5) |
| C01M-C012-C01J | 123.7 (6) | O3-C29-C30 | 112.1 (5) |
| C5-C6-C7 | 103.5 (5) | O3-C29-C32 | 104.7 (5) |
| C5-C6-C8 | 137.2 (6) | C28-C29-C30 | 110.6 (5) |
| C8-C6-C7 | 119.3 (6) | C28-C29-C32 | 111.1 (5) |
| N7-C28-C24 | 105.6 (5) | C30-C29-C32 | 109.7 (5) |
| N7-C28-C29 | 119.2 (5) | O2-C01W-C015 | 111.6 (5) |
| C24-C28-C29 | 135.0 (5) | O2-C01W-C01Y | 110.8 (5) |
| N6-C015-C01D | 106.6 (5) | O2-C01W-C022 | 103.7 (5) |
| N6-C015-C01W | 124.2 (6) | C01Y-C01W-C015 | 111.9 (5) |
| C01D-C015-C01W | 129.2 (6) | C022-C01W-C015 | 109.8 (5) |
| N8-C25-C24 | 113.3 (5) | C022-C01W-C01Y | 108.6 (5) |
| N8-C25-C26 | 128.5 (6) | F13-C32-C29 | 108.9 (5) |
| C26-C25-C24 | 118.2 (6) | F12-C32-F13 | 108.6 (5) |
| N1-C5-C6 | 106.2 (5) | F12-C32-F14 | 108.7 (6) |
| N1-C5-C1 | 118.4 (5) | F12-C32-C29 | 113.4 (5) |
| C6-C5-C1 | 135.1 (5) | F14-C32-F13 | 105.2 (5) |
| N2-C7-C6 | 112.8 (6) | F14-C32-C29 | 111.7 (5) |
| N2-C7-C11 | 128.1 (6) | O6-C19-C18 | 108.6 (5) |
| C11-C7-C6 | 119.0 (6) | O6-C19-C20 | 111.0 (5) |
| C22-C23-C24 | 118.0 (6) | O6-C19-C21 | 106.8 (6) |
| C28-C24-C25 | 103.1 (5) | C20-C19-C18 | 112.1 (6) |
| C23-C24-C28 | 136.5 (5) | C21-C19-C18 | 109.7 (6) |
| C23-C24-C25 | 120.3 (5) | C21-C19-C20 | 108.6 (6) |

TABLE I-continued

| Geometric parameters (Å, °) for (xx) | | | |
|---|---|---|---|
| N3-C14-C17 | 112.4 (6) | F8-C022-C01W | 112.6 (6) |
| N3-C14-C13 | 128.6 (6) | F6-C022-F8 | 106.9 (5) |
| C13-C14-C17 | 118.9 (6) | F6-C022-F7 | 107.2 (5) |
| C13-C12-C16 | 117.7 (6) | F6-C022-C01W | 112.3 (5) |
| C015-C01D-C01F | 103.9 (5) | F7-C022-F8 | 106.3 (5) |
| C015-C01D-C01M | 136.2 (6) | F7-C022-C01W | 111.1 (5) |
| C01M-C01D-C01F | 119.9 (6) | F2-C2-F1 | 106.7 (6) |
| C23-C22-Br3 | 119.6 (5) | F2-C2-F3 | 109.1 (6) |
| C23-C22-C27 | 123.1 (6) | F2-C2-C1 | 112.3 (6) |
| C27-C22-Br3 | 117.3 (5) | F1-C2-C1 | 109.3 (5) |
| N5-C01F-C01D | 111.9 (5) | F3-C2-F1 | 106.0 (5) |
| N5-C01F-C01L | 129.6 (6) | F3-C2-C1 | 113.1 (6) |
| C01L-C01F-C01D | 118.5 (6) | F9-C21-F10 | 107.2 (6) |
| C9-C8-C6 | 118.1 (6) | F9-C21-F11 | 107.3 (6) |
| C26-C27-C22 | 118.2 (5) | F9-C21-C19 | 113.2 (6) |
| C15-C17-C18 | 135.8 (6) | F10-C21-F11 | 106.8 (6) |
| C15-C17-C14 | 120.6 (6) | F10-C21-C19 | 111.4 (6) |
| C18-C17-C14 | 103.6 (5) | F11-C21-C19 | 110.7 (6) |

What is claimed:

1. A compound of

Formula (I)

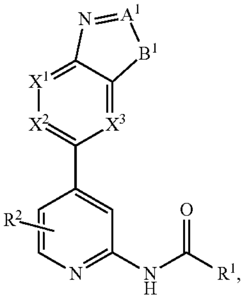

or

Formula (II)

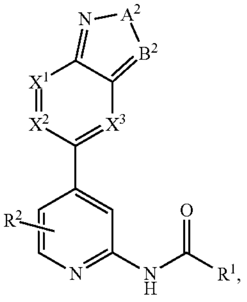

or a pharmaceutically acceptable salt or solvate thereof, wherein:

$X^1$, $X^2$, and $X^3$ are each independently N or $CR^3$;

$A^1$ is N or C—$R^4$, $B^1$ is C—$R^6R^7$, N—$R^5$;

$A^2$ is N—$R^8$, S, or O;

$B^2$ is C—$R^9$;

$R_1$ is $C_{3-10}$cycloalkyl or 4-10 membered heterocycloalkyl optionally substituted with 1, 2, 3, 4, 5, 6, 7 or 8 independently selected Rb substituents;

$R^2$ is $C_{1-6}$ alkyl;

$R^3$ is H, D, OH, halogen, CN, $C_{1-6}$ alkyl, $C_{3-10}$ cycloalkyl, $C_{1-6}$ alkoxyl, $C_{1-6}$ haloalkyl, or 4-14 membered heterocycloalkyl;

$R^4$ is H, D, $C_{1-6}$ alkyl, $C_{1-6}$ alkoxy, $C_{3-6}$ cycloalkyl, or 4-6 membered heterocycloalkyl;

$R^5$ is $C_{1-6}$ alkyl, $C_{1-6}$ alkoxy, —$CF_3(CH)CH_3$, $C_{3-6}$ cycloalkyl, —$CH_2$-($C_{3-6}$ cycloalkyl), or 4-6 membered heterocycloalkyl;

or $R^4$ and $R^5$, together with the atoms to which they are attached, form a 5-, 6-, or 7-membered heterocycloalkyl ring optionally substituted with 1, 2, 3, 4 or 5 independently selected Rb substituents;

$R^6$ is $C_{1-6}$ alkyl, $C_{1-6}$ alkoxy, $C_{3-6}$ cycloalkyl, or 4-6 membered heterocycloalkyl;

$R^7$ is $C_{1-6}$ alkyl, $C_{1-6}$ alkoxy, $C_{3-6}$ cycloalkyl, or 4-6 membered heterocycloalkyl;

or $R^6$ and $R^7$ together with the carbon atom to which they are both attached, form a $C_{4-7}$ spirocyclic ring;

$R^8$ is $C_{1-6}$ alkyl, $C_{1-6}$ alkoxy, $C_{3-6}$ cycloalkyl, or 4-6 membered heterocycloalkyl; and $R^9$ is $C_{1-6}$ alkyl, $C_{1-6}$ alkoxy, $C_{3-6}$ cycloalkyl, or 4-6 membered heterocycloalkyl;

or $R^8$ and $R^9$, together with the atoms to which they are attached, form an 5- or 6-membered heterocycloalkyl ring optionally substituted with 1, 2, 3, 4 or 5 independently selected Rb substituents;

$R^b$ is CN, $C_{1-4}$ alkyl, 5-10 membered heteroaryl, 4-14 membered heterocycloalkyl, $NR^cC({=}NR^c)NR^cR^c$, $NR^cC({=}NOH)NR^cR^c$, $NR^cC({=}NCN)NR^cR^c$, $NR^cC(O)R^c$, $NR^cC(O)OR^c$, $NR^cC(O)NR^cR^c$, $NR^cS(O)R^c$, or $NR^cS(O)_2R^c$, $NR^cS(O)_2NR^cR^c$;

each $R^c$ is independently H, OH, $C_{1-6}$ alkyl, $C_{1-6}$ alkoxy, $C_{2-6}$ alkenyl, $C_{2-6}$ alkynyl, $C_{6-10}$ aryl, $C_{3-10}$ cycloalkyl, 4-10 membered heterocycloalkyl, 5-10 membered heteroaryl, $C_{6-10}$ aryl-$C_{1-4}$ alkyl, $C_{3-10}$ cycloalkyl-$C_{1-4}$ alkyl, or (4-10 membered heterocycloalkyl)-$C_{1-4}$ alkyl, or (5-10 membered heteroaryl)-$C_{1-4}$ alkyl;

wherein when $R^c$ is $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl, then $R^c$ is optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

2. The compound of claim 1, wherein the compound has a formula:

Formula (I)

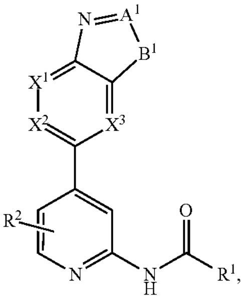

or

Formula (II)

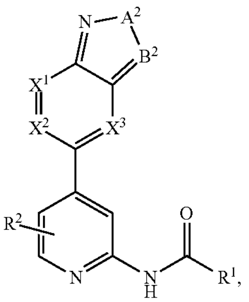

or a or a pharmaceutically acceptable salt or solvate thereof, wherein:

$X^1$, $X^2$, and $X^3$ are each independently N or $CR^3$;

$A^1$ is N or C—$R^4$;

$B^1$ is C—$R^6R^7$, N—$R^5$;

$A^2$ is N—$R^8$, S, or O;

$B^2$ is C—$R^9$;

$R_1$ is $C_{3-10}$cycloalkyl optionally substituted with 1, 2, 3, 4, 5, 6, 7 or 8 independently selected Rb substituents;

$R^2$ is $C_{1-6}$ alkyl;

$R^3$ is H, D, OH, halogen, CN, $C_{1-6}$ alkyl, $C_{3-10}$ cycloalkyl, $C_{1-6}$ alkoxyl, or 4-14 membered heterocycloalkyl;

$R^4$ is H, D, $C_{1-6}$ alkyl, or $C_{1-6}$ alkoxy;

$R^5$ is $C_{1-6}$ alkyl or $C_{1-6}$ alkoxy;

or $R^4$ and $R^5$, together with the atoms to which they are attached, form an 5-, 6-, or 7-membered heterocycloalkyl ring optionally substituted with 1, 2, 3, 4 or 5 independently selected Rb substituents;

$R^6$ is $C_{1-6}$ alkyl;

$R^7$ is $C_{1-6}$ alkyl;

or $R^6$ and $R^7$ together with the carbon atom to which they are both attached, form a $C_{4-7}$ spirocyclic ring;

$R^8$ is $C_{1-6}$ alkyl; and $R^9$ is $C_{1-6}$ alkyl;

or $R^8$ and $R^9$, together with the atoms to which they are attached, form an 5-, 6-, or 7-membered heterocycloalkyl ring optionally substituted with 1, 2, 3, 4 or 5 independently selected Rb substituents;

$R^b$ is $C_{1-4}$ alkyl, $NR^cC(=NR^c)NR^cR^c$, $NR^cC(=NOH)NR^cR^c$, $NR^cC(=NCN)NR^cR^c$, $NR^cC(O)R^c$, $NR^cC(O)OR^c$, $NR^cC(O)NR^cR^c$, $NR^cS(O)R^c$, $NR^cS(O)(=NR^c)R^c$, $NR^cS(O)_2R^c$, or $NR^cS(O)_2NR^cR^c$;

each $R^c$ is independently H, $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl;

wherein when $R^c$ is $C_{1-6}$ alkyl, $C_{1-6}$ alkoxy, $C_{3-10}$ cycloalkyl, 4-10 membered heterocycloalkyl, or (5-10 membered heteroaryl)-$C_{1-4}$ alkyl, then $R^c$ is optionally substituted with 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

3. The compound according to claim 1, or a pharmaceutically acceptable salt or solvate thereof, wherein $R^2$ is $CH_3$ or $CH_2CH_3$.

4. The compound according to claim 1, or a pharmaceutically acceptable salt or solvate thereof, wherein said compound is a compound of Formula (I):

Formula (I)

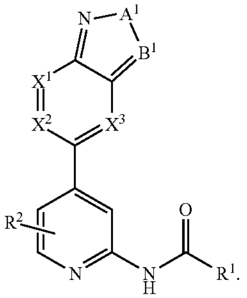

5. The compound according to claim 1, or a pharmaceutically acceptable salt or solvate thereof, wherein said compound is a compound of Formula (II):

Formula (II)

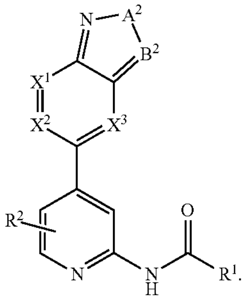

6. The compound of claim 1, wherein the compound has a formula of

Formula (III)

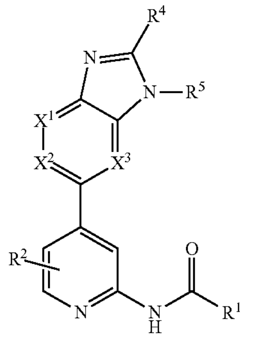

or

Formula (IV)

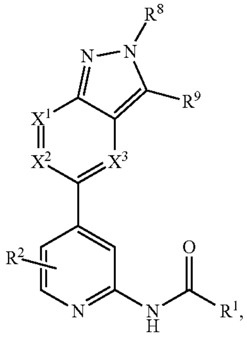

or a pharmaceutically acceptable salt or solvate thereof.

7. The compound of claim 1, wherein the compound has a formula of

Formula (V)

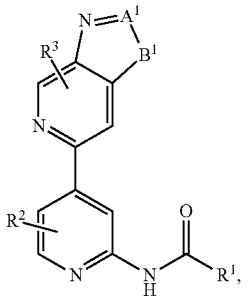

Formula (VI)

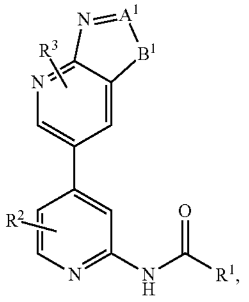

Formula (VII)

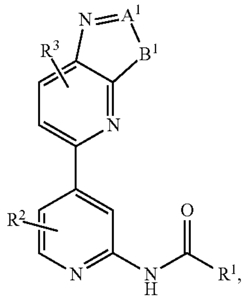

Formula (VIII)

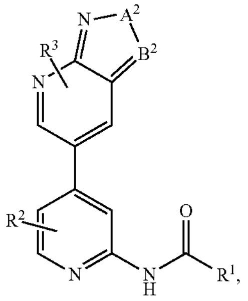

Formula (IX)

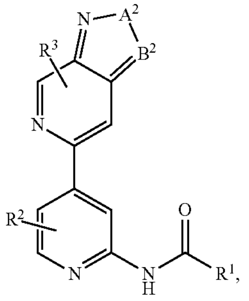

-continued

Formula (X)

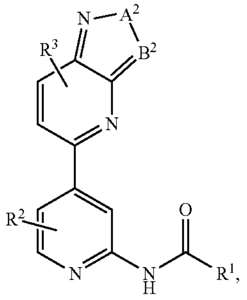

Formula (XI)

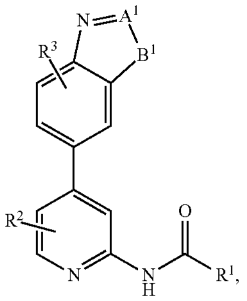

or

Formula (XII)

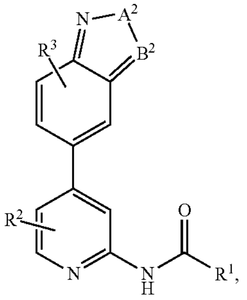

or a pharmaceutically acceptable salt or solvate thereof.

8. The compound according to claim 7, or a pharmaceutically acceptable salt or solvate thereof, wherein said compound is a compound of Formula (V), Formula (VI), Formula (VII), or Formula (XI):

Formula (V)

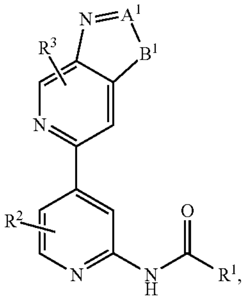

-continued

Formula (VI)

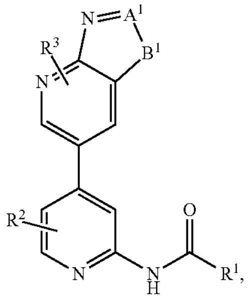

Formula (VII)

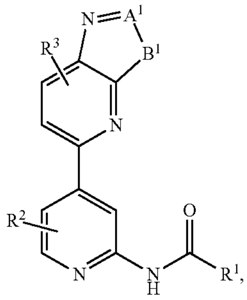

or

Formula (XI)

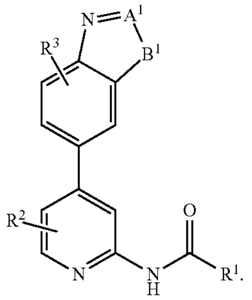

9. The compound according to claim 7, or a pharmaceutically acceptable salt or solvate thereof, wherein said compound is a compound of Formula (VIII), Formula (IX), Formula (X), or Formula (XII):

Formula (VIII)

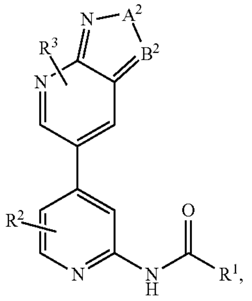

-continued

Formula (IX)

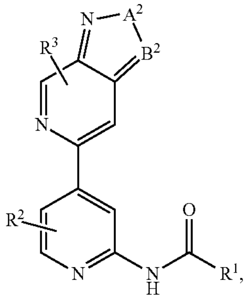

Formula (X)

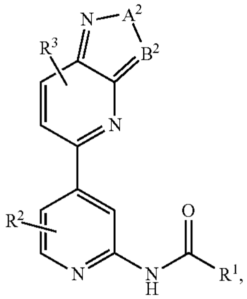

or

Formula (XII)

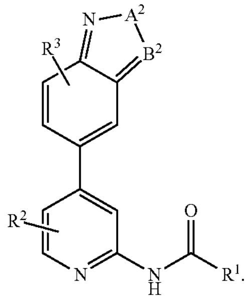

10. The compound of claim 1, or a pharmaceutically acceptable salt or solvate thereof, wherein $R^1$ is

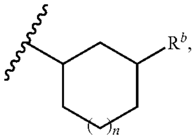

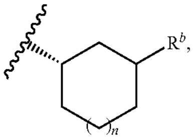

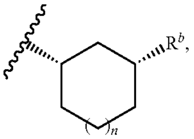

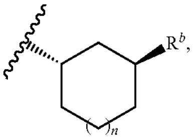

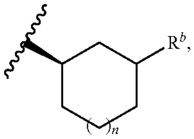

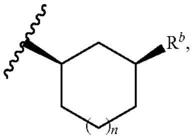

or

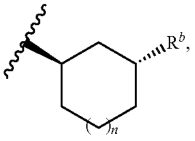

wherein n is 0 or 1.

11. The compound of claim 10, or a pharmaceutically acceptable salt or solvate thereof, wherein the 1 Rb substituent on $R^1$ is acetamido (—NHC(O)$CH_3$), 3-hydroxybutanamido (—NHC(O)$CH_2$CH(OH)$CH_3$), propionamido (—NHC(O)$CH_2CH_3$), 2-methoxyacetamido (—NHC(O)$CH_2$—$OCH_3$), 2-cyanoacetamido (—NHC(O)$CH_2$—CN),

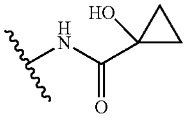
,
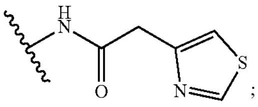
;

methylsulfonamido (—$NHSO_2CH_3$), 3-methylureido (—NHC(O)$NHCH_3$), 3-methoxyureido (—NHC(O)$NHOCH_3$), 3,3-dimethylureido (—NHC(O)N$(CH_3)_2$), 3-ethylureido (—NHC(O)$NHCH_2CH_3$),

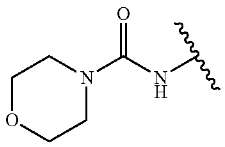
or
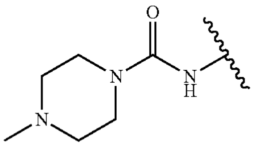
.

12. The compound of claim 1, wherein the compound, or a pharmaceutically acceptable salt or solvate thereof, has a formula of Formula (XIII)

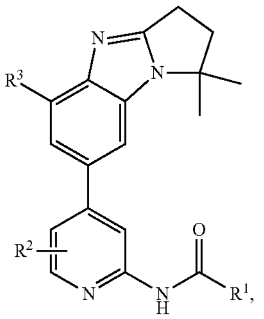

Formula (XV)

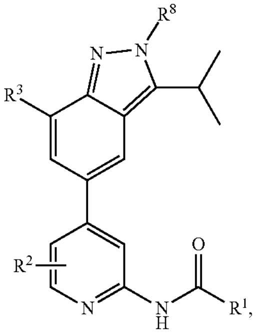
or

-continued

Formula (XVIII)

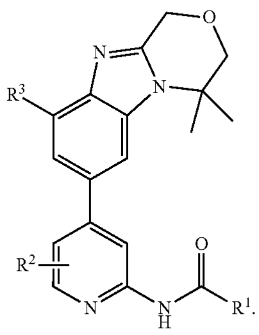

13. The compound of claim 1, wherein the compound, or a pharmaceutically acceptable salt or solvate thereof, has a formula of Formula (XIX-a)

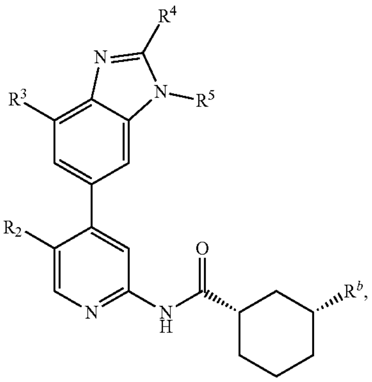

wherein $R^2$ is Me;

$R^3$ is H, D, or F;

$R^4$ is H or $C_{1-3}$ alkyl;

$R^5$ is isopropyl, —$CF_3$(CH)$CH_3$, —$C_{3-6}$ cycloalkyl, or —$CH_2$-($C_{3-6}$ cycloalkyl);

$R^b$ is $NHCOR^{13}$ or CN; and $R^{13}$ is H or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl.

14. The compound of claim 13, wherein the compound, or a pharmaceutically acceptable salt or solvate thereof, has a formula of Formula (XIX-e)

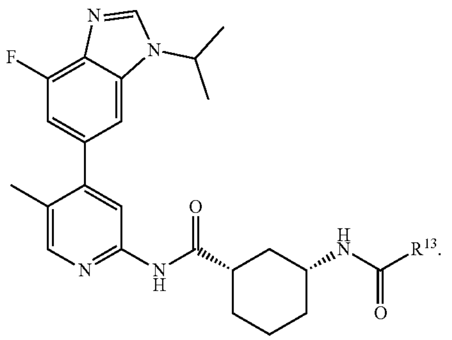

15. A compound, or a pharmaceutically acceptable salt or solvate thereof, wherein the compound has the formula;

Formula (XXIII-a)

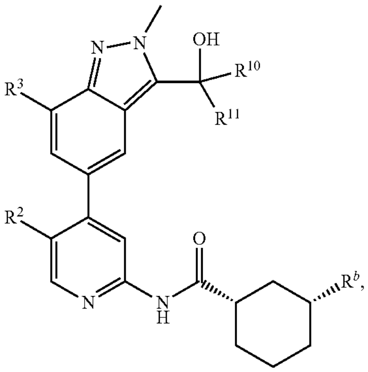

wherein:

$R^2$ is Me;

$R^3$ is H, D, or F;

$R^{10}$ is H, D, Me, or $C_{1-3}$ haloalkyl;

$R^{11}$ is H, D, Me, or $C_{1-3}$ haloalkyl;

$R^b$ is $NHCOR^{14}$; and $R^{14}$ is H, —$CH_2CN$, or optionally substituted $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-4}$ alkyl, $C_{3-10}$ cycloalkyl-$C_{1-4}$ alkyl, (5-10 membered heteroaryl)-$C_{1-4}$ alkyl- or (4-10 membered heterocycloalkyl)-$C_{1-4}$ alkyl;

wherein when $R^{14}$ is optionally substituted, the optional substituents are 1, 2, 3, 4, or 5 independently selected $R^f$ substituents;

each $R^f$ is independently halogen, CN, $C_{1-4}$ alkyl, or $OR^g$; and each $R^g$ is independently H or $C_{1-6}$ alkyl.

16. The compound of claim 15, wherein the compound, or a pharmaceutically acceptable salt or solvate thereof, has a formula of Formula (XXVII-e)

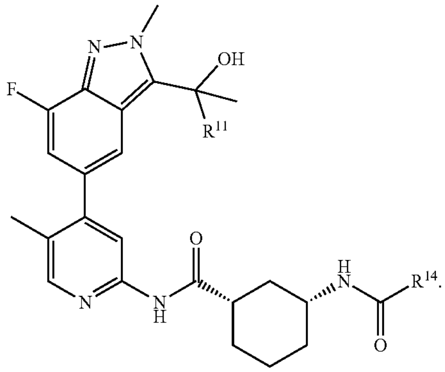

17. A pharmaceutical composition comprising a compound according to claim 1, or a pharmaceutically acceptable salt or solvate thereof, and a pharmaceutically acceptable excipient.

18. A method of inhibiting a CDK enzyme comprising: contacting the CDK enzyme with an effective amount of a compound of claim 1, or a pharmaceutically acceptable salt or solvate thereof.

19. The method of claim 18, wherein the CDK enzyme is CDK9.

20. A method of treating a disease or disorder associated with aberrant CDK activity in a subject or a subject in need thereof comprising administering to the subject, a compound of claim 1, or a pharmaceutically acceptable salt or solvate thereof.

21. The method of claim 20, wherein the disease or disorder associated with aberrant CDK activity is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

22. A method of treating cancer in a subject or a subject in need thereof comprising administering to the subject, a compound of claim 1, or a pharmaceutically acceptable salt or solvate thereof.

23. The method of claim 22, wherein the cancer is colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

* * * * *